US006488931B1

(12) United States Patent
Mitcham et al.

(10) Patent No.: US 6,488,931 B1
(45) Date of Patent: *Dec. 3, 2002

(54) COMPOSITIONS AND METHODS FOR THERAPY AND DIAGNOSIS OF OVARIAN CANCER

(75) Inventors: Jennifer L. Mitcham, Redmond, WA (US); Tony N. Frudakis, Sarasota, FL (US); Gordon E. King, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/338,933

(22) Filed: Jun. 23, 1999

Related U.S. Application Data

(63) Continuation-in-part of application No. 09/216,003, filed on Dec. 17, 1998, and a continuation-in-part of application No. 09/215,681, filed on Dec. 17, 1998.

(51) Int. Cl.[7] .................. A61K 39/00; C07K 14/00; C07K 17/00; C07K 1/00
(52) U.S. Cl. .................. 424/184.1; 424/192.1; 424/277.1; 435/6; 435/69.1; 435/69.3; 435/69.7; 530/300; 530/350; 530/828; 530/853
(58) Field of Search .................. 530/300, 350, 530/828, 853; 424/184.1, 192.1, 277.1; 435/6, 69.1, 69.3, 69.7

(56) References Cited

U.S. PATENT DOCUMENTS 5,480,795 A * 1/1996 Kurihara et al. ........... 435/91.4

OTHER PUBLICATIONS

Bookman et al., "Biological therapy of ovarian cancer: Current directions," *Seminars in Oncology*, 25(3):381–396.
Gillespie et al., "Mage, Bage and Gage: Tumour antigen expression in benign and malignant ovarian tissue," *British Journal of Cancer*, 78(6):816–821, Sep., 1998.
Heller et al., "Discovery and analysis of inflammatory disease–related genes using cDNA microarrays," *Proc. Natl. Acad. Sci. USA* 94:2150–2155, Mar., 1997.
Ishikawa et al., "Prediction of the coding sequence of unidentified human genes. The complete sequence of 100 new cDNA clones from brain which can code for large proteins in vitro," *DNA Res.*, 5:169–176, 1998.
Jin et al., "Human T cell leukemia virus type 1 oncoprotein tax targets the human mitotic checkpoint protein MAD1," *Cell* 93:81–91, Apr. 3, 1998.
Köhler et al., "Immotherapy of Ovarian Carcinoma with the Monoclonal Anti–Idiotype Antibody ACA125—Results of the Phase LB Study," *Gebrutshilfe und Fraenheilkunde*, 58(4):180–186, Apr. 1998, (English Abstract).
Ma et al., "Use of encapsulated single chain antibodies for induction of anti–idiotypic humoral and cellular immune responses," *Journal of Pharmaceutical Sciences*, 87(11):1375–1378, Nov., 1998.
Peoples et al., "Ovarian cancer–associated lymphocyte recognition of folate binding protein peptides," *Annals of Surgical Oncology*, 5(8):743–750, Dec., 1998.
Schena et al., "Parallel human genome analysis: Microarray–based expression monitoring of 1000 genes," *Proc. Natl. Acad. Sci.*, 93:10614–10619, Oct., 1996.

* cited by examiner

Primary Examiner—Mary K. Zeman
(74) Attorney, Agent, or Firm—Seed Intellectual Property Law Group PLLC

(57) ABSTRACT

Compositions and methods for the therapy of cancer, such as ovarian cancer, are disclosed. Compositions may comprise one or more ovarian carcinoma proteins, immunogenic portions thereof, polynucleotides that encode such portions or antibodies or immune system cells specific for such proteins. Such compositions may be used, for example, for the prevention and treatment of diseases such as ovarian cancer. Methods are further provided for identifying tumor antigens that are secreted from ovarian carcinomas and/or other tumors.

9 Claims, 91 Drawing Sheets

11729.1 contig

```
TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC
```

11729-45.21.21.cons1

```
TAGGATGTGTTGGACCCTCTGTGTCAAAAAAAACCTCACAAAGAATCCCCTGCTCATTACAGAAGAAGATGCATTT
AAAATATGGGTTATTTTCAACTTTTTATCTGAGGACAAGTATCCATTAATTATTGTGTCAGAAGAGATTGAATACC
TGCTTAAGAAGCTTACAGAAGCTATGGGAGGAGGTTGGCAGCAAGAACAATTTGAACATTATAAAATCAACTTTGA
TGACAGTAAAAATGGCCTTTCTGCATGGGAACTTATTGAGCTTATTGGAAATGGACAGTTTAGCAAAGGCATGGAC
CGGCAGACTGTGTCTATGGCAATTAATGAAGTCTTTAATGAACTTATATTAGATGTGTTAAAGCAGGGTTACATGA
TGAAAAAGGGCCACAGACGGAAAAACTGGACTGAAAGATGGTTTGTACTAAAACCCAACATAATTTCTTACTATGT
GAGTGAGGATCTGAAGGATAAGAAAGGAGACATTCTCTTGGATGAAAATTGCTGTGTAGAGTCCTTGCCTGACAAA
GATGGAAA
```

11729-45.21.21.cons2

```
TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC
```

11731.1contig

```
TCTTTTTCTTTCGATTTCCTTCAATTTGTCACGTTTGATTTTATGAAGTTGTTCAAGGGCTAACTGCTGTGTATTA
TAGCTTTCTCTGAGTTCCTTCAGCTGATTGTTAAATGAATCCATTTCTGAGAGCTTAGATGCAGTTTCTTTTTCAA
GAGCATCTAATTGTTCTTTAAGTCTTTGGCATAATTCTTCCTTTTCTGATGACTTTTTATGAAGTAAACTGATCCC
TGAATCAGGTGTGTTACTGAGCTGCATGTTTTTAATTCTTTCGTTTAATAGCTGCTTCTCAGGGACCAGATAGATA
AGCTTATTTTGATATTCCTTAAGCTCTTGTTGAAGTTGTTTGATTTCCATAATTTCCAGGTCACACTGTTTATCCA
AAACTTCTAGCTCAGTCTTTTGTGTTTGCTTTCTGATTTGGACATCTTGTAGTCTGCCTGAGATCTGCTGATGXTT
TCCATTCACTGCTTCCAGTTCCAGGTGGAGACTTTXCTTTCTGGAGCTCAGCCTGACAATGCCTTCTTGXTCCCT
```

*Fig. 1A*

11731.2contig

```
AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTA
```

11734.1contig

```
AATAGATTTAATGCAGAGTGTCAACTTCAATTGATTGATAGTGGCTGCCTAGAGTGCTGTGTTGAGTAGGTTTCTG
AGGATGCACCCTGGCTTGAAGAGAAAGACTGGCAGGATTAACAATATCTAAAATCTCACTTGTAGGAGAAACCACA
GGCACCAGAGCTGCCACTGGTGCTGGCACCAGCTCCACCAAGGCCAGCGAAGAGCCCAAATGTGAGAGTGGCGGTC
AGGCTGGCACCAGCACTGAAGCCACCACTGGTGCTGGCACTGGCACTGGCACTGTTATTGGTACTGGTACTGGCAC
CAGTGCTGGCACTGCCACTCTCTTGGGCTTTGGCTTTAGCTTCTGCTCCCGCCTGGATCCGGGCTTTGGCCCAGGG
TCCGATATCAGCTTCGTCCCAGTTGCAGGGCCCGGCAGCATTCTCCGAGCCGAGCCCAATGCCCATTCGAGCTCTA
ATCTCGGCCCTAGCCTTGGCTTCAGCTGCAGCCTCAGCTGCAGCCTTCAAATCCGCTTCCATCGCCTCTCGGTAC
```

11734.2contig

```
GCCAAGAAAGCCCGAAAGGTGAAGCATCTGGATGGGGAAGAGGATGGCAGCAGTGATCAGAGTCAGGCTTCTGGAA
CCACAGGTGGCCGAAGGGTCTCAAAGGCCCTAATGGCCTCAATGGCCCGCAGGGCTTCAAGGGGTCCCATAGCCTT
TTGGGCCCGCAGGGCATCAAGGACTCGGTTGGCTGCTTGGGCCCGGAGAGCCTTGCTCTCCCTGAGATCACCTAAA
GCCCGTAGGGGCAAGGCTCGCCGTAGAGCTGCCAAGCTCCAGTCATCCCAAGAGCCTGAAGCACCACCACCTCGGG
ATGTGGCCCTTTTGCAAGGGAGGGCAAATGATTTGGTGAAGTACCTTTTGGCTAAAGACCAGACGAAGATTCCCAT
CAAGCGCTCGGACATGCTGAAGGACATCATCAAAGAATACACTGATGTGTACCCCGAAATCATTGAACGAGCAGGC
TATTCCTTGGAGAAGGTATTTGGGATTCAATTGAAGGAAATTGATAAGAATGACCACTTGTACATTCTTCTCAGC
```

11736.1contg

```
GAGGTCTCACTATGTTGCCCAGGCTGTTCTTGAACTCCTGGGATCAAGCAATCCACCCATGTTGGTCTCCAAAAGT
GCTGGGATCATAGGCGTGAGCCACCTCACCCAGCCACCAATTTTCAATCAGGAAGACTTTTTCCTTCTTCAAGAAG
TGAAGGGGTTTCCAGAGTATAGCTACACTATTGCTTGCCTGAGGGTGACTACAAAATTGCTTGCTAAAAGGTTAGGA
TGGGTAAAGAATTAGATTTTCTGAATGCAAAAATAAAATGTGAACTAATGAACTTTAGGTAATACATATTCATAAA
ATAATTATTCACATATTTCCTGATTTATCACAGAAATAATGTATGAAATGCTTTGAGTTTCTTGGAGTAAACTCCA
TTACTCATCCCAAGAAACCATATTATAAGTATCACTGATAATAAGAACAACAGGACCTTGTCATAAATTCTGGATA
AGAGAAATAGTCTCTGGGTGTTTGXTCTTAATTGATAAAATTTACTTGTCCATCTTTTAGTTCAGAATCACAAAA
```

*Fig. 1B*

11736.2contig

```
AAGCGGAAATGAGAAAGGAGGGAAAATCATGTGGTATTGAGCGGAAAACTGCTGGATGACAGGGCTCAGTCCTGTT
GGAGAACTCTGGGTGGTGCTGTAGAACAGGGCCACTCACAGTGGGGTGCACAGACCAGCACGGCTCTGTGACCTGT
TTGTTACAGGTCCATGATGAGGTAAACAATACACTGAGTATAAGGGTTGGTTTAGAAACTCTTACAGCAATTTGAC
AAAGTAATCTTCTGTGCAGTGAATCTAAGAAAAAAATTGGGGCTGTATTTGTATGTTCCTTTTTTTCATTTCATGT
TCTGAGTTACCTATTTTTATTGCATTTTACAAAAGCATCCTTCCATGAAGGACCGGAAGTTAAAAACAAAGCAGGT
CCTTTATCACAGCACTGTCGTAGAACACAGTTCAGAGTTATCCACCCAAGGAGCCAGGGAGCTGGGCTAAACCAAA
GAATTTTGCTTTTGGTTAATCATCAGGTACTTGAGTTGGAATTGTTTTAATCCCATCATTACCAGGCTGGAXGTG
```

11739-1&2

```
CCGCGGCTCCTGTCCAGACCCTGACCCTCCCTCCCAAGGCTCAACCGTCCCCCAACAACCGCCAGCCTTGTACTGA
TGTCGGCTGCGAGAGCCTGTGCTTAAGTAAGAATCAGGCCTTATTGGAGACATTCAAGCAAAGGTTGGACAACTAC
TTTTCCAGAACAGAAAGGAAACTCATGCATCAGAAAAGGTGACTAATAAAGGTACCAGAAGAATATGGCTGCACAA
ATACCAGAATCTGATCAGATAAAACAGTTTAAGGAATTTCTGGGGACCTACAATAAACTTACAGAGACCTGCTTTT
TGGACTGTGTTAGAGACTTCACAACAAGAGAAGTAAAACCTGAAGAGACCACCTGTTCAGAACATTGCTTACAGAA
ATATTTAAAAATGACACAAAGAATATCCATGAGATTTCAGGAATATCATATTCAGCAGAATGAAGCCCTGGCAGCC
AAAGCAGGACTCCTTGGCCAACCACGATAGAGAAGTCCTGATGGATGAACTTTTGATGAAAGATTGCCAACAGCTG
CTTTATTGGAAATGAGGACTCATCTGATAGAATCCCCTGAAAGCAGTAGCCACCATGTTCAACCATCTGTCATGAC
TGTTTGGCAAATGGAAACCGCTGGAGAAACAAAATTGCTATTTACCAGGAATAATCACAATAGAAGGTCTTATTGT
TCAGTGAAATAATAAGATGCAACATTTGTTGAGGCCTTATGATTCAGCAGCTTGGTCACTTGATTAGAAAAATAAA
CCATTGTTTCTTCAATTGTGACTGTTAATTTTAAAGCAACTTATGTGTTCGATCATGTATGAGATAGAAAAATTTT
TATTACTCAAAGTAAAATAAATGGA
```

11740.1.contig

```
GAAAAAAAATATAAAACACACTTTTGCGAAAACGGTGGCCCTAAAAGAGGAAAAGAATTTCACCAATATAAATCCA
ATTTTATGAAAACTGACAATTTAATCCAAGAATCACTTTTGTAAATGAAGCTAGCAAGTGATGATATGATAAAATA
AACGTGGAGGAAATAAAAACACAAGACTTGGCATAAGATATATCCACTTTTGATATTAAACTTGTGAAGCATATTC
TTCGACAAATTGTGAAAGCGTTCCTGATCTTGCTTGTTCTCCATTTCAAATAAGGAGGCATATCACATCCCAAGAG
TAACAGAAAAAGAAAAAAGACATTTTTGCATTTTGAGATGAACCAAAGACACAAAACAAAACGAACAAAGTGTCAT
GTCTAATTCTAGCCTCTGAAATAAACCTTGAACATCTCCTACAAGGCACCGTGATTTTTGTAATTCTAACCTGAAG
AAATGTGATGACTTTTGTGGACATGAAAATCAGATGAGAAAACTGTGGTCTTTCCAAAGCCTGAACTCCCCTGAAA
ACCTTTGCA
```

*Fig. 1C*

11766.1.contig

```
CTGGGATCATTTCTCTTGATGTCATAAAAGACTCTTCTTCTTCCTCTTCATCCTCTTCTTCATCCTCTTCTGTACA
GTGCTGCCGGGTACAACGGCTATCTTTGTCTTTATCCTGAGATGAAGATGATGCTTCTGTTTCTCCTACCATAACT
GAAGAAATTTCGCTGGAAGTCGTTTGACTGGCTGTTTCTCTGACTTCACCTTCTTTGTCAAACCTGAGTCTTTTTA
CCTCATGCCCCTCAGCTTCCACAGCATCTTCATCTGGATGTTTATTTTTCAAAGGGCTCACTGAGGAAACTTCTGA
TTCAGAGGTCGAAGAGTCACTGTGATTTTTCTCCTCATTTTGCTGCAAATTTGCCTCTTTGCTGTCTGTGCTCTCA
GGCAACCCATTTGTTGTCATGGGGGCTGACAAAGAAACCTTTGGTCGATTAAGTGGCCTGGGTGTCCCAGGCCCAT
TTATATTAGACCTCTCAGTATAGCTTGGTGAATTTCCAGGAAACATAACACCATTCATTCGATTTAAACTATTGGA
ATTGGTTTT
```

11766.2.contig

```
GAGGGTTGGTGGTAGCGGCTTGGGGAGGTGCTCGCTCTGTCGGTCTTGCTCTCTCGCACGCTTCCCCCGGCTCCCT
TCGTTTCCCCCCCCGGTCGCCTGCGTGCCGGAGTGTGTGCGAGGGAGGGGGAGGGCGTCGGGGGGGTGGGGGGAG
GCGTTCCGGTCCCCAAGAGACCCGCGGAGGGAGGCGGAGGCTGTGAGGGACTCCGGGAAGCCATGGACGTCGAGAG
GCTCCAGGAGGCGCTGAAAGATTTTGAGAAGAGGGGGAAAAAGGAAGTTTGTCCTGTCCTGGATCAGTTTCTTTGT
CATGTAGCCAAGACTGGAGAAACAATGATTCAGTGGTCCCAATTTAAAGGCTATTTTATTTTCAAACTGGAGAAAG
TGATGGATGATTTCAGAACTTCAGCTCCTGAGCCAAGAGGTCCTCCCAACCCTAATGTCGA
```

11773.2.contig

```
AAGCAGGCGGCTCCCGCGCTCGCAGGGCCGTGCCACCTGCCCGCCCGCCCGCTCGCTCGCTCGCCCGCCGCGCCGC
GCTGCCGACCGCCAGCATGCTGCCGAGAGTGGGCTGCCCCGCGCTGCCGXTGCCG
```

11775-1&2

```
ATCTCTTGTATGCCAAATATTTAATATAAATCTTTGAAACAAGTTCAGATGAAATAAAAATCAAAGTTTGCAAAAA
CGTGAAGATTAACTTAATTGTCAAATATTCCTCATTGCCCCAAATCAGTATTTTTTTTATTTCTATGCAAAAGTAT
GCCTTCAAACTGCTTAAATGATATATGATATGATACACAAACCAGTTTTCAAATAGTAAAGCCAGTCATCTTGCAA
TTGTAAGAAATAGGTAAAAGATTATAAGACACCTTACACACACACACACACACACGTGTGCACGCCAATGAC
AAAAAACAATTTGGCCTCTCCTAAAATAAGAACATGAAGACCCTTAATTGCTGCCAGGAGGGAACACTGTGTCACC
CCTCCCTACAATCCAGGTAGTTTCCTTTAATCCAATAGCAAATCTGGGCATATTTGAGAGGAGTGATTCTGACAGC
CACGTTGAAATCCTGTGGGGAACCATTCATGTCCACCCACTGGTGCCCTGAAAAAATGCCAATAATTTTTCGCTCC
CACTTCTGCTGCTGtCTCTTCCACATCCTCACATAGACCCCAGACCCGCTGGCCCCTGGCTGGGCATCGCATTGCT
GGTAGAGCAAGTCATAGGTCTCGTCTTTGACGTCACAGAAGCGATACACCAAATTGCCTGGTCGGTCATTGTCATA
ACCAGAGA
```

*Fig. 1D*

11777.1&2.cons

```
CAGACGGGGTTTCACTATGTTGGCTAGGCTGGTCTTGAACTCCTGACTTCAGGTGATCTGCCTGCCTTGGCCTCCC
AAAGTGCTGGGATTACAGGCATAAGCCACTGCGCCCGGCTGATCTGATGGTTTCATAAGGCTTTTCCCCCTTTTGC
TCAGCACTTCTCCTTCCTGCCGCCATGTGAAGAAGGACATGTTTGCTTCCCCTTCCACCACGATTGTAAGTTGTTT
CCTGAGGCCTCCCCGGCCATGCTGAACTGTGAGTCAATTAAACCTCTTTCCTTTATAAATTATCCAGTTTTGGGTA
TGTCTTTATTAGTAGAATGAGAACAGACTAATACAACCCTTAAAGGAGACTGACGGAGAGGATTCTTCCTGGATCC
CAGCACTTCCTCTGAATGCTACTGACATTCTTCTTGAGGACTTTAAACTGGGAGATAGAAAACAGATTCCATGGCT
CAGCAGCCTGAGAGCAGGGAGGGAGCCAAGCTATAGATGACATGGGCAGCCTCCCCTGAGGCCAGGTGTGGCCGAA
CCTGGGCAGTGCTGCcACCCACCCCACCAGGGCCAAGTCCTGTCCTTGGAGAGCCAAGCCTCAATCACTGCTAGCC
TCAAGTGTCCCCAAGCCACAGTGGCTAGGGGGACTCAGGGAACAGTTCCCAGTCTGCCCTACTTCTCTTACCTTTA
CCCCTCATACCTCCAAAGTAGACCATGTTCATGAGGTCCAAAGG
```

11779.2.contig

```
AAGCGAGGAAGCCACTGCGGCTCCTGGCTGAAAAGCGGCGCCAGGCTCGGGAACAGAGGGAACGCGAAGAACAGGA
GCGGAAGCTGCAGGCTGAAAGGGACAAGCGAATGCGAGAGGAGCAGCTGGCCCGGGAGGCTGAAGCCCGGGCTGAA
CGTGAGGCCGAGGCGCGGAGACGGGAGGAGCAGGAGGCTCGAGAGAAGGCGCAGGCTGAGCAGGAGGAGCAGGAGC
GACTGCAGAAGCAGAAAGAGGAAGCCGAAGCCCGGTCCCGGGAAGAAGCTGAGCGCCAGCGCCAGGAGCGGGAAAA
GCACTTTCAGAAGGAGGAACAGGAGAGACAAGAGCGAAGAAAGCGGCTGGAGGAGATAATGAAGAGGACTCGGAAA
TCAGAAGCCGCCGAAACCAAGAAGCAGGATGCAAAGGAGACCGCAGCTAACAATTCCGGCCCAGACCCTTGTGAAA
GCTGTAGAGACTCGGCCCTCTGGGCTTCCAGAAAGGATTCTATTGCAGAAAGGAAGGAGCTXGGCCCCCCAXGGA
```

11781 & 37.cons

```
CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACXTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAAT
```

```
CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACCTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAATTA
```

11784-1 & 2

```
GGACGACAAGGCCATGGCGATATCGGATCCGAATTCAAGCCTTTGGAATTAAATAAACCTGGAACAGGGAAGGTGA
AAGTTGGAGTGAGATGTCTTCCATATCTATACCTTTGTGCACAGTTGAATGGGAACTGTTTGGGTTTAGGGCATCT
TAGAGTTGATTGATGGAAAAAGCAGACAGGAACTGGTGGGAGGTCAAGTGGGGAAGTTGGTGAATGTGGAATAACT
TACCTTTGTGCTCCACTTAAACCAGATGTGTTGCAGCTTTCCTGACATGCAAGGATCTACTTTAATTCCACACTCT
CATTAATAAATTGAATAAAAGGGAATGTTTTGGCACCTGATATAATCTGCCAGGCTATGTGACAGTAGGAAGGAAT
GGTTTCCCCTAACAAGCCCAATGCACTGGTCTGACTTTATAAATTATTTAATAAAATGAACTATTATC
```

11785.2.contig

```
GGCAGTGACATTCACCATCATGGGAACCACCTTCCCTTTTCTTCAGGATTCTCTGTAGTGGAAGAGAGCACCCAGT
GTTGGGCTGAAAACATCTGAAAGTAGGGAGAAGAACCTAAAATAATCAGTATCTCAGAGGGCTCTAAGGTGCCAAG
AAGTCTCACTGGACATTTAAGTGCCAACAAAGGCATACTTTCGGAATCGCCAAGTCAAAACTTTCTAACTTCTGTC
TCTCTCAGAGACAAGTGAGACTCAAGAGTCTACTGCTTTAGTGGCAACTACAGAAAACTGGTGTTACCCAGAAAAA
CAGGAGCAATTAGAAATGGTTCCAATATTTCAAAGCTCCGCAAACAGGATGTGCTTTCCTTTGCCCATTTAGGGTT
TCTTCTCTTTCCTTTCTCTTTATTAACCACT
```

*Fig. 1F*

11718-1&2 cons

```
TGCGCTGAAAACAACGGCCTCCTTTACTGTTAAAATGCAGCCACAGGTGCTTAGCCGTGGGCATCTCAACCACCAG
CCTCTGTGGGGGGCAGGTGGGCGTCCCTGTGGGCCTCTGGGCCCACGTCCAGCCTCTGTCCTCTGCCTTCCGTTCT
TCGACAGTGTTCCCGGCATCCCTGGTCACTTGGTACTTGGCGTGGGCCTCCTGTGCTGCTCCAGCAGCTCCTCCAG
GXGGTCGGCCCGCTTCACCGCAGCCTCATGTTGTGTCCGGAGGCTGCTCACGGCCTCCTCCTTCCTCGCGAGGGCT
GTCTTCACCCTCCGGXGCACCTCCTCCAGCTCCAGCTGCTGGCGGGCCTGCAGCGTGGCCAGCTCGGCCTTGGCCT
GCCGCGTCTCCTCCTCARAGGCTGCCAGCCGGTCCTCGAACTCCTGGCGGATCACCTGGGCCAGGTTGCTGCGCTC
GCTAGAAAGCTGCTCGTTCACCGCCTGCGCATCCTCCAGCGCCCGCTCCTTCTGCCGCACAAGGCCCTGCAGACGC
AGATTCTCGCCCTCGGCcTCCCCAAGCTGGCCCTTCAGCTCCGAGCACCGCTCCTGAAGCTTCCGCTCCGACTGCT
CCAGCTCGGAGAGCTCGGCCTCGTACTTGTCCCGTAAGCGCTTGATGCGGCTCTCGGCAGCCTTCTCACTCTCCTC
CTTGGCCAGCGCCATGTCGGCCTCCAGCCGGTGAATGACCAGCTCAATCTCCTTGTCCCGGCCTTTCCGGATTTCT
TCCCTCAGCTCCTGTTCCCGGTTCAGCAGCCACGCCTCCTCCTTCCTGGTGCGGCCGGCCTCCCACGCCTGCCTCT
CCAGCTCCAGCTGCTGCTTCAGGGTATTCAGCTCCATCTGGCGGGCCTGCAGCGTGGCCA
```

13690.4

```
CAACTTATTACTTGAAATTATAATATAGCCTGTCCGTTTGCTGTTTCCAGGCTGTGATATATTTTCCTAGTGGTTT
GACTTTAAAAATAAATAAGGTTTAATTTTCTCCCC
```

13693.1

```
TGCAAGTCACGGGAGTTTATTTATTTAATTTTTTTCCCCAGATGGAGACTCTGTCGCCCAGGCTGGAGTGCAATGG
TGTGATCTTGGCTCACTGCAACCTCCACCTCCTGGGTTCAAGCGATTCTCCTGCCACAGCCTCCCGAGTAGCTGGG
ATTACAGGTGCCCGCCACCACACCCAGCTAATTTTTATATTTTTAGTAAAGACAGGGTTTCCCCATGTTGGCCAGG
CTGGTCTTGAACTTCTGACCTCAGGTGATCCACCTGCCTCGGCCTCCCAAAGTGTTGGGATTACAGGCGTGAGCTA
CCCGTGCCTGGCCAGCCACTGGAGTTTAAAGGACAGTCATGTTGGCTCCAGCCTAAGGCGGCATTTTCCCCCATCA
GAAAGCCCGCGGCTCCTGTACCTCAAAATAGGGCACCTGTAAAGTCAGTCAGTGAAGTCTCTGCTCTAACTGGCCA
CCCGGGGCCATTGGCNTCTGACACAGCCTTGCCAGGANGCCTGCATCTGCAAAAGAAAAGTTCACTTCCTTTCCG
```

13694.1

```
CAGAGAATCTKAGAAAGATGTCGCGTTTTCTTTTAATGAATGAGAGAAGCCCATTTGTATCCCTGAATCATTGAGA
AAAGGCGGCGGTGGCGACAGCGGCGACCTAGGGATCGATCTGGAGGGACTTGGGGAGCGTGCAGAGACCTCTAGCT
CGAGCGCGAGGGACCTCCCGCCGGGATGCCTGGGGAGCAGATGGACCCTACTGGAAGTCAGTTGGATTCAGATTTC
TCTCAGCAAGATACTCCTTGCCTGATAATTGAAGATTCTCAGCCTGAAAGCCAGGTTCTAGAGGATGATTCTGGTT
CTCACTTCAGTATGCTATCTCGACACCTTCCTAATCTCCAGACGCACAAAGAAAATCCTGTGTTGGATGTTGNGTC
CAATCCTTGAACAAACAGCTGGAGAAGAACGAGGAGACCGGTAATAGTGGGTTCAATGAACATTTGAAAGAAAACC
AGGTTGCAGACCCTG
```

GACTGTCCTGAACAAGGGACCTCTGACCAGAGAGCTGCAGGAGATGCAGAGTGGTGGCAGGAGTGGAAGCCAAAGA
ACACCCACCTTCCTCCCTTGAAGGAGTAGAGCAACCATCAGAAGATACTGTTTTATTGCTCTGGTCAAACAAGTCT
TCCTGAGTTGACAAAACCTCAGGCTCTGGTGACTTCTGAATCTGCAGTCCACTTTCCATAAGTTCTTGTGCAGACA
ACTGTTCTTTTGCTTCCATAGCAGCAACAGATGCTTTGGGGCTAAAAGGCATGTCCTCTGACCTTGCAGGTGGTGG
ATTTTGCTCTTTTACAACATGTACATCCTTACTGGGCTGTGCTGTCACAGGGATGTCCTTGCTGGACTGTTCTGCT
ATGGGGATATCTTCGTTGGACTGTTCTTCATGCTTAATTGCAGTATTAGCATCCACATCAGACAGCCTGGTATAAC
CAGAGTTGGTGGTTACTGATTGTAGCTGCTCTTTGTCCACTTCATATGGCACAAGTATTTTCCTCAACATCCTGGC
TCTGGGAAG

13695.1

GAAATGTATATTTAATCATTCTCTTGAACGATCAGAACTCTRAAATCAGTTTTCTATAACARCATGTAATACAGTC
ACCGTGGCTCCAAGGTCCAGGAAGGCAGTGGTTAACACATGAAGAGTGTGGGAAGGGGGCTGGAAACAAAGTATTC
TTTTCCTTCAAAGCTTCATTCCTCAAGGCCTCAATTCAAGCAGTCATTGTCCTTGCTTTCAAAAGTCTGTGTGTGC
TTCATGGAAGGTATATGTTTGTTGCCTTAATTTGAATTGTGGCCAGGAAGGGTCTGGAGATCTAAATTCAGAGTAA
GAAAACCTGAGCTAGAACTCAGGCATTTCTCTTACAGAACTTGGCTTGCAGGGTAGAATGAAGGAAAGAAACTTA
GAAGCTCAACAAGCTGAAGATAATCCCATCAGGCATTTCCCATAGGCCTTGCAACTCTGTTCACTGAGAGATGTTA
TCCTG

13695.2

AGTCTGGAGTGAGCAAACAAGAGCAAGAAACAARRAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGAGTGATAAGTAA
AATGCACGTGGAGACAAGTGCATCCCCAGATCTCAGGGACCTCCCCCTGCCTGTCACCTGGGGAGTGAGAGGACAG
GATAGTGCATGTTCTTTGTCTCTGAATTTTTAGTTATATGTGCTGTAATGTTGCTCTGAGGAAGCCCCTGGAAAGT
CTATCCCAACATATCCACATCTTATATTCCACAAATTAAGCTGTAGTATGTACCCTAAGACGCTGCTAATTGACTG
CCACTTCGCAACTCAGGGGCGGCTGCATTTTAGTAATGGGTCAAATGATTCACTTTTTATGATGCTTCCCAAGGTG
CCTTGGCTTCTCTTCCCAACTGACAAATGCCCAAGTTGAGAAAAATGATCATAATTTTAGCATAAACCGAGCAATC
GGCGACCCC

13697.1

TAGCTGTCTTCCTCACTCTTATGGCAATGACCCCATATCTTAATGGATTAAGATAATGAAAGTGTATTTCTTACAC
TCTGTATCTATCACCAGAAGCTGAGGTGATAGCCCGCTTGTCATTGTCATCCATATTCTGGGACTCAGGCGGGAAC
TTTCTGGAATATTGCCAGGGAGCATGGCAGAGGGGCACAGTGCATTCTGGGGGAATGCACATTGGCTCAGCCTGGG
TAATGAGTGATATACATTACCTCTGTTCACAACTCATTGCCCAGCACCAGTCACAAGGCCCCACCAAATACCAGAG
CCCAAGAAATGTAGTCCTGTTGATATGGTTTTGCTGTGTCCCAACCCAAATCTCATCTTGAATTGTAAGCTCCCAT
AATTCCCATGTGTTGTGGGAGGGACCTGGTG

```
ATCATGAGGATGTTACCAAAGGGATGGTACTAAACCATTTGTATTCGTCTGTTTTCACACTGCTTTGAAGATACTA
CCTGAGACTGGGTAATTTATAAACAAAAGAGATTTAATTGACTCACAGTTCTGCATGGCTGAAGAGGCCTCAGGAA
ACTTACAGTCATGGTGGAAGGCAAAGGAGGAGCAAGGCATGTCTTACATGTCAGTAGGAGAGAGAGCGAGAGCAGG
AGAACCTGCCACTTATAAACCATTCAGATCTCATAACTCCCTATCATGAGAAAAACATGGAGGAAACCACCCTCAT
GATCCAATCACCTCCCGCCAGGTCCCTCCCTCGACACGTGGGGATTATAATTCAGGATTAGAGGGACACAGAGACA
AACCATATCATCATTCATGAGAAATCCACCCTCATAGTCCAATCAGCTCCTACCAGGCCCCACCTCCAACACTGGG
GATTGCAATTCAACATGAGATTTGGATGGGGACACAGATTCAAACCATATCATAC
```

13699.1&2

```
CATGGCCTTTCTCCTTAGAGGCCAGAGGTGCTGCCCTGGCTGGGAGTGAAGCTCCAGGCACTACCAGCTTTCCTGA
TTTTCCCGTTTGGTCCATGTGAAGAGCTACCACGAGCCCCAGCCTCACAGTGTCCACTCAAGGGCAGCTTGGTCCT
CTTGTCCTGCAGAGGCAGGCTGGTGTGACCCTGGGAACTTGACCCGGGAACAACAGGTGGCCCAGAGTGAGTGTGG
CCTGGCCCCTCAACCTAGTGTCCGTCCTCCTCTCTCCTGGAGCCAGTCTTGAGTTTAAAGGCATTAAGTGTTAGAT
ACAAGCTCCTTGTGGCTGGAAAAACACCCCTCTGCTGATAAAGCTCAGGGGGCACTGAGGAAGCAGAGGCCCCTTG
GGGGTGCCCTCCTGAAGAGAGCGTCAGGCCATCAGCTCTGTCCCTCTGGTGCTCCACGTCTGTTCCTCACCCTCC
ATCTCTGGGAGCAGCTGCACCTGACTGGCCACGCGGGGGCAGTGGAGGCACAGGCTCAGGGTGGCCGGGCTACCTG
GCACCCTATGGCTTACAAAGTAGAGTTGGCCCAGTTTCCTTCCACCTGAGGGGAGCACTCTGACTCCTAACAGTCT
TCCTTGCCCTGCCATCATCTGGGGTGGCTGGCTGTCAAGAAAGGCCGGGCATGCTTTCTAAACACAGCCACAGGAG
GCTTGTAGGGCATCTTCCAGGTGGGGAAACAGTCTTAGATAAGTAAGGTGACTTGCCTAAGGCCTCCCAGCACCCT
TGATCTTGGAGTCTCACAGCAGACTGCATGTSAACAACTGGAACCGAAAACATGCCTCAGTATAAAA
```

13703.3

```
CCAGAACCTCCTTCTCTTTGGAGAATGGGGAGGCCTCTTGGAGACACAGAGGGTTTCACCTTGGATGACCTCTAGA
GAAATTGCCCAAGAAGCCCACCTTCTGGTCCCAACCTGCAGACCCCACAGCAGTCAGTTGGTCAGGCCCTGCTGTA
GAAGGTCACTTGGCTCCATTGCCTGCTTCCAACCAATGGGCAGGAGAGAAGGCCTTTATTTCTCGCCCACCCATTC
TCCTGTACCAGCACCTCCGTTTTCAGTCAGYGTTGTCCAGCAACGGTACCGTTTACACAGTCA
```

13705.1

```
TGCATGTAGTTTTATTTATGTGTTTTSGTCTGGAAAACCAAGTGTCCCAGCAGCATGACTGAACATCACTCACTTC
CCCTACTTGATCTACAAGGCCAACGCCGAGAGCCCAGACCAGGATTCCAAACACACTGCACGAGAATATTGTGGAT
CCGCTGTCAGGTAAGTGTCCGTCACTGACCCARACGCTGTTACGTGGCACATGACTGTACAGTGCCACGTAACAGC
ACTGTACTTTTCTCCCATGAACAGTTACCTGCCATGTATCTACATGATTCAGAACATTTTGAACAGTTAATTCTGA
CACTTGAATAATCCCATCAAAAACCGTAAAATCACTTTGATGTTTGTAACGACAACATAGCATCACTTTACGACAG
AATCATCTGGAAAAACAGAACAACGAATACATACATCTTAAAAAATGCTGGGGTGGGCCAGGCACAGCTTCACGCC
TGTAATCCCAGCACTTTGGGAGGCTTAAGCGGGTG
```

```
TGGGGCGGAAAGAAGCCAAGGCCAAGGAGCTGGTGCGGCAGCTGCAGCTGGAGGCCGAGGAGCAGAGGAAGCAGAA
GAAGCGGCAGAGTGTGTCGGGCCTGCACAGATACCTTCACTTGCTGGATGGAAATGAAAATTACCCGTGTCTTGTG
GATGCAGACGGTGATGTGATTTCCTTCCCACCAATAACCAACAGTGAGAAGACAAAGGTTAAGAAAACGACTTCTG
ATTTGTTTTTGGAAGTAACAAGTGCCACCAGTCTGCAGATTTGCAAGGATGTCATGGATGCCCTCATTCTGAAAAT
GGCAAGAAATGAAAAAGTACACTTTAGAAAATAAAGAGGAAGGATCACTCTCAGATACTGAAGCCGATGCAGTCTC
TGGACAACTTCCAGATCCCACAACGAATCCCAGTGCTGGAAAGGACGGGCCCTTCCTTCTGGTGGTGGAACANGTC
CCGGTGGTGGATCTTGGAANGGAACCTGAANGTGGTGTACCCCGTCCAAGGCCGACCTTGGCCAC
```

13707.4

```
TCCCGCGCTCGCAGGGCNCGTGCCACCTGCCYGTCCGCCCGCTCGCTCGCTCGCCCGCCGCGCCGCGCTGCCGACC
GYCAGCATGCTGCCGAGAGTGGGCTGCCCCGCGCTGCCGCTGCCGCCGCCGCCGCTGCTGCCGCTGCTGCCGCTGC
TGCTGCTGC
```

13708.1&2

```
GGCGGGTAGGCATGGAACTGAGAAGAACGAAGAAGCTTTCAGACTACGTGGGGAAGAATGAAAAAACCAAAATTAT
CGCCAAGATTCAGCAAAGGGGACAGGGAGCTCCAGCCCGAGAGCCTATTATTAGCAGTGAGGAGCAGAAGCAGCTG
ATGCTGTACTATCACAGAAGACAAGAGGAGCTCAAGAGATTGGAAGAAAATGATGATGATGCCTATTTAAACTCAC
CATGGGCGGATAACACTGCTTTGAAAAGACATTTTCATGGAGTGAAAGACATAAAGTGGAGACCAAGATGAAGTTC
ACCAGCTGATGACACTTCCAAAGAGATTAGCTCACCT
```

13709.1

```
TCTGAAGGTTAAATGTTTCATCTAAATAGGGATAATGRTAAACACCTATAGCATAGAGTTGTTTGAGATTAAATGA
GATAATACATGTAAAATTATGTGCCTGGCATACAGCAAGATTGTTGTTGTTGATGATGATGATGATGATGATA
ATATTTTTCTATCCCCAGTGCACAACTGCTTGAACCTATTAGATAATCAATACATGTTTCTTGAACTGAGATCAAT
TTCCCCATGTTGTCTGACTGATGAAGCCCTACATTTTCTTCTAGAGGAGATGACATTTGAGCAAGATCTTAAAGAA
AATCAGATGCCTTCACCTGACCACTGCTTGGTGATCCCATGGCACTTTGTACATCTCTCCATTAGCTCTCATCTCA
CCAGCCCATCATTATTGTATGTGCTGCCTTCTGAAGCTTGCAGCTGGCTACCATCMGGTAGAATAAAAATCATCCT
TTCATAAAATAGTGACCCTCCTTTTTTATTTGCATTTCCCAAAGCCAAGCACCGTGGGANGGTAG
```

TATGAAGAAGGGAAAAGAAGATAATTTGTGAAAGAAATGGGTCCAGTTACTAGTCTTTGAAAAGGGTCAGTCTGTA
GCTCTTCTTAATGAGAATAGGCAGCTTTCAGTTGCTCAGGGTCAGATTTCCTTAGTGGTGTATCTAATCACAGGAA
ACATCTGTGGTTCCCTCCAGTCTCTTTCTGGGGGACTTGGGCCCACTTCTCATTTCATTTAATTAGAGGAAATAGA
ACTCAAAGTACAATTTACTGTTGTTTAACAATGCCACAAAGACATGGTTGGGAGCTATTTCTTGATTTGTGTAAAA
TGCTGTTTTTGTGTGCTCATAATGGTTCCAAAAATTGGGTGCTGGCCAAAGAGAGATACTGTTACAGAAGCCAGCA
AGAAGACCTCTGTTCATTCACACCCCCGGGGATATCAGGAATTGACTCCAGTGTGTGCAAATCCAGTTTGGCCTAT
CTTCT 13712.1&2

TGAGGGACTGATTGGTTTGCTCTCTGCTATTCAATTCCCCAAGCCCACTTGTTCCTGCAGCGTCCTCCTTCTCATT
CCCTTTAGTTGTACCCTCTCTTTCATCTGAGACCTTTCCTTCTTGATGTCGCCTTTTCTTCTTCTTGCTTTTTCTG
ATGTTCTGCTCAGCATGTTCTGGGTGCTTCTCATCTGCATCATTCCTTTCAGATGCTGTAGCTTCTTCCTCCTCTT
TCTGCCTCCTTTTCTTTTTCTTTTTTTTGGGGGGCTTGCTCTCTGACTGCAGTTGAGGGGCCCCAGGGTCCTGGCC
TTTGAGACGAGCCAGGAAGGCCTGCTCCTGGGCCTCTAGGCGAGCAAGCTTGGCCTTCATTGTGATCCCAAGACGG
GCAGCCTTGTGTGCTGTTCGCCCCTCACAGGCTTGGAGCAGCATCTCATCAGTCAGAATCTTTGGGGACTTGGACC
CCTGGTTGTCGTCATCACTGCAGCTCTCCAAGTCTTTGTTTGGCTTCTCTCCACCTGAAGTCAATGTAGCCATCTT
CACAAACTTCTGATACAGCAAGTTGGGCTTGGGATGATTATAACGGGTGGTCTCCTTAGAAAGGCTCCTTATCTGT
ACTCCATCCTGCCCAGTTTCCACTACCAAGTTGGCCGCAGTCTTGTTGAAGAGCTCATTCCACCAGTGGTTTGTGA
ACTCCTTGGCAGGGTCATGTCCTACCCCATGAGTGTCTTGCTTCAGYGTCACCCTGAGAGCCTGAGTGATACCATT
CTCCTTCCG 13714.1&2

GACAACATGAAATAAATCCTAGAGGACAAAATTAAACTCAATAGAGTGTAGTCTAGTTAAAAACTCGAAAAATGAG
CAAGTCTGGTGGGAGTGGAGGAAGGGCTATACTATAAATCCAAGTGGGCCTCCTGATCTTAACAAGCCATGCTCAT
TATACACATCTCTGAACTGGACATACCACCTTTACGCAGGAAACAGGGCTTGGAACTTCTAAGGGAAATTAACATG
CACCACCCACATCTAACCTACCTGCCGGGTAGGTACCATCCCTGCTTCGCTGAAATCAGTGCTC 13716.1&2

TTGGAATTAAATAAACCTGGAACAGGGAAGGTGAAAGTTGGAGTGAGATGTCTTCCATATCTATACCTTTGTGCAC
AGTTGAATGGGAACTGTTTGGGTTTAGGGCATCTTAGAGTTGATTGATGGAAAAAGCAGACAGGAACTGGTGGGAG
GTCAAGTGGGGAAGTTGGTGAATGTGGAATAACTTACCTTTGTGCTCCACTTAAACCAGATGTGTTGCAGCTTTCC
TGACATGCAAGGATCTACTTTAATTCCACACTCTCATTAATAAATTGAATAAAAGGGAATGTTTTGGCACCTGATA
TAATCTGCCAGGCTATGTGACAGTAGGAAGGAATGGTTTCCCCTAACAAGCCCAATGCACTGGTCTGACTTTATAA
ATTATTTAATAAAATGAACTATTATC

```
AAACTGGACCTGCAACAGGGACATGAATTTACTGCARGGTCTGAGCAAGCTCAGCCCCTCTACCTCAGGGCCCCAC
AGCCATGACTACCTCCCCCAGGAGCGGGAGGGTGAAGGGGGCCTGTCTCTGCAAGTGGAGCCAGAGTGGAGGAATG
AGCTCTGAAGACACAGCACCCAGCCTTCTCGCACCAGCCAAGCCTTAACTGCCTGCCTGACCCTGAACCAGAACCC
AGCTGAACTGCCCCTCCAAGGGACAGGAAGGCTGGGGGAGGGAGTTTACAACCCAAGCCATTCCACCCCCTCCCCT
GCTGGGGAGAATGACACATCAAGCTGCTAACAATTGGGGGAAGGGGAAGGAAGAAAACTCTGAAAACAAAATCTTG
T
```

13722.3

```
CATGCGTTTCACCACTGTTGGCCAGGCTGGTCTCGAACTCCTGGCCTCAAGCAATCCACCCGCCTCAGCCTCCAAA
AGTGCTGGGATTACAGATGTGAGCCATGGCACCATGCCAAAAGGCTATATTCCTGGCTCTGTGTTTCCGAGACTGC
TTTTAATCCCAACTTCTCTACATTTAGATTAAAAAATATTTTATTCATGGTCAATCTGGAACATAATTACTGCATC
TTAAGTTTCCACTGATGTATATAGAAGGCTAAAGGCACAATTTTTATCAAATCTAGTAGAGTAACCAAACATAAAA
TCATTAATTACTTTCAACTTAATAACTAATTGACATTCCTCAAAAGAGCTGTTTTCAATCCTGATAGGTTCTTTAT
TTTTTCAAAATATATTTGCCATGGGATGCTAATTTGCAATAAGGCGCATAATGAGAATACCCCAAACTGGA
```

13722.4

```
GTTGGACCCCCAGGGACTGGAAAGACACTTCTTGCCCGAGCTGTGGCGGGAGAAGCTGATGTTCCTTTTTATTATG
CTTCTGGATCCGAATTTGATGAGATGTTTGTGGGTGTGGGAGCCAGCCGTATCAGAAATCTTTTTAGGGAAGCAAA
GGCGAATGCTCCTTGTGTTATATTTATTGATGAATTAGATTCTGTTGGTGGGAAGAGAATTGAATCTCCAATGCAT
CCATATTCAAGGCAGACCATAAATCAACTTCTTGCTGAAATGGATGGTTTTAAACCCAATGAAGGAGTTATCATAA
TAGGAGCCACAAACTTCCCAGAGGCATTAGATAATGCCTTAATACCGTCCTGGTCGTTTTGACATGCAAGTTACAG
TTCCAAGGCCAGATGTAAAAGGTCGAACAGAAATTTTGAAATGGTATCTCAATAAAATAAAGTTTGATCAATCCCG
TTGATCCAGAAATTATAGCCTCGAGGTACTGGTGGCTTTTCCGGAAGCAGAGTTGGGAGAATCTT
```

13724-13698-13748

```
GCCTACAACATCCAGAAAGAGTCTACCCTGCACCTGGTGCTSCGTCTCAGAGGTGGGATGCAGATCTTCGTGAAGA
CCCTGACTGGTAAGACCATCACTCTCGAAGTGGAGCCGAGTGACACCATYGAGAACGTCAAAGCAAAGATCCARGA
CAAGGAAGGCRTYCCTCCTGACCAGCAGAGGTTGATCTTTGCCGGAAAGCAGCTGGAAGATGGDCGCACCCTGTCT
GACTACAACATCCAGAAAGAGTCYACCCTGCACCTGGTGCTCCGTCTCAGAGGTGGGATGCARATCTTCGTGAAGA
CCCTGACTGGTAAGACCATCACCCTCGAGGTGGAGCCCAGTGACACCATCGAGAATGTCAAGGCAAAGATCCAAGA
TAAGGAAGGCATCCCTCCTGATCAGCAGAGGTTGATCTTTGCTGGGAAACAGCTGGAAGATGGACGCACCCTGTCT
GACTACAACATCCAGAAAGAGTCCACTCTGCACTTGGTCCTGCGCTTGAGGGGGGGTGTCTAAGTTTCCCCTTTTA
AGGTTTCMACAAATTTCATTGCACTTTCCTTTCAATAAAGTTGTTGCATTCCC
```

13730.1

```
GAACTGGGCCCTGAGCCCAAGTCATGCCTTGTGTCCGCATCTGCCGTGTCACCTCTGTKCCTGCCCCTCACCCCTC
CCTCCTGGTCTTCTGAGCCAGCACCATCTCCAAATAGCCTATTCCTTCCTGCAAATCACACACACATGCGGGCCAC
ACATACCTGCTGCCCTGGAGATGGGGAAGTAGGAGAGATGAATAGAGGCCCATACATTGTACAGAAGGAGGGGCAG
GTGCAGATAAAAGCAGCAGACCCAGCGGCAGCTGAGGTGCATGGAGCACGGTTGGGGCCGGCATTGGGCTGAGCAC
CTGATGGGCCTCATCTCGTGAATCCTCGAGGCAGCGCCACAGCAGAGGAGTTAAGTGGCACCTGGGCCGAGCAGAG
CAGGAGACTGAGGGTCAGAGTGGAGGCTAAGCTGCCCTGGAACTCCTCAATCTTGCCTGCCCCCTAGTATGAAGCC
CCCTTCCTGCCCCTACAATTCCTGA
```

13732.1

```
ATGGATCTTACTTTGCCACCCAGGTTGGAGTGCAGTGCTGCAATCTTGGCTCACTGCAGCCTTAACCTCCCAGGCT
CAAGCTATCCTCCTGCCAAAGCCTTCCACATAGCTGGGACTACAGGTACACNGCCACCACACCCAGCTAAAATTTT
TGTATTTTTTGTAGAGACGGGATCTCGCCACGTTGCCCAGGCTGGTCCCATCCTGACCTCAAGCAGATCTGCCCAC
CTCAGCCCCCCAACGTGCTAGGATTACAGGCGTGAGCCACCGCACCCAGCCTTTGTTTTGCTTTTAATGGAATCAC
CAGTTCCCCTCCGTGTCTCAGCAGCAGCTGTGAGAAATGCTTTGCATCTGTGACCTTTATGAAGGGGAACTTCCAT
GCTGAATGAGGGTAGGATTACATGCTCCTGTTTCCCGGGGGTCAAGAAAGCCTCAGACTCCAGCATGATAAGCAGG
GTGAG
```

13732.2

```
ATAGGGGCTTTAAGGAGGGAATTCAGGTTCAATGAGGTCGTAAGGCCAGGGCTCTTATCCAGTAAGACTGGGGTCC
TTAGATGAGAAAGAGACACCCGAGGTCCTTCTCTCTGCCGTGTGAGGATGCATCAAGAAGGCGGCCGTCTGCAAGC
GAAGGAGAGGCCGCACCAGAAACCGACACCTTCATCTTGGACTTGCAGCCTCTAGAACTGAGAAAATAACTGTCTG
TTGGTTAAGCCACCCAGTTTGTAGTATTCTCTTATGGCTTCCTAAGCAGACTAACAAACAAACACCCAAAATTAAC
TGATGGCTTCGCTGTCTTCTGTAAAAATTGCTATGAGAGAACTTTTCACTCACTGTTTTGCAGTTTCTCCCTCAGT
CCCTGGTTCTTTCTTCTCACATAATCCCAATTTCAATTTATAGTTCATGGCCCAGGCAGAGTCATTCATCACGGCA
TCTCCTGAGCTAAACCAGCACCTGCTCTGCTCACTTCTTGACTGGCTGCTCATCATCAGCCCTCTTGCAGAGATTT
CATTTCCTCCCGTGCCAGGTACTTCACGCACCAAGCTCA
```

GGATAATGAAGTTGTTTTATTTAGCTTGGACAAAAAGGCATATTCCTCTATTTTCTTATACAACAAATATCCCCAA
AATAAAGCAAGCATATATATCTTGAATGTGTAATAATCCAGTGATAAACAAGAGCAGTACTTTAAAAGAAAAAAAA
ATATGTATTTCTGTCAGGTTAAAATGAGAATCAAAACCATTTACTCTGCTAACTCATTATTTTTTGCTTTCTTTTT
GGTTAAGAGAGGCAATGCAATACACTGAAAAAGGTTTTTATCTTATCTGGCATTGGAATTAGACATATTCAAACCC
CAGCCCCCATTTCCAAACTTTAAGACCACAAACAAGTAATTTACTTTTCTGAACATTGGTTTTTTCTGGAAAATGG
GAATTATAAAATAGACTTTGCAGACTCTTATGAGATTAAATAAGATAATGTATGAAATTCTTTCTTCTTTTTTACT
TCTTTTTCCTTTTTGAGATGGAGTCTCACCCCGTCACCCAGGCTGGAGTACAGTG

13735.2

CCACTGCACTCCAGCCTGGGTGACGGAGTGAGACTCTGTCTCAAAAAAACAAACAAACAAACAAACAAAAAACTGA
AAAGGAAATAGAGTTCCTCTTTCCTCATATATGAATATATTATTTCAACAGATTGTTGATCACCTACCATATGCTT
GGTATTGTTCTAATTGCTGGGGATACAGCAAGAGGTTCTGCAGAACTTCATGGAGCATGAAAGTAAATAAACAAAG
TTAATTTCAAGGCCAGGCATGGTTGCTCACACCTTTAGTCCCAGCACTTTGGGAGGCTGAGGCAGGTGGATCACTT
GGGCCCAGGAGTTCAAGGCTGCAGTGAGCCAAGATTGTGCCACTACTCTCCAGGCTGGGCAACAGAGCAAGACCCT
GTCTCAGGGGGAACAAAAAGTTAATTTCAGATTTTGTTAAGTGCTGTAAAGGAAGTAAATAGGTTGATATTCAAGA
GAGCACCTGAAGGCCAGGCGTGGTGGCTCACGCCTGTGGTCTAACGCTTTGGGAAGCCCGAGCGGGCGGATCACAA
GGTCAGGAGAATTTTGGCCAGGCATGGTG

13736.1

AGAATCCATTTATTGGGTTTTAAACTAGTTACACAACTGAAATCAGTTTGGCACTACTTTATACAGGGATTACGCC
TGTGTATGCCGACACTTAAATACTGTACCAGGACCACTGCTGTGCTTAGGTCTGTATTCAGTCATTCAGCATGTAG
ATACTAAAAATATACTGTAGTGTTCCTTTAAGGAAGACTGTACAGGGTGTGTTGCAAGATGACATTCACCAATTTG
TGAATTATTTCAACCCAGAAGATACCTTTCACTCTATAAACTTGTCATAGGCAAACATGTGGTGTTAGCATTGAGA
GATGCACACAAAAATGTTACATAAAAGTTCAGACATTCTAATGATAAGTGAACTGAAAAAAAAAAAAACCCCACAT
CTCAATTTTTGTAACAAGATAAAGAAAATAATTTAAAAACACAAAAAATGGCATTCAGTGGGTACAAAGCC

13737.1&2

CAAATATTTAATATAAATCTTTGAAACAAGTTCAGAKGAAATAAAAATCAAAGTTTGCAAAAACGTGAAGATTAAC
TTAATTGTCAAATATTCCTCATTGCCCCAAATCAGTATTTTTTTTATTTCTATGCAAAAGTATGCCTTCAAACTGC
TTAAATGATATATGATATGATACACAAACCAGTTTTCAAATAGTAAAGCCAGTCATCTTGCAATTGTAAGAAATAG
GTAAAAGATTATAAGACACCTTACACACACACACACACACACACACACGTGTGCACcGCCAATGACAAAAAACA
ATTTGGCCTCTCCTAAAATAAGAACATGAAGACCCTTAATTGCTGCCAGGAGGGAACACTGTGTCACCCCTCCCTA
CAATCCAGGTAGTTTCCTTTAATCCAATAGCAAATCTGGGCATATTTGAGAGGAGTGATTCTGACAGCCACSGTTG
AAATCCTGTGGGGAACCATTCATGTCCACCCACTGGTGCCCTGAAAAAATGCCAATAATTTTTCGCTCCCACTTCT
GCTGCTGTCTCTTCCACATCCTCACATAGACCCCAGACCCGCTGGCCCCTGGCTGGGCATCGCATTGCTGGTAGAG
CAAGTCATAGGTCTCGTCTTTGACGTCACAGAAGCGATACACCAAATTGCCTGGTCGGTCATTGTCATAACCAG

TTTGACTTTAGTAGGGGTCTGAACTATTTATTTTACTTTGCCMGTAATATTTARACCYTATATATCTTTCATTATG
CCATCTTATCTTCTAATGBCAAGGGAACAGWTGCTAAMCTGGCTTCTGCATTWATCACATTAAAAATGGCTTTCTT
GGAAAATCTTCTTGATATGAATAAAGGATCTTTTAVAGCCATCATTTAAAGCMGGNTTCTCTCCAACACGAGTCTG
CTSASGGGGGGKGAGCTGTGAACTCTGGCTGAAGGCTTTCCCATACACACTGCAATGACMTGGTTTCTGACCAGBG
TGAGTTA

13738.2

AGAGAAGCCCCATAAATGCAATCAGTGTGGGAAGGCCTTCAGTCAGAGCTCAAGCCTTTTCCTCCATCATCGGGTT
CATACTGGAGAGAAACCCTATGTATGTAATGAATGCGGCAGAGCCTTTGGTTTTAACTCTCATCTTACTGAACACG
TAAGGATTCACACAGGAGAAAAACCCTATGTTTGTAATGAGTGCGGCAAAGCCTTTCGTCGGAGTTCCACTCTTGT
TCAGCATCGAAGAGTTCACACTGGGGAGAAGCCCTACCAGTGCGTTGAATGTGGGAAAGCTTTCAGCCAGAGCTCC
CAGCTCACCCTACATCAGCCGAGTTCACACTGGAGAGAAGCCCTATGACTGTGGTGACTGTGGGAAGGCCTTCAGC
CGGAGGTCAACCCTCATTCAGCATCAGAAAGTTCACAGCGGAGAGACTCGTAAGTGCAGAAAACATGGTCCAGCCT
TTGTTCATGGCTCCAGCCTCACAGCAGATGGACAGATTCCCACTGGAGAGAAGCACGGCAGAACCTTTAACCATGG
TGCAAATCTCATTCTGCGCTGGACAGTTC

13739.1&2

GAGACAGGGTCTCACTTTGTCACCCAGGCTGGAATGCAGTGGTGCGATCTTACGTAGCTCACTGCAGCCCTGACCT
CCTGGACTCAAACAATTCTCCTGCCTCAGCCCTGCAAGTAGCTGGGACTGTGGGTGCATGCCACCATGCCTGGCTA
ACTTTTGTAGTTTTTGTAAAGATGGGGTTTTGCCATGTTGCACATGCTGGTCTTGAACTCCTGAGCTCAAACGATC
TGCCCACCTCGGCCTCCCAGAATGTTGGGATTACAGGGGTAAACCACCACGCCTGGCCCCATTAGGGTATTCTTAG
CATCCACTTGCTCACTGAGATTAATCATAAGAGATGATAAGCACTGGAAGAAAAAAATTTTTACTAGGCTTTGGAT
ATTTTTTTCCTTTTTCAGCTTTATACAGAGGATTGGATCTTTAGTTTTCCTTTAACTGATAATAAAACATTGAAAG
GAAATAAGTTTACCTGAGATTCACAGAGATAACCGGCATCACTCCCTTGCTCAATTCCAGTCTTTACCACATCAAT
TATTTTCAGAGGTGCAGGATAAAGGCCTTTAGTCTGCTTTCGCACTTTTTCTTCCACTTTTTTGTAAACCTGTTGC
CTGACAAATGGAATTGACAGCGTATGCCATGACTATTCCATTTGTCAGGCATACGCTGTCAATTTTTCCACCAATC
CCTTGTCTCTCTTTGGAGAGATCTTCTTATCAGCTAGTCCTTTGGCAAAAGTAATTGCAACTTCTTCTAGGTATTC
TATTGTCCGTTCCACTGGTGGAACCCCTGGGACCAGGACTAAAACCTCCAG

13741.1

ATCTCATATATATATTTCTTCCTGACTTTATTTGCTTGCTTCTGNCACGCATTTAAAATATCACAGAGACCAAAAT
AGAGCGGCTTTCTGGTGGAACGCATGGCAGTCACAGGACAAAATACAAAACTAGGGGGCTCTGTCTTCTCATACAT
CATACAATTTTCAAGTATTTTTTTTTATGTACAAAGAGCTACTCTATCTGAAAAAAAATTAAAAAAATAAATGAGACA
AGATAGTTTATGCATCCTAGGAAGAAAGAATGGGAAGAAAGAACGGGGCAGTTGGGTACAGATTCCTGTCCCCTGT
TCCCAGGGACCACTACCTTCCTGCCACTGAGTTCCCCCACAGCCTCACCCATCATGTCACAGGGCAAGTGCCAGGG
TAGGTGGGGACCAGTGGAGACAGGAACCAGCAACATACTTTGGCCTGGAAGATAAGGAGAAAGTCTCAGAAACACA
CTGGTGGGAAGCAATCCCACNGGCCGTGCCCCANGAGCTTCCCACCTGCTGCTGGCTCCCTGGGTGGCTTTGGGAA
CAGCTTGGGCAGGCCCTTTTGGGTGGGGNCCAACTGGGCCTTTGGGCCCGTGTGGAAAG

AAACATTGAGATGGAATGATAGGGTTTCCCAGAATCAGGTCCATATTTTAACTAAATGAAAATTATGATTTATAGC
CTTCTCAAATACCTGCCATACTTGATATCTCAACCAGAGCTAATTTTACCTCTTTACAAATTAAATAAGCAAGTAA
CTGGATCCACAATTTATAATACCTGTCAATTTTTTCTGTATTAAACCTCTATCATAGTTTAAGCCTATTAGGGTAC
TTAATCCTTACAAATAAACAGGTTTAAAATCACCTCAATAGGCAACTGCCCTTCTGGTTTTCTTCTTTGACTAAAC
AATCTGAATGCTTAAGATTTTCCACTTTGGGTGCTAGCAGTACACAGTGTTACACTCTGTATTCCAGACTTCTTAA
ATTATAGAAAAAGGAATGTACACTTTTTGTATTCTTTCTGAGCAGGGCCGGGAGGCAACATCATCTACCATGGTAG
GGACTTGTATGCATGGACTACTTTA 14351.1

ACTCTGTCGCCCAGGCTGGAGCCCABTGGMGCGATCTCGACTCCCTGCAAGCTMCGCCTCACAGGWTCATGCCATT
CTCCTGCCTCAGCATCTGGAGTAGCTGGGACTACAGGCGCCAGCCACCATGCCCAGCTAATTTTT 14351.2

ACCTTAAAGACATAGGAGAATTTATACTGGGAGAGAAAGCTTACAAATGTAAGGTTTCTGACAAGACTTGGGAGTG
ATTCACACCTGGAACAACATACTGGACTTCACACTGGABAGAAACCTTACAAGTGTAATGAGTGTGGCAAAGCCTT
TGGCAAGCAGTCAACACTTATTCACCATCAGGCAATTCA 14354.2

AGTCAGGATCATGATGGCTCAGTTTCCCACAGCGATGAATGGAGGGCCAAATATGTGGGCTATTACATCTGAAGAA
CGTACTAAGCATGATAAACAGTTTGATAACCTCAAACCTTCAGGAGGTTACATAACAGGTGATCAAGCCCGTACTT
TTTTCCTACAGTCAGGTCTGCCGGCCCCGGTTTTAGCTGAAATATGGGCCTTATCAGATCTGAACAAGGATGGGAA
GATGGACCAGCAAGAGTTCTCTATAGCTATGAAACTCATCAAGTTAAAGTTGCAGGGCCAACAGCTGCCTGTAGTC
CTCCCTCCTATCATGAAACAACCCCCTATGTTCTCTCCACTAATCTCTGCTCGTTTTGGGATGGGAAGCATGCCCA
ATCTGTCCATTCATCAGCCATTGCCTCCAGTTGCACCTATAGCAACACCCTTGTCTTCTGCTACTTCAGGGACCAG
TATTCCTCCCTAATGATGCCTGCT 14354.1

CTTTCGATTTCCTTCAATTTGTCACGTTTGATTTTATGAAGTTGTTCAAGGGCTAACTGCTGTGTATTATAGCTTT
CTCTGAGTTCCTTCAGCTGATTGTTAAATGAATCCATTTCTGAGAGCTTAGATGCAGTTTCTTTTTCAAGAGCATC
TAATTGTTCTTTAAGTCTTTGGCATAATTCTTCCTTTTCTGATGACTTTCTATGAAGTAAACTGATCCCTGAATCA
GGTGTGTTACTGAGCTGCATGTTTTTAATTCTTTCGTTTAATAGCTGCTTCTCAGGGACCAGATAGATAAGCTTAT
TTTGATATTCCTTAAGCTCTTGGTGAAGTTGTTCGATTTCCATAATTTCCAGGTCACACTGGTTATCCCAAACTTC
T

```
TGGAGGTGAAACGGAGGCAAGAAAGGGGGCTACCTCAGGAGCGAGGGACAAAGGGGGCGTGAGGCACCTAGGCCGC
GGCACCCCGGCGACAGGAAGCCGTCCTGAACCGGGCTACCGGGTAGGGGAAGGGCCCGCGTAGTCCTCGCAGGGCC
CCAGAGCTGGAGTCGGCTCCACAGCCCCGGGCCGTCGGCTTCTCACTTCCTGGACCTCCCCGGCGCCCGGGCCTGA
GGACTGGCTCGGCGGAGGGAGAAGAGGAAACAGACTTGAGCAGCTCCCCGTTGTCTCGCAACTCCACTGCCGAGGA
ACTCTCATTTCTTCCCTCGCTCCTTCACCCCCCACCTCATGTAGAAAGGTGCTGAAGCGTCCGGAGGGAAGAAGAA
CCTGGGCTACCGTCCTGGCCTTCCCMCCCCCTTCCCGGGGCGCTTTGGTGGGCGTGGAGTTGGGGTTGGGGGGGTG
GGTGGGGGTTCTTTTTTGGAGTGCTGGGGAACTTTTTTCCCTTCTTCAGGTCAGGGGAAAGGGAATGCCCAATTCA
GAGAGACATGGGGGCAAGAAGGACGGGAGTGGAGGAGCTTCTGGAACTTTGCAGCCGTCATCGGGAGGCGGCAGCT
CTAACAGCAGAGAGCGTCACCGCTTGGTATCGAAGCACAAGCGGCATAAGTCCAAACACTCCAAAGACATGGGGTT
GGTGACCCCGAAGCAGCATCCCTGGGCACAGTTATCAAACCTTTGGTGGAGTATGATGATATCAGCTCTGATTCC
GACACCTTCTCCGATGACATGGCCTTCAAACTAGACCGAAGGGAGAACGACGAACGTCGTGGATCAGATCGGAGCG
ACCGCCTGCACAAACATCGTCACCACCAGCACAGGCGTTCCCGGGACTTACTAAAAGCTAAACAGACCG
```

16432-1

```
GACATGTTTGCCTGCAGGGGACCAGAGACAATGGGATTAGCCAGTGCTCACTGTTCTTTATGCTTCCAGAGAGGAT
GGGGACAGCTCTCAGGTCAGAATCCAGGCTGAGAAGGCCATGCTGGTTGGGGGCCCCCGGAAGCACGGTCCGGATC
CTCCCTGGCATCAGCGTAGACCCGCTGCTCAGGCTTGGGGTACCAAACTCATGCTCTGTACTGTTTTGGCCCCATG
CGGTGAGAGGAAAACCTAGAAAAAGATTGGTCGTGCTAAGGAATCAGCTGCCCCCTCATCCTCCGCATCCAATGCT
GGTGACAACATATTCCCTCTCCCAGGACACAGACTCGGTGACTCCACACTGGGCTGAGTGGCCTCTGGAGGCTCGT
GGCCTAAGGCAGGGCTCCGTAAGGCTGATCGGCTGAACTGGGTGGGGTGAGGGTTTCTGACCCTTCGCTTCCCATC
CCATAACCGCTGTCAATGAGCTCACACTGTGGTCA
```

16432-2

```
GATGGCATGGTCGTTGCTAATGTGCCTGCTGGGATGGAGCACTTCCTCCTGTGAGCCCAGGGGACCCGCCTGTCCC
TGGAGCTTGGGGCAAGGAGGGAAGAGTGATACCAGGAAGGTGGGGCTGCAGCCAGGGGCCAGAGTCAGTTCAGGGA
GTGGTCCTCGGCCCTCAAAGCTCCTCCGGGGACTGCTCAGGAGTGATGGTGCCCTGGAGTTTGCCCCAACTTCCCT
GGCCACCCTGGAAGGTGCCTGGCTGCTCCAGGCCTCTAGGCTGGGCTGATGGGTTTCTCCAGGACACAAGTATCAT
TAAAGCCACCCTCTCCTCAGCTTGTCAGGCCGCACATGTGGGACAGGCTGTGCTCACAACCCCCTCGCCTGCCCTG
CCCTCCATCAGGAGGAGCCAGTGGAACCTTCGGAAAGCTCCCAGCATCTCAGCAGCCCTCAAAAGTCGTCCTGGGG
CAAGCTCTGGTTCTCCTGACTGGAGGTCATCTGGGCTTGGCCTGCTCTCTCTCGC
```

17184.3

```
TAAAAAAGTGTAACAAAGGTTTATTTAGACTTTCTTCATGCCCCCAGATCCAGGATGTCTATGTAAACCGTTATCT
TACAAAGAAAGCACAATATTTGGTATAAACTAAGTCAGTGACTTGCTTAACTGAAATAGCGTCCATCCAAAAGTGG
GTTTAAGGTAAAACTACCTGACGATATTGGCGGGGATCCTGCAGTTTGGACTGCTTGCCGGGTTTGTCCAGGGTTC
CGGGTCTGTTCTTGGCACTCATGGGGACAGGCATCCTGCTCGTCTGTGGGGCCCCGCTGGAGCCCTTACGTGAAGC
TGAAGGTATCGACCSTAGGGGGCTCTAGGGCAGTGGGACCTTCATCCGGAACTAACAAGGGTCGGGGAGAGGCCTC
TTGGGCTATGTGGG
```

CAAGCGTTCCTTTATGGATGTAAATTCAAACAGTCATGCTGAGCCATCCCGGGCTGACAGTCACGTTWAAGACACT
AGGTCGGGCGCCACAGTGCCACCCAAGGAGAAGAAGAATTTGGAATTTTTCCATGAAGATGTACGGAAATCTGATG
TTGAATATGAAAATGGCCCCCAAATGGAATTCCAAAAGGTTACCACAGGGGCTGTAAGACCTAGTGACCCTCCTAA
GTGGGAAAGAGGAATGGAGAATAGTATTTCTGATGCATCAAGAACATCAGAATATAAAACTGAGATCATAATGAAG
GAAAATTCCATATCCAATATGAGTTTACTCAGAGACAGTAGAAACTATTCCCAGG 17185.1

TAGGAATAACAAATGTTTATTCAGAAATGGATAAGTAATACATAATCACCCTTCATCTCTTAATGCCCCTTCCTCT
CCTTCTGCACAGGAGACACAGATGGGTAACATAGAGGCATGGGAAGTGGAGGAGGACACAGGACTAGCCCACCACC
TTCTCTTCCCGGTCTCCCAAGATGACTGCTTATAGAGTGGAGGAGGCAAACAGGTCCCCTCAATGTACCAGATGGT
CACCTATAGCACCAGCTCCAGATGGCCACGTGGTTGCAGCTGGACTCAATGAAACTCTGTGACAACCAGAAGATAC
CTGCTTTGGGATGAGAGGGAGGATAAAGCCATGCAGGGAGGATATTTACCATCCCTACCCTAAGCACAGTGCAAGC
AGTGAGCCCCGGCTCCCAGTACCTGAAAAACCAAGGCCTACTGNCTTTTGGATGCTCTCTTGGGCCACG 17188.2

AAGCCTCCTGCCCTGGAAATCTGGAGCCCCTTGGAGCTGAGCTGGACGGGGCAGGGAGGGGCTGAGAGGCAAGACC
GTCTCCCTCCTGCTGCAGCTGCTTCCCCAGCAGCCACTGCTGGGCACAGCAGAAACGCCAGCAGAGAAAATGGGAG
CCGAGAGTCCTTAGCCCTGGAGCTGAGGCTGCCTCTGGGCTGACCCGCTGGCTGTACGTGGCCAGAACTGGGGTTG
GCATCTGGCATCCATTTGAGGCCAGGGTGGAGGAAAGGGAGGCCAACAGAGGAAAACCTATTCCTGCTGTGACAAC
ACAGCCCTTGTCCCACGCAGCCTAAGTGCAGGGAGCGTGATGAAGTCAGGCAGCCAGTCGGGGAGGACGAGGTAAC
TCAGCAGCAATGTCACCTTGTAGCCTATGCGCTCAATGGCCCGGAGGGGCAGCAACCCCCCGCACACGTCAGCCAA
CAGCAGTGCCTCTGCAGGCACCAAGAGAGCGATGATGGACTTGAGCGCCGTGTTC 17190.1

GTTTGGCAGAAGACATGTTTAATAACATTTTCATATTTAAAAAATACAGCAACAATTCTCTATCTGTCCACCATCT
TGCCTTGCCCTTCCTGGGGCTGAGGCAGACAAAGGAAAGGTAATGAGGTTAGGGCCCCCAGGCGGGCTAAGTGCTA
TTGGCCTGCTCCTGCTCAAAGAGAGCCATAGCCAGCTGGGCACGGCCCCCTAGCCCCTCCAGGTTGCTGAGGCGGC
AGCGGTGGTAGAGTTCTTCACTGAGCCGTGGGCTGCAGTCTCGCAGGGAGAACTTCTGCACCAGCCCTGGCTCTAC
GGCCCGAAAGAGGTGGAGCCCTGAGAACCGGAGGAAAACATCCATCACCTCCAGCCCCTCCAGGGCTTCCTCCTCT
TCCTGGCCTGCCAGTTCACCTGCCAGCCGGGCTCGGGCCGCCAGGTAGTCAGCGTTGTAGAAGCAGCCCTCCGCAG
AAGCCTGCCGGTCAAATCTCCCCGCTATAGGAGCCCCCCGGGAGGGGTCAGCACC

```
CAAGTTGAACGTCAGGCTTGGCAGAGGTGGAGTGTAGATGAAAACAAAGGTGTGATTATGAAGAGGATGTGAGTCC
TTTGGGTGTAGGAGAGAAAGGCTGTTGAGCTTCTATTTCAAGATACTTTTACCTGTGCAAAAAGCACATTTTCCAC
CTCCTTCTCATGGCATTTGTGTAAGGTGAGTATGATTCCTATTCCATCTGCATTTTAGAGGTGAAGAATAACGTAC
AAGGGATTCAGTGATTAGCAAGGGACCCCTCACTAAGTGTTGATGGAGTTAGGACAGAGCTCAGCTGTTTGAATCT
CAGAGCCCAGGCAGCTGGAGCTGGGTAGGATCCTGGAGCTGGCACTAATGTGAGGTGCATTCCCTCCAACCCAGGC
TCAGATCCGGAACCTGACCGTGCTGACCCCCGAAGGGGAGGCAGGGCTGAGCTGGCCCGTTGGGCTCCCTGCTCCT
TTCACACCACACTCTCGCTTTGAGGTGCTGGGCTGGGACTACTTCACAGAGCAGC
```

17191.2&89.2

```
TGGCCTGGGCAGGATTGGGAGAGAGGTAGCTACCCGGATGCAGTCCTTTGGGATGAAGACTATAGGGTATGACCCC
ATCATTTCCCCAGAGGTCTCGGCCTCCTTTGGTGTTCAGCAGCTGCCCCTGGAGGAGATCTGGCCTCTCTGTGATT
TCATCACTGTGCACACTCCTCTCCTGCCCTCCACGACAGGCTTGCTGAATGACAACACCTTTGCCCAGTGCAAGAA
GGGGGTGCGTGTGGTGAACTGTGCCCGTGGAGGGATCGTGGACGAAGGCGCCCTGCTCCGGGCCCTGCAGTCTGGC
CAGTGTGCCGGGGCTGCACTGGACGTGTTTACGGAAGAGCCGCCACGGGACCGGGCCTTGGTGGACCATGAGAATG
TCATCAGCTGTCCCCACCTGGGTGCCAGCACCAAGGAGGCTCAGAGCCGCTGTGGGGAGGAAATTGCTGTTCAGTT
CGTGGACATGGTGAAGGGGAAATCTCTCACGGGGGTTGTGAATGCCCAGGCCCTT
```

*Fig. 1S*

```
AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTAC
ATCCTCATTACCAAATGGAACTGCCAGTCTCATTCAGCCTTTATCCATTCCTTATTCTTCTTCAACATTGCCTCAT
GCATCATCTTACAGCCTGATGATGGGAGGATTTGGTGGTGCTAGTATCCAGAAGGCCCAGTCTCTGATTGATTTAG
GATCTAGTAGCTCAACTTCCTCAACTGCTTCCCTCTCAGGGAACTCACCTAAGACAGGGACCTCAGAGTGGGCAGT
TCCTCAGCCTTCAAGATTAAAGTATCGGCAAAAATTTAATAGTCTAGACAAAGGCATGAGCGGATACCTCTCAGGT
TTTCAAGCTAGAAATGCCCTTCTTCAGTCAAATCTCTCTCAAACTCAGCTAGCTACTATTTGGACTCTGGCTGACA
TCGATGGTGACGGACAGTTGAAAGCTGAAGAATTTATTCTGGCGATGCACCTCACTGACATGGCCAAAGCTGGACA
GCCACTACCACTGACGTTGCCTCCCGAGCTTGTCCCTCCATCTTTCAGAGGGGGAAAGCAAGTTGATTCTGTTAAT
GGAACTCTGCCTTCATATCAGAAAACACAAGAAGAAGAGCCTCAGAAGAAACTGCCAGTTACTTTTGAGGACAAAC
GGAAAGCCAACTATGAACGAGGAAACATGGAGCTGGAGAAGCGACGCCAAGTGTTGATGGAGCAGCAGCAGAGGGA
GGCTGAACGCAAAGCCCAGAAAGAGAAGGAAGAGTGGGAGCGGAAACAGAGAGAACTGCAAGAGCAAGAATGGAAG
AAGCAGCTGGAGTTGGAGAAACGCTTGGAGAAACAGAGAGAGCTGGAGAGACAGCGGGAGGAAGAGAGGAGAAAGG
AGATAGAAAGACGAGAGGCAGCAAAACAGGAGCTTGAGAGACAACGCCGTTTAGAATGGGAAAGACTCCGTCGGCA
GGAGCTGCTCAGTCAGAAGACCAGGGAACAAGAAGACATTGTCAGGCTGAGCTCCAGAAAGAAAAGTCTCCACCTG
GAACTGGAAGCAGTGAATGGAAAACATCAGCAGATCTCAGGCAGACTACAAGATGTCCAAATCAGAAAGCAAACAC
AAAAGACTGAGCTAGAAGTTTTGGATAAACAGTGTGACCTGGAAATTATGGAAATCAAACAACTTCAACAAGAGCT
TAAGGAATATCAAAATAAGCTTATCTATCTGGTCCCTGAGAAGCAGCTATTAAACGAAAGAATTAAAAACATGCAG
CTCAGTAACACACCTGATTCAGGGATCAGTTTACTTCATAAAAAGTCATCAGAAAAGGAAGAATTATGCCAAAGAC
TTAAAGAACAATTAGATGCTCTTGAAAAAGAAACTGCATCTAAGCTCTCAGAAATGGATTCATTTAACAATCAGCT
GAAGGAACTCAGAGAAAGCTATAATACACAGCAGTTAGCCCTTGAACAACTTCATAAAATCAAACGTGACAAATTG
AAGGAAATCGAAAGAAAAAGATTAGAGCAAAAAAAAAAAAA
```

*Fig. 2A*

ATGGCAGTGACATTCACCATCATGGGAACCACCTTCCCTTTTCTTCAGGATTCTCTGTAGTGGAAGAGAGCACCCA
GTGTTGGGCTGAAAACATCTGAAAGTAGGGAGAAGAACCTAAAATAATCAGTATCTCAGAGGGCTCTAAGGTGCCA
AGAAGTCTCACTGGACATTTAAGTGCCAACAAAGGCATACTTTCGGAATCGCCAAGTCAAAACTTTCTAACTTCTG
TCTCTCTCAGAGACAAGTGAGACTCAAGAGTCTACTGCTTTAGTGGCAACTACAGAAAACTGGTGTTACCCAGAAA
AACAGGAGCAATTAGAAATGGTTCCAATATTTCAAAGCTCCGCAAACAGGATGTGCTTTCCTTTGCCCATTTAGGG
TTTCTTCTCTTTCCTTTCTCTTTATTAACCACTA

*Fig. 2B*

```
ATATCTAGAAGTCTGGAGTGAGCAAACAAGAGCAAGAAACAAAAAGAAGCCAAAAGCAGAAGGCTCCAATATGAAC
AAGATAAATCTATCTTCAAAGACATATTAGAAGTTGGGAAAATAATTCATGTGAACTAGACAAGTGTGTTAAGAGT
GATAAGTAAAATGCACGTGGAGACAAGTGCATCCCCAGATCTCAGGGACCTCCCCCTGCCTGTCACCTGGGGAGTG
AGAGGACAGGATAGTGCATGTTCTTTGTCTCTGAATTTTTAGTTATATGTGCTGTAATGTTGCTCTGAGGAAGCCC
CTGGAAAGTCTATCCCAACATATCCACATCTTATATTCCACAAATTAAGCTGTAGTATGTACCCTAAGACGCTGCT
AATTGACTGCCACTTCGCAACTCAGGGGCGGCTGCATTTTAGTAATGGGTCAAATGATTCACTTTTTATGATGCTT
CCAAAGGTGCCTTGGCTTCTCTTCCCAACTGACAAATGCCAAAGTTGAGAAAAATGATCATAATTTTAGCATAAAC
AGAGCAGTCGGCGACACCGATTTTATAAATAAACTGAGCACCTTCTTTTTAAACAAACAAATGCGGGTTTATTTCT
CAGATGATGTTCATCCGTGAATGGTCCAGGGAAGGACCTTTCACCTTGACTATATGGCATTATGTCATCACAAGCT
CTGAGGCTTCTCCTTTCCATCCTGCGTGGACAGCTAAGACCTCAGTTTTCAATAGCATCTAGAGCAGTGGGACTCA
GCTGGGGTGATTTCGCCCCCCATCTCCGGGGGAATGTCTGAAGACAATTTTGTTACCTCAATGAGGGAGTGGAGGA
GGATACAGTGCTACTACCAACTAGTGGATAAAGGCCAGGGATGCTGCTCAACCTCCTACCATGTACAGGACGTCTC
CCCATTACAACTACCCAATCCGAAGTGTCAACTGTGTCAGGACTAAGAAACCCTGGTTTTGAGTAGAAAAGGGCCT
GGAAAGAGGGGAGCCAACAAATCTGTCTGCTTCCTCACATTAGTCATTGGCAAATAAGCATTCTGTCTCTTTGGCT
GCTGCCTCAGCACAGAGAGCCAGAACTCTATCGGGCACCAGGATAACATCTCTCAGTGAACAGAGTTGACAAGGCC
TATGGGAAATGCCTGATGGGATTATCTTCAGCTTGTTGAGCTTCTAAGTTTCTTTCCCTTCATTCTACCCTGCAAG
CCAAGTTCTGTAAGAGAAATGCCTGAGTTCTAGCTCAGGTTTTCTTACTCTGAATTTAGATCTCCAGACCCTTCCT
GGCCACAATTCAAATTAAGGCAACAAACATATACCTTCCATGAAGCACACACAGACTTTTGAAAGCAAGGACAATG
ACTGCTTGAATTGAGGCCTTGAGGAATGAAGCTTTGAAGGAAAAGAATACTTTGTTTCCAGCCCCCTTCCCACACT
CTTCATGTGTTAACCACTGCCTTCCTGGACCTTGGAGCCACGGTGACTGTATTACATGTTGTTATAGAAAACTGAT
TTTAGAGTTCTGATCGTTCAAGAGAATGATTAAATATACATTTCCTA
```

```
TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT
```

*Fig. 4*

```
TAGCGYGGTCGCGGCCGAGGYCTGCTTYTCTGTCCAGCCCAGGGCCTGTGGGGTCAGGGCGGTGGGTGCAGATGGC
ATCCACTCCGGTGGCTTCCCCATCTTTCTCTGGCCTGAGCAAGGTCAGCCTGCAGCCAGAGTACAGAGGGCCAACA
CTGGTGTTCTTGAACAAGGGCCTTAGCAGGCCCTGAAGGRCCCTCTCTGTAGTGTTGAACTTCCTGGAGCCAGGCC
ACATGTTCTCCTCATACCGCAGGYTAGYGATGGTGAAGTTGAGGGTGAAATAGTATTMANGRAGATGGCTGGCARA
CCTGCCCGGGCGGCCGCTCSAAATCC
```

*Fig. 5*

```
AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA
```

```
TTGGGGNTTTMGAGCGGCCGCCCGGGCAGGTACCGGGGTGGTCAGCGAGGAGCCATTCACACTGAACTTCACCATC
AACAACCTGCGGTATGAGGAGAACATGCAGCACCCTGGCTCCAGGAAGTTCAACACCACGGAGAGGGTCCTTCAGG
GCCTGCTCAGGTCCCTGTTCAAGAGCACCAGTGTTGGCCCTCTGTACTCTGGCTGCAGACTGACTTTGCTCAGACT
TGAGAAACATGGGGCAGCCACTGGAGTGGACGCCATCTGCACCCTCCGCCTTGATCCCACTGGTCCTGGACTGGAC
AGAGAGCGGCTATACTGGGAGCTGAGCCAGTCCTCTGGCGGNGACNCCNCTT
```

Fig. 7B

```
AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA
```

```
TGTGGTGTTGAACTTCCTGGAGNCAGGGTGACCCATGTCCTCCCCATACTGCAGGTTGGTGATGGTGAAGTTGAGG
GTGAATGGTACCAGGAGAGGGCCAGCAGCCATAATTGTSGRGCKGSMGMSSGAGGMWGGWGTYYCWGAGGTTCYRA
RRTCCACTGTGGAGGTCCCAGGAGTGCTGGTGGTGGGCACAGAGSTCYGATGGGTGAAACCATTGACATAGAGACT
GTTCCTGTCCAGGGTGTAGGGGCCCAGCTCTTYRATGYCATTGGYCAGTTKGCTYAGCTCCCAGTACAGCCRCTCT
CKGYYGMGWCCAGSGCTTTTGGGGTCAAGATGATGGATGCAGATGGCATCCACTCCAGTGGCTGCTCCATCCTTCT
CGGACCTGAGAGAGGTCAGTCTGCAGCCAGAGTACAGAGGGCCAACACTGGTGTTCTTTGAATA
```

*Fig. 8*

```
TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG
```

```
ACGGTTTCAATGGACACTTTTATTGTTTACTTAATGGATCATCAATTTTGTCTCACTACCTACAAATGGAATTTCA
TCTTGTTTCCATGCTGAGTAGTGAAACAGTGACAAAGCTAATCATAATAACCTACATCAAAAGAGAACTAAGCTAA
CACTGCTCACTTTCTTTTTAACAGGCAAAATATAAATATATGCACTCTAXAATGCACAATGGTTTAGTCACTAAAA
AATTCAAATGGGATCTTGAAGAATGTATGCAAATCCAGGGTGCAGTGAAGATGAGCTGAGATGCTGTGCAACTGTT
TAAGGGTTCCTGGCACTGCATCTCTTGGCCACTAGCTGAATCTTGACATGGAAGGTTTTAGCTAATGCCAAGTGGA
GATGCAGAAAATGCTAAGTTGACTTAGGGGCTGTGCACAGGAACTAAAAGGCAGGAAAGTACTAAATATTGCTGAG
AGCATCCACCCCAGGAAGGACTTTACCTTCCAGGAGCTCCAAACTGGCACCACCCCCAGTGCTCACATGGCTGACT
TTATCCTCCGTGTTCCATTTGGCACAGCAAGTGGCAGTG
```

11721-2

```
AAGGCTGGTGGGTTTTTGATCCTGCTGGAGAACCTCCGCTTTCATGTGGAGGAAGAAGGGAAGGGAAAAGATGCTT
CTGGGAACAAGGTTAAAGCCGAGCCAGCCAAAATAGAAGCTTTCCGAGCTTCACTTTCCAAGCTAGGGGATGTCTA
TGTCAATGATGCTTTTGGCACTGCTCACAGAGCCCACAGCTCCATGGTAGGAGTCAATCTGCCACAGAAGGCTGGT
GGGTTTTTGATGAAGAAGGAGCTGAACTACTTTGCAAAGGCCTTGGAGAGCCCAGAGCGACCCTTCCTGGCCATCC
TGGGCGGAGCTAAAGTTGCAGACAAGATCCAGCTCATCAATAATATGCTGGACAAAGTCAATGAGATGATTATTGG
TGGTGGAATGGCTTTTACCTTCCTTAAGGTGCTCAACAACATGGAGATTGGCACTTCTCTGTTTGATGAAGAGGGA
GCCAAGATTGTCAAAGACCTAATGTCCAAAGCTGAGAAGAATGGTGTGAAGATTACCTTGCCTGTTGACTTTGTCA
CTGCTGACAAGTTTGATGA
```

11724-1

```
TTTGTTCCTTACATTTTTCTAAAGAGTTACTTAAATCAGTCAACTGGTCTTTGAGACTCTTAAGTTCTGATTCCAA
CTTAGCTAATTCATTCTGAGAACTGTGGTATAGGTGGCGTGTCTCTTCTAGCTGGGACAAAAGTTCTTTGTTTTCC
CCCTGTAGAGTATCACAGACCTTCTGCTGAAGCTGGACCTCTGTCTGGGCCTTGGACTCCCAAATCTGCTTGTCAT
GTTCAAGCCTGGAAATGTTAATCTTTAATTCTTCCATATGGATGGACATCTGTCTAAGTTGATCCTTTAGAACACT
GCAATTATCTTCTTTGAGTCTAATTTCTTCTTCTTTGCTTTGAATCGCATCACTAAACTTCCTCTCCCATTTCTTA
GCTTCATCTATCACCCTGTCACGATCATCCTGGAGGGAAGACATGCTCTTAGTAAAGGCTGCAAGCTGGGTCACAG
TACTGTCCAAGTTTTCCTGAAGTTGCTGAACTTCCTTGTCTTTCTTGTTCAAAGTAACCTGAATCTCTCCAATTGT
CTCTTCCAAGTGGACTTTTTCTCTGCGCAAAGCATCCAG
```

11724-2

```
TCATTGCCTGTGATGGCATCTGGAATGTGATGAGCAGCCAGGAAGTTGTAGATTTCATTCAATCAAAGGATTCAGC
ATGTGGTGGAAGCTGTGAGGCAAGAGAAACAAGAACTGTATGGCAAGTTAAGAAGCACAGAGGCAAACAAGAAGGA
GACAGAAAAGCAGTTGCAGGAAGCTGAGCAAGAAATGGAGGAAATGAAAGAAAAGATGAGAAAGTTTGCTAAATCT
AAACAGCAGAAAATCCTAGAGCTGGAAGAAGAGAATGACCGGCTTAGGGCAGAGGTGCACCCTGCAGGAGATACAG
CTAAAGAGTGTATGGAAACACTTCTTTCTTCCAATGCCAGCATGAAGGAAGAACTTGAAAGGGTCAAAATGGAGTA
TGAAACCCTTTCTAAGAAGTTTCAGTCTTTAATGTCTGAGAAAGACTCTCTAAGTGAAGAGGTTCAAGATTTAAAG
CATCAGATAGAAGGTAATGTATCTAAACAAGCTAACCTAGAGGCCACCGAGAAACATGATAACCAAACGAATGTCA
CTGAAGAGGGAACACAGTCTATACCAGGT
```

*Fig. 15A*

16455.1.edit

TCGAGCGGCCGCCCGGGCAGGTCCATTTTCTCCCTGACGGTCCCACTTCTCTCCAATCTTGTAGTTCACACCATTG
TCATGACACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAAGTTGCCCACGGTAACAACCTCTTCCCGAACCTTATGCCTCTGCTG
GTCTTTCAAGTGCCTCCACTATGATGTTGTAGGTGGCACCTCTGGTGAGGACCTCGGCCGCGACCACGCT

16455.2.edit

AGCGTGGTTTGCGGCCGAGGTCCTCACCANAGGTGCCACCTACAACATCATAGTGGAGGCACTGAAAGACCAGCAG
AGGCATAAGGTTCGGGAAGAGGTTGTTACCGTGGGCAACTCTGTCAACGAAGGCTTGAACCAACCTACGGATGACT
CGTGCTTTGACCCCTACACAGNTTCCCATTATGCCGTTGGAGATGAGTGGGAACGAATGTCTGAATCAGGCTTTAA
ACTGTTGTGCCAGTGCTTANGCTTTGGAAGTGGTCATTTCAGATGTGATTCATCTANATGGTGTCATGACAATGGT
GNGAACTACAAGATTGGAGAGAAGTGGNACCGTCAGGGGANAAAATGGACCTGCCCGGGCGGCNCGCTCGA

16456.1.edit

AGCGTGGTCGCGGCCGAGGTCTGGCTTNCTGCTCANGTGATTATCCTGAACCATCCAGGCCAAATAAGCGCCGGCT
ATGCCCCTGNATTGGATTGCCACACGGCTCACATTGCATGCAAGTTTGCTGAGCTGAAGGAAAAGATTGATC

16456.2.edit

TCGAGCGGCCGCCCGGGCAGGTCCAATTGAAACAAACAGTTCTGAGACCGTTCTTCCACCACTGATTAAGAGTGGG
GNGGCGGGTATTAGGGATAATATTCATTTAGCCTTCTGAGCTTTCTGGGCAGACTTGGTGACCTTGCCAGCTCCAG
CAGCCTTCTGGTCCACTGCTTTGATGACACCCACCGCAACTGTCTGTCTCATATCACGAACAGCAAAGCGACCCAA
AGGTGGATAGTCTGAGAAGCTCTCAACACACATGGGCTTGCCAGGAACCATATCAACAATGGGCAGCATCACCAGA
CTTCAAGAATTTAAGGGCCATCTTCCAGCTTTTTACCAGAACGGCGATCAATCTTTTCCTTCAGCTCAGCAAACTT
GCATGCAATGTGAGCCG

*Fig. 15A-1*

16524.2.edit

```
TCGAGCGGCCGCCCGGGCAGGTCTGGGCCAGGAGGACCAATAGGACCAGTAGGACCCCTTGGGCCATCTTTCCCTG
GGACACCATCAGCACCTGGACCGCCTGGTTCACCCTTGTCACCCTTTGGACCAGGACTTCCAAGACCTCCTCTTTC
TCCAGGCATTCCTTGCAGACCAGGAGTACCANCAGCACCAGGTGGCCCAGGAGGACCAGCAGCACCCTTTCCTCCT
TCGGGACCAGGGGGACCAGCTCCACCTCTAAGTCCTGGGGCCCCTGCCAATCCAGGAGGGCCTCCTTCACCTTTCT
CACCCGGAGCCCCTCTTTCT
```

16526.1.edit

```
TCGAGCGGCCGCCCGGGCAGGTCCACCGGGATATTCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGACAACCGGAG
GCTGGAGAGCAAAATCCGGGAGCACTTGGAGAAGAAGGGACCCCAGGTCAGAGACTGGAGCCATTACTTCAAGATC
ATCGAGGACCTGAGGGCTCANATCTTCGCAAATACTGCNGACAATGCCCG
```

16526.2.edit

```
ATGCGNGGTCGCGGCCGANGACCANCTCTGGCTCATACTTGACTCTAAAGNCNTCACCAGNANTTACGGNCATTGC
CAATCTGCAGAACGATGCGGGCATTGTCCGCANTATTTGCGAAGATCTGAGCCCTCAGGNCCTCGATGATCTTGAA
GTAANGGCTCCAGTCTCTGACCTGGGGTCCCTTCTTCTCCAAGTGCTCCCGGATTTTGCTCTCCAGCCTCCGGTTC
TCGGTCTCCAAGNCTTCTCACTCTGTCCAGGAAAAGAGGCCAGGCGGNCGATCAGGGCTTTTGCATGGACT
```

16527.1.edit

```
AGCGTGGTCGCGGCCGAGGTTGTACAAGCTTTTTTTTTTTTTTTTTTTTTTTTTTTTTTTTTTTTTTTTTTTTTTT
TTTTTTTTTTTTTTTTTTTTTTTT
```

16527.2.edit

```
TCGAGCGGCCGCCCGGGCAGGTCTGCCAACACCAAGATTGGCCCCCGCCGCATCCACACAGTTNGTGTGCGGGGAG
GTAACAAGAAATACCGTGCCCTGAGGNTGGACGNGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATNGACAGCACACCGTACCGACAGTGGGTACCGAAGTCCCACTATGCNCCT
```

```
AAGCCAATAATCACCATTTATTACTTAATATATGCCAACCACTGTACTTGGCAGTTCACAAATTCTCACCGTTACA
ACAACCCCATGAGGTATTTATTCCCATTCTATAGATAGGGAAACCACAGCTCAAGTAAGTTAGGAAACTGAGCCAA
GTATACACAGAATACGAAGTGGCAAAACTAGAAGGAAAGACTGACACTGCTATCTGCTGGCCTCCAGTGTCCTGGC
TCTTTTCACACGGGtTCAATGTCTCCAGCGCTGCTGCTGCTGCTGCATTACCATGCCCTCATTGTTTTTCTTCCTC
TGGTGTTCAACTGCATCCTTCAAAGAATCTAACTCATTCCAGAGACCACTTATTTCTTTCTCTCTTTCTGAAATTA
CTTTTAATAATTCTTCATGAGGGGGAAAAGAAGATGCCTGTTGGTAGTTTTGTTGTTTAAGCTGCTCAATTTGGGA
CTTAAACAATTTGTTTTCATCTTGTACATCCTGTAACAGCTGTGTTTTGCTAGAAAGATCACTCTCCCTCTCTTTT
AGCATGGCTTCTAACCTCTTCAATTCATTTTCCTTTTCTTTCAACACAATCTCAAGTTCTTCAAACTGTGATGCAG
AAGAGGCCTCTTTCAAGTTATGTTGTGCTACTTCCTGAACATGTGCTTTTAAAGATTCATTTTCTTCTTGAAGATC
CTGTAACCACTTCCCTGTATTGGCTAGGTCTTTCTCTTTCTCTTCCAAAACAGCCTTCATGGTATTCATCTGTTCC
TCTTTTCCTTTTAATAAGTTCAGGAGCTTCAGAAC
```

11726-1&2

```
CAAGCTTTTTTTTTTTTTTTAAAAAGTGTTAGCATTAATGTTTTATTGTCACGCAGATGGCAACTGGGTTTATGTC
TTCATATTTTATATTTTTGTAAATTAAAAAAAATTACAAGTTTTAAATAGCCAATGGCTGGTTATATTTTCAGAAAA
CATGATTAGACTAATTCATTAATGGTGGCTTCAAGCTTTTCCTTATTGGCTCCAGAAAATTCACCCACCTTTTGTC
CCTTCTTAAAAAACTGGAATGTTGGCATGCATTTGACTTCACACTCTGAAGCAACATCCTGACAGTCATCCACATC
TACTTCAAGGAATATCACGTTGGAATACTTTTCAGAGAGGGAATGAAAGAAAGGCTTGATCATTTTGCAAGGCCCA
CACCACGTGGCTGAGAAGTCAACTACTACAAGTTTATCACCTGCAGCGTCCAAGGCTTCCTGAAAAGCAGTCTTGC
TCTCGATCTGCTTCACCATCTTGGCTGCTGGAGTCTGACGAGCGGCTGTAAGGACCGATGGAAATGGATCCAAAGC
ACCAAACAGAGCTTCAAGACTCGCTGCTTGGCTTGAATTCGGATCCGATATCGCCATGGCCT
```

11727-1&2

```
AAGTGTTAGCATTAATGTTTTATTGTCACGCAGATGGCAACTGGGTTTATGTCTTCATATTTTATATTTTTGTAAA
TTAAAAAAATTMCAAGTTTTAAATAGCCAATGGCTGGTTATATTTTCAGAAAACATGATTAGACTAATTCATTAAT
GGTGGCTTCAAGCTTTTCCTTATTGGCTCCAGAAAATTCACCCACCTTTTGTCCCTTCTTAAAAAACTGGAATGTT
GGCATGCATTTGACTTCACACTCTGAAGCAACATCCTGACAGTCATCCACATCTACTTCAAGGAATATCACGTTGG
AATACTTTTCAGAGAGGGAATGAAAGAAAGGCTTGATCATTTTGCAAGGCCCACACCACGTGGCTGAGAAGTCAAC
TACTACAAGTTTATCACCTGCAGCGTCCAAGGCTTCCTGAAAAGCAGTCTTGCTCTCGATCTGCTTCACCATCTTG
GCTGCTGGAGTCTGACGAGCGGCTGTAAGGACCGATGGAAATGGATCCAAAGCACCAAACAGAGCTTCAAGACTCG
CTGCTTGGCATGAATTCGGATCCGA
```

*Fig. 15B*

16459.1.edit

```
TCGAGCGGCCGCCCGGGCAGGTCCAGAGGGCTGTGCTGAAGTTTGCTGCTGCCACTGGAGCCACTCCAATTGCTGG
CCGCTTCACTCCTGGAACCTTCACTAACCAGATCCAGGCAGCCTTCCGGGAGCCACGGCTTCTTGTGGNTACTGAC
CCCAGGGCTGACCACCAGCCTCTCACGGAGGCATCTTATGTTAACCTACCTACCATTGCGCTGTGTAACACAGATT
CTCCTCTGCGCTATGTGGACATTGCCATCCCATGCAACAACAAGGGAGCTCACTCAGNGGGGTTTGATGTGGTGGA
TGCTGGCTCGGGAAGTTCTGCGCATGCGTGGCACCATTTCCCGTGAACACCCATGGGANGNCATGCCTGATCTGGA
CTTCTACAGAGATCCTGAAGAGATTGAAAAAGAAGAACAGGCTGNTTGCTGANAAAAGCAAGTGACCAAGGANGAAA
TTTCANGGGTGAAANGGACTGCTCCCGCTCCTGAATTCACTGCTACTCAACCTGANGNTGCAGACTGGTCTTGAAG
GNGNACANGGGCCCTCTGGGCCTATTTAAGCANCTTCGGTCGCGAACACGNT
```

16459.2.edit

```
AGCGTGNGTCGCGGCCGAGGTGCTGAATAGGCACAGAGGGCACCTGTACACCTTCAGACCAGTCTGCAACCTCAGG
CTGAGTAGCAGTGAACTCAGGAGCGGGAGCAGTCCATTCACCCTGAAATTCCTCCTTGGNCACTGCCTTCTCAGCA
GCAGCCTGCTCTTCTTTTTCAATCTCTTCAGGATCTCTGTAGAAGTACAGATCAGGCATGACCTCCCATGGGTGTT
CACGGGAAATGGTGCCACGCATGCGCAGAACTTCCCGAGCCAGCATCCACCACATCAAACCCACTGAGTGAGCTCC
CTTGTTGTTGCATGGGATGGGCAATGTCCACATAGCGCAGAGGAGAATCTGTGTTACACAGCGCAATGGTAGGTAG
GTTAACATAAGATGCCTCCGCGAGAAGCTGGTGGTCAGCCCTGGGGTCAAGTAACCACAAGAAGCCGTGGCTCCCG
GAAGGCTGCCTGGATCTGGTTAGTGAAGGNTCCAGGAGTGAAGCGGCCAACAATTGGAGTGGCTTCAGTGGCAAGC
AGCAAACTTCAGCACAAGCCCTCTGGACCTGCCCGGCGGCCGCTCGA
```

16460.1.edit

```
TCGAGCGGCCGCCCGGGCAGGTCCATTTTCTCCCTGACGGNCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCNTCCCCGAACCTTATGCCTCTGCTG
GGCTTTCAGNGCCTCCACTATGATGNTGTAGGGGGGCACCTCTGGNGANGACCTCGGCCGCGACCACGCT
```

16460.2.edit

```
AGCGTGGTCGCGGCCGAGGTCCTCACCAGAGGTGCCACCTACAACATCATAGTGGAGGCACTGAAAGACCAGCAGA
GGCATAAGGCTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGGTCATTTCAGATGTGATTCATCTAGATGGTGCCATGACAATGGN
GNGAACTACAAGATTGGAGAGAAGTGGNACCGNCAGGGAGAAAATGGACCTGCCCGGGCGGCCGCTCGA
```

Fig. 15B-1

16528.1.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAG
```

16528.2.edit

```
AGCGTGNTCNCGGCCGAGGATGGGGAAGCTCGNCTGTCTTTTTCCTTCCAATCAGGGGCTNNNTCTTCTGATTATT
CTTCAGGGCAANGACATAAATTGTATATTCGGNTCCCGGTTCCAGNCCAGTAATAGTAGCCTCTGTGACACCAGGG
CGGGGCCGAGGGACCACTTCTCTGGGAGGAGACCCAGGCTTCTCATACTTGATGATGAAGCCGGTAATCCTGGCAC
GTGGGCGGCTGCCATGATACCACCAANGAATTGGGTGTGGTGGACCTGCCCGGGCGGGCCGCTCGAAAANCCGAAT
TCNTGCAAGAATATCCATCACACTTGGGCGGGCCGNTCGAACCATGCATCNTAAAAGGGCCCCAATTTCCCCCCTA
TTAGGNGAAGCCNCATTTAACAAATTCCACTTGG
```

16529.1.edit

```
TCGAGCGGCCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTTGAGCCAGCAGAATCGAAAACATTCGGAACCCAAGAAGGGCAAGCCCGCAAAGAAACCCCGCCCGCAC
CTGGCCGNGAACCTCCAAGAANGTGCCCACNTCTTGACTGGGAAAAAAAGGGAAAANTACTTGGAATTGGAC
```

16529.2.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAAGTGGCACATCTTGAGGTCACGGCAGGGTGCGGGCGG
GGTTCTTGCGGGCTGCCCTTCTGGGCTCCCGGAATGTTCTNNGAACTTGCTGG
```

```
TACAAACTTTATTGAAACGCACACGCGCACACACACAAACACCCCTGTGGATAGGGAAAAGCACCTGGCCACAGGG
TCCACTGAAACGGGGAGGGGATGGCAGCTTGTAATGTGGCTTTTGCCACAACCCCCTTCTGACAGGGAAGGCCTTA
GATTGAGGCCCCACCTCCCATGGTGATGGGGAGCTCAGAATGGGGTCCAGGGAGAATTTGGTTAGGGGGAGGTGCT
AGGGAGGCATGAGCAGAGGGCACCCTCCGAGTGGGGTCCCGAGGGCTGCAGAGTCTTCAGTACTGTCCCTCACAGC
AGCTGTCTCAAGGCTGGGTCCCTCAAAGGGGCGTCCCAGCGCGGGGCCTCCCTGCGCAAACACTTGGTACCCCTGG
CTGCGCAGCGGAAGCCAGCAGGACAGCAGTGGCGCCGATCAGCACAACAGACGCCCTGGCGGTAGGGACAGCAGGC
CCAGCCCTGTCGGTTGTCTCGGCAGCAGGTCTGGTTATCATGGCAGAAGTGTCCTTCCCACACTTCACGTCCTTCA
CACCCACGTGAXGGCTACXGGCCAGGAAG
```

11728.2.40.19.19

```
CCCGTGGGTGCCATCCACGGAGTTGTTACCTGATCTTTGGAAGCAGGATCGCCCGTCTGCACTGCAGTGGAAGCCC
CGTGGGCAGCAGTGATGGCCATCCCCGCATGCCACGGCCTCTGGGAAGGGGCAGCAACTGGAAGTCCCTGAGACGG
TAAAGATGCAGGAGTGGCCGGCAGAGCAGTGGGCATCAACCTGGCAGGGGCCACCCAGATGCCTGCTCAGTGTTGT
GGGCCATTTGTCCAGAAGGGGACGGCAGCAGCTGTAGCTGGCTCCTCCGGGGTCCAGGCAGCAGGCCACAGGGCAG
AACTGACCATCTGGGCACCGCGTTCCAGCCACCAGCCCTGCTGTTAAGGCACCCAGCTCACCAGGGTCCACATGG
TCTGCCTGCGTCCGACTCCGCGGTCCTTGGGCCCTGATGGTTCTACCTGCTGTGAGCTGCCCAGTGGGAAGTATGG
CTGCTGCCAATGCCCAACGCCACCTGCTGCTCCGATCACCTGCACTGCTGCCCCAAGACACTGTGTGTGACCTGAT
CCAGAGTAAGTGCCTCTCCAAGGAGAACG
```

11730-1

```
GAATCACCTTTCTGGTTTAGCTAGTACTTTGTACAGAACAATGAGGTTTCCCACAGCGGAGTCTCCCTGGGCTCTG
TTTGGCTCTCGGTAAGGCAGGCCTACACCTTTTCCTCTCCTCTATGGAGAGGGGAATATGCATTAAGGTGAAAAGT
CACCTTCCAAAAGTGAGAAAGGGATTCGATTGCTGCTTCAGGACTGTGGAATTATTTGGAATGTTTTACAAATGGT
TGCTACAAAACAACAAAAAAGGTAATTACAAAATGTGTACATCACAACATGCTTTTTAAAGACATTATGCATTGTG
CTCACATTCCCTTAAATGTTGTTTCCAAAGGTGCTCAGCCTCTAGCCCAGCTGGATTCTCCGGGAAGAGGCAGAGA
CAGTTTGGCGAAAAAGACACAGGGAAGGAGGGGGTGGTGAAAGGAGAAAGCAGCCTTCCAGTTAAAGATCAGCCCT
CAGTTAAAGGTCAGCTTCCCGCAXGCTGGCCTCAXGCGGAGTCTGGGTCAGAGGGAGGAGCAGCAGCAGGGTGGGA
CTGGGGCGT
```

11730-2

```
AACCGGAGCGCGAGCAGTAGCTGGGTGGGCACCATGGCTGGGATCACCACCATCGAGGCGGTGAAGCGCAAGATCC
AGGTTCTGCAGCAGCAGGCAGATGATGCAGAGGAGCGAGCTGAGCGCCTCCAGCGAGAAGTTGAGGGAGAAAGGCG
GGCCCGGGAACAGGCTGAGGCTGAGGTGGCCTCCTTGAACCGTAGGATCCAGCTGGTTGAAGAAGAGCTGGACCGT
GCTCAGGAGCGCCTGGCCACTGCCCTGCAAAAGCTGGAAGAAGCTGAAAAAGCTGCTGATGAGAGTGAGAGAGGTA
TGAAGGTTATTGAAAACCGGGCCTTAAAAGATGAAGAAAAGATGGAACTCCAGGAAATCCAACTCAAAGAAGCTAA
GCACATTGCAGAAGAGGCAGATAGGAAGTATGAAGAGGTGGCTCGTAAGTTGGTGATCATTGAAGGAGACTTGGAA
CGCACAGAGGAACGAGCTGAGCTGGCAGAGTCCCGTTGCCGAGAGATGGATGAGCAGATTAGACTGATGGACCAGA
ACCTGAAGTGTCTGAGTGC
```

*Fig. 15C*

16461.1.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGNTGCAACCTTG
GTTGGGGTCAATCCAGTACTCTCCACTCTTCCAGCCAGAGTGGCACATCTTGAGGTCACGGCAGGTGCGGNCGGGG
GNTTTTGCGGCTGCCCTCTGGNCTTCGGNTGTNCTCNATCTGCTGGCTCA
```

16461.2.edit

```
TCGAGCGGCCGCCCGGGCAGGTCTCGCGGTCGCACTGGTGATGCTGGTCCTGTTGGTCCCCCCGGCCCTCCTGGAC
CTCCTGGCCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGNCGCAAGAACCCCGCCCGCACCTGCCGTG
ACCTCAAGATGTGCCACTCTGACTGGAAGAGTGGAGAGTACTGGATTGACCCCAACCAAGCTGCAACCTGGATGCC
ATCAAAGTCTTCTGCAACATGGAGACTGGTGAGACCTGCGTGTACCCCACTCAGCCCAGTGTGGCCCAAAAGAACT
GGTACATCAGCAAGAACCCCAAGGACAAGAAGCATGTCTGGTTCGGCGAGAACATGACCGATGGATTCCAGTTCGA
GTATGGCGGGCAGGGCTCCGACCCTGCCGATGGGGACCTTGGCCGCGAACACGCT
```

16463.1.edit

```
AGCGTGGNNGCGGCCGAGGTATAAATATCCAGNCCATATCCTCCCTCCACACGCTGANAGATGAAGCTGTNCAAAG
ATCTCAGGGTGGANAAAACCAT
```

16463.2.edit

```
TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT
```

*Fig. 15C-1*

16530.1.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTTGCTTGTGCGCCACGTGTTGCTCANACANGGGTGGGCTGGGCATCAAG
GNG

16530.2.edit

TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAAGTGTCAACGTAAGTAAGTTAACAGGGTCTCCGCTGTGGATC
ATCAGGCCATCCACAAACTTCATGGATTTAACCCTCTGTCCTCGGAG

16531.1.edit

TCGAGCGGCCGCCCGGGCAGGTGTTTCAGAGGTTCCAAGGTCCACTGTGGAGGTCCCAGGAGTGCTGGTGGTGGGC
ACAGAGGTCCGATGGGTGAAACCATTGACATAGAGACTGTTCCTGTCCAGGGTGTAGGGGCCCAGCTCTTTGATGC
CATTGGCCAGTTGGCTCAGCTCCCAGTACAGCCGCTCTCTGTTGAGTCCAGGGCTTTTGGGGTCAAGATGATGGAT
GCAGATGGCATCCACTCCAGTGGCTGCTCCATCCTTCTCGGACCTGAGAGAGGTCAGTCTGCAGCCAGAGTACAGA
GGGCCAACACTGGTGTTCTTTGAATA

16531.2.edit

AGCGTGGTCGCGGCCGAGGTCTGTACTGGGAGCTAAGCAAACTGACCAATGACATTGAAGAGCTGGGCCCCTACAC
CCTGGACAGGAACAGTCTCTATGTCAATGGTTTCACCCATCAGAGCTCTGTGNCCACCACCAGCACTCCTGGGACC
TCCACAGTGGATTTCAGAACCTCAGGGACTCCATCCTCCCTCTCCAGCCCCACAATTATGGCTGCTGGCCCTCTCC
TGGTACCATTCACCCTCAACTTCACCATCACCAACCTGCAGTATGGGGAGGACATGGGTCACCCTGNCTCCAGGAA
GTTCAACACCACA

16532.1.edit

TCGAGCGGCCGCCCGGACAGGTCTGGGCGGATAGCACCGGGCATATTTTGGAATGGATGAGGTCTGGCACCCTGAG
CAGTCCAGCGAGGACTTGGTCTTAGTTGAGCAATTTGGCTAGGAGGATAGTATGCAGCACGGNTCTGAGNCTGTGG
GATAGCTGCCATGAAGTAACCTGAAGGAGGTGCTGGCTGGTANGGGTTGATTACAGGGTTGGGAACAGCTCGTACA
CTTGCCATTCTCTGCATATACTGGTTAGTGAGGTGAGCCTGGCCCTCTTCTTTTG

*Fig. 15C-2*

11732.1contig

```
GAGAACTTGGCCTTTATTGTGGGCCCAGGAGGGCACAAAGGTCAGGAGGCCCAAGGGAGGGATCTGGTTTTCTGGA
TAGCCAGGTCATAGCATGGGTATCAGTAGGAATCCGCTGTAGCTGCACAGGCCTCACTTGCTGCAGTTCCGGGGAG
AACACCTGCACTGCATGGCGTTGATGACCTCGTGGTACACGACAGAGCCATTGGTGCAGTGCAAGGGCACGCGCAT
GGGCTCCGTCCTCGAGGGCAGGCAGCAGGAGCATTGCTCCTGCACATCCTCGATGTCAATGGAGTACACAGCTTTG
CTGGCACACTTTCCCTGGCAGTAATGAATGTCCACTTCCTCTTGGGACTTACAATCTCCCACTTTGATGTACTGCA
CCTTGGCTGTGATGTCTTTGCAATCAGGCTCCTCACATGTGTCACAGCAGGTGCCTGGAATTTTCACGATTTTGCC
TCCTTCAGCCAGACACTTGTGTTCATCAAATGGTGGGCAGCCCGTGACCCTCTTCTCCCAGATGTACTCTCCTCT
```

11732.2contig

```
GCCTGGACCTTGCCGGATCAGTGCCACACAGTGACTTGCTTGGCAAATGGCCAGACCTTGCTGCAGAGTCATCGTG
TCAATTGTGACCATGGACCCCGGCCTTCATGTGCCAACAGCCAGTCTCCTGTTCGGGTGGAGGAGACGTGTGGCTG
CCGCTGGACCTGCCCTTGTGTGTGCACGGGCAGTTCCACTCGGCACATCGTCACCTTCGATGGGCAGAATTTCAAG
CTTACTGGTAGCTGCTCCTATGTCATCTTTCAAAACAAGGAGCAGGACCTGGAAGTGCTCCTCCACAATGGGGCCT
GCAGCCCCGGGGCAAAACAAGCCTGCATGAAGTCCATTGAGATTAAGCATGCTGGCGTCTCTGCTGAGCTGCACAG
TAACATGGAGATGGCAGTGGATGGGAGACTGGTCCTTGCCCCGTACGTTGGTGAAAACATGGAAGTCAGCATCTAC
GGCGCTATCATGTATGAAGTCAGGTTTACCCATCTTGGCCACATCCTCACATACACCGCCXCAAAACAACGAGTT
```

11735-1-2

```
AGATCAACCTCTGCTGGTCAGGAGGAATGCCTTCCTTGTCTTGGATCTTTGCTTTGACGTTCTCGATAGTRWCAaC
TKKRYTSRAMSKMAAGKGYRATGRWMTTKSYWGWRASYKTMWWMRSGRARAYTTaGaCAYCCCMCCTCWgAGaCGS
AGKACCARGTGCAgAgGTGGACTCTTTCTGGATGTTGTAGTCAGACAGGGTGCGTCCATCTTCCAGCTGTTTCCCA
GCAAAGATCAACCTCTGCTGATCAGGAGGGATGCCTTCCTTATCTTGGATCTTTGCCTTGACATTCTCGATGGTGT
CACTGGGCTCCACCTCGAGGGTGATGGTCTTACCAGTCAGGGTCTTCACGAAGATYTGCATCCCACCTCTGAGACG
GAGCACCAGGTGCAGGGTRGACTCTTTCTGGATGTTGTAGTCAGACAGGGTGCGYCCATCTTCCAGCTGcTTTCCS
aGCAAAGATCAACCTCTGCTGGTCAGGAGGRATGCCTTCCTTGTCYTGGATCTTTGCYTTGACRTTCTCRATGGTG
TCACTCGGCTCCACTTCGAGAGTGATGGTCTTACCAGTCAGGGTCTTCACGAAGATCTGCATCCCACCTCTAA
```

11740.2.contig

```
AAGTCACAAACAGACAAAGATTATTACCAGCTGCAAGCTATATTAGAAGCTGAACGAAGAGACAGAGGTCATGATT
CTGAGATGATTGGAGACCTTCAAGCTCGAATTACATCTTTACAAGAGGAGGTGAAGCATCTCAAACATAATCTCGA
AAAAGTGGAAGGAGAAAGAAAAGAGGCTCAAGACATGCTTAATCACTCAGAAAAGGAAAAGAATAATTTAGAGATA
GATTTAAACTACAAACTTAAATCATTACAACAACGGTTAGAACAAGAGGTAAATGAACACAAAGTAACCAAAGCTC
GTTTAACTGACAAACATCAATCTATTGAAGAGGCAAAGTCTGTGGCAATGTGTGAGATGGAAAAAAAGCTGAAAGA
AGAAAGAGAAGCTCGAGAGAAGGCTGAAAATCGGGTTGTTCAGATTGAGAAACAGTGTTCCATGCTAGACGTTGAT
CTGAAGCAATCTCAGCAGAAACTAGAACATTTGACTGGAAATAAAGAAAGGATGGAGGATGAAGTTAAGAATCTA
```

*Fig. 15D*

16464.1.edit

```
CGAGCGGGCGACCGGGCAGGTNCAGACTCCAATCCANANAACCATCAAGCCAGATGTCAGAAGCTACACCATCACA
GGTTTACAACCAGGCACTGACTACAAGANCTACCTGCACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGTACATCATCNAGTATGANAAGCCTGGGCCTCCTCCCAGAGAAGNGG
TCCCTCGGCCCCGCCCTGNTGTCCCANAGGNTACTATTACTGNGCCNGCAACCGGCAACCGATATCNATTTTGNCA
TTGGCCTTCAACAATAATTA
```

16464.2.edit

```
AGCGTGGTTCGCGGCCGANGTCCTGTCAGAGTGGCACTGGTAGAAGTTCCAGGAACCCTGAACTGTAAGGGTTCTT
CATCAGNGCCAACAGGATGACATGAAATGATGTACTCAGAAGTGTCCTGGAATGGGGCCCATGAGATGGTTGTCTG
AGAGAGAGCTTCTTGNCCTGTCTTTTTCCTTCCAATCAGGGGCTCGCTCTTCTGATTATTCTTCAGGGCAATGACA
TAAATTGTATATTCGGGTCCCGGNTCCAGGCCAGTAATAGTANCCTCTGTGACACCAGGGCGGNGCCGAGGGACCA
CTTCTCTGGGAGGAGACCCAGGCTTCTCATACTTGATGATGTAACCGGTAATCCTGGCACGTGGCGGCTGCCATGA
TACCAGCAAGGAATTGGGGTGTGGTGGCCAGGAAACGCAGGTTGGATGGNGCATCAATGGCAGTGGAGGCCGTCGA
TGACCACAGGGGGAGCTCCGACATTGTCATTCAAGGTG
```

16465.1.edit

```
AGCGTGGNCGCGGCCGAGGTGCAGCGCGGGCTGTGCCACCTTCTGCTCTCTGCCCAACGATAAGGAGGGTNCCTGC
CCCCAGGAGAACATTAACTNTCCCCAGCTCGGCCTCTGCCGG
```

16465.2.edit

```
TCGAGCGGCCGCCCGGGCAGGTTTTTTTTGCTGAAAGTGGNTACTTTATTGGNTGGGAAAGGGAGAAGCTGTGGTC
AGCCCAAGAGGGAATACAGAGNCCCGAAAAAGGGGAGGGCAGGTGGGCTGGAACCAGACGCAGGGCCAGGCAGAAA
CTTTCTCTCCTCACTGCTCAGCCTGGTGGTGGCTGGAGCTCANAAATTGGGAGTGACACAGGACACCTTCCCACAG
CCATTGCGGCGGCATTTCATCTGGCCAGGACACTGGCTGTCCACCTGGCACTGGTCCCGACAGAAGCCCGAGCTGG
GGAAAGTTAATGTTCACCTGGGGGCAGGAACCCTCCTTATCATTGNGCAGAGAGCAGAAGGTGGCACAGCCCGCGC
TGCACCTCGGCCGCGACCACGCT
```

16466.2.edit

```
TCGAGCGGCCGCCCGGGCAGGTCCACCATAAGTCCTGATACAACCACGGATGAGCTGTCAGGAGCAAGGTTGATTT
CTTTCATTGGTCCGGNCTTCTCCTTGGGGGNCACCCGCACTCGATATCCAGTGAGCTGAACATTGGGTGGCGTCCA
CTGGGCGCTCAGGCT
```

16467.2.edit

```
TCGAGCGGTTCGCCCGGGCAGGTCCACCACACCCAATTCCTTGCTGGTATCATGGCAGCCGCCACGTGCCAGGATT
ACCGGCTACATCATCAAGTATGAGAAGCCTGGGTCTCCTCCCAGAGAAGCGGTCCCTCGGCCCCGCCCTGGTGTCA
CAGAGGCTACTATTACTGGCCTGGAACCGGGAACCGAATATACAATTTATGTCATTGNCCTGAAGAATAATCANNA
ANAGCGANCCCCTGATTGGAAGGA
```

*Fig. 15D-1*

01_16558.3.edit

AGCGTGGTCGCGGCCGAGGTGAGCCACAGGTGACCGGGGCTGAAGCTGGGGCTGCTGGNCCTGCTGGTCCTG

02_16558.4.edit

CAGCNGCTCCNACGGGGCCTGNGGGACCAACAACACCGTTTTCACCCTTAGGCCCTTTGGCTCCTCTTTCTCCTTT
AGCACCAGGTTGACCAGCAGCNCCANCAGGACCAGCAAATCCATTGGGGCCAGCAGGACCGACCTCACCACGTTCA
CCAGGGCTTCCCCGAGGACCAGCAGGACCAGCAGGACCAGCAGCCCCAGCTTCGCCCCGGTCACCTGTGGCTCACC
TCGGCCGCGACCACGCT

03_16535.1.edit

TCGAGCGGTCGCCCGGGCAGGTCCACCGGGATAGCCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGANAACCGGAG
GCTGGANAGCAAAATCCGGGAGCACTTGGAGAAGAAGGGACCCCAGGTCAAGAGACTGGAGCCATTACTTCAAGAT
CATCGAGGGACCTGGAGG

04_16535.2.edit

AGCGNGGTCGCGGCCGAGGTCCAGCTCTGTCTCATACTTGACTCTAAAGTCATCAGCAGCAAGACGGGCATTGTCA
ATCTGCAGAACGATGCGGGCATTGTCCGCAGTATTTGCGAAGATCTGAGCCCTCAGGTCCTCGATGATCTTGAAGT
AATGGCTCCAGTCTCTGACCTGGGGTCCCTTCTTCTCCAAGTGCTCCCGGATTTTGCTCTCCAGCCTCCGGTTCTC
GGTCTCCAGGCTCCTCACTCTGTCCAGGTAAGAAGGCCCAGGCGGTCGTTCAGGCTTTGCATGGTCTCCTTCTCGT
TCTGGATGCCTCCCATTCCTGCCAGACCC

05_16536.1.edit

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 15D-2*

11765.2&64.2.contig

```
CGCCTCCACCATGTCCATCAGGGTGACCCAGAAGTCCTACAAGGTGTCCACCTCTGGCCCCCGGGCCTTCAGCAGC
CGCTCCTACACGAGTGGGCCCGGTTCCCGCATCAGCTCCTCGAGCTTCTCCCGAGTGGGCAGCAGCAACTTTCGCG
GTGGCCTGGGCGGCGGCTATGGTGGGGCCAGCGGCATGGGAGGCATCACCGCAGTTACGGTCAACCAGAGCCTGCT
GAGCCCCCTTGTCCTGGAGGTGGACCCCAACATCCAGGCCGTGCGCACCCAGGAGAAGGAGCAGATCAAGACCCTC
AACAACAAGTTTGCCTCCTTCATAGACAAGGTACGGTTCCTGGAGCAGCAGAACAAGATGCTGGAGACCAAGTGGA
GCCTCCTGCAGCAGCAGAAGACGGCTCGAAGCAACATGGACAACATGTTCGAGAGCTACATCAACARCCTTAGGCG
GCAGCTGGAGACTCTGGGCCAGGAGAAGCTGAAGCTGGAGGCGGAGCTTGGCAACATGCAGGGGCTGGTGGAGGAC
TTCAAGAACAAGTATGAGGATGAGATCAATAAGCGTACAGAGATGGAGAACGAATTTGTCCTCATCAAGAAGGATG
TGGATGAAGCTTACATGAACAAGGTAGAGCTGGAGTCTCGCCTGGAAGGGCTGACCGACGAGATCAACTTCCTCAG
GCAGCTGTATGAAGAGGAGATCCGGGAGCTGCAGTCCCAGATCTCGGACACATCTGTGGTGCTGTCCATGGACAAC
AGCCGCTCCCTGGACATGGACAGCATCATTGCTGAGGTCAAGGCACAGTACGAGGATATTGCCAACCGCAGCCGGG
CTGAGGCTGAGAGCATGTACCAGGTCAAGTATGAGGAGCTGCAGAGCCTGGCTGGGAAGCACGGGGATGACCTGCG
GCGCACAAAGACTGAGATCTCTGAGATGAACCCGGAACATCAGCCCGGCTXCAGGCTGAGATTGAGGGCCTCAAAG
GCCAGAXGGCTTXCCTGGAXGXCCGCCAT
```

11767.2.contig

```
CCCGGAGCCAGCCAACGAGCGGAAAATGGCAGACAATTTTTCGCTCCATGATGCGTTATCTGGGTCTGGAAACCCA
AACCCTCAAGGATGGCCTGGCGCATGGGGGAACCAGCCTGCTGGGGCAGGGGGCTACCCAGGGGCTTCCTATCCTG
GGGCCTACCCCGGGCAGGCACCCCCAGGGGCTTATCCTGGACAGGCACCTCCAGGCGCCTACCCTGGAGCACCTGG
AGCTTATCCCGGAGCACCTGCACCTGGAGTCTACCCAGGGCCACCCAGCGGCCCTGGGGCCTACCCATCTTCTGGA
CAGCCAAGTGCCACCGGAGCCTACCCTGCCACTGGCCCCTATGGCGCCCCTGCTGGGCCACTGATTGTGCCTTATA
ACCTGCCTTTGCCTGGGGGAGTGGTGCCTCGCATGCTGATAACAATTCTGGGCACGGTGAAGCCCAATGCAAACAG
AATTGCTTTAGATTTCCAAAGAGGGAATGATGTTGCCTTCCACTTTAACCCACGCTTCAATGAGAACAACAGGAGA
GTCATTGGTTGCAATACAAAGCTGGATAA
```

11768-1&2

```
GGGAATGCAACAACTTTATTGAAAGGAAAGTGCAATGAAATTTGTTGAAACCTTAAAAGGGGAAACTTAGACACCC
CCCCTCRAgCGMAGKACCARGTGCARAgGTGGACTCTTTCTGGATGTTGTAGTCAGACAGGGTRCGWCCATCTTCC
AGCTGTTTYCCRGCAAAGATCAACCTCTGCTGATCAGGAGGRATGCCTTCCTTATCTTGGATCTTTGCCTTGACAT
TCTCGATGGTGTCACTGGGCTCCACCTCGAGGGTGATGGTCTTACCAGTCAGGGTCTTCACGAAGATYTGCATCCC
ACCTCTGAGACGGAGCACCAGGTGCAGGGTRGACTCTTTCTGGATGTTGTAGTCAGACAGGGTGCGYCCATCTTCC
AGCTGcTTTCCSaGCAAAGATCAACCTCTGCTGGTCAGGAGGRATGCCTTCCTTGTCYTGGATCTTTGCYTTGACR
TTCTCAATGGTGTCACTCGGCTCCACTTCGAGAGTGATGGTCTTACCAGTCAGGGTCTTCACGAAGATCTGCATCC
CACCTCTAAGACGGAGCACCAGGTGCAGGGTGGACTCTTTCTGGATGgTTGTAGTCAGACAGGGTGCGTCCATCTT
CCAGCTGTTTCCCAGCAAAGATCAACCT
```

*Fig. 15E*

01_16469.edit

AGCGTGGTCGCGGCCGAGGTTGTACAAGCTTTTTTTTTTTTTTTTTTTTTTTTTTTTTTTTTTTTTTTTTTTTT
TTTTTTTTTTTTTTT

02_16469.edit

TCGAGCGGNCGCCCGGGCAGGTCTGCCAACACCAAGATTGGCCCCCGCCGCATCCACACAGTCCGTGTGCGGGGAG
GTAACAAGAAATACCGTGCCCTGAGGTTGGACGTGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATCGACAGCACACCGTACCGACAGTGGTACGAGTCCCACTATGCGCTGCCCCTGGGCCGCAAGAAGGGAG
CCAAGCTGACTCCTGAGGAAGAAGAGATTTTAAACAAAAAACGATCTAANAAAAAAAAAACAAT

03_16470.edit

AGCGTGGTCGCGGCCGAGGTGAAATGGTATTCAGCTTCCTGGCACTTCTGGTCAGCAACCCAGTGTTGGGCAACAA
ATGATCTTTGAGGAACATGGTTTTAGGCGGACCACACCGCCCACAACGGCCACCCCCATAAGGCATAGGCCAAGAC
CATACCCGCCGAATGTAGGACAAGAAGCTCTCTCTCAGACAACCATCTCATGGGCCCCATTCCAGGACACTTCTGA
GTACATCATTTCATGTCATCCTGTTGGCACTGATGAAGAACCCTTACAGTTCAGGGTTCCTGGAACTTCTACCAGT
GCCACTCTGACAGGACCTGCCCGGGCGGCCGCTCGA

04_16470.edit

TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCACCTCGGCCGCGACCACGCTA

05_16471.edit

TCGAGCGGCCGCCCGGGCAGGTCTCCCTTCTTGCGGCCCAGGGGCAGCGCATAGTGGGACTCGTACCACTGTCGGT
ACGGTGTGCTGTCGATGAGCACGATGCAATTCTTCACCAGGGTCTTGGTACGAACCAGCTCGTTATTAGATGCATT
GTAGACAACATCGATGATCCTTGTTTTACGAGTACAACACTCTGAGCCCCAGGAGAAATTCCCCACGTCCAACCTC
AGGGCACGGTATTTCTTGTTACCTCCCCGCACACGGACTGTGTGGATGCGGCGGGGGCCAAGCTGACTCCTGAGGA
AGAAGAGATTTTAAACAAAAAACGATCTAAAAAAAATTCAGAAGAAATATGATGAAAGGAAAAAGAATGCCAAAATC
AGCAGTCTCCTGGAGGAGCAGTTCCAGCAGGGCAAGCTTCTTGCGTGCATCGCTTCAAGGCCGGGACAGTGTGACC
GAGCAGATGGCTATGTGCTAGAGGGCAAAGAAGTGGAGTTCTATCTTAAGAAAATCAGGGCCCAGAATGGTGNGTC
TTCAACTAATCCAAAGGGGAGTTTCAGACCAGTGCAATCAGCAAAAACATTGATACTGNTGGCCAAATTTATTGGT
GCAGGGCTTGCACANTANGANNGGCTGGGTCTTGGGGCTTGGATTGGNACAAGCTTTGGCAGCCTTTTCTTTGGTT
TTGCCAAAAACCTTTTGNTGAAGANGANACCTNGGGCGGACCCCTTAACCGATTCCACNCCNGGNGGCGTTCTANG
GNCCCNCTTG

*Fig. 15E-1*

07_16537.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACCGCAGGTCTCACCAGTCTCCATGTTGCAGAAGACTTTGATGGCATCCAGGTTGCAGCCTT
GGTTGGGGTCAATCCAGTACTCTCCACTCTTCCAGTCAGAAGTGGGCACATCTTGAGGTCACCGGCAGGTGCCGGG
CCGGGGGTTCTTGCGGCTTGCCCTCTGGGCTCCGGATGTTCTCGATCTGCTTGGCTCAGGCTCTTGAGGGTGGGTG
TCCACCTCGAGGTCACGGTCACCGAAACCTGCCCGGGCGGCCCGCTCGA

08_16537.2.edit

TCGAGCGGTCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGGCCCAGAAGAAACTGGTACATCAGCAAGGA
ACCCCAAGGACAAGAGGCATTGTCTTGGTTCGGCGAGNAGCATGACCCGATGGATTCCAGTTTCGAGTATTGGCGG
CCAGGGCTTCCCGACCCTTGCCGATGTGGACCTCGGCCGCGACCACCGCT

```
AGGTTGATCTTTGCTGGGAAACAGCTGGAAGATGGACGCACCCTGTCTGACTACAAcCATCCAGAAAGAGTCCACC
CTGCACCTGGTGCTCCGTCTTAGAGGTGGGATGCAGATCTTCGTGAAGACCCTGACTGGTAAGACCATCACTCTCG
AAGTGGAGCCGAGTGACACCATTGAGAAYGTCAARGCAAAGATCCARGACAAGGAAGGCATYCCTCCTGACCAGCA
GAGGTTGATCTTTGCtSGGAAAgCAGCTGGAAGATGGRCGCACCCTGTCTGACTACAACATCCAGAAAGAGTCYAC
CCTGCACCTGGTGCTCCGTCTCAGAGGTGGGATGCARATCTTCGTGAAGACCCTGACTGGTAAGACCATCACCCTC
GAGGTGGAGCCCAGTGACACCATCGAGAATGTCAAGGCAAAGATCCAAGATAAGGAAGGCATCCCTCCTGATCAGC
AGAGGTTGATCTTTGCTGGGAAACAGCTGGAAGATGGACGCACCCTGTCTGACTACAACATCCAGAAAGAGTCCAC
cTYTGCACYTGGTMCTBCGtCTYaGAGGKGGGRTGcaaaTCTWMGTKWagaCaCtCaCTKKYAAGRYYaTCAMCMW
tgAKKTCgAKYSCASTKWCaCTWTCRAKAAMGTYRWWGCAWagaTCCMAGACAAGGAAGGCATTCCTCCTGACCAG
CAGAGGTTGATCT
```

11769.1.contig

```
ATGGAGTCTCACTCTGTCGACCAGGCTGGAGCGCTGTGGTGCGATATCGGCTCACTGCAGTCTCCACTTCCTGGGT
TCAAGCGATCCTCCTGCCTCAGCCTCCCGAGTAGCTGGGACTACAGGCAGGCGTCACCATAATTTTTGTATTTTTA
GTAGAGACATGGTTTCGCCATGTTGGCTGGGCTGGTCTCGAACTCCTGACCTCAAGTGATCTGTCCTGGCCTCCCA
AAGTGTTGGGATTACAGGCGAAAGCCAACGCTCCCGGCCAGGGAACAACTTTAGAATGAAGGAAATATGCAAAAGA
ACATCACATCAAGGATCAATTAATTACCATCTATTAATTACTATATGTGGGTAATTATGACTATTTCCCAAGCATT
CTACGTTGACTGCTTGAGAAGATGTTTGTCCTGCATGGTGGAGAGTGGAGAAGGGCCAGGATTCTTAGGTT
```

11769.2.contig

```
AGCGCGGTCTTCCGGCGCGAGAAAGCTGAAGGTGATGTGGCCGCCCTCAACCGACGCATCCAGCTCGTTGAGGAGG
AGTTGGACAGGGCTCAGGAACGACTGGCCACGGCCCTGCAGAAGCTGGAGGAGGCAGAAAAAGCTGCAGATGAGAG
TGAGAGAGGAATGAAGGTGATAGAAAACCGGGCCATGAAGGATGAGGAGAAGATGGAGATTCAGGAGATGCAGCTC
AAAGAGGCCAAGCACATTGCGGAAGAGGCTGACCGCAAATACGAGGAGGTAGCTCGTAAGCTGGTCATCCTGGAGG
GTGAGCTGGAGAGGGCAGAGGAGCGTGCGGAGGTGTCTGAACTAAAATGTGGTGACCTGGAAGAAGAACTCAAGAA
TGTTACTAACAATCTGAAATCTCTGGAGGCTGCATCTGAAAAGTATTCTGAAAAGGAGGACAAATATGAAGAAGAA
ATTAAACTTCTGTCTGACAAACTGAAAGAGGCTGAGACCCGTGCTGAATTTGCAGAGAGAACGGTTGCAAAACTGG
AAAAGACAATTGATGACCTGGAAGAGAAACTTGCCCAGC
```

11770.1.contig

```
GTGCACAGGTCCCATTTATTGTAGAAAATAATAATAATTACAGTGATGAATAGCTCTTCTTAAATTACAAAACAGA
AACCACAAAGAAGGAAGAGGAAAAACCCCAGGACTTCCAAGGGTGAAGCTGTCCCCTCCTCCCTGCCACCCTCCCA
GGCTCATTAGTGTCCTTGGAAGGGGCAGAGGACTCAGAGGGGATCAGTCTCCAGGGGCCCTGGGCTGAAGCGGGTG
AGGCAGAGAGTCCTGAGGCCACAGAGCTGGGCAACCTGAGCCGCCTCTCTGGCCCCCTCCCCCACCACTGCCCAAA
CCTGTTTACAGCACCTTCGCCCCTCCCCTCTAAACCCGTCCATCCACTCTGCACTTCCCAGGCAGGTGGGTGGGCC
AGGCCTCAGCCATACTCCTGGGCGCGGGTTTCGGTGAGCAAGGCACAGTCCCAGAGGTGATATCAAGGCCT
```

*Fig. 15F*

06_16471.edit

AGCGTGGTCGCGGCCGAGGTCTGCTGCTTCAGCGAAGGGTTTCTGGCATAACCAATGATAAGGCTGCCAAAGACTG
TTCCAATACCAGCACCAGAACCAGCCACTCCTACTGTTGCAGCACCTGCACCAATAAATTTGGCAGCAGTATCAAT
GTCTCTGCTGATTGCACTGGTCTGAAACTCCCTTTGGATTAGCTGAGACACACCATTCTGGGCCCTGATTTTCCTA
AGATAGAACTCCAACTCTTTGCCCTCTAGCACATAGCCATCTGCTCGGTCACACTGTCCCGGCCTTGAAGCGATGC
ACGCAAGAAGCTTGCCCTGCTGGAACTGCTCCTCCAGGAGACTGCTGATTTTGGCATTCTTTTTCCTTTCATCATA
TTTCTTCTGAATTTTTTTAGATCGTTTTTTGTTTAAAATCTCTTCTTCCTCAGGAGTCAGCTTGGCCCCCGCCGCA
TCCACACAGTCCGTGTGCGGGGAGGTAACAAGAAATACCGTGCCCTGAGGTTGGACGTGGGGAATTTCTCCTGGGG
CTCAGAGTGGTGTACTCGTAAAACAAGGATCATCGATGGTGNCTACAATGCATCTAATAACGAGCTGGGTCGGACC
CAAAGAACCTGGNGAANAAATGGATCGNCTCATCGACAGGACACCGTACCCGACAGGGGNACGANTCCCACTATGC
GCTTGCCCCTGGGCCGCAANAAAGGAAAACTGCCCGGGCGGCCNTCGAAAGCCCAATTNTGGAAAAAATCCATCAC
ACTGGGNGGCCNGTCGAGCATGCATNTANAGGGGCCCATTCCCCCTNANN

07_16472.edit

TCGAGCGGCCGCCCGGGCAGGTCCCCAACCAAGGCTGCAACCTGGATGCCATCAAAGTCTTCTGCAACATGGAGAC
TGGTGAGACCTGCGTGTACCCCACTCAGCCCAGTGTGGCCCAGAAGAACTGGTACATCAGCAAGAACCCCAAGGAC
AAGAGGCATGTCTGGTTCGGCGAGAGCATGACCGATGGATTCCAGTTCGAGTATGGCGGCCAGGGCTCCGACCCTG
CCGATGTGGACCTCGGCCGCGACCACGCT

08_16472.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGACCTGCCCGGGCGGCCGCTCGA

09_16473.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGNTTT
AGGCGGACCACACCGCCCACAACGGCCACCCCCATAAGGCATAGGCCAAGACCATACCCGCCGAATGTAGGACAAG
AAGCTNTNTNTCANACACCATNTATGGGCCCCATTCCAGGACACTTCTGAGTACATCATTTATGNCATCTGTGGC
ACTTGATGAAAACCCTTACAGTTCAGGGTTCTGGAACTTTTACCAGGCCTNTTACAGGACTNGGCCGGACNCCTTA
AGCCNATTNCACCCTGGGGCGTTCTANGGTCCCACTCGNNCACTGGNGAAAATGGCTACTGTN

*Fig. 15F-1*

11770.2.contig

```
GCAAGGAACTGGTCTGCTCACACTTGCTGGCTTGCGCATCAGGACTGGCTTTATCTCCTGACTCACGGTGCAAAGG
TGCACTCTGCGAACGTTAAGTCCGTCCCCAGCGCTTGGAATCCTACGGCCCCCACAGCCGGATCCCCTCAGCCTTC
CAGGTCCTCAACTCCCGTGGACGCTGAACAATGGCCTCCATGGGGCTACAGGTAATGGGCATCGCGCTGGCCGTCC
TGGGCTGGCTGGCCGTCATGCTGTGCTGCGCGCTGCCCATGTGGCGCGTGACGGCCTTCATCGGCAGCAACATTGT
CACCTCGCAGACCATCTGGGAGGGCCTATGGATGAACTGCGTGGTGCAGAGCACCGGCCAGATGCAGTGCAAGGTG
TACGACTCGCTGCTGGCACTGCCGCAGGACCTGCAGGCGGCCCGCGCCCTCGTCATCATCA
```

11773.1.contig

```
TGCAAAAGGGACACAGGGGGTTCAAAAATAAAAATTTCTCTTCCCCCTCCCCAAACCTGTACCCCAGCTCCCCGACC
ACAACCCCCTTCCTCCCCCGGGGAAAGCAAGAAGGAGCAGGTGTGGCATCTGCAGCTGGGAAGAGAGAGGCCGGGG
AGGTGCCGAGCTCGGTGCTGGTCTCTTTCCAAATATAAATACXTGTGTCAGAACTGGAAAATCCTCCAGCACCCAC
CACCCAAGCACTCTCCGTTTTCTGCCGGTGTTTGGAGAGGGGCGGGGGGCAGGGGCGCCAGGCACCGGCTGGCTGC
GGTCTACTGCATCCGCTGGGTGTGCACCCCGCGAGCCTCCTGCTGCTCATTGTAGAAGAGATGACACTCGGGGTCC
CCCCGGATGGTGGGGGCTCCCTGGATCAGCTTCCCGGTGTTGGGGTTCACACACCAGCACTCCCCACGCTGCCCGT
TCAGAGACATCTTGCACTGTTTGAGGTTGTACAGGCCATGCTTGTCACAGTTG
```

11778.1.contig

```
GGGTTGGAGGGACTGGTTCTTTATTTCAAAAAGACACTTGTCAATATTCAGTATCAAAACAGTTGCACTATTGATT
TCTCTTTCTCCCAATCGGCCCCAAAGAGACCACATAAAAGGAGAGTACATTTTAAGCCAATAAGCTGCAGGATGTA
CACCTAACAGACCTCCTAGAAACCTTACCAGAAAATGGGGACTGGGTAGGGAAGGAAACTTAAAAGATCAACAAAC
TGCCAGCCCACGGACTGCAGAGGCTGTCACAGCCAGATGGGGTGGCCAGGGTGCCACAAACCCAAAGCAAAGTTTC
AAAATAATATAAAATTTAAAAAGTTTTGTACATAAGCTATTCAAGATTTCTCCAGCACTGACTGATACAAAGCACA
ATTGAGATGGCACTTCTAGAGACAGCAGCTTCAAACCCAGAAAAGGGTGATGAGATGAGTTTCACATGGCTAAATC
AGTGGCAAAAACACAGTCTTCTTTCTTTCTTTCTTTCAAGGAGGCAGGAAAGCAATTAAGTGGTCACCTCAACATA
AGGGGGACATGATCCATTCTGTAAGCAGTTGTGAAGGGG
```

11778-2&30-2

```
CAGGAACCGGAGCGCGAGCAGTAGCTGGGTGGGCACCATGGCTGGGATCACCACCATCGAGGCGGTGAAGCGCAAG
ATCCAGGTTCTGCAGCAGCAGGCAGATGATGCAGAGGAGCGAGCTGAGCGCCTCCAGCGAGAAGTTGAGGGGAGAAA
GGCGGGCCCGGGAACAGGCTGAGGCTGAGGTGGCCTCCTTGAACCGTAGGATCCAGCTGGTTGAAGAAGAGCTGGA
CCGTGCTCAGGAGCGCCTGGCCACTGCCCTGCAAAAGCTGGAAGAAGCTGAAAAAGCTGCTGATGAGAGTGAGAGA
GGTATGAAGGTTATTGAAAACCGGGCCTTAAAAGATGAAGAAAAGATGGAACTCCAGGAAATCCAACTCAAAGAAG
CTAAGCACATTGCAGAAGAGGCAGATAGGAAGTATGAAGAGGTGGCTCGTAAGTTGGTGATCATTGAAGGAGACTT
GGAACGCACAGAGGAACGAGCTGAGCTGGCAGAGTCCCGTTGCCGAGAGATGGATGAGCAGATTAGACTGATGGAC
CAGAACCTGAAGTGTCTGAGTGC
```

*Fig. 15G*

11_16474.edit

```
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGNGAAACTCCNAGGACANGAGGGCTAAATTCCATGAAGTTTGTGGATGGCCTGATGATCCACAAT
CGGAGACCCTGTTAACTACTACCGTCTNACCNCCTGCTGTNCNCCCCCNTTTCTGCTNAANACATNGGGNTNNTNC
TTGNCCNTCCTTGGGTNGAAANATNNAATNGCCTNCCCNTTCNTANCNCTACTNGNTCCANANTTGGCCTTTAAANA
ATCCNCCTTGCCTTNNNCACTGTTCANNTNTTTNNTCGTAAACCCTATNANTTNNATTANATNNTNNNNNNCTCAC
CCCCCTCNTCATTNANCCNATANGCTNNNAANTCCTTNANNCCTCCCNCCCNNTCNCTCNTACTNANTNCTTCTN
NCCCATTACNNAGCTCTTTCNTTTAANATAATGNNGCCNNGCTCTNCATNTCTACNATNTGNNNAATNCCCCCNCC
CCCNANCGNNTTTTTGACCTNNNAACCTCCTTTCCTCTTCCCTNCNNAAATTNCNNANTTCCNCNTTCCNNCNTTT
CGGNTNNTCCCATNCTTTCCANNNCTTCANTCTANCNCNCTNCAACTTATTTTCCTNTCATCCCTTNTTCTTTACA
NNCCCCCTNNTCTACTCNNCNNTTNCATTANATTTGAAACTNCCACNNCTANTTNCCTCNCTCTACNNTTTTATTT
TNCGNTCNCTCTACNTAATANTTTAATNANTTNTCN
```

12_16474.edit

```
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAAGCAGTGTCAACGTAGTAAGTTAACAGGGTCTCCGCTGTGGATCA
TCAGGCCATCCACAAACTTCATGGATTTAGCCCTCTGTCCTCGGAGTTTCCCAGACACCACAACCTCGCAGCCTTT
GGCCCCACTCTCCATGATGAACCGCAGCACACCATAGCAGGCCCTCCGCACAAGCAAGCCCTCCTAAGAATTTGTA
ACGCANANACTCTGCTGGCAATGGCACACAAACCTCTAGTGGACCTCGGNCGCGACCACGC
```

13_16475.edit

```
TCGAGCGGCCGCCCGGGCAGGTCTGGTCCAGGATAGCCTGCGAGTCCTCCTACTGCTACTCCAGACTTGACATCAT
ATGAATCATACTGGGGAGAATAGTTCTGAGGACCAGTAGGGCATGATTCACAGATTCCAGGGGGGCCAGGAGAACC
AGGGGACCCTGGTTGTCCTGGAATACCAGGGTCACCATTTCTCCCAGGAATACCAGGAGGGCCTGGATCTCCCTTG
GGGCCTTGAGGTCCTTGACCATTAGGAGGGCGAGTAGGAGCAGTTGGAGGCTGTGGGCAAACTGCACAACATTCTC
CAAATGGAATTTCTGGGTTGGGGCAGTCTAATTCTTGATCCGTCACATATTATGTCATCGCAGAGAACGGATCCTG
AGTCACAGACACATATTTGGCATGGTTCTGGCTTCCAGACATCTCTATCCGNCATAGGACTGACCAAGATGGGAAC
ATCCTCCTTCAACAAGCTTNCTGTTGTGCCAAAAATAATAGTGGGATGAAGCAGACCGAGAAGTACCAGCTCCCC
TTTTTGCACAAAGCNTCATCATGTCTAAATATCAGACATGAGACTTCTTTGGGCAAAAAAGGAGAAAAAGAAAAAG
CAGTTCAAAGTANCCNCCATCAAGTTGGTTCCTTGCCCNTTCAGCACCCGGGCCCCGTTATAAAACACCTNGGGCC
GGACCCCCCTT
```

*Fig. 15G-1*

11782.1.contig

```
ATCTACGTCATCAATCAGGCTGGAGACACCATGTTCAATCGAGCTAAGCTGCTCAATATTGGCTTTCAAGAGGCCT
TGAAGGACTATGATTACAACTGCTTTGTGTTCAGTGATGTGGACCTCATTCCGATGGACGACCGTAATGCCTACAG
GTGTTTTTCGCAGCCACGGCACATTTCTGTTGCAATGGACAAGTTCGGGTTTAGCCTGCCATATGTTCAGTATTTT
GGAGGTGTCTCTGCTCTCAGTAAACAACAGTTTCTTGCCATCAATGGATTCCCTAATAATTATTGGGGTTGGGGAG
GAGAAGATGACGACATTTTTAACAGATTAGTTCATAAAGGCATGTCTATATCACGTCCAAATGCTGTAGTAGGGAG
GTGTCGAATGATCCGGCATTCAAGAGACAAGAAAAATGAGCCCAATCCTCAGAGGTTTGACCGGATCGCACATACA
AAGGAAACGATGCGCTTCGATGGTTTGAACTCACTTACCTACAAGGTGTTGGATGTCAGAGATACCCGTTATATAC
CCAAATCAC
```

11782.2.contig

```
CTAGACCTCTAATTAAAAGGCACAATCATGCTGGAGAATGAACAGTCTGACCCCGAGGGCCACAGCGAATTTTAGG
GAAGGAGGCAAAGAGGTGAGAAGGGAAAGGAAAGAAGGAAGGAAGGAGAACAATAAGAACTGGAGACGTTGGGTGG
GTCAGGGAGTGTGGTGGAGGCTCGGAGAGATGGTAAACAAACCTGACTGCTATGAGTTTTCAACCCCATAGTCTAG
GGCCATGAGGGCGTCAGTTCTTGGTGGCTGAGGGTCCTTCCACCCAGCCCACCTGGGGGAGTGGAGTGGGGAGTTC
TGCCAGGTAAGCAGATGTTGTCTCCCAAGTTCCTGACCCAGATGTCTGGCAGGATAACGCTGACCTGTTCCCTCAA
CAAGGGACCTGAAAGTAATTTTGCTCTTTAC
```

11783-1 & 2

```
CCGAATTCAAGCGTCAACGATCCYTCCCTTACCATCAAATCAATTGGCCACCAATGGTACTGAACCTACGAGTACA
CCGACTACgGGCGGACTAATCTTCAACTCCTACATACTTCCCCCATTATTCCTAGAACCAGGCGACCTGCGACTCC
TTGACGTTGACAATCGAGTAGTACTCCCGATTGAAGCCCCCATTCGTATAATAATTACATCACAAGACGTCTTGCA
CTCATGAGCTGTCCCCACATTAGGCTTAAAAACAGATGCAATTCCCGGACGTCTAAGCCAAACCACTTTCACCGCT
ACACGACCGGGGGTATACTACGGTCAATGCTCTGAAATCTGTGGAGCAAACCACAGTTTCATGCCCATCGTCCTAG
AATTAATTCCCCTAAAAATCTTTGAAATAGGGCCCGTATTTACCCTATAGCACCCCCTCTACCCCCTCTAG
```

11786.1.contig

```
GCTCTTCACACTTTTATTGTTAATTCTCTTCACATGGCAGATACAGAGCTGTCGTCTTGAAGACCACCACTGACCA
GGAAATGCCACTTTTACAAAATCATCCCCCCTTTTCATGATTGGAACAGTTTTCCTGACCGTCTGGGAGCGTTGAA
GGGTGACCAGCACATTTGCACATGCAAAAAAGGAGTGACCCCAAGGCCTCAACCACACTTCCCAGAGCTCACCATG
GGCTGCAGGTGACTTGCCAGGTTTGGGGTTCGTGAGCTTTCCTTGCTGCTGCGGTGGGGAGGCCCTCAAGAACTGA
GAGGCCGGGGTATGCTTCATGAGTGTTAACATTTACGGGACAAAAGCGCATCATTAGGATAAGGAACAGCCACAGC
ACTTCATGCTTGTGAGGGTTAGCTGTAGGAGCGGGTGAAAGGATTCCAGTTTATGAAAATTTAAAGCAAACAACGG
TTTTTAGCTGGGTGGGAAACAGGAAAACTGTGATGTCGGCCAATGACCACCATTTTTCTGCCCATGTGAAGGTCCC
CATGAAACC
```

*Fig. 15H*

14_16475.edit

```
AGCGTGGTCGCGGCCGAGGTGTTTTATGACGGGCCCGGTGCTGAAGGGCAGGGAACAACTTGATGGTGCTACTTTG
AACTGCTTTTCTTTTCTCCTTTTTGCACAAAGAGTCTCATGTCTGATATTTAGACATGATGAGCTTTGTGCAAAAG
GGGAGCTGGCTACTTCTCGCTCTGCTTCATCCCACTATTATTTTGGCACAACAGGAAGCTGTTGAAGGAGGATGTT
CCCATCTTGGTCAGTCCTATGCGGATAGAGATGTCTGGAAGCCAGAACCATGCCAAATATGTGTCTGTGACTCAGG
ATCCGTTCTCTGCGATGACATAATATGTGACGATCAAGAATTAGACTGCCCCAACCCAGAAATTCCATTTGGAGAA
TGTTGTGCAGTTTGCCCACAGCCTCCAACTGCTCCTACTCGCCCTCCTAATGGTCAAGGACCTCAAGGCCCCAAGG
GAGATCCAGGCCCTCCTGGTATTCCTGGGAGAAATGGTGACCCTGGTATTCCAGGACAACCAGGGTCCCCTGGTTC
TCCTGGCCCCCCTGGAATCNGGNGAATCATGCCCTACTGGTCCTCAAACTATTCTCCCANATGATTCATATGATGT
CAAGTCTGGGATAGCNAGTANGGANGGACTCGCAGGCTATTCTGGACCANACCTGCCGGGGGGGCGTTCGAAAGCC
CGAATCTGCANANNTNCNTTCACACTGGCGGCCGTCGAGCTGCTTTAAAAGGGCCATTCCNCCTTTAGNGNGGGGG
ANTACAATTACTNGGCGGCGTTTTANANCGCGNGNCTGGGAAAT
```

15_16476.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAGGCTCTTGAGGGTGGTGTCCACCTCGA
GGTCACGGTCACGAACCACATTGGCATCATCAGCCCGGTAGTAGCGGCCACCATCGTGAGCCTTCTCTTGANGTGG
CTGGGGCAGGAACTGAAGTCGAAACCAGCGCTGGGAGGACCAGGGGGACCAANAGGTCCAGGAAGGGCCCGGGGGG
GACCAACAGGACCAGCATCACCAAGTGCGACCCGCGAGAACCTGCCCGGCCGNCCGCTCGAA
```

16_16476.edit

```
TCGAGCGNNCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGCCGCAAGAACCCCGCCCGCACCTGCCGTG
ACCTCAAGATGTGCCACTCTGACTGGAAGAGTGGAGAGTACTGGATTGACCCCAACCAAGGCTGCAACCTGGATGC
CATCAAAGTCTTCTGCAACATGGAGACTGGTGAGACCTGCGTGTACCCCACTCAGCCCAGTGTGGCCCAGAAGAAC
TGGTACATCAGCAAGAACCCCAAGGACAAGAGGCATGTCTGGTTCGGCGAGAGCATGACCGATGGATTCCAGTTCG
AGTATGGCGGCCAGGGCTCCCACCCTGCCGATGTGGACCTCCGGCCGCGACCACCCTT
```

*Fig. 15H-1*

11786.2.contig

```
CAAGCGCTTGGCGTTTGGACCCAGTTCAGTGAGGTTCTTGGGTTTTGTGCCTTTGGGGATTTTGGTTTGACCCAGG
GGTCAGCCTTAGGAAGGTCTTCAGGAGGAGGCCGAGTTCCCCTTCAGTACCACCCCTCTCTCCCCACTTTCCCTCT
CCCGGCAACATCTCTGGGAATCAACAGCATATTGACACGTTGGAGCCGAGCCTGAACATGCCCCTCGGCCCCAGCA
CATGGAAAACCCCCTTCCTTGCCTAAGGTGTCTGAGTTTCTGGCTCTTGAGGCATTTCCAGACTTGAAATTCTCAT
CAGTCCATTGCTCTTGAGTCTTTGCAGAGAACCTCAGATCAGGTGCACCTGGGAGAAAGACTTTGTCCCCACTTAC
AGATCTATCTCCTCCCTTGGGAAGGGCAGGGAATGGGGACGGTGTATGGAGGGGAAGGGATCTCCTGCGCCCTTCA
TTGCCACACTTGGTGGGACCATGAACATCTTTAGTGTCTGAGCTTCTCAAATTACTGCAATAGGA
```

13691.1&2

```
AGCGTCAAATCAGAATGGAAAAGACTCAAAACCATCATCAACACCAAGATCAAAAGGACAAGRATCCTTCAAGAAA
CAGGAAAAAACTCCTAAAACACCAAAAGGACCTAGTTCTGTAGAAGACATTAAAGCAAAAATGCAAGCAAGTATAG
AAAAAGGTGGTTCTCTTCCCAAAGTGGAAGCCAAATTCATCAATTATGTGAAGAATTGCTTCCGGATGACTGACCA
AGAGGCTATTCAAGATCTCTGGCAGTGGAGGAAGTCTCTTTAAGAAAATAGTTTAAACAATTTGTTAAAAAATTTT
CCGTCTTATTTCATTTCTGTAACAGTTGATATCTGGCTGTCCTTTTTATAATGCAGAGTGAGAACTTTCCCTACCG
TGTTTGATAAATGTTGTCCAGGTTCTATTGCCAAGAATGTGTTGTCCAAAATGCCTGTTTAGTTTTTAAAGATGGA
ACTCCACCCTTTGCTTGGTTTTAAGTATGTATGGAATGTTATGATAGGACATAGTAGTAGCGGTGGTCAGACATGG
AAATGGTGGGSMGACAAAAATATACATGTGAAATAA
```

13692.1&2

```
TCCGAATTCCAAGCGAATTATGGACAAACGATTCCTTTTAGAGGATTACTTTTTTCAATTTCGGTTTTAGTAATCT
AGGCTTTGCCTGTAAAGAATACAACGATGGATTTTAAATACTGTTTGTGGAATGTGTTTAAAGGATTGATTCTAGA
ACCTTTGTATATTTGATAGTATTTCTAACTTTCATTTCTTTACTGTTTGCAGTTAATGTTCATGTTCTGCTATGCA
ATCGTTTATATGCACGTTTCTTTAATTTTTTTAGATTTTCCTGGATGTATAGTTTAAACAACAAAAAGTCTATTTA
AAACTGTAGCAGTAGTTTACAGTTCTAGCAAAGAGGAAAGTTGTGGGGTTAAACTTTGTATTTTCTTTCTTATAGA
GGCTTCTAAAAAGGTATTTTTATATGTTCTTTTTAACAAATATTGTGTACAACCTTTAAAACATCAATGTTTGGAT
CAAAACAAGACCCAGCTTATTTTCTGC
```

13693.2

```
TGTGGTGGCGCGGGCTGAGGTGGAGGCCCAGGACTCTGACCCTGCCCCTGCCTTCAGCAAGGCCCCCGGCAGCGCC
GGCCACTACGAACTGCCGTGGGTTGAAAAATATAGGCCAGTAAAGCTGAATGAAATTGTCGGGAATGAAGACACCG
TGAGCAGGCTAGAGGTCTTTGCAAGGGAAGGAAATGTGCCCAACATCATCATTGCGGGCCCTCCAGGAACCGGCAA
GACCACAAGCATTCTGTGCTTGGCCCGGGCCCTGCTGGGCCCAGCACTCAAAGATGCCATGTTGGAACTCAATGCT
TCAAATGACAGGGGCATTGACGTTGTGAGGAATAAAATTAAAATGTTTGCTCAACAAAAGTCACTCTTCCCAAAG
GCCGACATAAGATCATCATTCTGGATGAAGCAGACAGCATGACCGACGGAGCCCAGCAAGCCTTGAGGAGAACCAT
GGAAATCTACTCTAAAACCACTCGTTCGCCCTTGCTTGTAATGCTTCGGATAAGATCATCGAGCC
```

*Fig. 15I*

17_16477.edit

```
TNGAGCGGCCGCCCGGGCAGGNTGNNAACGCTGGTCCTGCTGGTCCTCCTGGCAAGGCTGGTGAAGATGGTCACCC
TGGAAAAACCCGGACGACCTGGTGAGAGAGGAGTTGTTGGACCACAGGGTGCTCGTGGTTTCCCTGGAACTCCTGGA
CTTCCTGGCTTCAAAGGCATTAGGGGACACAATGGTCTGGATGGATTGAAGGGACAGCCCGGTGCTCCTGGTGTGA
AGGGTGAACCTGGTGCCCCTGGTGAAAATGGAACTCCAGGTCAAACAGGAGCCCGTGGGCTTCCTGGTGAGAGAGG
ACCGTGTTGGTGCCCCTGGCCCANACCTCGGCCGCGACCACGCTAAGCCCGAATTTCCAGCACACTGGNGGCCGTT
ACTANTGGATCCGAGCTCGGTACCAAGCTTGGCGTAATCATGGTCATAGCTGTTTCCTGNGTGAAATTGTTATCCG
CTCACAATTTCACACANCATACGAAGCCGGAAAGCATAAAGTGTAAAGCCTTGGGGTGCTAATGAGTGAGCTAACT
CNCATTAAATTGCGTTGCGCTCACTGCCCGCTTTTCCANNNGGGAAACCNTGGCNTNGCCNGCTTGCNTTAANTGA
AATCCGCCNACCCCCGGGGAAAAGNCGGTTTGCNGTATTGGGGCNCTTTTTCCCTTTCCTCGGNTTACTTGANTTA
NTGGGCTTTGGNCGNTTCGGGTTGNGGCGANCNGGTTCAACNTCACNCCAAAGGNGGNAANACGGTTTTCCCANAA
TCCGGGGGNTANCCCAANGNAAAACATNNGNCNAANGGGCT
```

18_16477.edit

```
AGCGTGGTTNGCGGCCGAGGTCTGGGCCAGGGGCACCAACACGTCCTCTCTCACCAGGAAGCCCACGGGCTCCTGT
TTGACCTGGAGTTCCATTTTCACCAGGGGCACCAGGTTCACCCTTCACACCAGGAGCACCGGGCTGTCCCTTCAAT
CCATNCAGACCATTGTGNCCCCTAATGCCTTTGAAGCCAGGAAGTCCAGGAGTTCCAGGGAAACCACCGAGCACCC
TGTGGTCCAACAACTCCTCTCTCACCAGGTCGTCCGGGTTTTCCAGGGTGACCATCTTCACCAGCCTTGCCAGGAG
GACCAGCAGGACCAGCGTTACCAACCTGCCCGGGCGGCCGCTCGA
```

21_16479.edit

```
TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT
```

22_16479.edit

```
AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAAGATGTGATTCATCTAGATGGTGCCATGACAATGGT
GTGAACTACAAGATTGGAGAGAAGTGGGACCGTCAGGGAGAAAATGGACCTGCCCGGGCCGGCCGCTCGA
```

```
CTTTGCAAAGCTTTTATTTCATGTCTGCGGCATGGAATCCACCTGCACATGGCATCTTAGCTGTGAAGGAGAAAGC
AGTGCACGAGAAGGAATGAGTGGGCGGAACCAACGGCCTCCACAAGCTGCCTTCCAGCAGCCTGCCAAGGCCATGG
CAGAGAGAGACTGCAAACAAACACAAGCAAACAGAGTCTCTTCACAGCTGGAGTCTGAAAGCTCATAGTGGCATGT
GTGAATCTGACAAAATTAAAAGTGTGCATAGTCCATTACATGCATAAAACACTAATAATAATCCTGTTTACACGTG
ACTGCAGCAGGCAGGTCCAGCTCCACCACTGCCCTCCTGCCACATCACATCAAGTGCCATGGTTTAGAGGGTTTTT
CATATGTAATTCTTTTATTCTGTAAAAGGTAACAAAATATACAGAACAAAACTTTCCCTTTTTAAAACTAATGTTA
CAAATCTGTATTATCACTTGGATATAAATAGTATATAAGCTGATC
```

13700.1

```
CAAGGGATATATGTTGAGGGTACRGRGTGACACTGAACAGATCACAAAGCACGAGAAACATTAGTTCTCTCCCTCC
CCAGCGTCTCCTTCGTCTCCCTGGTTTTCCGATGTCCACAGAGTGAGATTGTCCCTAAGTAACTGCATGATCAGAG
TGCTGKCTTTATAAGACTCTTCATTCAGCGTATCCAATTCAGCAATTGCTTCATCAAATGCCGTTTTTGCCAGGCT
ACAGGCCTTTTCAGGAGAGTTTAGAATCTCATAGTAAAAGACTGAGAAATTTAGTGCCAGACCAAGACGAATTGGG
TGTGTAGGCTGCATTNCTTTCTTACTAATTTCAAATGCTTCCTGGTAAGCCTGCTGGGAGTTCGACACAAGTGGTT
TGTTTGTTGCTCCAGATGCCACTTCAGAAAGATACCTAAAATAATCTCCTTTCATTTTCAAAGTAGAACAC
```

13700.2

```
TCCGGAGCCGGGGTAGTCGCCGCCGCCGCCGCCGGTGCAGCCACTGCAGGCACCGCTGCCGCCGCCTGAGTAGTGG
GCTTAGGAAGGAAGAGGTCATCTCGCTCGGAGCTTCGCTCGGAAGGGTCTTTGTTCCCTGCAGCCCTCCCACGGGA
ATGACAATGGATAAAAGTGAGCTGGTACAGAAAGCCAAACTCGCTGAGCAGGCTGAGCGATATGATGATATGGCTG
CAGCCATGAAGGCAGTCACAGAACAGGGGCATGAACTCTCCAACGAAGAGAGAAATCTGCTCTCTGTTGCCTACAA
GAATGTGGTAAGGCCGCCCGCCGCTCTTCCTGGCGTGTCATCTCCAGCATTGAGCAGAAAACAGAGAGGAATGAGA
AGAAGCAGCAGATGGGCAAAGAGTACCGTGAGAAGATAGAGGCAGAACTGCAGGACATCTGCAATGATGTTCTGGA
GCTTGTTGGACAAATATCTTATTCCAATGCTACACAACCCAGAAA
```

13701.1

```
AAAAAGCAGCARGTTCAACACAAAATAGAAATCTCAAATGTAGGATAGAACAAAACCAAGTGTGTGAGGGGGGAAG
CAACAGCAAAAGGAAGAAATGAGATGTTGCAAAAAAGATGGAGGAGGGTTCCCCTCTCCTCTGGGGACTGACTCAA
ACACTGATGTGGCAGTATACACCATTCCAGAGTCAGGGGTGTTCATTCTTTTTTGGGAGTAAGAAAAGGTGGGGAT
TAAGAAGACGTTTCTGGAGGCTTAGGGACCAAGGCTGGTCTCTTTCCCCCCTCCCAACCCCCTTGATCCCTTTCTC
TGATCAGGGGAAAGGAGCTCGAATGAGGGAGGTAGAGTTGGAAAGGGAAAGGATTCCACTTGACAGAATGGGACAG
ACTCCTTCCCA
```

*Fig. 15J*

24_16480.edit

```
TCGAGCGNNCGCCCGGGCAGGTCCAGTAGTGCCTTCGGGACTGGGTTCACCCCCAGGTCTGCGGCAGTTGTCACAG
CGCCAGCCCCGCTGGCCTCCAAAGCATGTGCAGGAGCAAATGGCACCGAGATATTCCTTCTGCCACTGTTCTCCTA
CGTGGTATGTCTTCCCATCATCGTAACACGTTGCCTCATGAGGGTCACACTTGAATTCTCCTTTTCCGTTCCCAAG
ACATGTGCAGCTCATTTGGCTGGCTCTATAGTTTGGGGAAAGTTTGTTGAAACTGTGCCACTGACCTTTACTTCCT
CCTTCTCTACTGGAGCTTTCGTACCTTCCACTTCTGCTGTTGGTAAAATGGTGGATCTTCTATCAATTTCATTGAC
AGTACCCACTTCTCCCAAACATCCAGGGAAATAGTGATTTCAGAGCGATTAGGAGAACCAAATTATGGGGCAGAAA
TAAGGGGCTTTTCCACAGGTTTTCCTTTGGAGGAAGATTTCAGTGGTGACTTTAAAAGAATACTCAACAGTGTCTT
CATCCCCATAGCAAAAGAAGAAACNGTAAATGATGGAANGCTTCTGGAGATGCCNNCATTTAAGGGACNCCCAGAA
CTTCACCATCTACAGGACCTACTTCAGTTTACANNAAGNCACATANTCTGACTCANAAAGGACCCAAGTAGCNCCA
TGGNCAGCACTTTNAGCCTTTCCCCTGGGGAAAANNTTACNTTCTTAAANCCTNGGCCNNGACCCCCTTAAGNCCA
AATTNTGGAAAANTTCCNTNCNNCTGGGGGGCNGTTCNACATGCNTTTNAAGGGCCCAATTNCCCCNT
```

25_16481.edit

```
TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAGCCAGTCCTGGTGCAGGAC
GGTGAGGACGCTGACCACACGGTACGTGCTGTTGTACTGCTCCTCCCGCGGCTTTGTCTTGGCATTATGCACCTCC
ACGCCGTCCACGTACCAGTTGAACTTGACCTCAGGGTCTTCGTGGCTCACGTCCACCACCACGCATGTAACCTCAG
ACCTCGGCCGCGACCACGCT
```

26_16481.edit

```
AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAAGCCCCGAGAACCACAGGTGTACACCCT
GCCCCCATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACA
CCTGCCCGGGCGGCCGCTCGA
```

27_16482.edit

```
TCGAGCGGCCGCCCGGGCAGGTTGAATGGCTCCTCGCTGACCACCCCGGTGCTGGTGGTGGGTACAGAGCTCCGAT
GGGTGAAACCATTGACATAGAGACTGTCCCTGTCCAGGGTGTAGGGGCCCAGCTCAGTGATGCCGTGGGTCAGCTG
GCTCAGCTTCCAGTACAGCCGCTCTCTGTCCAGTCCAGGGCTTTTGGGGTCAGGACGATGGGTGCAGACAGCATCC
ACTCTGGTGGCTGCCCCATCCTTCTCAGGCCTGAGCAAGGTCAGTCTGCAACCAGAGTACAGAGAGCTGACACTGG
TGTTCTTGAACAAGGGCATAAGCAGACCCTGAAGGACACCTCGGCCGCGACCACGCT
```

TGGCAATAGCACAGCCATCCAGGAGCTCTTCARGCGCATCTCGGAGCAGTTCACTGCCATGTTCCGCCGGAAGGCC
TTCCTCCACTGGTACACAGGCGAGGGCATGGACGAGATGGAGTTCACCGAGGCTGAGAGCAACATGAACGACCTCG
TCTCTGAGTATCAAGCAGTACCAGGATGCCACCGCAGAAGAGGAGGAGGATTTCGGTGAGGAGGCCGAAGAGGAGG
CCTAAGGCAGAGCCCCCATCACCTCAGGCTTCTCAGTTCCCTTAGCCGTCTTACTCAACTGCCCCTTTCCTCTCCC
TCAGAATTTGTGTTTGCTGCCTCTATCTTGTTTTTTGTTTTTTCTTCTGGGGGGGTCTAGAACAGTGCCTGGCACA
TAGTAGGCGCTCAATAAATACTTGGTTGNTGAATGTCTCCT 13702.2

AGCTGGCGCTAGGGCTCGGTTGTGAAATACAGCGTRGTCAGCCCTTGCGCTCAGTGTAGAAACCCACGCCTGTAAG
GTCGGTCTTCGTCCATCTGCTTTTTTCTGAAATACACTAAGAGCAGCCACAAAACTGTAACCTCAAGGAAACCATA
AAGCTTGGAGTGCCTTAATTTTTAACCAGTTTCCAATAAAACGGTTTACTACCT 13704.2-13740.2

GGAGATGAAGATGAGGAAGCTGAGTCAGCTACGGGCARGCGGGCAGCTGAAGATGATGAGGATGACGATGTCGATA
CCAAGAAGCAGAAGACCGACGAGGATGACTAGACAGCAAAAAAGGAAAAGTTAAA 13706.1

GATGAAAATTAAATACTTAAATTAATCAAAAGGCACTACGATACCACCTAAAACCTACTGCCTCAGTGGCAGTAKG
CTAAKGAAGATCAAGCTACAGSACATYATCTAATATGAATGTTAGCAATTACATAKCARGAAGCATGTTTGCTTTC
CAGAAGACTATGGNACAATGGTCATTWGGGCCCAAGAGGATATTTGGCCNGGAAAGGATCAAGATAGATNAANGTA
AAG 13706.2

GAGTAGCAACGCAAAGCGCTTGGTATTGAGTCTGTGGGSGACTTCGGTTCCGGTCTCTGCAGCAGCCGTGATCGCT
TAGTGGAGTGCTTAGGGTAGTTGGCCAGGATGCCGAATATCAAAATCTTCAGCAGGCAGCTCCCACCAGGACTTAT
CTCASAAAATTGCTGACCGCCTGGGCCTGGAGCTAGGCAAGGTGGTGACTAAGAAATTCAGCAACCAGGAGACCTG
TGTGGAAATTGGTGAAAGTGTACCGTGGAGAGGATGTCTACATTGTTCAGAGTGGNTGTGGCGAAATCAATGACAA
TTTAATGGAGCTTTTGATCATGATTAATGCCTGCAAGATTGCTTCAGCCAGCCGGGTTACTGCAGTCATCCCATGC
TTCCCTTATGCCCCGGCAGGATAAGAAAGATNAGAGCCGGGCCGCCAATCTCAGCCAAGCTTGGTGCAAATATGCT
ATCTGTAGCAGTGCAGATCATATTATCACCATGGACCTACATGCTTCTCAAATTCANGGCTTTTT

*Fig. 15K*

28_16482.edit

```
AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA
```

29_16483.edit

```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTCCCGGTTCCAGGCCAGTAATA
GTAGCCTCTGTGACACCAGGGCGGGGCCGAGGGACCCTTCTNTTGGAAGAGACCAGCTTCTCATACTTGATGATGA
GNCCGGTAATCCTGGCACGTGGNGGTTGCATGATNCCACCAAGGAAATNGGNGGGGGNGGACCTGCCCGGCGGCCG
TTCNAAAGCCCAATTCCACACACTTGGNGGCCGTACTATGGATCCCACTCNGTCCAACTTGGNGGAATATGGCATA
ACTTTT
```

31_16484.edit

```
TCGAGCGGCCGCCCGGGCAGGTCCTTGACCTTTTCAGCAAGTGGGAAGGTGTAATCCGTCTCCACAGACAAGGCCA
GGACTCGTTTGTACCCGTTGATGATAGAATGGGGTACTGATGCAACAGTTGGGTAGCCAATCTGCAGACAGACACT
GGCAACATTGCGGACACCCTCCAGGAAGCGAGAATGCAGAGTTTCCTCTGTGATATCAAGCACTTCAGGGTTGTAG
ATGCTGCCATTGTCGAACACCTGCTGGATGACCAGCCCAAAGGAGAAGGGGGAGATGTTGAGCATGTTCAGCAGCG
TGGCTTCGCTGGCTCCCACTTTGTCTCCAGTCTTGATCAGACCTCGGCCGCGACCACGCT
```

37_16487.edit

```
AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCG
```

```
ATGCAAAAGGGGACACAGGGGGTTCAAAAATAAAAATTTCTCTTCCCCCTCCCCAAACCTGTACCCCAGCTCCCCG
ACCACAACCCCCTTCCTCCCCCGGGGAAAGCAAGAAGGAGCAGGTGTGGCATCTGCAGCTGGGAAGAGAGAGGCCG
GGGAGGTGCCGAGCTCGGTGCTGGTCTCTTTCCAAATATAAATACGTGTGTCAGAACTGGAAAATCCTCCAGCACC
CACCACCCAAGCACTCTCCGTTTTCTGCCGGTGTTTGGAGAGGGGCGGNGGGCAGGGGCGCCAGGCACCGGCTGGC
TGCGGTCTACTGCATCCGCTGGGTGTGCACCCCGCGA
```

13710.2

```
AGGTTGGAGAAGGTCATGCAGGTGCAGATTGTCCAGGSKCAGCCACAGGGTCAAGCCCAACAGGCCCAGAGTGGCA
CTGGACAGACCATGCAGGTGATGCAGCAGATCATCACTAACACAGGAGAGATCCAGCAGATCCCGGTGCAGCTGAA
TGCCGGCCAGCTGCAGTATATCCGCTTAGCCCAGCCTGTATCAGGCACTCAAGTTGTGCAGGGACAGATCCAGACA
CTTGCCACCAATGCTCAACAGATTACACAGACAGAGGTCCAGCAAGGACAGCAGCAGTTCAAGCCAGTTCACAAGA
TGGACAGCAGCTCTACCAGATCCAGCAAGTCACCATGCCTGCGGGCCANGACCTCGCCAGCCCATGTTCATCCAGT
CAAGCCAACCAGCCCTTCNACGGGCAGGCCCCCAGGTGACCGGCGACTGAAGGGCCTGAGCTGGCAAGGCCAANG
ACACCCAACACAATTTTTTGCCATACAGCCCCCAGGCAATGGGCACAGCCTTTCTTCCCAGAGGAC
```

13710-1

```
TGAGATTTATTGCATTTCATGCAGCTTGAAGTCCATGCAAAGGRGACTAGCACAGTTTTTAATGCATTTAAAAAAT
AAAAGGGAGGTGGGCAGCAAACACACAAAGTCCTAGTTTCCTGGGTCCCTGGGAGAAAAGAGTGTGGCAATGAATC
CACCCACTCTCCACAGGGAATAAATCTGTCTCTTAAATGCAAAGAATGTTTCCATGGCCTCTGGATGCAAATACAC
AGAGCTCTGGGGTCAGAGCAAGGGATGGGGAGAGGACCACGAGTGAAAAAGCAGCTACACACATTCACCTAATTCC
ATCTGAGGGCAAGAACAACGTGGCAAGTCTTGGGGGTAGCAGCTGTT
```

13711.1

```
TCCAGACATGCTCCTGTCCTAGGCGGGGAGCAGGAACCAGACCTGCTATGGGAAGCAGAAAGAGTTAAGGGAAGGT
TTCCTTTCATTCCTGTTCCTTCTCTTTTGCTTTTGAACAGTTTTTAAATATACTAATAGCTAAGTCATTTGCCAGC
CAGGTCCCGGTGAACAGTAGAGAACAAGGAGCTTGCTAAGAATTAATTTTGCTGTTTTTCACCCCATTCAAACAGA
GCTGCCCTGTTCCCTGATGGAGTTCCATTCCTGCCAGGGCACGGCTGAGTAACACGAAGCCATTCAAGAAAGGCGG
GTGTGAAATCACTGCCACCCCATGGACAGACCCCTCACTCTTCCTTCTTAGCCGCAGCGCTACTTAATAAATATAT
TTATACTTTGAAATTATGATAACCGATTTTTCCCATGCGGCATCCTAAGGGCACTTGCCAGCTCTTATCCGGACAG
TCAAGCACTGTTGTTGGACAACAGATAAAGGAAAAGAAAAAGAAGAAAACAACCGCAACTTCTGT
```

*Fig. 15L*

38_16487.edit

```
CGAGCGGCCGCCCGGGCAGGTTTGGAAGGGGGATGCGGGGGAAGAGGAAGACTGACGGTCCCCCCAGGAGTTCAGG
TGCTGGGCACGGTGGGCATGTGTGAGTTTTGTCACAAGATTTGGGCTCAACTCTCTTGTCCACCTTGGTGTTGCTG
GGCTTGTGATCTACGTTGCAGGTGTAGGTCTGGGTGCCGAAGTTGCTGGAGGGCACGGTCACCACGCTGCTGAGGG
AGTAGAGTCCTGAGGACTGTAGGACAGACCTCGGCCGCGACCACGCT
```

39_16488.edit

```
NGGNNGGTCCGGNCNGNCAGGACCACTCNTCTTCGAAATA
```

41_16489.edit

```
AGCGTGGTCGCGGCCGAGGTCCTCACTTGCCTCCTGCAAAGCACCGATAGCTGCGCTCTGGAAGCGCAGATCTGTT
TTAAAGTCCTGAGCAATTTCTCGCACCAGACGCTGGAAGGGAAGTTTGCGAATCAGAAGTTCAGTGGACTTCTGAT
AACGTCTAATTTCACGGAGCGCCACAGTACCAGGACCTGCCCGGGCGGCCGCTCGA
```

42_16489.edit

```
TCGAGCGGCCGCCCGGGCAGGTCCTGGTACTGNGGCGCTCCGTGAAATTAGACGTTATCAGAAGTCCACTGAACTT
CTGATTCGCAAACTTCCCTTCCAGCGTCTGGTGCGAGAAATTGCTCAGGACTTTAAAACAGATCTGCGCTTCCAGA
GCGCAGCTATCGGTGCTTTGCAGGAGGCAAGTGAGGACCTCGGCCGCGACCACGCT
```

45_16491.edit

```
TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT
```

TGAGACGGACCACTGGCCTGGTCCCCCCTCATKTGCTGTCGTAGGACCTGACATGAAACGCAGATCTAGTGGCAGA
GAGGAAGATGATGAGGAACTTCTGAGACGTCGGCAGCTTCAAGAAGAGCAATTAATGAAGCTTAACTCAGGCCTGG
GACAGTTGATCTTGAAAGAAGAGATGGAGAAAGAGAGCCGGGAAAGGTCATCTCTGTTAGCCAGTCGCTACGATTC
TCCCATCAACTCAGCTTCACATATTCCATCATCTAAAACTGCATCTCTCCCTGGCTATGGAAGAAATGGGCTTCAC
CGGCCTGTTTCTACCGACTTCGCTCAGTATAACAGCTATGGGGATGTCAGCGGGGGAGTGCGAGATTACCAGACAC
TTCCAGATGGCCACATGCCTGCAATGAGAATGGACCGAGGAGTGTCTATGCCCAACATGTTGGAACCAAAGATATT
TCCATATGAAATGCTCATGGTGACCAACAGAGGGCCGAAACCAAATCTCAGAGAGGTGGACAGAA

13713.1&2

TCACTTTATTTTTCTTGTATAAAAACCCTATGTTGTAGCCACAGCTGGAGCCTGAGTCCGCTGCACGGAGACTCTG
GTGTGGGTCTTGACGAGGTGGTCAGTGAACTCCTGATAGGGAGACTTGGTGAATACAGTCTCCTTCCAGAGGTCGG
GGGTCAGGTAGCTGTAGGTCTTAGAAATGGCATCAAAGGTGGCCTTGGCGAAGTTGCCCAGGGTGGCAGTGCAGCC
CCGGGCTGAGGTGTAGCAGTCATCGATACCAGCCATCATGAG

13715.4

CTGGAATATAGACCCGTGATCGACAAAACTTTGAACGAGGCTGACTGTGCCACCGTCCCGCCAGCCATTCGCTCCT
ACTGATGAGACAAGATGTGGTGATGACAGAATCAGCTTTTGTAATTATGTATAATAGCTCATGCATGTGTCCATGT
CATAACTGTCTTCATACGCTTCTGCACTCTGGGGAAGAAGGAGTACATTGAAGGGAGATTGGCACCTAGTGGCTGG
GAGCTTGCCAGGAACCCAGTGGCCAGGGAGCGTGGCACTTACCTTTGTCCCTTGCTTCATTCTTGTGAGATGATAA
AACTGGGCACAGCTCTTAAATAAAATATAAATGAACA

13717.1&2

TGAATGGGGAGGAGCTGACCCAGGAAATGGAGCTTGNGGAGACCAGGCCTGCAGGGGATGGAACCTTCCAGAAGTG
GGCATCTGTGGTGGTGCCTCTTGGGAAGGAGCAGAAGTACACATGCCATGTGGAACATGAGGGGCTGCCTGAGCCC
CTCACCCTGAGATGGGGCAAGGAGGAGCCTCCTTCATCCACCAAGACTAACACAGTAATCATTGCTGTTCCGGTTG
TCCTTGGAGCTGTGGTCATCCTTGGAGCTGTGATGGCTTTTGTGATGAAGAGGAGGAGAAACACAGGTGGAAAAGG
AGGGGACTATGCTCTGGCTCCAGGCTCCCAGAGCTCTGATATGTCTCTCCCAGATTGTAAAGTGTGAAGACAGCTG
CCTGGTGTGGACTTGGTGACAGACAATGTCTTCACACATCTCCTGTGACATCCAGAGACCTCAGTTCTCTTTAGTC
AAGTGTCTGATGTTCCCTGTGAGTCTGCGGGCTCAAAGTGAAGAACTGTGGAGCCCAGTCCACCCCTGCACACCAG
GACCCTATCCCTGCACTGCCCTGTGTTCCCTTCCACAGCCAACCTTGCTGCTCCAGCCAAACATTGGTGGACATCT
GCAGCCTGTCAGCTCCATGCTACCCTGACCTTCAACTCCTCACTTCCACACTGAGAATAATAATTTGAATGTGGGT
GGCTGGAGAGATGGCTCAGCGCTGACTGCTCTTCCAAAGGTCCTGAGTTCAAATCCCAGCAACCACATGGTGGCTC
ACAACCATCTGTAATGGGATCTAATACCCTCTTCTGCAGTGTCTGAAGACASCTACAGTGTACTTACATATAATAA
TAAATAAG

*Fig. 15M*

46_16491.edit

```
GTGGGNTTGAACCCNTTTNANCTCCGCTTGGTACCGAGCTCGGATCCACTAGTAACGGCCGCCAGTGTGCTGGAAT
TCGGCTTAGCGTGGTCGCGGCCGAGGTCAAGAACCCCGCCCGCACCTGCCGTGACCTCAAGATGTGCCACTCTGAC
TGGAAGAGTGGAGAGTACTGGATTGACCCCAACCAAGGCTGCAACCTGGATGCCATCAAAGTCTTCTGCAACATGG
AGACTGGTGAGACCTGCGTGTACCCCACTCAGCCCAGTGTGGCCCAGAAGAACTGGTACATCAGCAAGAACCCCAA
GGACAAGAGGCATGTCTGGTTCGGCGAGAGCATGACCGATGGATTCCAGTTCGAGTATGGCGGCCAGGGCTCCGAC
CCTGCCGATGTGGACCTGCCCGGGCGGCCGCTCGA
```

47_16492.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAAGTGT
CTATGCTCAGAATCCAAGCGGAGAGAAGTCAGCCTCTGGTTCAGACTGNAAGTAACCAACATTGATCGCCTAAAGG
ACTGGCATTCACTGATGNGGATGCCGATTCCATCAAAATTGNTTGGGAAAACCCACAGGGGCAAGTTTNCANGTCN
AGGNGGACCTACTCGAGCCCTGAGGATGGAATCCTTGACTNTTCCTTNNCCTGATGGGGAAAAAAAACCTTNAAAA
CTTGAAGGACCTGCCCGGGCGGCCGTNCAAAACCCAATTCCACCCCCTTGGGGGCGTTCTATGGGNCCCACTCGGA
CCAAACTTGGGGTAAN
```

48_16492.edit

```
TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGGCATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAGTTTTTGTTGGTCCTGGTCCATTTTTGGGAGTGGTGGTTACTCTGT
AACCAGTAACAGGGGAACTTGAAGGCAGCCACTTGACACTAATGCTGTTGTCCTGAACATCGGTCACTTGCATCTG
GGATGGTTTGTCAATTTCTGTTCGGTAATTAATGGAAATTGGCTTGCTGCTTGCGGGCTTGTCTCCACGGCCAGT
GACAGCATACACAGTGATGGTATAATCAACTCCAGGTTTAAGCCGCTGATGGTAGCTGAAACTTTGCTCCAGGCAC
AAGTGAACTCCTGACAGGGCTATTTCCTNCTGTTCTCCGTAAGTGATCCTGTAATATCTCACTGGGACAGCAGGAN
GCATTCCAAAACTTCGGGCGNGACCCCCTAAGCCGAATTNTGCAATATNCATCACACTGGCGGGCGCTCGANCATT
CATTAAAAGGCCCAATCNCCCCTATAGGGAGTNTANTACAATTNG
```

```
GGCCGGGCGCGCGCGCCCCCGCCACACGCACGCCGGGCGTGCCAGTTTATAAAGGGAGAGAGCAAGCAGCGAGTCT
TGAAGCTCTGTTTGGTGCTTTGGATCCATTTCCATCGGTCCTTACAGCCGCTCGTCAGACTCCAGCAGCCAAGATG
GTGAAGCAGATCGAGAGCAAGACTGCTTTTCAGGAAGCCTTGGACGCTGCAGGTGATAAACTTGTAGTAGTTGACT
TCTCAGCCACGTGGTGTGGGCCTTGCAAAATGATCAAGCCTTTCTTTCATTCCCTCTCTGAAAAGTATTCCAACGT
GATATTCCTTGAAGTAGATGTGGATGACTGTCAGGATGTTGCTTCAGAGTGTGAAGTCAAATGCATGCCAACATTC
CAGTTTTTTAAGAAGGGACAAAAGGTGGGTGAATTTTCTGGAGCCAATAAGGAAAAGCTTGAAGCCACCATTAATG
AATTAGTCTAATCATGTTTTCTGAAAATATAACCAGCCATTGGCTATTTAAAACTTGTAATTTTTTTAATTTACAA
AAATATAAAATATGAAGACATAAACCCMGTTGCCATCTGCGTGACAATAAAACATTAATGCTAACACTT
```

13721.1

```
TCACATAAGAAATTTAAGCAAGTTACRCTATCTTAAAAAACACAACGAATGCATTTTAATAGAGAAACCCTTCCCT
CCCTCCACCTCCCTCCCCCACCCTCCTCATGAATTAAGAATCTAAGAGAAGAAGTAACCATAAAACCAAGTTTTGT
GGAATCCATCATCCAGAGTGCTTACATGGTGATTAGGTTAATATTGCCTTCTTACAAAATTTCTATTTTAAAAAAA
ATTATAACCTTGATTGCTTATTACAAAAAAATTCAGTACAAAAGTTCAATATATTGAAAAATGCTTTTCCCCTCCC
TCACAGCACCGTTTTATATATAGCAGAGAATAATGAAGAGATTGCTAGTCTAGATGGGGCAATCTTCAAATTACAC
CAAGACGCACAGTGGTTTATTTACCCTCCCCTTCTCATAAG
```

13721.2

```
GGAAAGGATTCAAGAATTAGAGGACTTGCTTGCTRRAGAAAAAGACAACTCTCGTCGCATGCTGACAGACAAAGAG
AGAGAGATGGCGGAAATAAGGGATCAAATGCAGCAACAGCTGAATGACTATGAACAGCTTCTTGATGTAAAGTTAG
CCCTGGACATGGAAATCAGTGCTTACAGGAAACTCTTAGAAGGCGAAGAAGAGAGGTTGAAGCTGTCTCCAAGCCC
TTCTTCCCGTGTGACAGTATCCCGAGCATCCTCAAGTCGTAGTGTACCGTACAACTAGAGGAAAGCGGAAGAGGGT
TGATGTGGAAGAATCAGAGGCGAAGTAGTAGTGTTAGCATCTCTCATTCCGCCTCAACCACTGGAAATGTTTGCAT
CGAAGAAATTGATGTTGATGGGAAATTTATCCCGCTTGAAGAACACTTCTGAACAGGATCAACCAATGGGAAGGCT
TGGGAGATGATCAGAAAAATTGGAGACACATCAGTCAGTTATAAATATACCTCAA
```

13723.1

```
CATGGGTTTCACCAGGTTGGCCAGGCTGCTCTTGAACTSCTGACCTCAGGTGATCCACCCGCCTCGGCCTCCCAAA
GTGCTGGGATTACAGGCGTGAGCCACCACGCCCGGCCCCCAAAGCTGTTTCTTTTGTCTTTAGCGTAAAGCTCTCC
TGCCATGCAGTATCTACATAACTGACGTGACTGCCAGCAAGCTCAGTCACTCCGTGGTCTTTTTCTCTTTCCAGTT
CTTCTCTCTCTCTTCAAGTTCTGCCTCAGTGAAAGCTGCAGGTCCCCAGTTAAGTGATCAGGTGAGGGTTCTTTGA
ACCTGGTTCTATCAGTCGAATTAATCCTTCATGATGG
```

*Fig. 15N*

49_16493.edit

```
TCGAGCGGCCGCCCGGGCAGGTCACTTTTGGTTTTTGGTCATGTTCGGTTGGTCAAAGATAAAAACTAAGTTTGAG
AGATGAATGCAAAGGAAAAAAATATTTTCCAAAGTCCATGTGAAATTGTCTCCCATTTTTTTGGCTTTTGAGGGGG
TTCAGTTTGGGTTGCTTGTCTGTTTCCGGGTTGGGGGGAAAGTTGGTTGGGTGGGAGGGAGCCAGGTTGGGATGGA
GGGAGTTTACAGGAAGCAGACAGGGCCAACGTCG
```

55_16496.edit

```
AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA
```

56_16496.edit

```
TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT
```

59_16498.edit

```
TCGAGCGGCCGCCCGGGCAGGTCCACCATAAGTCCTGATACAACCACGGATGAGCTGTCAGGAGCAAGGTTGATTT
CTTTCATTGGTCCGGTCTTCTCCTTGGGGGTCACCCGCACTCGATATCCAGTGAGCTGAACATTGGGTGGTGTCCA
CTGGGCGCTCAGGCTTGTGGGTGTGACCTGAGTGAACTTCAGGTCAGTTGGTGCAGGAATAGTGGTTACTGCAGTC
TGAACCAGAGGCTGACTCTCTCCGCTTGGATTCTGAGCATAGACACTAACCACATACTCCACTGTGGGCTGCAAGC
CTTCAATAGTCATTTCTGTTTGATCTGGACCTGCAGTTTTAGTTTTTGTTGGTCCTGGTCCATTTTTGGGAGTGGT
GGTTACTCTGTAACCAGTAACAGGGGAACTTGAAGGCAGCCACTTGACACTAATGCTGTTGTCCTGAACATCGGTC
ACTTGCATCTGGGATGGTTTGNCAATTTCTGTTCGGTAATTAATGGAAATTGGCTTGCTGCTTGCGGGCTGTCTC
CACGGCCAGTGACAGCATACACAGNGATGGNATNATCAACTCCAAGTTTAAGGCCCTGATGGTAACTTTAAACTTG
CTCCCAGCCAGNGAACTTCCGGACAGGGTATTTCTTCTGGTTTTCCGAAAGNGANCCTGGAATNNTCTCCTTGGAN
CAGAAGGANCNTCCAAAACTTGGGCCGGAACCCCTT
```

GATGTGTTGGACCCTCTGTGTCAAAAAAAACCTCACAAAGAATCCCCTGCTCATTACAGAAGAAGATGCATTTAAA
ATATGGGTTATTTTCAACTTTTTATCTGAGGACAAGTATCCATTAATTATTGTGTCAGAAGAGATTGAATACCTGC
TTAAGAAGCTTACAGAAGCTATGGGAGGAGGTTGGCAGCAAGAACAATTTGAACATTATAAAATCAACTTTGATGA
CAGTAAAAATGGCCTTTCTGCATGGGAACTTATTGAGCTTATTGGAAATGGACAGTTTAGCAAAGGCATGGACCGG
CAGACTGTGTCTATGGCAATTAATGAAGTCTTTAATGAACTTATATTAGATGTGTTAAAGCAGGGTTACATGATGA
AAAAGGGCCACAGACGGAAAAACTGGACTGAAAGATGGTTTGTACTAAAACCCAACATAATTTCTTACTATGTGAG
TGAGGATCTGAAGGATAAGAAAGGAGACATTCTCTTGGATGAAAATTGCTGTGTAGAAGTCCTTGCCTGACAAAAG
ATGGAAAGAAATGCCTTTT 13725.1

GACTGGTTCTTTATTTCAAAAAGACACTTGTCAATATTCAGTRTCAAAACAGTTGCACTATTGATTTCTCTTTCTC
CCAATCGGCCCCAAAGAGACCACATAAAAGGAGAGTACATTTTAAGCCAATAAGCTGCAGGATGTACACCTAACAG
ACCTCCTAGAAACCTTACCAGAAAATGGGGACTGGGTAGGGAAGGAAACTTAAAAGATCAACAAACTGCCAGCCCA
CGGACTGCAGAGGCTGTCACAGCCAGATGGGGTGGCCAGGGTGCCACAAACCCAAAGCAAAGTTTCAAAATAATAT
AAAATTTAAAAAGTTTTGTACATAAGCTATTCAAGATTTCTCCAGCACTGACTGATACAAAGCACAATTGAGATGG
CACTTCTAGAGACAGCAGCTTCAAACCCAGAAAAGGGTGATGAGATGAAGTTTCACATGGCTAAATCAGTGGCAAA
AACACAGTCTTCTTTCTTTCTTTCAAGGANGCAGGAAAGCAATTAAGTGGTCACCTTAACATAAGGGGGAC 13725.2

TGGGTGGGCACCATGGCTGGGATCACCACCATCGAGGCGGTGAAGCGCAAGATCCAGGTTCTGCAGCAGCAGGCAG
ATGATGCAGAGGAGCGAGCTGAGCGCCTCCAGCGAGAAGTTGAGGGAGAAAGGCGGGCCCGGGAACAGGCTGAGGC
TGAGGTGGCCTCCTTGAACCGTAGGATCCAGCTGGTTGAAGAAGAGCTGGACCGTGCTCAGGAGCGCCTGGCCACT
GCCCTGCAAAAGCTGGAAGAAGCTGAAAAAGCTGCTGATGAGAGTGAGAGAGGTATGAAGGTTATTGAAAACCGGG
CCTTAAAAGATGAAGAAAAGATGGAACTCCAGGAAATCCAACTCAAAGAAGCTAAGCACATTGCAGAAGAGGCAGA
TAGGAAGTATGAAGAGGTGGCTCGTAAGTTGGTGATCATTGAAGGAGACTTGGAACCGCACAGAAGGAACGAGCTT
GAGCTTGGCAAAAGTCCCGTTGCCCAGAGATGGGATGAACCAGATTAGACTGATGGACCANAACC 13726.1&2

AGGGGCNGCGGGTGCGTGGGCCACTGGGTGACCGACTTAGCCTGGCCAGACTCTCAGCACCTGGAAGCGCCCCGAG
AGTGACAGCGTGAGGCTGGGAGGGAGGACTTGGCTTGAGCTTGTTAAACTCTGCTCTGAGCCTCCTTGTCGCCTGC
ATTTAGATGGCTCCCGCAAAGAAGGGTGGCGAGAAGAAAAAGGGCCGTTCTGCCATCAACGAAGTGGTAACCCGAG
AATACACCATCAACATTCACAAGCGCATCCATGGAGTGGGCTTCAAGAAGCGTGCACCTCGGGCACTCAAAGAGAT
TCGGAAATTTGCCATGAAGGAGATGGGAACTCCAGATGTGCGCATTGACACCAGGCTCAACAAAGCTGTCTGGGCC
AAAGGAATAAGGAATGTGCCATACCGAATCCGGTGTGCGGCTGTCCAGAAAACGTAATGAGGATGAAGATTCACCA
AATAAGCTATATACTTTGGTTACCTATGTACCTGTTACCACTTTCAAAAATCTACAGACAGTCAATGTGGATGAGA
ACTAATCGCTGATCGTCAGATCAAATAAAGTTATAAAAT

Fig. 15O

60_16473.edit

```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTTCCCGGTTCCAGGCCAGTAAT
AGTAGCCTCTTGTGACACCAGGCGGGGCCCANGGACCACTTCTCTGGGANGAGACCCAGCTTCTCATACTTGATGA
TGTAACCCGGTAATCCTGCACGTGGCGGCTGNCATGATACCANCAAGGAATTGGGTGNGGNGGACCTGCCCGGCGG
CCCTCNA
```

60_16498.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAGTGTC
TATGCTCAGAATCCAAGCGGAGAGAGTCAGCCTCTGGTTCAGACTGCAGTAACCACTATTCCTGCACCAACTGACC
TGAAGTTCACTCAGGTCACACCCACAAGCCTGAGCCGCCAGTGGACACCACCCAATGTTCACTCACTGGATATCGA
GTGCGGGTGACCCCCAAGGAGAAGACCCGGACCCATGAAAGAAATCAACCTTGCTCCTGACAGCTCATCCGNGGGT
GTATCAGGACTTATGGGGGACTGCCCCGGCNGGCCGNTCGAAANCGAATTNTGAAATTTCCTTCNCACTGGGNGGC
GNTTCGAGCTTNCTTNTANANGGCCCAATTCNCCTNTAGNGGGTCGTN
```

61_16499.edit

```
AGCGTGGTCGCGGCCGAGGTCNAGG
```

62_16483.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGTTTT
AGGCGGACCACACCGCCCACAACGGGCACCCCCATAAGGNATAGGCCAAGACCATACCCCGCCGAATGTAGGACAA
GAAGCTCTNTCTCAACAACCATCTCATGGGCCCCATTCCAGGACACTTCTGAGTACATCATTTCATGTCATCCTGG
TGGGCACTTGATGAANAACCCTTACAGTTCAGGGTTCCTGGAACTTCTACCAGNGCCACTTCTGACAGGANCTTGG
GCGNGACCACCCT
```

```
TCGGGAGCCACACTTGGCCCTCTTCCTCTCCAAAGSGCCAGAACCTCCTTCTCTTTGGAGAATGGGGAGGCCTCTT
GGAGACACAGAGGGTTTCACCTTGGATGACCTCTAGAGAAATTGCCCAAGAAGCCCACCTTCTGGTCCCAACCTGC
AGACCCCACAGCAGTCAGTTGGTCAGGCCCTGCTGTAGAAGGTCACTTGGCTCCATTGCCTGCTTCCAACCAATGG
GCAGGAGAGAAGGCCTTTATTTCTCGCCCACCCATTCCTCCTGTACCAGCACCTCCGTTTTCAGTCAGTGTTGTCC
AGCAACGGTACCGTTTACACAGTCACCTCAGACACACCATTTCACCTCCCTTGCCAAGCTGTTAGCCTTAGAGTGA
TTGCAGTGAACACTGTTTACACACCGTGAATCCATTCCCATCAGTCCATTCCAGTTGGCACCAGCCTGAACCATTT
GGTACCTGGTGTTAACTGGAGTCCTGTTTACAAGGTGGAGTCGGGGCTTGCTGACTTCTCTTCATTTGAGGGCAC
```

13727.2

```
ACCTAGACAGAAGGTGGGTGAGGGAGGACTGGTAGGAGGCTGAGGCAATTCCTTGGTAGTTTGTCCTGAAACCCTA
CTGGAGAAGTCAGCATGAGGCACCTACTGAGAGAAGTGCCCAGAAACTGCTGACTGCATCTGTTAAGAGTTAACAG
TAAAGAGGTAGAAGTGTGTTTCTGAATCAGAGTGGAAGCGTCTCAAGGGTCCCACAGTGGAGGTCCCTGAGCTACC
TCCCTTCCGTGAGTGGGAAGAGTGAAGCCCATGAAGAACTGAGATGAAGCAAGGATGGGGTTCCTGGGCTCCAGGC
AAGGGCTGTGCTCTCTGCAGCAGGGAGCCCCACGAGTCAGAAGAAAAGAACTAATCATTTGTTGCAAGAAACCTTG
CCCGGATACTAGCGGAAAACTGGAGGCGGNGGTGGGGGCACAGGAAAGTGGAAGTGATTTGATGGAGAGCAGAGAA
GCCTATGCACAGTGGCCGAGTCCACTTGTAAAGTG
```

13728.1&2

```
TTCAAGCAATTGTAACAAGTATATGTAGATTAGAGTGAGCAAAATCATATACAATTTTCATTTCCAGTTGCTATTT
TCCAAATTGTTCTGTAATGTCGTTAAAATTACTTAAAAATTAACAAAGCCAAAAATTATATTTATGACAAGAAAGC
CATCCCTACATTAATCTTACTTTTCCACTCACCGGCCCATCTCCTTCCTCTTTTTCCTAACTATGCCATTAAAACT
GTTCTACTGGGCCGGGCGTGTGGCTCATGCCTGTAATCCCAGCATTTTGGGAGGCCAAGGCAGGCGGATCATGAGG
TCAAGAGATTGAGACCATCCTGGCCAACATGGTGAAACCCCGCCTCGACTAAGAATACAAAAATTAGCTGGGCATG
GTGGCGCATGCCTGTAGTCTCAGCTACTCGGGAGGCTGAGGCAGAAGAATCGCTTGAACCCGGGAGGCAGAGGATG
CAGTGAGCCCCGATCGCGCCACTGCACTCTAGCCTGGGCGACAGACTGAGACTCTGCTC
```

13731.1&2

```
TGTGCCAGTCTACAGGCCTATCAGCAGCGACTCCTTCAGCAACAGATGGGGTCCCCTGTTCAGCCCAACCCCATGA
GCCCCCAGCAGCATATGCTCCCAAATCAGGCCCAGTCCCCACACCTACAAGGCCAGCAGATCCCTAATTCTCTCTC
CAATCAAGTGCGCTCTCCCCAGCCTGTCCCTTCTCCACGGCCACAGTCCCAGCCCCCCCACTCCAGTCCTTCCCCA
AGGATGCAGCCTCAGCCTTCTCCACACCACGTTTCCCCACAGACAAGTTCCCCACATCCTGGACTGGTAGTTGCCC
AGGCCAACCCCATGGAACAAGGGCATTTTGCCAGCC
```

*Fig. 15P*

63_16500.edit

```
AGCGTGGTCGCGGCCGAGGTCCATTTTCTCCCTGACGGTCCCACTTCTCTCCAATCTTGTAGTTCACACCATTGTC
ATGGCACCATCTAGATGAATCACATCTGAAATGACCACTTCCAAAGCCTAAGCACTGGCACAACAGTTTAAAGCCT
GATTCAGACATTCGTTCCCACTCATCTCCAACGGCATAATGGGAAACTGTGTAGGGGTCAAAGCACGAGTCATCCG
TAGGTTGGTTCAAGCCTTCGTTGACAGAGTTGCCCACGGTAACAACCTCTTCCCGAACCTTATGCCTCTGCTGGTC
TTTCAGTGCCTCCACTATGATGTTGTAGGTGGCACCTCTGGTGAGGACCTGCCCGGGCGGCCCGCTCGA
```

64_16493.edit

```
AGCGTGGTCGCGGCCGAGGTGTGCCCCAGACCAGGAATTCGGCTTCGACGTTGGCCCTGTCTGCTTCCTGTAAACT
CCCTCCATCCCAACCTGGCTCCCTCCCACCCAACCAACTTTCCCCCCAACCCGGAAACAGACAAGCAACCCAAACT
GAACCCCCTCAAAAGCCAAAAAAATGGGAGACAATTTCACATGGACTTTGGAAAATATTTTTTTCCTTTGCATTCA
TCTCTCAAACTTAGTTTTTATCTTTGACCAACCGAACATGACCAAAAACCAAAAGTGACCTGCCCGGGCGGCCGCT
CGA
```

64_16500.edit

```
TCGAGCGGCCGCCCGGGCAGGTCCTCACCAGAGGTGCCACCTACAACATCATAGTGGAGGCACTGAAAGACCAGCA
GAGGCATAAGGTTCGGGAAGAGGTTGTTACCGTGGGCAACTCTGTCAACGAAGGCTTGAACCAACCTACGGATGAC
TCGTGCTTTGACCCCTACACAGTTTCCCATTATGCCGTTGGAGATGAGTGGGAACGAATGTCTGAATCAGGCTTTA
AACTGTTGTGCCAGTGCTTAGGCTTTGGAAGTGGTCATTTCAGATGTGATTCATCTAGATGGTGCCATGACAATGG
TGTGAACTACAAGATTGGAGAGAAGTGGGACCGTCAGGGAGAAAATGGACCTCGGCCGCGACCACGCT
```

```
TGTAAAAACTTGTTTTTAATTTTGTATAAAATAAAGGTGGTCCATGCCCACGGGGGCTGTAGGAAATCCAAGCAGACCA
GCTGGGGTGGGGGGATGTAGCCTACCTCGGGGGACTGTCTGTCCTCAAAACGGGCTGAGAAGGCCCGTCAGGGGCCCAG
GTCCCACAGAGAGGCCTGGGATACTCCCCCAACCCGAGGGGCAGACTGGGCAGTGGGGAGCCCCCATCGTGCCCCAGAG
GTGGCCACAGGCTGAAGGAGGGGCCTGAGGCACCGCAGCCTGCAACCCCCAGGGCTGCAGTCCACTAACTTTTTACAGA
ATAAAAGGAACATGGGGATGGGGAAAAAAGCACCAGGTCAGGCAGGGCCCGAGGGCCCCAGATCCCAGGAGGGCCAGGA
CTCAGGATGCCAGCACCACCCTAGCAGCTCCCACAGCTCCTGGCACAGGAGGCCGCCACGGATTGGCACAGGCCGCTGC
TGGCCATCACGCCACATTTGGAGAACTTGTCCCGACAGAGGTCAGCTCGGAGGAGCTCCTCGTGGGCACACACTGTACG
AACACAGATCTCCTTGTTAATGACGTACACACGGCGGAGGCTGCGGGGACAGGGCACGGGAGGTCTCAGCCCCACTT
```

13736.2

```
ATGGCTGCTGGATTTAGGTGGTAATAGGGGCTGTGGGCCATAAATCTGAAGCCTTGAGAACCTTGGGTCTGGAGAGCCA
TGAAGAGGGAAGGAAAAGAGGGCAAGTCCTGAACCTAACCAATGACCTGATGGATTGCTCGACCAAGACACAGAAGTGA
AGTCTGTGTCTGTGCACTTCCCACAGACTGGAGTTTTTGGTGCTGAATAGAGCCAGTTGCTAAAAAATTGGGGGTTTGG
TGAAGAAATCTGATTGTTGTGTGTATTCAATGTGTGATTTTAAAAATAAACAGCAACAACAATAAAAACCCTGACTGGC
TGTTTTTTCCCTGTATTCTTTACAACTATTTTTTGACCCTCTGAAAATTATTATACTTCACCTAAATGGAAGACTGCTG
TGTTTGTGGAAATTTTGTAATTTTTTAATTTATTTTATTCTCTCTCCTTTTTATTTTGCCTGCAGAATCCGTTGAGAGA
CTAATAAGGCTTAATATTTAATTGATTTGTTTAATATGTATATAAAT
```

13744.2-13696.2

```
GGCATGCGAGCGCACTCGGCGGACGCAAGGGCGGCGGGGAGCACACGGAGCACTGCAGGCGCCGGGTTGGGACAGCGTC
TTCGCTGCTGCTGGATAGTCGTGTTTTCGGGGATCGAGGATACTCACCAGAAACCGAAAATGCCGAAACCAATCAATGT
CCGAGTTACCACCATGGATGCAGAGCTGGAGTTTGCAATCCAGCCAAATACAACTGGAAAACAGCTTTTTGATCAGGTG
GTAAAGACTATCGGCCTCCGGGAAGTGTGGTACTTTGGCCTCCACTATGTGGATAATAAAGGATTTCCTACCTGGCTGA
AGCTGGATAAGAAGGTGTCTGCCCAGGAGGTCAGGAAGGAGAATCCCCTCCAGTTCAAGTTCCGGGCCAAaGTTCTACC
CTGAAGATGTGGCTGAGGAGCTCATCCAGGACATCACCCAGAAACTTTTCTTCCTTCAAGTGAAGGAAGGAATCCTTAG
CGATGAGATCTACTGCCCCCCCTTGARACTGCCGTGCTCTTGGGGTCCTACGCTTGTGCATGCCAAGTTTGGGGACTACC
ACCAAGAAG
```

13746.1&2-13720.1&2

```
GAAGGAGTCGGGATACTCAGCATTGATGCACCCCAATTTCAAAGCGGCATTCTTCGGCAGGTCTCTGGGACAATCTCTA
GGGTCACTACCTGGAAACTCGTTAGGGTACAACTGAATGCTGAAAGGAAAGAACACCTGCAGAACCGGACAGAAATTCA
CCCCGGCGATCAGCTGATTGATCTCGGTCGACCAGAAGTCATGGCTAAAGATGACGAGGACGTTGTCAATTCCCTGGGC
TTTTCGAAGTGAGTCCAGCAGCAGTCTGAGGTATTCGGGCCGGTTATGCACCTGGACCACCAGCACCAGCTCCCGGGGG
GCCCAGGTGCCAGCCTTATCTACATTCCTCAGGGTCTGATCAAAGTTCAGCTGGTACACCAGGGACCGGTACCGCAGCG
TCAGGTTGTCCGCTCGGGCTGGGGGACCGCCGGGACCAGGGAAGCCGCCGACACGTTGGAGACCCTGCGGATGCCCACA
GCCACAGAGGGGTGGTCCCCACCGCGGCCGCCGGCACCCCGCGCGGGTTCGGCGTCCAGCAACGGTGGGGCGAGGGCCT
CGTTCTTCCTTTGTCGCCCATTGCTGCTCCAGAGGACGAAGCCGCAGGCGGCCACCACGAGCGTCAGGATTAGCACCTT
CCGTTTGTAGATGCGGAACCTCATGGTCTCCAGGGCCGGGAGCGCAGCTACAGCTCGAGCGTCGGCGCCGCCGCTAGGA
GCCGCGGCTCGGCTTCGTCTCCGTCCTCTCCATTCAGCACCACGGGTCCCGGAAAAAGCTCAGCCSCGGTCCCAACCGC
ACCCTAGCTTCGTTACCTGCGCCTCGCTTG
```

*Fig. 15Q*

16501.edit

```
TCGAGCGGCCGCCCGGGCAGGTACCGGGGTGGTCAGCGAGGAGCCATTCACACTGAACTTCACCATCAACAACCTG
CGGTATGAGGAGAACATGCAGCACCCTGGCTCCAGGAAGTTCAACACCACGGAGAGGGTCCTTCAGGGCCTGCTCA
GGTCCCTGTTCAAGAGCACCAGTGTTGGCCCTCTGTACTCTGGCTGCAGACTGACTTTGCTCAGACCTGAGAAACA
TGGGGCAGCCACTGGAGTGGACGCCATCTGCACCCTCCGCCTTGATCCCACTGGTNCTGGACTGGACANANAGCGG
CTATACTTGGGAGCTGANCCNAACCTTTGGCGGNGACNCCNCTT
```

16501.2.edit

```
GAGGACTGGCTCAGCTCCCAGTATAGCCGCTCTCTGTCCAGTCCAGGACCAGTGGGATCAAGGCGGAGGGTGCAGA
TGGCGTCCACTCCAGTGGCTGCCCCATGTTTCTCAAGTCTGAGCAAAGNCAGTCTGCAGCCAGAGTACAGAGGGCC
AACACTGGTGCTCTTGAACAGGGACCTGAGCAGGCCCTGAAGGACCCTCTCCGTGGTGTTGAACTTCCTGGAGCCA
GGGTGCTGCATGTTCTCCTCATACCGCAGGTTGTTGATGGTGAAGTTCAGTGTGAATGGCTCCTCGCTGACCACCC
```

16502.1.edit

```
AGCGTGGTCGCGGCCGAGGTCCACCACACCCAATTCCTTGCTGGTATCATGGCAGCCGCCACGTGCCAGGATTACC
GGCTACATCATCAAGTATGAGAAGCCTGGGTCTCCTCCCAGAGAAGTGGTCCCTCGGCCCCGCCCTGGTGTCACAG
AGGCTACTATTACTGGCCTGGAACCGGGAACCGAATATACAATTTATGTCATTGCCCTGAAGAATAATCAGAAGAG
CGAGCCCCTGATTGGAAGGAAAAAGACAGACGAGCTTCCCCAACTGGTAACCCTTCCACACCCCAATCTTCATGGA
CCANANANCTTGGATNGTCCTTTCACNGGTTNAAAAAACCCTTTTCGCCCCCCCACCTTGGGGATTAACCTTGGGA
AANGGGGATTTNACCNTTCC
```

16502.2.edit

```
TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCCAGTGTCATACCCAGGGNGGGTGACCAAAGGGGGTCNTTTNGACCTGGNGAAAGGAACCA
TCCAAAANCTCTGNCCCATG
```

CAGATTTTTATTTGCAGTCGTCACTGGGGCCGTTTCTTGCTGCTTATTTGTCTGCTAGCCTGCTCTTCCAGCTGCA
TGGCCAGGCGCAAGGCCTTGATGACATCTCGCAGGGCTGAGAAATGCTTGGCTTGCTGGGCCAGAGCAGATTCCGC
TTTGTTCACAAAGGTCTCCAGGTCATAGTCTGGCTGCTCGGTCATCTCAGAGAGCTCAAGCCAGTCTGGTCCTTGC
TGTATGATCTCCTTGAGCTCTTCCATAGCCTTCTCCTCCAGCTCCCTGATCTGAGTCATGGCTTCGTTAAAGCTGG
ACATCTGGGAAGACAGTTCCTCCTCTTCCTTGGATAAATTGCCTGGAATCAGCGCCCGTTAGAGCAGGCTTCCAT
CTCTTCTGTTTCCATTTGAATCAACTGCTCTCCACTGGGCCCACTGTGGGGGCTCAGCTCCTTGACCCTGCTGCAT
ATCTTAAGGGTGTTTAAAGGATATTCACAGGAGCTTATGCCTGGT 14347.2

CTCCTCTTGGTACATGAACCCAAGTTGAAAGTGGACTTAACAAAGTATCTGGAGAACCAAGCATTCTGCTTTGACT
TTGCATTTGATGAAACAGCTTCGAATGAAGTTGTCTACAGGTTCACAGCAAGGCCACTGGTACAGACAATCTTTGA
AGGTGGAAAAGCAACTTGTTTTGCATATGGCCAGACAGGAAGTGGCAAGACACATACTATGGGCGGAGACCTCTCT
GGGAAAGCCCAGAATGCATCCAAAGGGATCTATGCCATGGCCTTCCGGGACGTCTTCTTCTGAAGAATCAACCCTG
CTACCGGAAGTTGGGCCTGGAAGTCTATGTGACATTCTTCGAGATCTACAATGGGAAGCTGTTTGACCTGCTCAAC
AAGAAGGCCAAGCTTGCGCGTGCTGGAAGACGGCAAGCAACAGGTGCAAGTGGTGGGGGCTTGCAGGAACATCTGG
NTAACTCTGCTTGATGATGGCANTCAAGATGATCGACATGGGCAGCGCCTGCAGA 14348.2&14350.1&2

TCCCGAATTCAAGCGACAAATTGGAWAGTGAAATGGAAGATGCCTATCATGAACATCAGGCAAATCTTTTGCGCCA
AGATCTGATGAGACGACAGGAAGAATTAAGACGCATGGAAGAACTTCACAATCAAGAAATGCAGAAACGTAAAGAA
ATGCAATTGAGGCAAGAGGAGGAACGACGTAGAAGAGAGGAAGAGATGATGATTCGTCAACGTGAGATGGAAGAAC
AAATGAGGCGCCAAAGAGAGGAAAGTTACAGCCGAATGGGCTACATGGATCCACGGGAAAGAGACATGCGAATGGG
TGGCGGAGGAGCAATGAACATGGGAGATCCCTATGGTTCAGGAGGCCAGAAATTTCCACCTCTAGGAGGTGGTGGT
GGCATAGGTTATGAAGCTAATCCTGGCGTTCCACCAGCAACCATGAGTGGTTCCATGATGGGAAGTGACATGCGTA
CTGAGCGCTTTGGGCAGGGAGGTGCGGGGCCTGTGGGTGGACAGGGTCCTAGAGGAATGGGGCCTGGAACTCCAGC
AGGATATGGTAGAGGGAGAGAAGAGTACGAAGGC 14349.1&2

TTCGTGAAGACCCTGACTGGTAAGACCATCACTCTCGAAGTGGAGCCCGAGTGACACCATTGAGAATGTCAAGGCA
AAGATCCAAGACAAGGAAGGCATCCCTCCTGACCAGCAKAGGTTGATCTTTGCTGGGAAACAGCTGGAAGATGGAC
GCACCCTGTCTGACTACAACATCCAGAAAGAGTCCACCCTGCACCTGGTGCTCCGTCTCAGAGGTGGGATGCAAAT
CTTCGTGAAGACCCTGACTGGTAAGACCATCACCCTCGAGGTGGAGCCCAGTGACACCATCGAGAATGTCAAGGCA
AAGATCCAAGATAAGGAAGGCATCCCTCCTGATCAGCAGAGGTTGATCTTTGCTGGGAAACAGCTGGAAGATGGAC
GCACCCTGTCTGACTACAACATCCAGAAAGAGTCCACTCTGCACTTGGTCCTGCGCTTGAGGGGGGGTGTCTAAGT
TTCCCCTTTTAAGGTTTCAACAAATTTCATTGCACTTTCCTTTCAATAAAGTTGTTGCATTC

*Fig. 15R*

16503.1.edit

AGCGTGGNCGCGGCCGAGGTCTGAGGATGTAAACTCTTCCCAGGGGAAGGCTGAAGTGCTGACCATGGTGCTACTG
GGTCCTTCTGAGTCAGATATGTGACTGATGNGAACTGAAGTAGGTACTGTAGATGGTGAAGTCTGGGTGTCCCTAA
ATGCTGCATCTCCAGAGCCTTCCATCATTACCGTTTCTTCTTTTGCTATGGGATGAGACACTGTTGAGTATTCTCT
AAAGTCACCACTGAAATCTTCCTCCAAAGGAAAACCTGTGGAAAAGCCCCTTATTTCTGCCCCATAATTTGGTTCT
CCTAATCNCTCTGAAATCACTATTTCCCTGGAANGTTTGGGAAAAANNGGGCNACCTGNCANTGGAAANTGGATAN
AAAGATCCCACCATTTTACCCAACNAGCAGAAAGTGGGAANGGTACCGAAAAGCTCCAAGTAANAAAAAGGAGGGA
AGTAAAGGTCAAGTGGGCACCAGTTTCAAACAAAACTTTCCCCAAACTATANAACCCA

16503.2.edit

AAGCGGCCGCCCGGGCAGGNNCAGNAGTGCCTTCGGGACTGGGNTCACCCCCAGGTCTGCGGCAGTTGTCACAGCG
CCAGCCCCGCTGGCCTCCAAAGCATGTGCAGGAGCAAATGGCACCGAGATATTCCTTCTGCCACTGTTCTCCTACG
TGGTATGTCTTCCCATCATCGTAACACGTTGCCTCATGAGGGTCACACTTGAATTCTCCTTTTCCGTTCCCAAGAC
ATGTGCAGCTCATTTGGCTGGCTCTATAGTTTGGGGAAAGTTTGTTGAAACTGTGCCACTGACCTTTACTTCCTCC
TTCTCTACTGGAGCTTTTCCGTACCTTCCACTTCTGCTGNTGGNAAAAAGGGNGGAACNTCTTATCAATTTCATTGG
ACAGTANCCCNCTTTCTNCCCAAAACATNCAAGGGAAAATATTGATTNCNAGAGCGGATTAAGGAACAACCCNAAT
TATGGGGGCCAGAAATAAAGGGGGCTTTTCCACAGGTNTTTTCCT

16504.1.edit

TCGAGCGGCCGCCCGGGCAGGTCTGCAGGCTATTGTAAGTGTTCTGAGCACATATGAGATAACCTGGGCCAAGCTA
TGATGTTCGATACGTTAGGTGTATTAAATGCACTTTTGACTGCCATCTCAGTGGATGACAGCCTTCTCACTGACAG
CAGAGATCTTCCTCACTGTGCCAGTGGGCAGGAGAAAGAGCATGCTGCGACTGGACCTCGGCCGCGACCACGCT

16504.2.edit

AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

```
GCGCGGGTGCGTGGGCCACTGGGTGACCGACTTAGCCTGGCCAGACTCTCAGCACCTGGAAGCGCCCCGAGAGTGA
CAGCGTGAGGCTGGGAGGGAGGACTTGGCTTGAGCTTGTTAAACTCTGCTCTGAGCCTCCTTGTCGCCTGCATTTA
GATGGCTCCCGCAAAGAAGGGTGGCGAGAAGAAAAAGGGCCGTTCTGCCATCAACGAAGTGGTAACCCGAGAATAC
ACCATCAACATTCACAAGCGCATCCATGGAGTGGGCTTCAAGAAGCGTGCACCTCGGGCACTCAAAGAGATTCGGA
AATTTGCCATGAAGGAGATGGGAACTCCAGATGTGCGCATTGACACCAGGCTCAACAAAGCTGTCTGGGCCAAAGG
AATAAGGAATGTGCCATACCGAATCCGTGTGCGGCTGTCCAGAAAACGTAATGAGGATGAAGATTCACCAAATAAG
CTATATACTTTGGTTACCTATGTACCTGTTACCACTTTCAAAAATCTACAGACAGTCAATGTGGATGAGAACTAAT
CGCTGATCGT
```

14353.1

```
AATTCTTTATTTAAATCAACAAACTCATCTTCCTCAAGCCCCAGACCATGGTAGGCAGCCCTCCCTCTCCATCCCC
TCACCCCACCCCTTAGCCACAGTGAAGGGAATGGAAAATGAGAAGCCACGAGGGCCCCTGCCAGGGAAGGCTGCCC
CAGATGTGTGGTGAGCACAGTCAGTGCAGCTGTGGCTGGGGCAGCAGCTGCCACAGGCTCCTCCCTATAAATTAAG
TTCCTGCAGCCACAGCTGTGGGAGAAGCATACTTGTAGAAGCAAGGCCAGTCCAGCATCAGAAGGCAGAGGCAGCA
TCAGTGACTCCCAGCCATGGAATGAACGGAGGACACAGAGCTCAGAGACAGAACAGGCCAGGGGGAAGAAGGAGAG
ACAGAATAGGCCAGGGCATGGCGGTGAGGGA
```

14353.2

```
TGATGAATCTGGGTGGGCTGGCAGTAGCCCGAGATGATGGGCTCTTCTCTGGGGATCCCAACTGGTTCCCTAAGAA
ATCCAAGGAGAATCCTCGGAACTTCTCGGATAACCAGCTGCAAGAGGGCAAGAACGTGATCGGGTTACAGATGGGC
ACCAACCGCGGGGCGTCTCANGCAGGCATGACTGGCTACGGGATGCCACGCCAGATCCTCTGATCCCACCCCAGGC
CTTGCCCCTGCCCTCCCACGAATGGTTAATATATATGTAGATATATATTTTAGCAGTGACATTCCCAGAGAGCCCC
AGAGCTCTCAAGCTCCTTTCTGTCAGGGTGGGGGGTTCAAGCCTGTCCTGTCACCTCTGAAGTGCCTGCTGGCATC
CTCTCCCCCATGCTTACTAATACATTCCCTTCCCCATAGCC
```

17182.1&2

```
AGCGGAGCTCCCTCCCCTGGTGGCTACAACCCACACACGCCAGGCTCAGGCATCGAGCAGAACTCCAGCGACTGGG
TAACCACTGACATTCAGGTGAAGGTGCGGGACACCTACCTGGATACACAGGTGGTGGGACAGACAGGTGTCATCCG
CAGTGTCACGGGGGGCATGTGCTCTGTGTACCTGAAGGACAGTGAGAAGGTTGTCAGCATTTCCAGTGAGCACCTG
GAGCCTATCACCCCCACCAAGAACAACAAGGTGAAAGTGATCCTGGGCGAGGATCGGGAAGCCACGGGCGTCCTAC
TGAGCATTGATGGTGAGGATGGCATTGTCCGTATGGACCTTGATGAGCAGCTCAAGATCCTCAACCTCCGCTTCCT
GGGGAAGCTCCTGGAAGCCTGAAGCAGGCAGGGCCGGTGGACTTCGTCGGATGAAGAGTGATCCTCCTTCCTTCCC
TGGCCCTTGGCTGTGACACAAGATCCTCCTGCAGGGCTAGGCGGATTGTTCTGGATTTCCTTTTGTTTTTCCTTTT
AGGTTTCCATCTTTTCCCTCCCTGGTGCTCATTGGAATCTGAGTAGAGTCTGGGGGAGGGTCCCCACCTTCCTGTA
CCTCCTCCCCACAGCTTGCTTTTGTTGTACCGTCTTTCAATAAAAAGAAGCTGTTTGGTCTA
```

*Fig. 15S*

16505.1.edit

```
CGAGCGGCCGCCCGGGCAGGTCCAGACTCCAATCCAGAGAACCACCAAGCCAGATGTCAGAAGCTACACCATCACA
GGTTTACAACCAGGCACTGACTACAAGATCTACCTGTACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGCTACATCATCAAGTATGAGAAGCCTGGGTCTCCTCCCAGAGAAGTG
GTCCCTCGGCCCCGCCCTGGTGNCACAGAAGCTACTATTACTGGCCTGGAACCGGGAACCGAATATACAATTTATG
TCATTGCCCTGAAGAATAATCANAAGAGCGAGCCCCTGATTGGAAGG
```

16505.2.edit

```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTGTCTTTTTCCTTCCAATCAGGGGCTCGCTCTTCTGATTATTCTTCAGGGCAATGACAT
AAATTGTATATTCGGTTCCCGGTTCCAGGCCAGTAATAGTAGCCTCTGTGACACCAGGGCGGGGCCGAGGGACCAC
TTCTCTGGGAGGAGACCCAGGCTTCTCATACTTGATGATGTANCCGGTAATCCTGGCACCGTGGCGGCTGCCATGA
TACCAGCAAGGAATTGGGTGTGGTGGCCAAGAAACGCAGGTTGGATGGTGCATCAATGGCAGTGGAGGCGTCGATN
ACCACAGGGGAGCTCCGANCATTGTCATTCAAGGTGGACAGGTAGAATCTTGTAATCAGGTGCCTGGTTTGTAAAC
CTG
```

16506.1.edit

```
TCGAGCGGCCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGCCCAGAAGAACTGGTACATCAGCAAGAACC
CCAAGGACAAGAAGCATGTCTGGTTCGGCGAAAGCATGACCGATGGATTCCAGTTCGAGTATGGCGGCCAGGGCTC
CGACCCTGCCGATGTGGACCTCGGCCGCGACCACGCTAAGCCCGAATTCCAGCACACTGGCGGCCGTTACTAGTGG
GATCCGAGCTTCGGTACCAAGCTTGGCGTAATCATGGGNCATAGCTGTTTCCTGNGTGAAAATGGTATTCCGCTTC
ACAATTTCCCAC
```

16506.2.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAAGCTCTTGAAGGGTGGTGTCCACCTCG
AGGTCACGGTCACGAAACCTGCCCGGGCGGCCGCTCGA
```

```
GGTTCACAGCACTGCTGCTTGTGTGTTGCCGGCCAGGAATTCCAGGCTCACAAGGCTATCTTAGCAGCTCGTTCTC
CGGTTTTTAGTGCCATGTTTGAACATGAAATGGAGGAGAGCAAAAAGAATCGAGTTGAAATCAATGATGTGGAGCC
TGAAGTTTTTAAGGAAATGATGTGCTTCATTTACACGGGGAAGGCTCCAAACCTCGACAAAATGGCTGATGATTTG
CTGGCAGCTGCTGACAAGTATGCCCTGGAGCGCTTAAAGGTCATGTGTGAGGATGCCCTCTGCAGTAACCTGTCCG
TGGAGAACGCTGCAGAAATTCTCATCCTGGCCGACCTCCACAGTGCAGATCAGTTGAAAACTCAGGCAGTGGATTT
CATCAACTATCATGCTTCGGATGTCTTGGAGACCTCTTGGG
```

17186.1&2

```
TCGTAGCCATTTTTCTGCTTCTTTGGAGAATGACGCCACACTGACTGCTCATTGTCGTTGGTTCCATGCCAATTGG
TGAAATAGAACCTCATCCGGTAGTGGAGCCGGAGGGACATCTTGTCATCAACGGTGATGGTGCGATTTGGAGCATA
CCAGAGCTTGGTGTTCTCGCCATACAGGGCAAAGAGGTTGTGACAAAGAGGAGAGATACGGCATGCCTGTGCAGCC
CTGATGCACAGTTCCTCTGCTGTGTACTCTCCACTGCCCAGCCGGAGGGGCTCCCTGTCCGACAGATAGAAGATCA
CTTCCACCCCTGGCTTG
```

17187.1&2

```
TGGCACACTGCTCTTAAGAAACTATGAWGATCTGAGATTTTTTTGTGTATGTTTTTGACTCTTTTGAGTGGTAATC
ATATGTGTCTTTATAGATGTACATACCTCCTTGCACAAATGGAGGGGAATTCATTTTCATCACTGGGAGTGTCCTT
AGTGTATAAAAACCATGCTGGTATATGGCTTCAAGTTGTAAAAATGAAAGTGACTTTAAAAGAAAATAGGGGATGG
TCCAGGATCTCCACTGATAAGACTGTTTTTAAGTAACTTAAGGACCTTTGGGTCTACAAGTATATGTGAAAAAAAT
GAGACTTACTGGGTGAGGAAATTCATTGTTTAAAGATGGTCGTGTGTGTGTGTGTGTGTGTGTTGTGTTGTG
TTTTGTTTTTTAAGGGAGGGAATTTATTATTTACCGTTGCTTGAAATTACTGKGTAAATATATGTYTGATAATGAT
TTGCTYTTTGVCMACTAAAATTAGGVCTGTATAAGTWCTARATGCMTCCCTGGGKGTTGATYTTCCMAGATATTGA
TGATAMCCCTTAAAATTGTAACCYGCCTTTTTCCCTTTGCTYTCMATTAAAGTCTATTCMAAAG
```

17191.1&89.1

```
GGGGGTAGGCTCTTTATTAGACGGTTATTGCTGTACTACAGGGTCAGAGTGCAGTGTAAGCAGTGTCAGAGGCCCG
CGTTCAGCCCAAGAATGTGGATTTTCTCTCCCTATTGATCACAGTGGGTGGGTTTCTTCAGAAAAGCCCCAGAGGC
AGGGACCAGTGAGCTCCAAGGTTAGAAGTGGAACTGGAAGGCTTCAGTCACATGCTGCTTCCACGCTTCCAGGCTG
GGCAGCAAGGAGGAGATGCCCATGACGTGCCAGGTCTCCCCATCTGACACCAGTGAAGTCTGGTAGGACAGCAGCC
GCACGCCTGCCTCTGCCAGGAGGCCAATCATGGTAGGCAGCATTGCAGGGTCAGAGGTCTGAGTCCGGAATAGGAG
CAGGGGCAGGTCCCTGCGGAGAGGCACTTCTGGCCTGAAGACAGCTCCATTGAGCCCCTGCAGTACAGGYGTAGTG
CCTTGGACCAAGCCCACAGCCTGGTAAGGGGCGCCTGCCAGGGCCACGGCCAGGAGGCA
```

*Fig. 15T*

16507.1.edit

```
AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGNGCCGGNCCGCTCGAAAAGCCCNAATTTCCAGNCACACTTGGCCGGCCGTTACTACTG
```

16507.2.edit

```
TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT
```

16508.1.edit

```
CGAGCGGCCGCCCGGGCAGGTCCCCCCCCTTTTTTTTTTTTTTTTTTTTTTTTTTTTTTTTTTTTTTTTTTTTTTT
TTTTTTTTTTTTTTTTTT
```

16508.2.edit

```
AGCGTGGTCGCGGCCGAGGTCTGGCATTCCTTCGACTTCTCTCCAGCCGAGCTTCCCAGAACATCACATATCACTG
CAAAAATAGCATTGCATACATGGATCAGGCCAGTGGAAATGTAAAGAAGGCCCTGAAGCTGATGGGGTCAAATGAA
GGTGAATTCAAGGCTGAAGGAAATAGCAAATTCACCTACACAGTTCTGGAGGATGGTTGCACGAAACACACTGGGG
AATGGAGCAAAACAGTCTTTGAATATCGAACACGCAAGGCTGTGAGACTACCTATTGTAGATATTGCACCCTATGA
CATTGGTGGTCCTGATCAAGAATTTGGTGTGGACGTTGGCCCTGTTTGCTTTTTATAAACCAAACTCTATCTGAAA
TCCCAACAAAAAAAATTTAACTCCATATGTGNTCCTCTTGTTCTAATCTTGGCAACCAGTGCAAGTGACCGACAAA
ATTCCAGTTATTTATTTCCAAAATGTTTGGAAACAGTATAATTTGACAAAGAAAAAAGGATACTTCTCTTTTTTTG
GCTGGTCCACCAAATACAATTCAAAAGGCTTTTTGGTTTTATTTTTTTANCCAATTCCAATTTCAAAATGTCTCAA
TGGNGCTTATAATAAAATAAACTTTCACCCTTNTTTTNTGAT
```

```
TAATTTCTTAGTCGTTTGGAATCCTTAAGCATGCAAAAGCTTTGAACAGAAGGGTTCACAAAGGAACCAGGGTTGT
CTTATGGCATCCAGTTAAGCCAGAGCTGGGAATGCCTCTGGGTCATCCACATCAGGAGCAGAAGCACTTGACTTGT
CGGTCCTGCTGCCACGGTTTGGGCGCCCACCACGCCCACGTCCACCTCGTCCTCCCCTGCCGCCACGTCCTGGGCG
GCCAAGGTCTCCAAAATTGATCTCCAGCTGAGACGTTATATCATTTGCTGGCTTCCGGAAATGATGGTCCATAACC
GAATCTTCAGCATGAGCCTCTTCACTCTTTGATTTATGAAGAACAAATCCCTTCTTCCACTGCCCATCAGCACCTT
CATTTGGTTTTCGGATATTAAATTCTACTTTTGCCCGGTCCTTATTTTGAATAGCCTTCCACTCATCCAAAGTCAT
CTCTTTTGGACCCTCCTCTTTTACCTCTTCAACTTCATTCTCCTTATTTTCAGTGTCTGCCACTGGATGATGTTCT
TCACCTTCAGGTGTTTCCTCAGTCACATTTGATTGATCCAAGTCAGTTAATTCGTCTTTGACAGTTCCCCAGTTGT
GAGATCCGCTACCTCCACGTTTGTCCTCGTGCTTCAGGCCAGATCTATCACTTCCACTATGCCTATCAAATTCACG
TTTGCCACGAGAATCAAATCCATCTCCTCGGCCCATTCCACGTCCACGGCCCCCTCGACCTCTTCCAAGACCACCA
CGACCTCGAATAGGTCGGTCAATAATCGGTCTATCAACTGAAAATTCGCCTCCTTCACCCTTTTCTTCAAGTGGCT
TTTCGAATCTTCGTTCACGAGGTGGTCGCCTTTCTGGTCTTCTATCAATTATTTTCCCTTCACCCTGAAGTTGTTG
ATCAGGTCTTCTTCCAACTCGTGC
```

17193

```
AAGCGGATGGACCTGAGTCAGCCGAATCCTAGCCCCTTCCCTTGGGCCTGCTGTGGTGCTCGACATCAGTGACAGA
CGGAAGCAGCAGACCATCAAGGCTACGGGAGGCCCGGGGCGCTTGCGAAGATGAAGTTTGGCTGCCTCTCCTTCCG
GCAGCCTTATGCTGGCTTTGTCTTAAATGGAATCAAGACTGTGGAGACGCGCTGGCGTCCTCTGCTGAGCAGCCAG
CGGAACTGTACCATCGCCGTCCACATTGCTCACAGGGACTGGGAAGGCGATGCCTGTCGGGAGCTGCTGGTGGAGA
GACTCGGGATGACTCCTGCTCAGATTCAGGCCTTGCTCAGGAAAGGGGAAAAGTTTGGTCGAGGAGTGATAGCGGG
ACTCGTTGACATTGGGGAAACTTTGCAATGCCCCGAAGACTTAACTCCCGATGAGGTTGTGGAACTAGAAAATCAA
GCTGCACTGACCAACCTGAAGCAGAAGTACCTGACTGTGATTTCAAACCCCAGGTGGTTACTGGAGCCCATACCTA
GGAAAGGAGGCAAGGATGTATTCCAGGTAGACATCCCAGAGCACCTGATCCCTTTGGGGCATGAAGTGTGACAAGT
GTGGGCTCCTGAAAGGAATGTTCCRGAGAAACCAGCTAAATCATGGCACCTTCAATTTGCCATCGTGACGCAGACC
TGTATAAATTAGGTTAAAGATGAATTTCCACTGCTTTGGAGAGTCCCACCCACTAAGCACTGTGCATGTAAACAGG
TTCCTTTGCTCAGATGAAGGAAGTAGGGGGTGGGGCTTTCCTTGTGTGATGCCTCCTTAGGCACACAGGCAATGTC
TCAAGTACTTTGACCTTAGGGTAGAAGGCAAAGCTGCCAGTAAATGTCTCAGCATTGCTGCTAATTTTGGTCCTGC
TAGTTTCTGGATTGTACAAATAAATGTGTTGTAGATGA
```

*Fig. 15U*

16509.1.edit
```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAAGTAACCACCACTCCCAAAAATGGACCAGGACCAACAAAAA
CTAAAACTGCAGGTCCAGATCAAACAGAAAATGGACTATTGAAGGCTTGCAGCCCACAGTGGAAGTATGTGGNTAG
GNGTCTATGCTCAGAATCCCAAGCCGGAGAAAGTCAGCCTTCTGGTTTAGACTGCAGTAACCAACATTGATCGCCC
TAAAGGACTGGNCATTCACTTGGATGGTGGATGTCCAATTC
```

16509.2.edit
```
TCGAGCGGCCGCCCGGGCAGGTCCTTGCAGCTCTGCAGNGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGNGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGGTGGTCCTGNCCCATTTTTGGGAAGTGGGGGGTTACTC
TGTAACCAGTAACAGGGGAACTTGAAGGCAGCCACTTGACACTAATGCTGTTGTCCTGAACATCGGTCACTTGCAT
CTGGGGATGGTTTTGACAATTTCTGGTTCGGCAAATTAATGGAAATTGGCTTGCTGCTTGGCGGGGCTGNCTCCAC
GGGCCAGTGACAGCATAC
```

16510.1.edit
```
TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGTTGGNCCTGNNCCATTTTTGGGGAAGGGGTGGTTACTC
TTGTAACCAGTAACAGGGGAACTTGAAGCAGCCACTTGACACTAATGCTGGTGGCCTGAACATCGGTCACTTGCAT
CTGGGATGGTTTGGTCAATTTCTGTTCGGTAATTAATGGGAAATTGGCTTACTGGCTTGCGGGGGCTGTCTCCACG
GNCAGTGACAAGCATACACAGGNGATGGGTATAATCAACTCCAGGTTTAAGGCCNCTGATGGTA
```

16510.2.edit
```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGTAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGGACCAGGACCAACAAAAA
ACTAAAACTGCANGGTCCAGATCAAACAGAAATGACTATTGAAGGCTTGCAGCCCACAGTGGAGTATGTGGGTTAG
TGTCTATGCTCAGAATNCCAAGCGGAGAGAGTCAGCCTCTGGTTCAGACT
```

*Fig. 15U-1*

16443.1.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAACCAGTCCTGGTGCANGAC
GGTGAGGACGCTNACCACACGGTACGNGCTGGTGTACTGCTCCTCCCGCGGCTTTGTCTTGGCATTATGCACCTCC
ACGCCGTCCACGTACCAATTGAACTTGACCTCAGGGTCTTCGTGGCTCACGTCCACCACCACGCATGTAACCTCAA
ANCTCGGNCGCGANCACGC

16443.2.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGCGACA
TCGCCCGTGGAGTGGGAGAGCAATGGGCAGCCGGAGAACAACTACAAGACCACGCCTCCCGTGCTGGACTCCGACA
CCTGCCGGGCGGCCGCTCGA

16444.2.edit

AGCGTGGTTNCGGCCGAGGTCCCAACCAAGGCTGCANCCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGNCGCTCGA

16445.1.edit

AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGCCGCTCGA

*Fig. 15V*

16511.1.edit

```
TCGAGCGGCCGCCCGGGCAGGTCAGCGCTCTCAGGACGTCACCACCATGGCCTGGGCTCTGCTCCTCCTCACCCTC
CTCACTCAGGGCACAGGGTCCTGGGCCCAGTCTGCCCTGACTCAGCCTCCCTCCGCGTCCGGGTCTCCTGGACAGT
CAGTCACCATCTCCTGCACTGGAACCAGCAGTGACGTTGGTGCTTATGAATTTGTCTCCTGGTACCAACAACACCC
AGGCAAGGCCCCCAAACTCATGATTTCTGAGGTCACTAAGCGGCCCTCAGGGGTCCCTGATCGCTTCTCTGGCTCC
AAGTCTGGCAACACGGCCTCCCTGACCGTCTCTGGGCTCCANGCTGAGGATGANGCTGATTATTACTGGAAGCTCA
TATGCAGGCAACAACAATTGGGTGTTCGGCGGAAGGGACCAAGCTGACCGTNCTAAGGTCAAGCCCAAGGCTTGCC
CCCCTCGGTCACTCTGTTCCCACCCTCCTCTGAAGAAGCTTTCAAGCCAACAANGNCACACTGGGTGTGTCTCATA
AGTGGACTTTCTACCC
```

16511.2.edit

```
AGCGTGGTCGCGGCCGAGGTCTGTAGCTTCTGTGGGACTTCCACTGCTCAGGCGTCAGGCTCAGGTAGCTGCTGGC
CGCGTACTTGTTGTTGCTTTGNTTGGAGGGTGTGGTGGTCTCCACTCCCGCCTTGACGGGGCTGCTATCTGCCTTC
CAGGCCACTGTCACGGCTCCCGGGTAGAAGTCACTTATGAGACACACCAGTGTGGCCTTGTTGGCTTGAAGCTCCT
CAGAGGAGGGTGGGAACAGAGTGACCGAGGGGGCAGCCTTGGGCTGACCTAGGACGGTCAGCTTGGTCCCTCCGCC
GAACACCCAATTGTTGTTGCCTGCATATGAGCTGCAGTAATAATCAGCCTCATCCTCAGCCTGGAGCCCAGAGACN
GTCAAGGGAGGCCCGTGTTTGCCAAGACTTGGAAGCCAGANAAGCGATCAGGGACCCCTGAGGGCCGCTTTACNGA
CCTCAAAAAATCATGAATTTGGGGGGCCTTTGCCTGGGNGTTGGTTGGTNACCAGNAAAACAAAATTTCATAAAGC
ACCAACGTCACTGCTGGTTTCCAGTGCANGAANATGGTGAACTGAANTGTCC
```

16512.1.edit

```
AGCGTGGTCGCGGCCGAGGTCCAGCATCAGGAGCCCCGCCTTGCCGGCTCTGGTCATCGCCTTTCTTTTTGTGGCC
TGAAACGATGTCATCAATTCGCAGTAGCAGAACTGCCGTCTCCACTGCTGTCTTATAAGTCTGCAGCTTCACAGCC
AATGGCTCCCATATGCCCAGTTCCTTCATGTCCACCAAAGTACCCGTCTCACCATTTACACCCCAGGTCTCACAGT
TCTCCTGGGTGTGCTTGGCCCGAAGGGAGGTAAGTANACGGATGGTGCTGGTCCCACAGTTCTGGATCAGGGTACG
AGGAATGACCTCTAGGGCCTGGGCNACAAGCCCTGTATGGACCTGCCCGGGCGGGCCCGCTCGA
```

16512.2.edit

```
TCGAGCGGCCGCCCGGGCAGGTCCATACAGGGCTGTTGCCCAGGCCCTAGAGGNCATTCCTTGTACCCTGATCCAG
AACTGTGGGACCAGCACCATCCGTCTACTTACCTCCCTTCGGGCCAAGCACACCCAGGAGAACTGTGAGACCTGGG
GTGTAAATGGNGAGACGGGTACTTTGGTGGACATGAAGGAACTGGGCATATGGGAGCCATTGGCTGNGAAGCTGCA
NACTTATAAGACAGCAGTGGAGACGGCAGTTCTGCTACTGCGAATTGATGACATCGTTTCAGGCCACAAAAAGAAA
GGCGATGACCANAGCCGGCAAGGCGGGGCTTCCTGATGCTGGACCTCGGCCGCCGACCACGCTT
```

*Fig. 15V-1*

16445.2.edit

TCGAGCGGTCGCCCGGGCAGGTCCACATCGGCAGGGTCGGAGCCCTGGCCGCCATACTCGAACTGGAATCCATCGG
NCATGCTCTCGCCGAACCAGACATGCCTCTTGNCCTTGGGGTTCTTGCTGATGTACCAGNTCTTCTGGGCCACACT
GGGCTGAGTGGGGTACACGCAGGTCTCACCANTCTCCATGTTGCANAAGACTTTGATGGCATCCAGGTTGCAGCCT
TGGTTGGGGTCAATCCAGTACTCTCCACTCTTCCAGACAGAGTGGCACATCTTGAGGTCACGGCAGGTGCGGGCGG
GGTTCTTGACCTCGGTCGCGACCACGCT 16446.1.edit TCGAGCGGCCGCCCGGGCAGGTCCTCCTCAGAGCGGTAGCTGTTCTTATTGCCCCGGCAGCCTCCATAGATNAAGT
TATTGCANGAGTTCCTCTCCACGTCAAAGTACCAGCGTGGGAAGGATGCACGGCAAGGCCCAGTGACTGCGTTGGC
GGTGCAGTATTCTTCATAGTTGAACATATCGCTGGAGTGGACTTCAGAATCCTGCCTTCTGGGAGCACTTGGGACA
GAGGAATCCGCTGCATTCCTGCTGGTGGACCTCGGCCGCGACCACGCT 16446.2.edit AGCGTGGTCGCGGCCGAGGTCCACCAGCAGGAATGCAGCGGATTCCTCTGTCCCAAGTGCTCCCAGAAGGCAGGAT
TCTGAAGACCACTCCAGCGATATGTTCAACTATGAAGAATACTGCACCGCCAACGCAGTCACTGGGCCTTGCCGTG
CATCCTTCCCACGCTGGTACTTTGACGTGGAGAGGAACTCCTGCAATAACTTCATCTATGGAGGCTGCCGGGGCAA
TAAGAACAGCTACCGCTCTGAGGAGGACCTGCCCGGGCGGCCGCTCGA 16447.1.edit TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGCCAGAATGGCACATCTTGAGGTCACGGCANGTGCGGGCGG
GGTTCTTGACCTCGGCCGCGACCACGCT

*Fig. 15W*

16514.1.edit

```
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTGCTGTGCGCCACGTGTTGCTCANACAGGGTGTGCTGGGCATCAAGGTG
AAGATCATGCTGCCCTGGGACCCANCTGGCAAAAATGGCCCTTAAAAACCCCTTGCCNTGACCACGTGAACCATTT
GTGNGAACCCCAAGATGAANATACTTGCCCACCACCCCCATTC
```

16514.2.edit

```
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAGTGTCAACGTAGTAGTTAACAGGGTCTCCGCTGTGGATCATC
AGGCCATCCACAAACTTCATGGATTTAGCCCTCTGTCCTCGGAGTTTCCCAAAACACCACAACCTCGCCAGCCTTT
GGGCCCCACTTCTTCATGAATGAAACCGCAGCACACCATTANCAAGGCCCTTCCGCACAGGNAAGCCCTTCCTAAG
GAGTTTTGTAAACGCAAAAAACTCTTGCCTGGGGCAAATGGGCACACAGACCTNTANTNGGACCTTGGNCCGCGAA
CCACCGCTT
```

16515.1.edit

```
AGCGTGGTCGCGGCCGAGGTCTGGCCCTCCTGGCAAGGCTGGTGAAGATGGTCACCCTGGAAAACCCGGACGACCT
GGTGAGAGAGGAGTTGTTGGACCACAGGGTGCTCGTGGTTTCCCTGGAACTCCTGGACTTCCTGGCTTCAAAGGCA
TTAGGGGACACAATGGTCTGGATGGATTGAAGGGACAGCCCGGTGCTCCTGGTGTGAAGGGTGAACCTGGNGCCCC
TGGTGAAAATGGAACTCCAGGTCAAACAGGAGCCCGNGGGCTTCCTGGNGAGAGAGGACGTGTTGGTGCCCCTGGC
CCANACCTGCCCGGGCGGCCGCTCNAAAAGCCGAAATCCAGNACACTGGCGGCCGNTACTANTGGAATCCGAACTT
CGGTACCAAAGCTTGGCCGTAATCATGGCCATAGCTTGTTCCCTGGGGNGGAAATTGGTATTCCGCTNCCAATTCC
ACACAACATACCGAACCCGGAAAGCATTAAAGTGTAAAAGCCCTGGGGGGGCCTAAATGANGTGAGCNTAACTCNC
ATTTAATTGGCGTTGCGCTTCACTGCCCCGCTTTTCCAGTCCGGGNA
```

16515.2.edit

```
TCGAGCGGCCGCCCGGGCAGGTCTGGGCCAGGGGCACCAACACGTCCTCTCTCACCAGGAAGCCCACGGGCTCCTG
TTTGACCTGGAGTTCCATTTTCACCAGGGGCACCAGGTTCACCCTTCACACCAGGAGCACCGGGCTGTCCCTTCAA
TCCATCCAGACCATTGTGNCCCCTAATGCCTTTGAAGCCAGGAAGTCCAGGAGTTCCAGGGAAACCACGAGCACCC
TGTGGTCCAACAACTCCTCTCTCACCAGGTCGTCCGGGTTTTCCAGGGTGACCATCTTCACCAGCCTTGCCAGGAG
GGCCAGACCTCGGCCGCGACCACGCT
```

*Fig. 15W-1*

16447.2.edit

```
AGCGTGGTCGCGGCCGAGGTCAAGAAACCCCGCCCGCACCTGCCGTGACCTCAAGATGTGCCACTCTGGCTGGAAG
AGTGGAGAGTACTGGATTGACCCCAACCAAGGCTGCAACCTGGATGCCATCAAAGTCTTCTGCAACATGGAGACTG
GTGAGACCTGCGTGTACCCCACTCAGCCCAGTGTGGCCCAGAAGAACTGGTACATCAGCAAGAACCCCAAGGACAA
GAGGCATGTCTGGCTCGGCGAGAGCATGACCGATGGATTCCAGTTCGAGTATGGCGGCCAGGGCTCCGACCCTGCC
GATGTGGACCTGCCCGGGCGGCCGCTCGA
```

16449.1.edit

```
AGCGTGGTCGCGGCCGAGGTCCTGTCAGAGTGGCACTGGTAGAAGNTCCAGGAACCCTGAACTGTAAGGGTTCTTC
ATCAGTGCCAACAGGATGACATGAAATGATGTACTCAGAAGTGTCCTGNAATGGGGCCCATGANATGGTTGNCTGA
GAGAGAGCTTCTTGTCCTACATTCGGCGGGTATGGTCTTGGCCTATGCCTTATGGGGGTGGCCGTTGNGGGCGGTG
NGGTCCGCCTAAAACCATGTTCCTCAAAGATCATTTGTTGCCCAACACTGGGTTGCTGACCANAAGTGCCAGGAAG
CTGAATACCATTTCCAGTGTCATACCCAGGGTGGGTGACGAAAGGGGTCTTTTGAACTGTGGAAGGAACATCCAAG
ATCTCTGNTCCATGAAGATTGGGGTGTGGAAGGGTTACCAGTTGGGGAAGCTCGCTGTCTTTTTCCTTCCAATCAN
GGGCTCGCTCTTCTGAATATTCTTCAGGGCAATGACATAAATTGTATATTCGGTTCCCGGTTCCAGGCCAG
```

16450.1.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGANGAACATGGNTTT
AGGCGGACCACACCGGCCACAACGGGCACCCCCATAAGGCATAGGCCAAGAACATACCCGNCGAATGTAGGACAAG
AAGCTCTNTCTCANACAANCATCTCATGGGCCCCATTCCANGACACTTCTGAGTACATCANTTCATGGCATCCTGG
TGGCACTGATAAAAACCCTTACAGTTA
```

16450.2.edit

```
AGCGTGGTCGCGGGCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
NGGGCTCGCTCTTCTGATTATTCTTCAGGGCAATGACATAAATTGTATATTCGGNTCCCGGGTNCAGCCAATAATA
ATAACCCTCTGTGACACCANGGCGGGGCCGAAGGANCACT
```

*Fig. 15X*

16516.1.edit

ANCGTGGTCGCGGCCGAGGTCCTCACCAGAGGTGNCACCTACAACATCATAGTGGAGGCACTGAAAGACCANCAGA
GGCATAAGGTTCGGGAAGAGG

16516.2.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGTCCACGGTAACAACCTCTTCCCGAACCTTATGCCTCTGCTGG
TCTTTCAGTGCCTCCACTATGATGTTGTAGGTGGCACCTCTGGTGAGGACCTCNGNCCNGAACAACGCTTAAGCCC
GNATTCTGCAGAATAATCCCATCACACTTGGCGGCCGCTTCGANCATGCATCNTAAAAGGGGCCCCAATTTCCCCC
TTATAAGNGAANCCGTATTTNCCAATTTCACTGGNCCCGCCGNTTTTACAAACGNCGGTGAACTGGGGAAAAACCC
TGGCGGTTACCCAACTTTAATCGCCNTTGGCAGCACAATCCCCCCTTTTCGNCCANCNTGGGCGTAAATAACCGAA
AA

16517.1.edit

ANCGNGGTCGCGGCCGANGTNTTTTTTCTTNTTTTTT

16518.1.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GGGNGGTCAGCGTCCTCACCGTCCTGCACCAGAATTGGTTGAATGGCAAGGAGTACAAGNGCAAGGTTTCCAACAA
AGCCNTCCCAGCCCCCNTCGAAAAAACCATTTCCAAAGCCAAAGGGCAGCCCCGAGAACCACAGGTGTACACCCTG
CCCCCATCCCGGGAGGAAAAGANCAANAACCNGGTTCAGCCTTAACTTGCTTGGTCNAANGCTTTTTATCCCAACG
NACTTCCCCCNTGGAANTGGGAAAAACCAATGGGCCAANCCGAAAAACAATTACAANAACCCC

16518.2.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGAACACCTGGGGTTCTCGGGGCTTGCCCTTTGGTTTTGAANATGGTTTTC
TCGATGGGGGCTGGAAGGGCTTTGTTGNAAACCTTGCACTTGACTCCTTGCCATTCACCCAGNCCTGGNGCAGGAC
GGNGAGGACNCTNACCACACGGAACCGGGCTGGTGGACTGCTCC

*Fig. 15X-1*

16451.1.edit

```
AGCGTGGTCGCGGCCGAGGTCCTCACCAGAGGTACCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA
```

16451.2.edit

```
TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGNTGACAGAGTTGCCCACGGTAACAACCTCTTCCCGAACCTTATGCCTCTGCTGG
TCTTTCAGTGCCTCCACTATGATGTTGTAGGTGGTACCTCTGGTGAGGACCTCGGCCGCGACCACGCT
```

16452.1.edit

```
AGCGTGGCCGCGGCCGAGGTCCATTGGCTGGAACGGCATCAACTTGGAAGCCAGTGATCGTCTCAGCCTTGGTTCT
CCAGCTAATGGTGATGGNGGTCTCAGTAGCATCTGTCACACGAGCCCTTCTTGGTGGGCTGACATTCTCCAGAGTG
GTGACAACACCCTGAGCTGGTCTGCTTGTCAAAGTGTCCTTAAGAGCATAGACACTCACTTCATATTTGGCGNCCA
CCATAAGTCCTGATACAACCACGGAATGACCTGTCAGGAAC
```

16452.2.edit

```
TCGAGCGGCCGCCCGGGCAGGTCCTCAGACCGGGTTCTGAGTACACAGTCAGTGTGGTTGCCTTGCACGATGATAT
GGAGAGCCAGCCCCTGATTGGAACCCAGTCCACAGCTATTCCTGCACCAACTGACCTGAAGTTCACTCAGGTCACA
CCCACAAGCCTGAGCGCCCAGTGGACACCACCCAATGTTCAGCTCACTGGATATCGAGTGCGGGTGACCCCCAAGG
AGAAGACCGGACCAATGAAAGAAATCAACCTTGCTCCTGACAGCTCATCCGTGGTTGTATCAGGACTTATGGCGGC
CACCAAATATGAAGTGAGTGTCTATGCTCTTAAGGACACTTTGACAAGCAGACCAGCTCAGGGTGTTGTCACCACT
CTGGAGAATGTCAGCCCACCAAGAAGGGCTCGTGTGACAGATGCTACTGAGACCACCATCACCATTAGCTGGAGAA
CCAAGACTGAGACGATCACTGGCTTCCAAGTTGATGCCGTTCCAGCCAATGGACCTCGGCCGCGACCACGCTT
```

*Fig. 15Y*

16519.1.edit
AGCGTGGTCGCGGACGANGTCCTGTCAGAGTGGNACTGGTAGAAGTTCCANGAACCCTGAACTGTAAGGGTTCTTC
ATCAGTGCCAACAGGATGACATGAAATGATGTACTCAGAAGNGNCCTGGAATGGGGCCCATGANATGGTTGCC

16519.2.edit
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGGCACCCCCCCTGGGTATGAACCTGGGAA
AANGGNANTTAANCTTTCCTGGCA

16520.1.edit
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGGTNCCCTGGTACTGGGTTACAGANTAACCACCACTCCCAAAAATGGACCAGGAACCACAAAAA
CTTAAACTGCAGGGTCCAGATCAAAACAGAAATGACTATTGAANGCTTGCAGCCCACAGTGGGAGTATGNGGGTAG
TGNCTATGCTTCAGAATCCAAGCGGAAAAAANGTCAAGCCTTNTGGGTTCAA

16520.2.edit
TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGNCTGAACCAGAGG
CTGACTCTCTCCGCTTGGATTCTGAGCATAGACACTAACCACATACTCCACTGTGGGCTGCAANCCTTCAATAANN
CATTTCTGTTTGATCTGGACC

16521.2.edit
TCGAGCGGCCGCCCGGGCAGGTCTGGTGGGGTCCTGGCACACGCACATGGGGGNGTTGNTCTNATCCAGCTGCCCA
GCCCCCATTGGCGAGTTTGAGAAGGTGTGCAGCAATGACAACAANACCTTCGACTCTTCCTGCCACTTCTTTGCCA
CAAAGTGCACCCTGGAGGGCACCAAGAAGGGCCACAAGCTCCACCTGGACTACATCGGGCCTTGCAAATACATCCC
CCCTTGCCTGGACTCTGAGCTGACCGAATTCCCCCTTGCGCATGCGGGACTGGCTCAAGAACCGTCCTGGCACCCT
TGTATGANAGGGATGAAGACACNACCC

*Fig. 15Y-1*

16453.1.edit

```
AGCGTGGTCGCGGCCGAGGTCTGGCCGAACTGCCAGTGTACAGGGAAGATGTACATGTTATAGNTCTTCTCGAAGT
CCCGGGCCAGCAGCTCCACGGGGTGGTCTCCTGCCTCCAGGCGCTTCTCATTCTCATGGATCTTCTTCACCCGCAG
CTTCTGCTTCTCAGTCAGAAGGTTGTTGTCCTCATCCCTCTCATACAGGGTGACCAGGACGTTCTTGAGCCAGTCC
CGCATGCGCAGGGGGAATTCGGTCAGCTCAGAGTCCAGGCAAGGGGGGATGTATTTGCAAGGCCCGATGTAGTCCA
AGTGGAGCTTGTGGCCCTTCTTGGTGCCCTCCAAGGTGCACTTTGTGGCAAAGAAGTGGCAGGAAGAGTCGAAGGT
CTTGTTGTCATTGCTGCACACCTTCTCAAACTCGCCAATGGGGGCTGGGCAGACCTGCCCGGGCGGCCGCTCGA
```

16453.2.edit

```
TCGAGCGGCCGCCCGGGCAGGTCTGCCCAGCCCCCATTGGCGAGTTTGAGAAGGNGTGCAGCAATGACAACAAGAC
CTTCGACTCTTCCTGCCACTTCTTTGCCACAAAGTGCACCCTGGAGGGCACCAAGAAGGGCCACAAGCTCCACCTG
GACTACATCGGGCCTTGCAAATACATCCCCCCTTGCCTGGACTCTGAGCTGACCGAATTCCCCCTGCGCATGCGGG
ACTGGCTCAAGAACGTCCTGGTCACCCTGTATGAGAGGGATGAGGACAACAACCTTCTGACTGAGAAGCANAAGCT
GCGGGTGAAGAAATCCATGAGAATGANAAGCGCCTGNAGGCANGAGACCACCCCGTGGAGCTGCTGGCCCGGGAC
TTCGAGAAGAACTATAACATGTACATCTTCCCTGTACACTGGCAGTTCGGCCAGACCTCGGCCGCGACCACGCT
```

16454.1.edit

```
AGCGTGGNTGCGGACGACGCCCACAAAGCCATTGTATGTAGTTTTANTTCAGCTGCAAANAATACCNCCAGCATCC
ACCTTACTAACCAGCATATGCAGACA
```

16454.2.edit

```
TCGAGCGGTCGCCCGGGCAGGTCTGGGCGGATAGCACCGGGCATATTTTGGAATGGATGAGGTCTGGCACCCTGAG
CAGCCCAGCGAGGACTTGGTCTTAGTTGAGCAATTTGGCTAGGAGGATAGTATGCAGCACGGTTCTGAGTCTGTGG
GATAGCTGCCATGAAGNAACCTGAAGGAGGCGCTGGCTGGTANGGGTTGATTACAGGGCTGGGAACAGCTCGTACA
CTTGCCATTCTCTGCATATACTGGNTAGTGAGGCGAGCCTGGCGCTCTTCTTTGCGCTGAGCTAAAGCTACATACA
ATGGCTTTGNGGACCTCGGCCGCGACCACGCTT
```

*Fig. 15Z*

16522.1.edit

```
AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCGAAAGCCGAATTCCAGCACACTGGCGGCCG
GTACTAGTGGANCCNAACTTGGNANCCAACCTGGNGGAANTAATGGGCATAANCTGTTTCTGGGGGGAAATTGGTA
TCCNGTTTACAATTCCCNCACAACATACGAGCCGGAAGCATAAAAGNGTAAAAGCCTGGGGGNGGCCTANTGAAGT
GAAGCTAAACTCACATTAATTNGCGTTGCCGCTCACTGGCCCGCTTTTCCAGC
```

16522.2.edit

```
TCGAGCGGCCGCCCGGGCAGGTTTGGAAGGGGGATGCGGGGGAAGAGGAAGACTGACGGTCCCCCCAGGAGTTCAG
GTGCTGGGCACGGTGGGCATGTGTGAGTTTTGTCACAAGATTTGGGCTCAACTCTCTTGTCCACCTTGGTGTTGCT
GGGCTTGTGATCTACGTTGCAGGTGTAGGTCTGGGNGCCGAAGTTGCTGGAGGGCACGGTCACCACGCTGCTGAGG
GAGTAGAGTCCTGAGGACTGTANGACAGACCTCGGCCGNGACCACGCTAAGCCGAATTCTGCAGATATCCATCACA
CTGGCGGCCGCTCCGAGCATGCATTTTAGAGG
```

16523.1.edit

```
AGCGTGGNCGCGGACGANGACAACAACCCC
```

16523.2.edit

```
TCGAGCGGCCGCCCGGGCAGGNCCACATCGGCAGGGTCGGAGCCCTGGCCGCCATACTCGAACTGGAATCCATCGG
TCATGCTCTTGCCGAACCAGACATGCCTCTTGTCCTTGGGGTTCTTGCTGATGNACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCT
```

16524.1.edit

```
AGCGTGGTCGCGGCCGAGGTCCAGCCTGGAGATAANGGTGAAGGTGGTGCCCCCGGACTTCCAGGTATAGCTGGAC
CTCGTGGTAGCCCTGGTGAGAGAGGTGAAACTGGCCCTCCAGGACCTGCTGGTTTCCCTGGTGCTCCTGGACAGAA
TGGTGAACCTGGNGGTAAAGGAGAAAGAGGGGCTCCGGNTGANAAAGGTGAAGGAGGCCCTCCTGNATTGGCAGGG
GCCCCANGACTTAGAGGTGGAGCTGGCCCCCCTGGCCCCGAAGGAGGAAAGGGTGCTGCTGGTCCTCCTGGGCCAC
CTGG
```

*Fig. 15Z-1*

SEQUENCE LISTING

<160> NUMBER OF SEQ ID NOS: 312

<210> SEQ ID NO 1
<211> LENGTH: 461
<212> TYPE: DNA
<213> ORGANISM: Homo sapien

<400> SEQUENCE: 1

| | | | | | |
|---|---|---|---|---|---|
| ttagagaggc | acagaaggaa | gaagagttaa | aagcagcaaa | gccgggtttt | tttgttttgt | 60 |
| tttgttttgt | tttgttttga | gatggagtct | cactctgttg | cccaagctgg | agtacaacgg | 120 |
| catgatctca | gctcgctgca | acctccgcct | cccacgttca | agtgattctc | ctgcctcagc | 180 |
| ctcccaagta | gctgggatta | caggcgcccg | ccaccacgct | cagctaattt | tttttgtatt | 240 |
| tttagtagag | acagggtttc | accaggttgg | ccaggctgct | cttgaactcc | tgacctcagg | 300 |
| tgatccaccc | gcctcggcct | cccaaagtgc | tgggattaca | ggcgtgagcc | accacgcccg | 360 |
| gccccccaaag | ctgtttcttt | tgtctttagc | gtaaagctct | cctgccatgc | agtatctaca | 420 |
| taactgacgt | gactgccagc | aagctcagtc | actccgtggt | c | | 461 |

<210> SEQ ID NO 2
<211> LENGTH: 540
<212> TYPE: DNA
<213> ORGANISM: Homo sapien

<400> SEQUENCE: 2

| | | | | | |
|---|---|---|---|---|---|
| taggatgtgt | tggaccctct | gtgtcaaaaa | aaacctcaca | agaatccccc | tgctcattac | 60 |
| agaagaagat | gcatttaaaa | tatgggttat | tttcaacttt | ttatctgagg | acaagtatcc | 120 |
| attaattatt | gtgtcagaag | agattgaata | cctgcttaag | aagcttacag | aagctatggg | 180 |
| aggaggttgg | cagcaagaac | aatttgaaca | ttataaaatc | aactttgatg | acagtaaaaa | 240 |
| tggccttttct | gcatgggaac | ttattgagct | tattggaaat | ggacagttta | gcaaaggcat | 300 |
| ggaccggcag | actgtgtcta | tggcaattaa | tgaagtcttt | aatgaactta | tattagatgt | 360 |
| gttaaagcag | ggttacatga | tgaaaaaggg | ccacagacgg | aaaaactgga | ctgaaagatg | 420 |
| gtttgtacta | aaacccaaca | taatttctta | ctatgtgagt | gaggatctga | aggataagaa | 480 |
| aggagacatt | ctcttggatg | aaaattgctg | tgtagagtcc | ttgcctgaca | agatggaaa | 540 |

<210> SEQ ID NO 3
<211> LENGTH: 461
<212> TYPE: DNA
<213> ORGANISM: Homo sapien

<400> SEQUENCE: 3

| | | | | | |
|---|---|---|---|---|---|
| ttagagaggc | acagaaggaa | gaagagttaa | aagcagcaaa | gccgggtttt | tttgttttgt | 60 |
| tttgttttgt | tttgttttga | gatggagtct | cactctgttg | cccaagctgg | agtacaacgg | 120 |
| catgatctca | gctcgctgca | acctccgcct | cccacgttca | agtgattctc | ctgcctcagc | 180 |
| ctcccaagta | gctgggatta | caggcgcccg | ccaccacgct | cagctaattt | tttttgtatt | 240 |
| tttagtagag | acagggtttc | accaggttgg | ccaggctgct | cttgaactcc | tgacctcagg | 300 |
| tgatccaccc | gcctcggcct | cccaaagtgc | tgggattaca | ggcgtgagcc | accacgcccg | 360 |
| gccccccaaag | ctgtttcttt | tgtctttagc | gtaaagctct | cctgccatgc | agtatctaca | 420 |
| taactgacgt | gactgccagc | aagctcagtc | actccgtggt | c | | 461 |

<210> SEQ ID NO 4

```
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 4
tcttttcttt tcgatttcct tcaatttgtc acgtttgatt ttatgaagtt gttcaagggc      60
taactgctgt gtattatagc tttctctgag ttccttcagc tgattgttaa atgaatccat     120
ttctgagagc ttagatgcag tttcttttc aagagcatct aattgttctt taagtctttg     180
gcataattct tccttttctg atgactttt atgaagtaaa ctgatccctg aatcaggtgt     240
gttactgagc tgcatgtttt taattctttc gtttaatagc tgcttctcag ggaccagata     300
gataagctta ttttgatatt ccttaagctc ttgttgaagt tgtttgattt ccataatttc     360
caggtcacac tgtttatcca aaacttctag ctcagtcttt tgtgtttgct ttctgatttg     420
gacatcttgt agtctgcctg agatctgctg atgntttcca ttcactgctt ccagttccag     480
gtggagactt tnctttctgg agctcagcct gacaatgcct tcttgntccc t              531

<210> SEQ ID NO 5
<211> LENGTH: 531
<212> TYPE: DNA
<213> ORGANISM: Homo sapien

<400> SEQUENCE: 5
agccagatgg ctgagagctg caagaagaag tcaggatcat gatggctcag tttcccacag      60
cgatgaatgg agggccaaat atgtgggcta ttacatctga agaacgtact aagcatgata     120
aacagtttga taacctcaaa ccttcaggag gttacataac aggtgatcaa gcccgtactt     180
ttttcctaca gtcaggtctg ccggccccgg ttttagctga aatatgggcc ttatcagatc     240
tgaacaagga tgggaagatg gaccagcaag agttctctat agctatgaaa ctcatcaagt     300
taaagttgca gggccaacag ctgcctgtag tcctccctcc tatcatgaaa caccccta     360
tgttctctcc actaatctct gctcgttttg ggatgggaag catgcccaat ctgtccattc     420
atcagccatt gcctccagtt gcacctatag caacacccct gtcttctgct acttcaggga     480
ccagtattcc tccctaatg atgcctgctc ccctagtgcc ttctgttagt a                531

<210> SEQ ID NO 6
<211> LENGTH: 531
<212> TYPE: DNA
<213> ORGANISM: Homo sapien

<400> SEQUENCE: 6
aatagattta atgcagagtg tcaacttcaa ttgattgata gtggctgcct agagtgctgt      60
gttgagtagg tttctgagga tgcaccctgg cttgaagaga aagactggca ggattaacaa     120
tatctaaaat ctcacttgta ggagaaacca caggcaccag agctgccact ggtgctggca     180
ccagctccac caaggccagc gaagagccca aatgtgagag tggcggtcag gctggcacca     240
gcactgaagc caccactggt gctggcactg gcactggcac tgttattggt actggtactg     300
gcaccagtgc tggcactgcc actctcttgg gctttggctt tagcttctgc tcccgcctgg     360
atccgggctt tggcccaggg tccgatatca gcttcgtccc agttgcaggg ccggcagca     420
ttctccgagc cgagcccaat gcccattcga gctctaatct cggccctagc cttggcttca     480
gctgcagcct cagctgcagc cttcaaatcc gcttccatcg cctctcggta c              531
```

<210> SEQ ID NO 7
<211> LENGTH: 531
<212> TYPE: DNA
<213> ORGANISM: Homo sapien

<400> SEQUENCE: 7

| | | | | | |
|---|---|---|---|---|---|
| gccaagaaag | cccgaaaggt | gaagcatctg | gatggggaag | aggatggcag | cagtgatcag | 60 |
| agtcaggctt | ctggaaccac | aggtggccga | agggtctcaa | aggccctaat | ggcctcaatg | 120 |
| gcccgcaggg | cttcaagggg | tcccatagcc | ttttgggccc | gcagggcatc | aaggactcgg | 180 |
| ttggctgctt | gggcccggag | agccttgctc | tccctgagat | cacctaaagc | ccgtagggc | 240 |
| aaggctcgcc | gtagagctgc | caagctccag | tcatcccaag | agcctgaagc | accaccacct | 300 |
| cgggatgtgg | ccctttttgca | agggagggca | aatgatttgg | tgaagtacct | tttggctaaa | 360 |
| gaccagacga | agattcccat | caagcgctcg | gacatgctga | aggacatcat | caagaatac | 420 |
| actgatgtgt | accccgaaat | cattgaacga | gcaggctatt | ccttggagaa | ggtatttggg | 480 |
| attcaattga | aggaaattga | taagaatgac | cacttgtaca | ttcttctcag | c | 531 |

<210> SEQ ID NO 8
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 8

| | | | | | |
|---|---|---|---|---|---|
| gaggtctcac | tatgttgccc | aggctgttct | tgaactcctg | ggatcaagca | atccacccat | 60 |
| gttggtctcc | aaaagtgctg | ggatcatagg | cgtgagccac | ctcacccagc | caccaatttt | 120 |
| caatcaggaa | gacttttttcc | ttcttcaaga | agtgaagggt | ttccagagta | tagctacact | 180 |
| attgcttgcc | tgagggtgac | tacaaaattg | cttgctaaaa | ggttaggatg | ggtaaagaat | 240 |
| tagattttct | gaatgcaaaa | ataaaatgtg | aactaatgaa | ctttaggtaa | tacatattca | 300 |
| taaataatt | attcacatat | ttcctgattt | atcacagaaa | taatgtatga | aatgctttga | 360 |
| gtttcttgga | gtaaactcca | ttactcatcc | caagaaacca | tattataagt | atcactgata | 420 |
| ataagaacaa | caggaccttg | tcataaattc | tggataagag | aaatagtctc | tgggtgtttg | 480 |
| ntcttaattg | ataaaattta | cttgtccatc | ttttagttca | gaatcacaaa | a | 531 |

<210> SEQ ID NO 9
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 9

| | | | | | |
|---|---|---|---|---|---|
| aagcggaaat | gagaaaggag | ggaaaatcat | gtggtattga | gcggaaaact | gctggatgac | 60 |
| agggctcagt | cctgttggag | aactctgggt | ggtgctgtag | aacagggcca | ctcacagtgg | 120 |
| ggtgcacaga | ccagcacggc | tctgtgacct | gtttgttaca | ggtccatgat | gaggtaaaca | 180 |
| atacactgag | tataagggtt | ggtttagaaa | ctcttacagc | aatttgacaa | agtaatcttc | 240 |
| tgtgcagtga | atctaagaaa | aaaattgggg | ctgtatttgt | atgttccttt | ttttcatttc | 300 |

-continued

| | |
|---|---|
| atgttctgag ttacctattt ttattgcatt ttacaaaagc atccttccat gaaggaccgg | 360 |
| aagttaaaaa caaagcaggt cctttatcac agcactgtcg tagaacacag ttcagagtta | 420 |
| tccacccaag gagccaggga gctgggctaa accaaagaat tttgcttttg gttaatcatc | 480 |
| aggtacttga gttggaattg ttttaatccc atcattacca ggctggangt g | 531 |

<210> SEQ ID NO 10
<211> LENGTH: 861
<212> TYPE: DNA
<213> ORGANISM: Homo sapien

<400> SEQUENCE: 10

| | |
|---|---|
| ccgcggctcc tgtccagacc ctgaccctcc ctcccaaggc tcaaccgtcc cccaacaacc | 60 |
| gccagccttg tactgatgtc ggctgcgaga gcctgtgctt aagtaagaat caggccttat | 120 |
| tggagacatt caagcaaagg ttggacaact acttttccag aacagaaagg aaactcatgc | 180 |
| atcagaaaag gtgactaata aggtaccag aagaatatgg ctgcacaaat accagaatct | 240 |
| gatcagataa acagtttaa ggaatttctg gggacctaca ataaacttac agagacctgc | 300 |
| tttttggact gtgttagaga cttcacaaca agagaagtaa aacctgaaga gaccacctgt | 360 |
| tcagaacatt gcttacagaa atatttaaaa atgacacaaa gaatatccat gagatttcag | 420 |
| gaatatcata ttcagcagaa tgaagccctg gcagccaaag caggactcct tggccaacca | 480 |
| cgatagagaa gtcctgatgg atgaactttt gatgaaagat tgccaacagc tgctttattg | 540 |
| gaaatgagga ctcatctgat agaatcccct gaaagcagta gccaccatgt tcaaccatct | 600 |
| gtcatgactg tttggcaaat ggaaaccgct ggagaaacaa aattgctatt taccaggaat | 660 |
| aatcacaata gaaggtctta tgttcagtg aaataataag atgcaacatt tgttgaggcc | 720 |
| ttatgattca gcagcttggt cacttgatta gaaaaataaa ccattgtttc ttcaattgtg | 780 |
| actgttaatt ttaaagcaac ttatgtgttc gatcatgtat gagatagaaa aatttttatt | 840 |
| actcaaagta aaataaatgg a | 861 |

<210> SEQ ID NO 11
<211> LENGTH: 541
<212> TYPE: DNA
<213> ORGANISM: Homo sapien

<400> SEQUENCE: 11

| | |
|---|---|
| gaaaaaaat ataaaacaca cttttgcgaa aacggtggcc ctaaaagagg aaaagaattt | 60 |
| caccaatata aatccaattt tatgaaaact gacaatttaa tccaagaatc acttttgtaa | 120 |
| atgaagctag caagtgatga tatgataaaa taaacgtgga ggaaataaaa acacaagact | 180 |
| tggcataaga tatatccact tttgatatta aacttgtgaa gcatattctt cgacaaattg | 240 |
| tgaaagcgtt cctgatcttg cttgttctcc atttcaaata aggaggcata tcacatccca | 300 |
| agagtaacag aaaaagaaaa aagacatttt tgcattttga gatgaaccaa agacacaaaa | 360 |
| caaacgaac aaagtgtcat gtctaattct agcctctgaa ataaaccttg aacatctcct | 420 |
| acaaggcacc gtgattttg taattctaac ctgaagaaat gtgatgactt tgtggacat | 480 |
| gaaaatcaga tgagaaaact gtggtctttc caaagcctga actcccctga aaacctttgc | 540 |
| a | 541 |

<210> SEQ ID NO 12
<211> LENGTH: 541
<212> TYPE: DNA
<213> ORGANISM: Homo sapien

<400> SEQUENCE: 12

```
ctgggatcat ttctcttgat gtcataaaag actcttcttc ttcctcttca tcctcttctt      60
catcctcttc tgtacagtgc tgccgggtac aacggctatc tttgtcttta tcctgagatg     120
aagatgatgc ttctgtttct cctaccataa ctgaagaaat ttcgctggaa gtcgtttgac     180
tggctgtttc tctgacttca ccttctttgt caaacctgag tcttttttacc tcatgccct     240
cagcttccac agcatcttca tctggatgtt tattttttcaa agggctcact gaggaaactt     300
ctgattcaga ggtcgaagag tcactgtgat ttttctcctc attttgctgc aaatttgcct     360
ctttgctgtc tgtgctctca ggcaacccat ttgttgtcat gggggctgac aaagaaacct     420
ttggtcgatt aagtggcctg ggtgtcccag gcccatttat attagacctc tcagtatagc     480
ttggtgaatt tccaggaaac ataacaccat tcattcgatt taaactattg gaattggttt     540
t                                                                     541
```

<210> SEQ ID NO 13
<211> LENGTH: 441
<212> TYPE: DNA
<213> ORGANISM: Homo sapien

<400> SEQUENCE: 13

```
gagggttggt ggtagcggct tgggaggtg ctcgctctgt cggtcttgct ctctcgcacg       60
cttccccgg ctcccttcgt ttcccccccc cggtcgcctg cgtgccggag tgtgtgcgag      120
ggaggggag ggcgtcgggg gggtggggggg aggcgttccg gtccccaaga gacccgcgga    180
gggaggcgga ggctgtgagg gactccggga agccatggac gtcagagggc tccaggaggc    240
gctgaaagat tttgagaaga gggggaaaaa ggaagtttgt cctgtcctgg atcagtttct    300
ttgtcatgta gccaagactg gagaaacaat gattcagtgg tcccaattta aaggctattt     360
tattttcaaa ctggagaaag tgatggatga tttcagaact tcagctcctg agccaagagg    420
tcctcccaac cctaatgtcg a                                               441
```

<210> SEQ ID NO 14
<211> LENGTH: 131
<212> TYPE: DNA
<213> ORGANISM: Homo sapien
<220> FEATURE:
<221> NAME/KEY: misc_feature
<222> LOCATION: (1)...(131)
<223> OTHER INFORMATION: n = A,T,C or G

<400> SEQUENCE: 14

```
aagcaggcgg ctcccgcgct cgcagggccg tgccacctgc ccgcccgccc gctcgctcgc      60
tcgcccgccg cgccgcgctg ccgaccgcca gcatgctgcc gagagtgggc tgccccgcgc     120
tgccgntgcc g                                                          131
```

<210> SEQ ID NO 15
<211> LENGTH: 692
<212> TYPE: DNA
<213> ORGANISM: Homo sapien

<400> SEQUENCE: 15

```
atctcttgta tgccaaatat ttaatataaa tctttgaaac aagttcagat gaaataaaaa       60
tcaaagtttg caaaaacgtg aagattaact taattgtcaa atattcctca ttgccccaaa     120
tcagtatttt ttttatttct atgcaaaagt atgccttcaa actgcttaaa tgatatatga     180
```

-continued

| | |
|---|---|
| tatgatacac aaaccagttt tcaaatagta aagccagtca tcttgcaatt gtaagaaata | 240 |
| ggtaaaagat tataagacac cttacacaca cacacacaca cacacacgtg tgcacgccaa | 300 |
| tgacaaaaaa caatttggcc tctcctaaaa taagaacatg aagaccctta attgctgcca | 360 |
| ggagggaaca ctgtgtcacc cctccctaca atccaggtag tttcctttaa tccaatagca | 420 |
| aatctgggca tatttgagag gagtgattct gacagccacg ttgaaatcct gtggggaacc | 480 |
| attcatgtcc acccactggt gccctgaaaa atgccaata attttcgct cccacttctg | 540 |
| ctgctgtctc ttccacatcc tcacatagac cccagaccg ctggcccctg ctgggcatc | 600 |
| gcattgctgg tagagcaagt cataggtctc gtctttgacg tcacagaagc gatacaccaa | 660 |
| attgcctggt cggtcattgt cataaccaga ga | 692 |

<210> SEQ ID NO 16
<211> LENGTH: 728
<212> TYPE: DNA
<213> ORGANISM: Homo sapien

<400> SEQUENCE: 16

| | |
|---|---|
| cagacggggt ttcactatgt tggctaggct ggtcttgaac tcctgacttc aggtgatctg | 60 |
| cctgccttgg cctcccaaag tgctgggatt acaggcataa gccactgcgc ccggctgatc | 120 |
| tgatggtttc ataaggcttt tccccctttt gctcagcact tctccttcct gccgccatgt | 180 |
| gaagaaggac atgtttgctt cccttccac cacgattgta agttgtttcc tgaggcctcc | 240 |
| ccggccatgc tgaactgtga gtcaattaaa cctctttcct ttataaatta tccagttttg | 300 |
| ggtatgtctt tattagtaga atgagaacag actaatacaa cccttaaagg agactgacgg | 360 |
| agaggattct tcctggatcc cagcacttcc tctgaatgct actgacattc ttcttgagga | 420 |
| cttaaactg ggagatagaa aacagattcc atggctcagc agcctgagag cagggaggga | 480 |
| gccaagctat agatgacatg ggcagcctcc cctgaggcca ggtgtggccg aacctgggca | 540 |
| gtgctgccac ccaccccacc agggccaagt cctgtccttg gagagccaag cctcaatcac | 600 |
| tgctagcctc aagtgtcccc aagccacagt ggctaggggg actcagggaa cagttcccag | 660 |
| tctgccctac ttctcttacc tttacccctc atacctccaa agtagaccat gttcatgagg | 720 |
| tccaaagg | 728 |

<210> SEQ ID NO 17
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 17

| | |
|---|---|
| aagcgaggaa gccactgcgg ctcctggctg aaaagcggcg ccaggctcgg aacagaggg | 60 |
| aacgcgaaga acaggagcgg aagctgcagg ctgaaaggga caagcgaatg cgagaggagc | 120 |
| agctggcccg ggaggctgaa gcccgggctg aacgtgaggc cgaggcgcgg agacgggagg | 180 |
| agcaggaggc tcgagagaag gcgcaggctg agcaggagga gcaggagcga ctgcagaagc | 240 |
| agaaagagga agccgaagcc cggtcccggg aagaagctga gcgccagcgc caggagcggg | 300 |
| aaaagcactt tcagaaggag gaacaggaga gacaagagcg aagaaagcgg ctggaggaga | 360 |
| taatgaagag gactcggaaa tcagaagccg ccgaaaccaa gaagcaggat gcaaaggaga | 420 |
| ccgcagctaa caattccggc ccagacccctt gtgaaagctg tagagactcg gccctctggg | 480 |

| cttccagaaa ggattctatt gcagaaagga aggagctngg ccccccangg a | 531 |

<210> SEQ ID NO 18
<211> LENGTH: 1041
<212> TYPE: DNA
<213> ORGANISM: Homo sapien
<220> FEATURE:
<221> NAME/KEY: misc_feature
<222> LOCATION: (1)...(1041)
<223> OTHER INFORMATION: n = A,T,C or G

<400> SEQUENCE: 18

| ctctgtggaa aactgatgag gaatgaattt accattaccc atgttctcat ccccaagcaa | 60 |
| agtgctgggt ctgattactg caacacagag aacgaagaag aacttttcct catacaggat | 120 |
| cagcagggcc tcatcacact gggctggatt catactcacc ccacacagac cgcgtttctc | 180 |
| tccagtgtcg acctacacac tcactgctct taccagatga tgttgccaga gtcagtagcc | 240 |
| attgtttgct cccccaagtt ccaggaaact ggattcttta aactaactga ccatggacta | 300 |
| gaggagattt cttcctgtcg ccagaaagga tttcatccac acagcaagga tccacctctg | 360 |
| ttctgtagct gcagccacgt gactgttgtg gacagagcag tgaccatcac agaccttcga | 420 |
| tgagcgtttg agtccaacac cttccaagaa caacaaaacc atatcagtgt actgtagccc | 480 |
| cttaatttaa gctttctaga aagctttgga agttttgta gatagtagaa aggggggcat | 540 |
| cacntgagaa agagctgatt ttgtatttca ggtttgaaaa gaataactg aacatatttt | 600 |
| ttaggcaagt cagaaagaga acatggtcac ccaaaagcaa ctgtaactca gaaattaagt | 660 |
| tactcagaaa ttaagtagct cagaaattaa gaaagaatgg tataatgaac ccccatatac | 720 |
| ccttccttct ggattcacca attgttaaca ttttttttcct ctcagctatc cttctaattt | 780 |
| ctctctaatt tcaatttgtt tatatttacc tctgggctca ataagggcat ctgtgcagaa | 840 |
| atttggaagc catttagaaa atcttttgga ttttcctgtg gtttatggca atatgaatgg | 900 |
| agcttattac tggggtgagg gacagcttac tccatttgac cagattgttt ggctaacaca | 960 |
| tcccgaagaa tgattttgtc aggaattatt gttatttaat aaatatttca ggatatttt | 1020 |
| cctctacaat aaagtaacaa t | 1041 |

<210> SEQ ID NO 19
<211> LENGTH: 1043
<212> TYPE: DNA
<213> ORGANISM: Homo sapien

<400> SEQUENCE: 19

| ctctgtggaa aactgatgag gaatgaattt accattaccc atgttctcat ccccaagcaa | 60 |
| agtgctgggt ctgattactg caacacagag aacgaagaag aacttttcct catacaggat | 120 |
| cagcagggcc tcatcacact gggctggatt catactcacc ccacacagac cgcgtttctc | 180 |
| tccagtgtcg acctacacac tcactgctct taccagatga tgttgccaga gtcagtagcc | 240 |
| attgtttgct cccccaagtt ccaggaaact ggattcttta aactaactga ccatggacta | 300 |
| gaggagattt cttcctgtcg ccagaaagga tttcatccac acagcaagga tccacctctg | 360 |
| ttctgtagct gcagccacgt gactgttgtg gacagagcag tgaccatcac agaccttcga | 420 |
| tgagcgtttg agtccaacac cttccaagaa caacaaaacc atatcagtgt actgtagccc | 480 |
| cttaatttaa gctttctaga aagctttgga agttttgta gatagtagaa aggggggcat | 540 |
| cacctgagaa agagctgatt ttgtatttca ggtttgaaaa gaataactg aacatatttt | 600 |

```
ttaggcaagt cagaaagaga acatggtcac ccaaaagcaa ctgtaactca gaaattaagt      660
tactcagaaa ttaagtagct cagaaattaa gaaagaatgg tataatgaac ccccatatac      720
ccttccttct ggattcacca attgttaaca ttttttttcct ctcagctatc cttctaattt     780
ctctctaatt tcaatttgtt tatatttacc tctgggctca ataagggcat ctgtgcagaa      840
atttggaagc catttagaaa atcttttgga ttttcctgtg gtttatggca atatgaatgg      900
agcttattac tggggtgagg acagcttac tccatttgac cagattgttt ggctaacaca       960
tcccgaagaa tgattttgtc aggaattatt gttatttaat aaatatttca ggatattttt     1020
cctctacaat aaagtaacaa tta                                             1043
```

<210> SEQ ID NO 20
<211> LENGTH: 448
<212> TYPE: DNA
<213> ORGANISM: Homo sapien

<400> SEQUENCE: 20

```
ggacgacaag gccatggcga tatcggatcc gaattcaagc cttttggaatt aaataaacct     60 ggaacaggga aggtgaaagt tggagtgaga tgtcttccat atctatacct ttgtgcacag     120
ttgaatggga actgtttggg tttagggcat cttagagttg attgatggaa aaagcagaca     180
ggaactggtg ggaggtcaag tggggaagtt ggtgaatgtg aataactta cctttgtgct     240 ccacttaaac cagatgtgtt gcagctttcc tgacatgcaa ggatctactt taattccaca   300
ctctcattaa taaattgaat aaaagggaat gttttggcac ctgatataat ctgccaggct   360
atgtgacagt aggaaggaat ggtttcccct aacaagccca atgcactggt ctgactttat   420
aaattattta ataaaatgaa ctattatc                                       448
```

<210> SEQ ID NO 21
<211> LENGTH: 411
<212> TYPE: DNA
<213> ORGANISM: Homo sapien

<400> SEQUENCE: 21

```
ggcagtgaca ttcaccatca tgggaaccac cttcccttt cttcaggatt ctctgtagtg      60
gaagagagca cccagtgttg ggctgaaaac atctgaaagt agggagaaga acctaaaata    120
atcagtatct cagagggctc taaggtgcca agaagtctca ctggacattt aagtgccaac    180
aaaggcatac tttcggaatc gccaagtcaa aactttctaa cttctgtctc tctcagagac    240
aagtgagact caagagtcta ctgctttagt ggcaactaca gaaaactggt gttacccaga    300
aaaacaggag caattagaaa tggttccaat atttcaaagc tccgcaaaca ggatgtgctt    360
tcctttgccc atttagggtt tcttctcttt cctttctctt tattaaccac t             411
```

<210> SEQ ID NO 22
<211> LENGTH: 896
<212> TYPE: DNA
<213> ORGANISM: Homo sapien
<220> FEATURE:
<221> NAME/KEY: misc_feature
<222> LOCATION: (1)...(896)
<223> OTHER INFORMATION: n = A,T,C or G

<400> SEQUENCE: 22

```
tgcgctgaaa acaacggcct cctttactgt taaaatgcag ccacaggtgc ttagccgtgg       60
gcatctcaac caccagcctc tgtgggggc aggtgggcgt ccctgtgggc ctctgggccc      120
acgtccagcc tctgtcctct gccttccgtt cttcgacagt gttcccggca tccctggtca    180
```

```
cttggtactt ggcgtgggcc tcctgtgctg ctccagcagc tcctccaggn ggtcggcccg    240
cttcaccgca gcctcatgtt gtgtccggag gctgctcacg gcctcctcct tcctcgcgag    300
ggctgtcttc accctccggn gcacctcctc cagctccagc tgctggcggg cctgcagcgt    360
ggccagctcg gccttggcct gccgcgtctc ctcctcarag gctgccagcc ggtcctcgaa    420
ctcctggcgg atcacctggg ccaggttgct gcgctcgcta gaaagctgct cgttcaccgc    480
ctgcgcatcc tccagcgccc gctccttctg ccgcacaagg ccctgcagac gcagattctc    540
gccctcggcc tccccaagct ggcccttcag ctccgagcac cgctcctgaa gcttccgctc    600
cgactgctcc agctcggaga gctcggcctc gtacttgtcc cgtaagcgct tgatgcggct    660
ctcggcagcc ttctcactct cctccttggc cagcgccatg tcggcctcca gccggtgaat    720
gaccagctca atctccttgt cccggccttt ccggatttct tccctcagct cctgttcccg    780
gttcagcagc cacgcctcct ccttcctggt gcggccggcc tccacgcct gcctctccag    840 ctccagctgc tgcttcaggg tattcagctc catctggcgg gcctgcagcg tggcca        896

<210> SEQ ID NO 23
<211> LENGTH: 111
<212> TYPE: DNA
<213> ORGANISM: Homo sapien

<400> SEQUENCE: 23
caacttatta cttgaaatta taatatagcc tgtccgtttg ctgtttccag gctgtgatat     60
attttcctag tggtttgact ttaaaaataa ataaggttta attttctccc c             111

<210> SEQ ID NO 24
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 24
tgcaagtcac gggagtttat ttatttaatt ttttccca gatggagact ctgtcgccca      60
ggctggagtg caatggtgtg atcttggctc actgcaacct ccacctcctg ggttcaagcg    120
attctcctgc cacagcctcc cgagtagctg ggattacagg tgcccgccac cacacccagc    180 taattttat attttagta aagacagggt ttccccatgt tggccaggct ggtcttgaac      240
ttctgacctc aggtgatcca cctgcctcgg cctcccaaag tgttgggatt acaggcgtga    300
gctacccgtg cctggccagc cactggagtt taaaggacag tcatgttggc tccagcctaa    360
ggcggcattt tccccatca gaaagcccgc ggctcctgta cctcaaaata gggcacctgt     420
aaagtcagtc agtgaagtct ctgctctaac tggccacccg gggccattgg cntctgacac    480
agccttgcca ggangcctgc atctgcaaaa gaaagttca cttcctttcc g              531

<210> SEQ ID NO 25
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 25
```

| | |
|---|---|
| cagagaatct kagaaagatg tcgcgttttc ttttaatgaa tgagagaagc ccatttgtat | 60 |
| ccctgaatca ttgagaaaag gcggcggtgg cgacagcggc gacctaggga tcgatctgga | 120 |
| gggacttggg gagcgtgcag agacctctag ctcgagcgcg agggacctcc cgccgggatg | 180 |
| cctggggagc agatggaccc tactggaagt cagttggatt cagatttctc tcagcaagat | 240 |
| actccttgcc tgataattga agattctcag cctgaaagcc aggttctaga ggatgattct | 300 |
| ggttctcact tcagtatgct atctcgacac cttcctaatc tccagacgca caagaaaat | 360 |
| cctgtgttgg atgttgngtc caatccttga acaaacagct ggagaagaac gaggagaccg | 420 |
| gtaatagtgg gttcaatgaa catttgaaag aaaaccaggt tgcagaccct g | 471 |

<210> SEQ ID NO 26
<211> LENGTH: 541
<212> TYPE: DNA
<213> ORGANISM: Homo sapien

<400> SEQUENCE: 26

| | |
|---|---|
| gactgtcctg aacaagggac ctctgaccag agagctgcag gagatgcaga gtggtggcag | 60 |
| gagtggaagc caaagaacac ccaccttcct cccttgaagg agtagagcaa ccatcagaag | 120 |
| atactgtttt attgctctgg tcaaacaagt cttcctgagt tgacaaaacc tcaggctctg | 180 |
| gtgacttctg aatctgcagt ccactttcca taagttcttg tgcagacaac tgttcttttg | 240 |
| cttccatagc agcaacagat gctttggggc taaaaggcat gtcctctgac cttgcaggtg | 300 |
| gtggattttg ctcttttaca acatgtacat ccttactggg ctgtgctgtc acaggatgt | 360 |
| ccttgctgga ctgttctgct atggggatat cttcgttgga ctgttcttca tgcttaattg | 420 |
| cagtattagc atccacatca gacagcctgg tataaccaga gttggtggtt actgattgta | 480 |
| gctgctcttt gtccacttca tatggcacaa gtattttcct caacatcctg gctctgggaa | 540 |
| g | 541 |

<210> SEQ ID NO 27
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 27

| | |
|---|---|
| gaaatgtata tttaatcatt ctcttgaacg atcagaactc traaatcagt tttctataac | 60 |
| arcatgtaat acagtcaccg tggctccaag gtccaggaag gcagtggtta acacatgaag | 120 |
| agtgtgggaa gggggctgga aacaaagtat tcttttcctt caaagcttca ttcctcaagg | 180 |
| cctcaattca agcagtcatt gtccttgctt tcaaaagtct gtgtgtgctt catggaaggt | 240 |
| atatgtttgt tgccttaatt tgaattgtgg ccaggaaggg tctggagatc taaattcaga | 300 |
| gtaagaaaac ctgagctaga actcaggcat ttctcttaca gaacttggct tgcagggtag | 360 |
| aatgaangga aagaaactta gaagctcaac aagctgaaga taatcccatc aggcatttcc | 420 |
| cataggcctt gcaactctgt tcactgagag atgttatcct g | 461 |

<210> SEQ ID NO 28
<211> LENGTH: 541
<212> TYPE: DNA
<213> ORGANISM: Homo sapien

<400> SEQUENCE: 28
agtctggagt gagcaaacaa gagcaagaaa caarragaag ccaaaagcag aaggctccaa    60
tatgaacaag ataaatctat cttcaaagac atattagaag ttgggaaaat aattcatgtg   120
aactagacaa gtgtgttaag agtgataagt aaaatgcacg tggagacaag tgcatcccca   180
gatctcaggg acctcccct gcctgtcacc tggggagtga aggacagga tagtgcatgt    240 tctttgtctc tgaattttta gttatatgtg ctgtaatgtt gctctgagga agcccctgga   300
aagtctatcc caacatatcc acatcttata ttccacaaat taagctgtag tatgtaccct   360
aagacgctgc taattgactg ccacttcgca actcaggggc ggctgcattt tagtaatggg   420
tcaaatgatt cactttttat gatgcttccc aaggtgcctt ggcttctctt cccaactgac   480
aaatgcccaa gttgagaaaa atgatcataa ttttagcata aaccgagcaa tcggcgaccc   540
c                                                                   541

<210> SEQ ID NO 29
<211> LENGTH: 411
<212> TYPE: DNA
<213> ORGANISM: Homo sapien

<400> SEQUENCE: 29
tagctgtctt cctcactctt atggcaatga ccccatatct taatggatta agataatgaa    60
agtgtatttc ttacactctg tatctatcac cagaagctga ggtgatagcc cgcttgtcat   120
tgtcatccat attctgggac tcaggcggga actttctgga atattgccag ggagcatggc   180 agagggcac agtgcattct ggggaatgc acattggctc agcctgggta atgagtgata    240
tacattacct ctgttcacaa ctcattgccc agcaccagtc acaaggcccc accaaatacc   300
agagcccaag aaatgtagtc ctgttgatat ggttttgctg tgtcccaacc caaatctcat   360
cttgaattgt aagctcccat aattcccatg tgttgtggga gggacctggt g            411

<210> SEQ ID NO 30
<211> LENGTH: 511
<212> TYPE: DNA
<213> ORGANISM: Homo sapien

<400> SEQUENCE: 30
atcatgagga tgttaccaaa gggatggtac taaaccattt gtattcgtct gttttcacac    60
tgctttgaag atactacctg agactgggta atttataaac aaaagagatt taattgactc   120
acagttctgc atggctgaag aggcctcagg aaacttacag tcatggtgga aggcaaagga   180
ggagcaaggc atgtcttaca tgtcagtagg agagagagcg agagcaggag aacctgccac   240
ttataaacca ttcagatctc ataactccct atcatgagaa aaacatggag gaaaccaccc   300
tcatgatcca atcacctccc gccaggtccc tccctcgaca cgtgggatt ataattcagg    360 attagaggga cacagagaca aaccatatca tcattcatga gaaatccacc ctcatagtcc   420
aatcagctcc taccaggccc cacctccaac actggggatt gcaattcaac atgagatttg   480 gatgggaca cagattcaaa ccatatcata c                                   511

<210> SEQ ID NO 31
<211> LENGTH: 827
<212> TYPE: DNA
<213> ORGANISM: Homo sapien

<400> SEQUENCE: 31
catggccttt ctccttagag gccagaggtg ctgccctggc tgggagtgaa gctccaggca    60

```
ctaccagctt tcctgatttt cccgtttggt ccatgtgaag agctaccacg agccccagcc    120
tcacagtgtc cactcaaggg cagcttggtc ctcttgtcct gcagaggcag gctggtgtga    180
ccctgggaac ttgacccggg aacaacaggt ggcccagagt gagtgtggcc tggcccctca    240
acctagtgtc cgtcctcctc tctcctggag ccagtcttga gtttaaaggc attaagtgtt    300
agatacaagc tccttgtggc tggaaaaaca cccctctgct gataaagctc agggggcact    360
gaggaagcag aggcccttg ggggtgccct cctgaagaga gcgtcaggcc atcagctctg    420
tccctctggt gctcccacgt ctgttcctca ccctccatct ctgggagcag ctgcacctga    480
ctggccacgc gggggcagtg gaggcacagg ctcaggtgg ccgggctacc tggcacccta    540
tggcttacaa agtagagttg gcccagtttc cttccacctg aggggagcac tctgactcct    600
aacagtcttc cttgccctgc catcatctgg ggtggctggc tgtcaagaaa ggccgggcat    660
gctttctaaa cacagccaca ggaggcttgt agggcatctt ccaggtgggg aaacagtctt    720
agataagtaa ggtgacttgc ctaaggcctc ccagcaccct tgatcttgga gtctcacagc    780
agactgcatg tsaacaactg gaaccgaaaa catgcctcag tataaaa                  827
```

```
<210> SEQ ID NO 32
<211> LENGTH: 291
<212> TYPE: DNA
<213> ORGANISM: Homo sapien

<400> SEQUENCE: 32
ccagaacctc cttctctttg gagaatgggg aggcctcttg gagacacaga gggtttcacc     60
ttggatgacc tctagagaaa ttgcccaaga agcccacctt ctggtcccaa cctgcagacc    120
ccacagcagt cagttggtca ggccctgctg tagaaggtca cttggctcca ttgcctgctt    180
ccaaccaatg ggcaggagag aaggccttta tttctcgccc acccattctc ctgtaccagc    240
acctccgttt tcagtcagyg ttgtccagca acggtaccgt ttacacagtc a             291
```

```
<210> SEQ ID NO 33
<211> LENGTH: 491
<212> TYPE: DNA
<213> ORGANISM: Homo sapien

<400> SEQUENCE: 33
tgcatgtagt tttatttatg tgttttsgtc tggaaaacca agtgtcccag cagcatgact     60
gaacatcact cacttcccct acttgatcta caaggccaac gccgagagcc agaccagga    120 ttccaaacac actgcacgag aatattgtgg atccgctgtc aggtaagtgt ccgtcactga    180
cccaracgct gttacgtggc acatgactgt acagtgccac gtaacagcac tgtacttttc    240
tcccatgaac agttacctgc catgtatcta catgattcag acattttga acagttaatt    300 ctgacacttg aataatccca tcaaaaaccg taaaatcact ttgatgtttg taacgacaac    360
atagcatcac tttacgacag aatcatctgg aaaaacagaa caacgaatac atacatctta    420
aaaaatgctg gggtgggcca ggcacagctt cacgcctgta atcccagcac tttgggaggc    480
ttaagcgggt g                                                          491
```

```
<210> SEQ ID NO 34
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G
```

<400> SEQUENCE: 34

```
tggggcggaa agaagccaag gccaaggagc tggtgcggca gctgcagctg gaggccgagg      60
agcagaggaa gcagaagaag cggcagagtg tgtcgggcct gcacagatac cttcacttgc     120
tggatggaaa tgaaaattac ccgtgtcttg tggatgcaga cggtgatgtg atttccttcc     180
caccaataac caacagtgag aagacaaagg ttaagaaaac gacttctgat ttgttttggg     240
aagtaacaag tgccaccagt ctgcagattt gcaaggatgt catggatgcc ctcattctga     300
aaatggcaag aaatgaaaaa gtacacttta gaaataaag aggaaggatc actctcagat      360
actgaagccg atgcagtctc tggacaactt ccagatccca caacgaatcc cagtgctgga     420
aaggacgggc ccttccttct ggtggtggaa cangtcccgg tggtggatct tggaanggaa     480
cctgaangtg gtgtaccccg tccaaggccg accttggcca c                         521
```

<210> SEQ ID NO 35
<211> LENGTH: 161
<212> TYPE: DNA
<213> ORGANISM: Homo sapien
<220> FEATURE:
<221> NAME/KEY: misc_feature
<222> LOCATION: (1)...(161)
<223> OTHER INFORMATION: n = A,T,C or G

<400> SEQUENCE: 35

```
tcccgcgctc gcagggcncg tgccacctgc cygtccgccc gctcgctcgc tcgcccgccg      60
cgccgcgctg ccgaccgyca gcatgctgcc gagagtgggc tgccccgcgc tgccgctgcc     120
gccgccgccg ctgctgccgc tgctgccgct gctgctgctg c                         161
```

<210> SEQ ID NO 36
<211> LENGTH: 341
<212> TYPE: DNA
<213> ORGANISM: Homo sapien

<400> SEQUENCE: 36

```
ggcgggtagg catggaactg agaagaacga agaagctttc agactacgtg gggaagaatg      60
aaaaaaccaa aattatcgcc aagattcagc aaaggggaca gggagctcca gcccgagagc     120
ctattattag cagtgaggag cagaagcagc tgatgctgta ctatcacaga agacaagagg     180
agctcaagag attggaagaa atgatgatg atgcctattt aaactcacca tgggcggata      240
acactgcttt gaaaagacat tttcatggag tgaaagacat aaagtggaga ccaagatgaa     300
gttcaccagc tgatgacact tccaaagaga ttagctcacc t                         341
```

<210> SEQ ID NO 37
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 37

```
tctgaaggtt aaatgtttca tctaaatagg gataatgrta acacctata gcatagagtt       60
gtttgagatt aaatgagata atacatgtaa aattatgtgc ctggcataca gcaagattgt     120
tgttgttgtt gatgatgatg atgatgatga taatattttt ctatccccag tgcacaactg     180
cttgaaccta ttagataatc aatacatgtt tcttgaactg agatcaattt ccccatgttg     240
```

| | |
|---|---|
| tctgactgat gaagccctac attttcttct agaggagatg acatttgagc aagatcttaa | 300 |
| agaaaatcag atgccttcac ctgaccactg cttggtgatc ccatggcact ttgtacatct | 360 |
| ctccattagc tctcatctca ccagcccatc attattgtat gtgctgcctt ctgaagcttg | 420 |
| cagctggcta ccatcmggta gaataaaaat catcctttca taaaatagtg accctccttt | 480 |
| tttatttgca tttcccaaag ccaagcaccg tgggangGta g | 521 |

<210> SEQ ID NO 38
<211> LENGTH: 461
<212> TYPE: DNA
<213> ORGANISM: Homo sapien

<400> SEQUENCE: 38

| | |
|---|---|
| tatgaagaag ggaaaagaag ataatttgtg aaagaaatgg gtccagttac tagtctttga | 60 |
| aaagggtcag tctgtagctc ttcttaatga gaataggcag cttcagttg ctcagggtca | 120 |
| gatttcctta gtggtgtatc taatcacagg aaacatctgt ggttccctcc agtctctttc | 180 |
| tgggggactt gggcccactt ctcatttcat ttaattagag gaaatagaac tcaaagtaca | 240 |
| atttactgtt gtttaacaat gccacaaaga catggttggg agctatttct tgatttgtgt | 300 |
| aaaatgctgt ttttgtgtgc tcataatggt tccaaaaatt gggtgctggc caaagagaga | 360 |
| tactgttaca gaagccagca agaagacctc tgttcattca cacccccggg gatatcagga | 420 |
| attgactcca gtgtgtgcaa atccagtttg gcctatcttc t | 461 |

<210> SEQ ID NO 39
<211> LENGTH: 769
<212> TYPE: DNA
<213> ORGANISM: Homo sapien

<400> SEQUENCE: 39

| | |
|---|---|
| tgagggactg attggttttgc tctctgctat tcaattcccc aagcccactt gttcctgcag | 60 |
| cgtcctcctt ctcattccct ttagttgtac cctctctttc atctgagacc tttccttctt | 120 |
| gatgtcgcct tttcttcttc ttgcttttttc tgatgttctg ctcagcatgt tctgggtgct | 180 |
| tctcatctgc atcattcctt tcagatgctg tagcttcttc ctcctcttttc tgcctccttt | 240 |
| tcttttttctt tttttttgggg ggcttgctct ctgactgcag ttgaggggcc ccagggtcct | 300 |
| ggcctttgag acgagccagg aaggcctgct cctgggcctc taggcgagca agcttggcct | 360 |
| tcattgtgat cccaagacgg gcagccttgt gtgctgttcg cccctcacag gcttggagca | 420 |
| gcatctcatc agtcagaatc tttggggact tggaccccctg gttgtcgtca tcactgcagc | 480 |
| tctccaagtc tttgtttggc ttctctccac ctgaagtcaa tgtagccatc ttcacaaact | 540 |
| tctgatacag caagttgggc ttgggatgat tataacgggt ggtctcctta gaaaggctcc | 600 |
| ttatctgtac tccatcctgc ccagtttcca ctaccaagtt ggccgcagtc ttgttgaaga | 660 |
| gctcattcca ccagtggttt gtgaactcct tggcagggtc atgtcctacc ccatgagtgt | 720 |
| cttgcttcag ygtcaccctg agagcctgag tgataccatt ctccttccg | 769 |

<210> SEQ ID NO 40
<211> LENGTH: 292
<212> TYPE: DNA
<213> ORGANISM: Homo sapien

<400> SEQUENCE: 40

| | |
|---|---|
| gacaacatga aataaatcct agaggacaaa attaaactca atagagtgta gtctagttaa | 60 |
| aaactcgaaa aatgagcaag tctggtggga gtggaggaag ggctatacta taaatccaag | 120 |

```
tgggcctcct gatcttaaca agccatgctc attatacaca tctctgaact ggacatacca      180
cctttacgca ggaaacaggg cttggaactt ctaagggaaa ttaacatgca ccacccacat      240
ctaacctacc tgccgggtag gtaccatccc tgcttcgctg aaatcagtgc tc              292

<210> SEQ ID NO 41
<211> LENGTH: 406
<212> TYPE: DNA
<213> ORGANISM: Homo sapien

<400> SEQUENCE: 41
ttggaattaa ataaacctgg aacagggaag gtgaaagttg gagtgagatg tcttccatat       60
ctataccttt gtgcacagtt gaatgggaac tgtttgggtt tagggcatct tagagttgat      120
tgatggaaaa agcagacagg aactggtggg aggtcaagtg gggaagttgg tgaatgtgga      180
ataacttacc tttgtgctcc acttaaacca gatgtgttgc agctttcctg acatgcaagg      240
atctacttta attccacact ctcattaata aattgaataa agggaatgt tttggcacct      300 gatataatct gccaggctat gtgacagtag gaaggaatgt tttcccctaa caagcccaat      360
gcactggtct gactttataa attatttaat aaaatgaact attatc                     406

<210> SEQ ID NO 42
<211> LENGTH: 381
<212> TYPE: DNA
<213> ORGANISM: Homo sapien

<400> SEQUENCE: 42
aaactggacc tgcaacaggg acatgaattt actgcarggt ctgagcaagc tcagcccctc       60
tacctcaggg ccccacagcc atgactacct cccccaggag cgggagggtg aaggggggcct    120 gtctctgcaa gtggagccag agtggaggaa tgagctctga agacacagca cccagccttc      180
tcgcaccagc caagccttaa ctgcctgcct gaccctgaac cagaacccag ctgaactgcc      240
cctccaaggg acaggaaggc tgggggaggg agtttacaac ccaagccatt ccaccccctc      300
ccctgctggg gagaatgaca catcaagctg ctaacaattg ggggaagggg aaggaagaaa      360
actctgaaaa caaaatcttg t                                                381

<210> SEQ ID NO 43
<211> LENGTH: 451
<212> TYPE: DNA
<213> ORGANISM: Homo sapien

<400> SEQUENCE: 43
catgcgtttc accactgttg gccaggctgg tctcgaactc ctggcctcaa gcaatccacc       60
cgcctcagcc tccaaaagtg ctgggattac agatgtgagc catggcacca tgccaaaagg     120
ctatattcct ggctctgtgt ttccgagact gcttttaatc ccaacttctc tacatttaga      180
ttaaaaaata ttttattcat ggtcaatctg gaacataatt actgcatctt aagtttccac      240
tgatgtatat agaaggctaa aggcacaatt tttatcaaat ctagtagagt aaccaaacat      300
aaaatcatta attactttca acttaataac taattgacat tcctcaaaag agctgttttc      360
aatcctgata ggttctttat tttttcaaaa tatatttgcc atgggatgct aatttgcaat      420
aaggcgcata atgagaatac cccaaactgg a                                     451

<210> SEQ ID NO 44
<211> LENGTH: 521
<212> TYPE: DNA
```

<213> ORGANISM: Homo sapien

<400> SEQUENCE: 44

| | | | | | |
|---|---|---|---|---|---|
| gttggacccc | cagggactgg | aaagacactt | cttgcccgag | ctgtggcggg | agaagctgat | 60 |
| gttccttttt | attatgcttc | tggatccgaa | tttgatgaga | tgtttgtggg | tgtgggagcc | 120 |
| agccgtatca | gaaatctttt | tagggaagca | aaggcgaatg | ctccttgtgt | tatatttatt | 180 |
| gatgaattag | attctgttgg | tgggaagaga | attgaatctc | caatgcatcc | atattcaagg | 240 |
| cagaccataa | atcaacttct | tgctgaaatg | atggttttta | aacccaatga | aggagttatc | 300 |
| ataataggag | ccacaaactt | cccagaggca | ttagataatg | ccttaatacc | gtcctggtcg | 360 |
| ttttgacatg | caagttacag | ttccaaggcc | agatgtaaaa | ggtcgaacag | aaattttgaa | 420 |
| atggtatctc | aataaaataa | agtttgatca | atcccgttga | tccagaaatt | atagcctcga | 480 |
| ggtactggtg | gcttttccgg | aagcagagtt | gggagaatct | t | | 521 |

<210> SEQ ID NO 45
<211> LENGTH: 585
<212> TYPE: DNA
<213> ORGANISM: Homo sapien

<400> SEQUENCE: 45

| | | | | | |
|---|---|---|---|---|---|
| gcctacaaca | tccagaaaga | gtctaccctg | cacctggtgc | tscgtctcag | aggtgggatg | 60 |
| cagatcttcg | tgaagaccct | gactggtaag | accatcactc | tcgaagtgga | gccgagtgac | 120 |
| accatygaga | acgtcaaagc | aaagatccar | gacaaggaag | gcrtycctcc | tgaccagcag | 180 |
| aggttgatct | tgccggaaa | gcagctggaa | gatggdcgca | ccctgtctga | ctacaacatc | 240 |
| cagaaagagt | cyaccctgca | cctggtgctc | cgtctcagag | gtgggatgca | ratcttcgtg | 300 |
| aagaccctga | ctggtaagac | catcaccctc | gaggtggagc | ccagtgacac | catcgagaat | 360 |
| gtcaaggcaa | agatccaaga | taaggaaggc | atccctcctg | atcagcagag | gttgatcttt | 420 |
| gctgggaaac | agctggaaga | tggacgcacc | ctgtctgact | acaacatcca | gaaagagtcc | 480 |
| actctgcact | tggtcctgcg | cttgaggggg | ggtgtctaag | tttcccctt | taaggtttcm | 540 |
| acaaatttca | ttgcactttc | ctttcaataa | agttgttgca | ttccc | | 585 |

<210> SEQ ID NO 46
<211> LENGTH: 481
<212> TYPE: DNA
<213> ORGANISM: Homo sapien

<400> SEQUENCE: 46

| | | | | | |
|---|---|---|---|---|---|
| gaactgggcc | ctgagcccaa | gtcatgcctt | gtgtccgcat | ctgccgtgtc | acctctgtkc | 60 |
| ctgcccctca | ccctccctc | ctggtcttct | gagccagcac | catctccaaa | tagcctattc | 120 |
| cttcctgcaa | atcacacaca | catgcgggcc | acacatacct | gctgccctgg | agatggggaa | 180 |
| gtaggagaga | tgaatagagg | cccatacatt | gtacagaagg | aggggcaggt | gcagataaaa | 240 |
| gcagcagacc | cagcggcagc | tgaggtgcat | ggagcacggt | tggggccggc | attgggctga | 300 |
| gcacctgatg | ggcctcatct | cgtgaatcct | cgaggcagcg | ccacagcaga | ggagttaagt | 360 |
| ggcacctggg | ccgagcagag | caggagactg | agggtcagag | tggaggctaa | gctgccctgg | 420 |
| aactcctcaa | tcttgcctgc | ccctagtat | gaagcccct | tcctgcccct | acaattcctg | 480 |
| a | | | | | | 481 |

<210> SEQ ID NO 47
<211> LENGTH: 461

<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 47

| | | |
|---|---|---|
| atggatctta ctttgccacc caggttggag tgcagtgctg caatcttggc tcactgcagc | 60 |
| cttaacctcc caggctcaag ctatcctcct gccaaagcct tccacatagc tgggactaca | 120 |
| ggtacacngc caccacaccc agctaaaatt tttgtatttt ttgtagagac gggatctcgc | 180 |
| cacgttgccc aggctggtcc catcctgacc tcaagcagat ctgcccacct cagcccccca | 240 |
| acgtgctagg attacaggcg tgagccaccg cacccagcct ttgttttgct tttaatggaa | 300 |
| tcaccagttc ccctccgtgt ctcagcagca gctgtgagaa atgctttgca tctgtgacct | 360 |
| ttatgaaggg gaacttccat gctgaatgag gtaggattta catgctcctg tttcccgggg | 420 |
| gtcaagaaag cctcagactc cagcatgata agcagggtga g | 461 |

<210> SEQ ID NO 48
<211> LENGTH: 571
<212> TYPE: DNA
<213> ORGANISM: Homo sapien

<400> SEQUENCE: 48

| | | |
|---|---|---|
| atagggctt taaggaggga attcaggttc aatgaggtcg taaggccagg gctcttatcc | 60 |
| agtaagactg gggtccttag atgagaaaga dacacccgag gtccttctct ctgccgtgtg | 120 |
| aggatgcatc aagaaggcgg ccgtctgcaa gcgaaggaga ggccgcacca gaaaccgaca | 180 |
| ccttcatctt ggacttgcag cctctagaac tgagaaaata actgtctgtt ggttaagcca | 240 |
| cccagtttgt agtattctct tatggcttcc taagcagact aacaaacaaa cacccaaaat | 300 |
| taactgatgg cttcgctgtc ttctgtaaaa attgctatga gagaactttt cactcactgt | 360 |
| tttgcagttt ctccctcagt ccctggttct ttcttctcac ataatcccaa tttcaattta | 420 |
| tagttcatgg cccaggcaga gtcattcatc acggcatctc ctgagctaaa ccagcacctg | 480 |
| ctctgctcac ttcttgactg gctgctcatc atcagccctc ttgcagagat ttcatttcct | 540 |
| cccgtgccag gtacttcacg caccaagctc a | 571 |

<210> SEQ ID NO 49
<211> LENGTH: 511
<212> TYPE: DNA
<213> ORGANISM: Homo sapien

<400> SEQUENCE: 49

| | | |
|---|---|---|
| ggataatgaa gttgttttat ttagcttgga caaaaaggca tattcctcta ttttcttata | 60 |
| caacaaatat ccccaaaata aagcaagcat atatatcttg aatgtgtaat aatccagtga | 120 |
| taaacaagag cagtacttta aaagaaaaaa aaatatgtat ttctgtcagg ttaaaatgag | 180 |
| aatcaaaacc atttactctg ctaactcatt attttttgct ttcttttttgg ttaagagagg | 240 |
| caatgcaata cactgaaaaa ggtttttatc ttatctggca ttggaattag acatattcaa | 300 |
| accccagccc ccatttccaa actttaagac cacaaacaag taatttactt ttctgaacat | 360 |
| tggttttttc tggaaaatgg gaattataaa atagactttg cagactctta tgagattaaa | 420 |
| taagataatg tatgaaattc tttcttcttt tttacttctt tttccttttt gagatggagt | 480 |
| ctcaccccgt cacccaggct ggagtacagt g | 511 |

<210> SEQ ID NO 50
<211> LENGTH: 561
<212> TYPE: DNA
<213> ORGANISM: Homo sapien

<400> SEQUENCE: 50

```
ccactgcact ccagcctggg tgacggagtg agactctgtc tcaaaaaaac aaacaaacaa      60
acaaacaaaa aactgaaaag gaaatagagt tcctctttcc tcatatatga atatattatt     120
tcaacagatt gttgatcacc taccatatgc ttggtattgt tctaattgct ggggatacag     180
caagaggttc tgcagaactt catggagcat gaaagtaaat aaacaaagtt aatttcaagg     240
ccaggcatgg ttgctcacac ctttagtccc agcactttgg gaggctgagg caggtggatc     300
acttgggccc aggagttcaa ggctgcagtg agccaagatt gtgccactac tctccaggct     360
gggcaacaga gcaagaccct gtctcagggg aacaaaaag ttaatttcag attttgttaa      420
gtgctgtaaa ggaagtaaat aggttgatat tcaagagagc acctgaaggc caggcgtggt     480
ggctcacgcc tgtggtctaa cgctttggga agcccgagcg ggcggatcac aaggtcagga     540
gaattttggc caggcatggt g                                                561
```

<210> SEQ ID NO 51
<211> LENGTH: 451
<212> TYPE: DNA
<213> ORGANISM: Homo sapien

<400> SEQUENCE: 51

```
agaatccatt tattgggttt taaactagtt acacaactga atcagtttg gcactacttt       60
atacagggat tacgcctgtg tatgccgaca cttaaatact gtaccaggac cactgctgtg     120
cttaggtctg tattcagtca ttcagcatgt agatactaaa aatatactgt agtgttcctt     180
taaggaagac tgtacagggt gtgttgcaag atgacattac caatttgtg aattatttca      240
acccagaaga tacctttcac tctataaact tgtcataggc aaacatgtgg tgttagcatt     300
gagagatgca cacaaaaatg ttacataaaa gttcagacat tctaatgata agtgaactga     360
aaaaaaaaaa aaccccacat ctcaattttt gtaacaagat aagaaaata atttaaaaac      420
acaaaaaatg gcattcagtg ggtacaaagc c                                    451
```

<210> SEQ ID NO 52
<211> LENGTH: 682
<212> TYPE: DNA
<213> ORGANISM: Homo sapien

<400> SEQUENCE: 52

```
caaatattta atataaatct ttgaaacaag ttcagakgaa ataaaaatca agtttgcaa       60
aaacgtgaag attaacttaa ttgtcaaata ttcctcattg ccccaaatca gtattttttt     120
tatttctatg caaaagtatg ccttcaaact gcttaaatga tatatgatat gatacacaaa     180
ccagttttca aatagtaaag ccagtcatct tgcaattgta agaaataggt aaagagattat    240
aagacacctt acacacacac acacacacac acacacacgt gtgcaccgcc aatgacaaaa     300
aacaatttgg cctctcctaa aataagaaca tgaagaccct taattgctgc caggagggaa     360
cactgtgtca cccctcccta caatccaggt agtttccttt aatccaatag caaatctggg     420
catatttgag aggagtgatt ctgacagcca csgttgaaat cctgtgggga accattcatg     480
tccacccact ggtgccctga aaaaatgcca ataattttc gctcccactt ctgctgctgt      540
ctcttccaca tcctcacata gacccccagac ccgctggccc ctggctgggc atcgcattgc    600
```

```
tggtagagca agtcataggt ctcgtctttg acgtcacaga agcgatacac caaattgcct    660
ggtcggtcat tgtcataacc ag                                            682

<210> SEQ ID NO 53
<211> LENGTH: 311
<212> TYPE: DNA
<213> ORGANISM: Homo sapien
<220> FEATURE:
<221> NAME/KEY: misc_feature
<222> LOCATION: (1)...(311)
<223> OTHER INFORMATION: n = A,T,C or G

<400> SEQUENCE: 53
tttgacttta gtagggtct gaactattta ttttactttg ccmgtaatat ttaraccyta     60
tatatctttc attatgccat cttatcttct aatgbcaagg gaacagwtgc taamctggct   120
tctgcattwa tcacattaaa aatggctttc ttggaaaatc ttcttgatat gaataaagga   180
tcttttavag ccatcattta aagcmggntt ctctccaaca cgagtctgct sasggggggk   240
gagctgtgaa ctctggctga aggctttccc atacacactg caatgacmtg gtttctgacc   300
agbgtgagtt a                                                        311

<210> SEQ ID NO 54
<211> LENGTH: 561
<212> TYPE: DNA
<213> ORGANISM: Homo sapien

<400> SEQUENCE: 54
agagaagccc cataaatgca atcagtgtgg gaaggccttc agtcagagct caagccttt     60 cctccatcat cgggttcata ctggagagaa accctatgta tgtaatgaat gcggcagagc   120
cttggttttt aactctcatc ttactgaaca cgtaaggatt cacacaggag aaaaaccta   180 tgtttgtaat gagtgcggca aagcctttcg tcggagttcc actcttgttc agcatcgaag   240
agttcacact ggggagaagc cctaccagtg cgttgaatgt gggaaagctt tcagccagag   300
ctcccagctc accctacatc agccgagttc acactggaga gaagccctat gactgtggtg   360
actgtgggaa ggccttcagc cggaggtcaa ccctcattca gcatcagaaa gttcacagcg   420
gagagactcg taagtgcaga aaacatggtc cagcctttgt tcatggctcc agcctcacag   480
cagatggaca gattcccact ggagagaagc acggcagaac ctttaaccat ggtgcaaatc   540
tcattctgcg ctggacagtt c                                             561

<210> SEQ ID NO 55
<211> LENGTH: 811
<212> TYPE: DNA
<213> ORGANISM: Homo sapien

<400> SEQUENCE: 55
gagacagggt ctcactttgt cacccaggct ggaatgcagt ggtgcgatct tacgtagctc     60
actgcagccc tgacctcctg gactcaaaca attctcctgc ctcagccctg caagtagctg   120
ggactgtggg tgcatgccac catgcctggc taactttgt agttttgta aagatggggt   180 tttgccatgt tgcacatgct ggtcttgaac tcctgagctc aaacgatctg cccacctcgg   240
cctcccagaa tgttgggatt acaggggtaa accaccacgc ctggccccat tagggtattc   300
ttagcatcca cttgctcact gagattaatc ataagagatg ataagcactg gaagaaaaaa   360
attttactca ggctttggat atttttttcc tttttcagct ttatacagag gattggatct   420
```

```
ttagttttcc tttaactgat aataaaacat tgaaaggaaa taagtttacc tgagattcac      480
agagataacc ggcatcactc ccttgctcaa ttccagtctt taccacatca attattttca      540
gaggtgcagg ataaaggcct ttagtctgct ttcgcacttt ttcttccact tttttgtaaa      600
cctgttgcct gacaaatgga attgacagcg tatgccatga ctattccatt tgtcaggcat      660
acgctgtcaa ttttttccacc aatcccttgt ctctctttgg agagatcttc ttatcagcta     720
gtcctttggc aaaagtaatt gcaacttctt ctaggtattc tattgtccgt tccactggtg      780
gaacccctgg gaccaggact aaaacctcca g                                     811
```

<210> SEQ ID NO 56
<211> LENGTH: 591
<212> TYPE: DNA
<213> ORGANISM: Homo sapien
<220> FEATURE:
<221> NAME/KEY: misc_feature
<222> LOCATION: (1)...(591)
<223> OTHER INFORMATION: n = A,T,C or G

<400> SEQUENCE: 56

```
atctcatata tatatttctt cctgactttta tttgcttgct tctgncacgc atttaaaata      60
tcacagagac caaaatagag cggctttctg gtggaacgca tggcagtcac aggacaaaat     120
acaaaactag ggggctctgt cttctcatac atcatacaat tttcaagtat ttttttttatg    180 tacaaagagc tactctatct gaaaaaaaat taaaaaataa atgagacaag atagtttatg     240
catcctagga agaaagaatg ggaagaaaga acggggcagt tgggtacaga ttcctgtccc     300
ctgttcccag ggaccactac cttcctgcca ctgagttccc ccacagcctc acccatcatg     360
tcacagggca agtgccaggg taggtgggga ccagtggaga caggaaccag caacatactt     420
tggcctggaa gataaggaga aagtctcaga acacactgg tgggaagcaa tcccacnggc     480
cgtgccccan gagcttccca cctgctgctg gctccctggg tggctttggg aacagcttgg      540
gcaggccctt ttgggtgggg nccaactggg cctttgggcc cgtgtggaaa g                591
```

<210> SEQ ID NO 57
<211> LENGTH: 481
<212> TYPE: DNA
<213> ORGANISM: Homo sapien

<400> SEQUENCE: 57

```
aaacattgag atggaatgat agggtttccc agaatcaggt ccatatttta actaaatgaa      60
aattatgatt tatagccttc tcaaataccct gccatacttg atatctcaac cagagctaat    120
tttacctctt tacaaattaa ataagcaagt aactggatcc acaatttata atacctgtca     180 atttttttctg tattaaacct ctatcatagt ttaagcctat tagggtactt aatccttaca    240
aataaacagg tttaaaatca cctcaatagg caactgccct tctggttttc ttctttgact     300
aaacaatctg aatgcttaag attttccact ttgggtgcta gcagtacaca gtgttacact     360
ctgtattcca gacttcttaa attatagaaa aaggaatgta cacttttttgt attctttctg    420 agcagggccg ggaggcaaca tcatctacca tggtagggac ttgtatgcat ggactacttt     480
a                                                                       481
```

<210> SEQ ID NO 58
<211> LENGTH: 141
<212> TYPE: DNA
<213> ORGANISM: Homo sapien

<400> SEQUENCE: 58

```
actctgtcgc ccaggctgga gcccabtggm gcgatctcga ctccctgcaa gctmcgcctc    60
acaggwtcat gccattctcc tgcctcagca tctggagtag ctgggactac aggcgccagc   120
caccatgccc agctaattt t                                              141
```

<210> SEQ ID NO 59
<211> LENGTH: 191
<212> TYPE: DNA
<213> ORGANISM: Homo sapien

<400> SEQUENCE: 59

```
accttaaaga cataggagaa tttatactgg gagagaaagc ttacaaatgt aaggtttctg    60
acaagacttg ggagtgattc acacctggaa caacatactg gacttcacac tggabagaaa   120
ccttacaagt gtaatgagtg tggcaaagcc tttggcaagc agtcaacact tattcaccat   180
caggcaattc a                                                        191
```

<210> SEQ ID NO 60
<211> LENGTH: 480
<212> TYPE: DNA
<213> ORGANISM: Homo sapien

<400> SEQUENCE: 60

```
agtcaggatc atgatggctc agtttcccac agcgatgaat ggagggccaa atatgtgggc    60
tattacatct gaagaacgta ctaagcatga taaacagttt gataacctca aaccttcagg   120
aggttacata acaggtgatc aagcccgtac tttttttccta cagtcaggtc tgccggcccc   180
ggttttagct gaaatatggg ccttatcaga tctgaacaag gatgggaaga tggaccagca   240
agagttctct atagctatga aactcatcaa gttaaagttg cagggccaac agctgcctgt   300
agtcctccct cctatcatga acaaccccc tatgttctct ccactaatct ctgctcgttt   360
tgggatggga agcatgccca atctgtccat tcatcagcca ttgcctccag ttgcacctat   420
agcaacaccc ttgtcttctg ctacttcagg gaccagtatt cctccctaat gatgcctgct   480
```

<210> SEQ ID NO 61
<211> LENGTH: 381
<212> TYPE: DNA
<213> ORGANISM: Homo sapien

<400> SEQUENCE: 61

```
ctttcgattt ccttcaattt gtcacgtttg attttatgaa gttgttcaag ggctaactgc    60
tgtgtattat agctttctct gagttccttc agctgattgt taaatgaatc catttctgag   120
agcttagatg cagtttcttt ttcaagagca tctaattgtt ctttaagtct ttggcataat   180
tcttcctttt ctgatgactt tctatgaagt aaactgatcc ctgaatcagg tgtgttactg   240
agctgcatgt ttttaattct ttcgtttaat agctgcttct cagggaccag atagataagc   300
ttattttgat attccttaag ctcttggtga agttgttcga tttccataat ttccaggtca   360
cactggttat cccaaacttc t                                             381
```

<210> SEQ ID NO 62
<211> LENGTH: 906
<212> TYPE: DNA
<213> ORGANISM: Homo sapien

<400> SEQUENCE: 62

```
gtggaggtga aacggaggca agaaagggg ctacctcagg agcgagggac aaaggggggcg    60
```

```
tgaggcacct aggccgcggc accccggcga caggaagccg tcctgaaccg ggctaccggg        120
taggggaagg gcccgcgtag tcctcgcagg gccccagagc tggagtcggc tccacagccc        180
cgggccgtcg gcttctcact tcctggacct ccccggcgcc cggcctgag gactggctcg         240 gcggagggag aagaggaaac agacttgagc agctccccgt tgtctcgcaa ctccactgcc        300
gaggaactct catttcttcc ctcgctcctt caccccccac ctcatgtaga aaggtgctga        360
agcgtccgga gggaagaaga acctgggcta ccgtcctggc cttcccmccc ccttcccggg        420
gcgctttggt gggcgtggag ttgggtttgg gggtgtgggt ggggttctt ttttggagtg         480 ctggggaact tttttcccct cttcaggtca ggggaaaggg aatgcccaat tcagagagac        540 atggggcaa gaaggacggg agtggaggag cttctggaac tttgcagccg tcatcgggag         600
gcggcagctc taacagcaga gagcgtcacc gcttggtatc gaagcacaag cggcataagt        660
ccaaacactc caaagacatg gggttggtga ccccgaagc agcatccctg gcacagtta         720 tcaaaccttt ggtggagtat gatgatatca gctctgattc cgacaccttc tccgatgaca        780
tggccttcaa actagaccga agggagaacg acgaacgtcg tggatcagat cggagcgacc        840
gcctgcacaa acatcgtcac caccagcaca ggcgttcccg ggacttacta aaagctaaac        900
agaccg                                                                  906

<210> SEQ ID NO 63
<211> LENGTH: 491
<212> TYPE: DNA
<213> ORGANISM: Homo sapien

<400> SEQUENCE: 63
gacatgtttg cctgcagggg accagagaca atgggattag ccagtgctca ctgttctta        60 tgcttccaga gaggatgggg acagctctca ggtcagaatc caggctgaga aggccatgct       120
ggttgggggc cccggaagc acgtccgga tcctccctgg catcagcgta gacccgctgc         180
tcaggcttgg ggtaccaaac tcatgctctg tactgttttg gccccatgcg gtgagaggaa       240
aacctagaaa aagattggtc gtgctaagga atcagctgcc ccctcatcct ccgcatccaa       300
tgctggtgac aacatattcc ctctcccagg acacagactc ggtgactcca cactgggctg      360
agtggcctct ggaggctcgt ggcctaaggc agggctccgt aaggctgatc ggctgaactg       420
ggtggggtga gggtttctga cccttcgctt cccatcccat aaccgctgtc aatgagctca      480
cactgtggtc a                                                            491

<210> SEQ ID NO 64
<211> LENGTH: 511
<212> TYPE: DNA
<213> ORGANISM: Homo sapien

<400> SEQUENCE: 64
gatggcatgg tcgttgctaa tgtgcctgct gggatggagc acttcctcct gtgagcccag        60 ggacccgcc tgtccctgga gcttgggca aggaggaag agtgatacca ggaaggtggg          120
gctgcagcca ggggccagag tcagttcagg gagtggtcct cggccctcaa agctcctccg       180
gggactgctc aggagtgatg gtgccctgga gtttgcccca acttccctgg ccaccctgga       240
aggtgcctgg ctgctccagg cctctaggct gggctgatgg gtttctccag gacacaagta      300
tcattaaagc cacctctcc tcagcttgtc aggccgcaca tgtgggacag gctgtgctca       360 caacccccctc gcctgccctg ccctccatca ggaggagcca gtggaacctt cggaaagctc    420
ccagcatctc agcagccctc aaaagtcgtc ctggggcaag ctctggttct cctgactgga     480
```
ggtcatctgg gcttggcctg ctctctctcg c                                    511

<210> SEQ ID NO 65
<211> LENGTH: 394
<212> TYPE: DNA
<213> ORGANISM: Homo sapien

<400> SEQUENCE: 65
taaaaaagtg taacaaaggt ttatttagac tttcttcatg cccccagatc caggatgtct     60
atgtaaaccg ttatcttaca aagaaagcac aatatttggt ataaactaag tcagtgactt    120
gcttaactga aatagcgtcc atccaaaagt gggtttaagg taaaactacc tgacgatatt    180
ggcggggatc ctgcagtttg gactgcttgc cgggtttgtc cagggttccg ggtctgttct    240
tggcactcat ggggacaggc atcctgctcg tctgtggggc cccgctggag cccttacgtg    300
aagctgaagg tatcgaccst aggggctct agggcagtgg gaccttcatc cggaactaac     360
aagggtcggg gagaggcctc ttgggctatg tggg                                 394

<210> SEQ ID NO 66
<211> LENGTH: 359
<212> TYPE: DNA
<213> ORGANISM: Homo sapien

<400> SEQUENCE: 66
caagcgttcc tttatggatg taaattcaaa cagtcatgct gagccatccc gggctgacag     60
tcacgttwaa gacactaggt cgggcgccac agtgccaccc aaggagaaga agaatttgga    120 attttttccat gaagatgtac ggaaatctga tgttgaatat gaaaatggcc cccaaatgga    180
attccaaaag gttaccacag gggctgtaag acctagtgac cctcctaagt gggaaagagg    240
aatggagaat agtatttctg atgcatcaag aacatcagaa tataaaactg agatcataat    300
gaaggaaaat tccatatcca atatgagttt actcagagac agtagaaact attcccagg    359

<210> SEQ ID NO 67
<211> LENGTH: 450
<212> TYPE: DNA
<213> ORGANISM: Homo sapien
<220> FEATURE:
<221> NAME/KEY: misc_feature
<222> LOCATION: (1)...(450)
<223> OTHER INFORMATION: n = A,T,C or G

<400> SEQUENCE: 67
taggaataac aaatgtttat tcagaaatgg ataagtaata cataatcacc cttcatctct     60
taatgcccct tcctctcctt ctgcacagga gacacagatg ggtaacatag aggcatggga    120
agtggaggag gacacaggac tagcccacca ccttctcttc ccggtctccc aagatgactg    180
cttatagagt ggaggaggca aacaggtccc ctcaatgtac cagatggtca cctatagcac    240
cagctccaga tggccacgtg gttgcagctg gactcaatga aactctgtga caaccagaag    300
ataccgtctt tgggatgaga gggaggataa agccatgcag ggaggatatt taccatccct    360
accctaagca cagtgcaagc agtgagcccc cggctcccag tacctgaaaa accaaggcct    420 actgncttt ggatgctctc ttgggccacg                                      450

<210> SEQ ID NO 68
<211> LENGTH: 511
<212> TYPE: DNA
<213> ORGANISM: Homo sapien -continued

<400> SEQUENCE: 68

```
aagcctcctg ccctggaaat ctggagcccc ttggagctga gctggacggg gcagggaggg        60
gctgagaggc aagaccgtct ccctcctgct gcagctgctt ccccagcagc cactgctggg       120
cacagcagaa acgccagcag agaaaatggg agccgagagt ccttagccct ggagctgagg       180
ctgcctctgg gctgacccgc tggctgtacg tggccagaac tggggttggc atctggcatc       240
catttgaggc cagggtggag gaaagggagg ccaacagagg aaaacctatt cctgctgtga       300
caacacagcc cttgtcccac gcagcctaag tgcagggagc gtgatgaagt caggcagcca       360
gtcggggagg acgaggtaac tcagcagcaa tgtcaccttg tagcctatgc gctcaatggc       420
ccggaggggc agcaaccccc cgcacacgtc agccaacagc agtgcctctg caggcaccaa       480
gagagcgatg atggacttga gcgccgtgtt c                                      511
```

<210> SEQ ID NO 69
<211> LENGTH: 511
<212> TYPE: DNA
<213> ORGANISM: Homo sapien

<400> SEQUENCE: 69

```
gtttggcaga agacatgttt aataacattt tcatatttaa aaaatacagc aacaattctc        60
tatctgtcca ccatcttgcc ttgcccttcc tggggctgag gcagacaaag gaaaggtaat       120
gaggttaggg cccccaggcg ggctaagtgc tattggcctg ctcctgctca aagagagcca       180
tagccagctg ggcacggccc cctagcccct ccaggttgct gaggcggcag cggtggtaga       240
gttcttcact gagccgtggg ctgcagtctc gcagggagaa cttctgcacc agccctggct       300
ctacggcccg aaagaggtgg agccctgaga accggaggaa aacatccatc acctccagcc       360
cctccagggc ttcctcctct tcctggcctg ccagttcacc tgccagccgg gctcgggccg       420
ccaggtagtc agcgttgtag aagcagccct ccgcagaagc ctgccggtca aatctccccg       480
ctataggagc ccccgggag gggtcagcac c                                       511
```

<210> SEQ ID NO 70
<211> LENGTH: 511
<212> TYPE: DNA
<213> ORGANISM: Homo sapien

<400> SEQUENCE: 70

```
caagttgaac gtcaggcttg gcagaggtgg agtgtagatg aaaacaaagg tgtgattatg        60
aagaggatgt gagtcctttg ggtgtaggag agaaaggctg ttgagcttct atttcaagat       120
acttttacct gtgcaaaaag cacattttcc acctccttct catggcattt gtgtaaggtg       180
agtatgattc ctattccatc tgcattttag aggtgaagaa taacgtacaa gggattcagt       240
gattagcaag ggaccctca ctaagtgttg atggagttag acagagctc agctgtttga        300
atctcagagc ccaggcagct ggagctgggt aggatcctgg agctggcact aatgtgaggt       360
gcattccctc caacccaggc tcagatccgg aacctgaccg tgctgacccc cgaaggggag       420
gcagggctga gctggcccgt tgggctccct gctcctttca ccacactc tcgctttgag         480
gtgctgggct gggactactt cacagagcag c                                      511
```

<210> SEQ ID NO 71
<211> LENGTH: 511
<212> TYPE: DNA
<213> ORGANISM: Homo sapien

<400> SEQUENCE: 71

```
tggcctgggc aggattggga gagaggtagc tacccggatg cagtcctttg ggatgaagac    60
tatagggtat gacccatca tttccccaga ggtctcggcc tcctttggtg ttcagcagct   120 gccctggag gagatctggc ctctctgtga tttcatcact gtgcacactc ctctcctgcc   180
ctccacgaca ggcttgctga atgacaacac ctttgcccag tgcaagaagg gggtgcgtgt   240
ggtgaactgt gcccgtggag ggatcgtgga cgaaggcgcc ctgctccggg ccctgcagtc   300
tggccagtgt gccggggctg cactggacgt gtttacggaa gagccgccac gggaccgggc   360
cttggtggac catgagaatg tcatcagctg tccccacctg ggtgccagca ccaaggaggc   420
tcagagccgc tgtggggagg aaattgctgt tcagttcgtg gacatggtga gggggaaatc   480
tctcacgggg gttgtgaatg cccaggccct t                                  511

<210> SEQ ID NO 72
<211> LENGTH: 2017
<212> TYPE: DNA
<213> ORGANISM: Homo sapien

<400> SEQUENCE: 72
agccagatgg ctgagagctg caagaagaag tcaggatcat gatggctcag tttcccacag    60
cgatgaatgg agggccaaat atgtgggcta ttacatctga agaacgtact aagcatgata   120
aacagtttga taacctcaaa ccttcaggag gttacataac aggtgatcaa gcccgtactt   180
ttttcctaca gtcaggtctg ccggccccgg ttttagctga aatatgggcc ttatcagatc   240
tgaacaagga tgggaagatg gaccagcaag agttctctat agctatgaaa ctcatcaagt   300
taaagttgca gggccaacag ctgcctgtag tcctccctcc tatcatgaaa caaccccta   360 tgttctctcc actaatctct gctcgttttg ggatgggaag catgcccaat ctgtccattc   420
atcagccatt gcctccagtt gcacctatag caacacccctt gtcttctgct acttcaggga   480
ccagtattcc tcccctaatg atgcctgctc ccctagtgcc ttctgttagt acatcctcat   540
taccaaatgg aactgccagt ctcattcagc ctttatccat tccttattct tcttcaacat   600
tgcctcatgc atcatcttac agcctgatga tgggaggatt tggtggtgct agtatccaga   660
aggcccagtc tctgattgat ttaggatcta gtagctcaac ttcctcaact gcttccctct   720
cagggaactc acctaagaca gggacctcag agtgggcagt tcctcagcct tcaagattaa   780
agtatcggca aaatttaat agtctagaca aaggcatgag cggatacctc tcaggttttc   840
aagctagaaa tgcccttctt cagtcaaatc tctctcaaac tcagctagct actatttgga   900
ctctggctga catcgatggt gacggacagt tgaaagctga agaatttatt ctggcgatgc   960
acctcactga catggccaaa gctggacagc cactaccact gacgttgcct cccgagcttg  1020
tccctccatc tttcagaggg ggaaagcaag ttgattctgt taatggaact ctgccttcat  1080
atcagaaaac acaagaagaa gagcctcaga gaaactgcc agttactttt gaggacaaac  1140
ggaaagccaa ctatgaacga ggaaacatgg agctggagaa gcgacgccaa gtgttgatgg  1200
agcagcagca gagggaggct gaacgcaaag cccagaaaga gaaggaagag tgggagcgga  1260
aacagagaga actgcaagag caagaatgga agaagcagct ggagttggag aaacgcttgg  1320
agaaacagag agagctggag agacagcggg aggaagagag gagaaaggag atagaaagac  1380
gagaggcagc aaaacaggag cttgagagac aacgccgttt agaatgggaa agactccgtc  1440
ggcaggagct gctcagtcag aagaccaggg aacaagaaga cattgtcagg ctgagctcca  1500
gaaagaaaag tctccacctg gaactggaag cagtgaatgg aaaacatcag cagatctcag  1560
```

-continued

| | |
|---|---|
| gcagactaca agatgtccaa atcagaaagc aaacacaaaa gactgagcta gaagttttgg | 1620 |
| ataaacagtg tgacctggaa attatggaaa tcaaacaact tcaacaagag cttaaggaat | 1680 |
| atcaaaataa gcttatctat ctggtccctg agaagcagct attaaacgaa agaattaaaa | 1740 |
| acatgcagct cagtaacaca cctgattcag ggatcagttt acttcataaa aagtcatcag | 1800 |
| aaaaggaaga attatgccaa agacttaaag aacaattaga tgctcttgaa aaagaaactg | 1860 |
| catctaagct ctcagaaatg gattcattta acaatcagct gaaggaactc agagaaagct | 1920 |
| ataatacaca gcagttagcc cttgaacaac ttcataaaat caaacgtgac aaattgaagg | 1980 |
| aaatcgaaag aaaaagatta gagcaaaaaa aaaaaaa | 2017 |

<210> SEQ ID NO 73
<211> LENGTH: 414
<212> TYPE: DNA
<213> ORGANISM: Homo sapien

<400> SEQUENCE: 73

| | |
|---|---|
| atggcagtga cattcaccat catgggaacc accttcccctt tcttcagga ttctctgtag | 60 |
| tggaagagag cacccagtgt tgggctgaaa acatctgaaa gtagggagaa gaacctaaaa | 120 |
| taatcagtat ctcagagggc tctaaggtgc caagaagtct cactggacat ttaagtgcca | 180 |
| acaaaggcat actttcggaa tcgccaagtc aaaactttct aacttctgtc tctctcagag | 240 |
| acaagtgaga ctcaagagtc tactgcttta gtggcaacta cagaaaactg gtgttaccca | 300 |
| gaaaaacagg agcaattaga aatggttcca atatttcaaa gctccgcaaa caggatgtgc | 360 |
| tttcctttgc ccatttaggg tttcttctct ttcctttctc tttattaacc acta | 414 |

<210> SEQ ID NO 74
<211> LENGTH: 1567
<212> TYPE: DNA
<213> ORGANISM: Homo sapien

<400> SEQUENCE: 74

| | |
|---|---|
| atatctagaa gtctggagtg agcaaacaag agcaagaaac aaaaagaagc caaaagcaga | 60 |
| aggctccaat atgaacaaga taaatctatc ttcaaagaca tattagaagt tgggaaaata | 120 |
| attcatgtga actagacaag tgtgttaaga gtgataagta aaatgcacgt ggagacaagt | 180 |
| gcatccccag atctcaggga cctcccccctg cctgtcacct ggggagtgag aggacaggat | 240 |
| agtgcatgtt cttttgtctct gaattttttag ttatatgtgc tgtaatgttg ctctgaggaa | 300 |
| gccccctggaa agtctatccc aacatatcca catcttatat tccacaaatt aagctgtagt | 360 |
| atgtacccta agacgctgct aattgactgc cacttcgcaa ctcaggggcg gctgcatttt | 420 |
| agtaatgggt caaatgattc acttttttatg atgcttccaa aggtgccttg gcttctcttc | 480 |
| ccaactgaca aatgccaaag ttgagaaaaa tgatcataat tttagcataa acagagcagt | 540 |
| cggcgacacc gattttataa ataaactgag caccttctttt ttaaacaaac aaatgcgggt | 600 |
| ttatttctca gatgatgttc atccgtgaat ggtccaggga aggacctttc accttgacta | 660 |
| tatggcatta tgtcatcaca agctctgagg cttctccttt ccatcctgcg tggacagcta | 720 |
| agacctcagt tttcaatagc atctagagca gtgggactca gctggggtga tttcgccccc | 780 |
| catctccggg ggaatgtctg aagacaattt tgttacctca atgagggagt ggaggaggat | 840 |
| acagtgctac taccaactag tggataaagg ccagggatgc tgctcaacct cctaccatgt | 900 |
| acaggacgtc tccccattac aactacccaa tccgaagtgt caactgtgtc aggactaaga | 960 |
| aaccctggtt tgagtagaa aagggcctgg aaagagggga gccaacaaat ctgtctgctt | 1020 |

```
cctcacatta gtcattggca aataagcatt ctgtctcttt ggctgctgcc tcagcacaga    1080
gagccagaac tctatcgggc accaggataa catctctcag tgaacagagt tgacaaggcc    1140
tatgggaaat gcctgatggg attatcttca gcttgttgag cttctaagtt tctttcccct    1200
cattctaccc tgcaagccaa gttctgtaag agaaatgcct gagttctagc tcaggttttc    1260
ttactctgaa tttagatctc cagacccttc ctggccacaa ttcaaattaa ggcaacaaac    1320
atataccttc catgaagcac acacagactt tgaaagcaa ggacaatgac tgcttgaatt    1380
gaggccttga ggaatgaagc tttgaaggaa agaatactt tgtttccagc cccttccca    1440 cactcttcat gtgttaacca ctgccttcct ggaccttgga ccacggtga ctgtattaca    1500 tgttgttata gaaaactgat tttagagttc tgatcgttca agagaatgat taaatataca    1560
tttccta                                                              1567

<210> SEQ ID NO 75
<211> LENGTH: 240
<212> TYPE: DNA
<213> ORGANISM: Homo sapien

<400> SEQUENCE: 75
tcgagcggcc gcccgggcag gtccttcaga cttggactgt gtcacactgc caggcttcca     60
gggctccaac ttgcagacgg cctgttgtgg gacagtctct gtaatcgcga aagcaaccat    120
ggaagacctg ggggaaaaca ccatggtttt atccaccctg agatctttga acaacttcat    180
ctctcagcgt gcggagggag gctctggact ggatatttct acctcggccg cgaccacgct    240

<210> SEQ ID NO 76
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 76
tagcgyggtc gcggccgagg yctgcttytc tgtccagccc agggcctgtg gggtcagggc     60
ggtgggtgca gatggcatcc actccggtgg cttccccatc tttctctggc ctgagcaagg    120
tcagcctgca gccagagtac agagggccaa cactggtgtt cttgaacaag gccttagca    180 ggccctgaag grccctctct gtagtgttga acttcctgga gccaggccac atgttctcct    240
cataccgcag gytagygatg gtgaagttga gggtgaaata gtattmangr agatggctgg    300
caracctgcc cgggcggccg ctcsaaatcc                                     330

<210> SEQ ID NO 77
<211> LENGTH: 361
<212> TYPE: DNA
<213> ORGANISM: Homo sapien

<400> SEQUENCE: 77
agcgtggtcg cggccgaggt gtccttcagg gtctgcttat gcccttgttc aagaacacca     60
gtgtcagctc tctgtactct ggttgcagac tgaccttgct caggcctgag aaggatgggg    120
cagccaccag agtggatgct gtctgcaccc atcgtcctga ccccaaaagc cctggactgg    180
acagagagcg gctgtactgg aagctgagcc agctgaccca cggcatcact gagctgggcc    240
cctacaccct ggacagggac agtctctatg tcaatggttt cacccatcgg agctctgtac    300
```

-continued

```
ccaccaccag caccggggtg gtcagcgagg agccattcaa cctgcccggg cggccgctcg      360
a                                                                     361

<210> SEQ ID NO 78
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 78
ttggggnttt mgagcggccg cccgggcagg taccggggtg gtcagcgagg agccattcac       60
actgaacttc accatcaaca acctgcggta tgaggagaac atgcagcacc ctggctccag      120
gaagttcaac accacggaga gggtccttca gggcctgctc aggtccctgt tcaagagcac      180
cagtgttggc cctctgtact ctggctgcag actgactttg ctcagacttg agaaacatgg     240
ggcagccact ggagtggacg ccatctgcac cctccgcctt gatcccactg gtcctggact     300
ggacagagag cggctatact gggagctgag ccagtcctct ggcggngacn ccnctt        356

<210> SEQ ID NO 79
<211> LENGTH: 226
<212> TYPE: DNA
<213> ORGANISM: Homo sapien

<400> SEQUENCE: 79
agcgtggtcg cggccgaggt ccagtcgcag catgctcttt ctcctgccca ctggcacagt       60
gaggaagatc tctgctgtca gtgagaaggc tgtcatccac tgagatggca gtcaaaagtg      120
catttaatac acctaacgta tcgaacatca tagcttggcc caggttatct catatgtgct     180
cagaacactt acaatagcct gcagacctgc ccgggcggcc gctcga                    226

<210> SEQ ID NO 80
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 80
tgtggtgttg aacttcctgg agncaggtg acccatgtcc tccccatact gcaggttggt       60
gatggtgaag ttgagggtga atggtaccag gagagggcca gcagccataa ttgtsgrgck     120
gsmgmssgag gmwggwgtyy cwgaggttcy rarrtccact gtggaggtcc caggagtgct    180
ggtggtgggc acagagstcy gatgggtgaa accattgaca tagagactgt tcctgtccag     240
ggtgtagggg cccagctctt yratgycatt ggycagttkg ctyagctccc agtacagccr    300
ctctckgyyg mgwccagsgc tttgggggtc aagatgatgg atgcagatgg catccactcc     360
agtggctgct ccatccttct cggacctgag agaggtcagt ctgcagccag agtacagagg    420
gccaacactg gtgttctttg aata                                            444

<210> SEQ ID NO 81
<211> LENGTH: 310
<212> TYPE: DNA
<213> ORGANISM: Homo sapien

<400> SEQUENCE: 81
```

```
tcgagcggcc gcccgggcag gtcaggaagc acattggtct tagagccact gcctcctgga      60
ttccacctgt gctgcggaca tctccaggga gtgcagaagg gaagcaggtc aaactgctca     120
gatcagtcag actggctgtt ctcagttctc acctgagcaa ggtcagtctg cagccagagt     180
acagagggcc aacactggtg ttcttgaaca agggcttgag cagaccctgc agaaccctct     240
tccgtggtgt tgaacttcct ggaaaccagg gtgttgcatg tttttcctca taatgcaagg     300
ttggtgatgg                                                            310
```

<210> SEQ ID NO 82
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 82

```
acggtttcaa tggacacttt tattgtttac ttaatggatc atcaattttg tctcactacc      60
tacaaatgga atttcatctt gtttccatgc tgagtagtga acagtgaca aagctaatca     120 taataaccta catcaaaaga gaactaagct aacactgctc actttctttt taacaggcaa     180
aatataaata tatgcactct anaatgcaca atggtttagt cactaaaaaa ttcaaatggg     240
atcttgaaga atgtatgcaa atccagggtg cagtgaagat gagctgagat gctgtgcaac     300
tgtttaaggg ttcctggcac tgcatctctt ggccactagc tgaatcttga catggaaggt     360
tttagctaat gccaagtgga gatgcagaaa atgctaagtt gacttagggg ctgtgcacag     420
gaactaaaag gcaggaaagt actaaatatt gctgagagca tccaccccag gaaggacttt     480
accttccagg agctccaaac tggcaccacc cccagtgctc acatggctga ctttatcctc     540
cgtgttccat ttggcacagc aagtggcagt g                                    571
```

<210> SEQ ID NO 83
<211> LENGTH: 551
<212> TYPE: DNA
<213> ORGANISM: Homo sapien

<400> SEQUENCE: 83

```
aaggctggtg ggttttttgat cctgctggag aacctccgct ttcatgtgga ggaagaaggg      60
aagggaaaag atgcttctgg gaacaaggtt aaagccgagc cagccaaaat agaagctttc     120
cgagcttcac tttccaagct agggatgtc tatgtcaatg atgcttttgg cactgctcac     180
agagcccaca gctccatggt aggagtcaat ctgccacaga aggctggtgg gttttttgatg     240 aagaaggagc tgaactactt tgcaaaggcc ttggagagcc cagagcgacc cttcctggcc     300
atcctgggcg gagctaaagt tgcagacaag atccagctca tcaataatat gctggacaaa     360
gtcaatgaga tgattattgg tggtggaatg gcttttacct tccttaaggt gctcaacaac     420
atggagattg gcacttctct gtttgatgaa gagggagcca agattgtcaa agacctaatg     480
tccaaagctg agaagaatgg tgtgaagatt accttgcctg ttgactttgt cactgctgac     540
aagtttgatg a                                                          551
```

<210> SEQ ID NO 84
<211> LENGTH: 571
<212> TYPE: DNA
<213> ORGANISM: Homo sapien

<400> SEQUENCE: 84

```
tttgttcctt acatttttct aaagagttac ttaaatcagt caactggtct ttgagactct      60
taagttctga ttccaactta gctaattcat tctgagaact gtggtatagg tggcgtgtct     120
cttctagctg ggacaaaagt tctttgtttt cccctgtag agtatcacag accttctgct     180
gaagctggac ctctgtctgg gccttggact cccaaatctg cttgtcatgt tcaagcctgg     240
aaatgttaat ctttaattct tccatatgga tggacatctg tctaagttga tcctttagaa     300
cactgcaatt atcttctttg agtctaattt cttcttcttt gctttgaatc gcatcactaa     360
acttcctctc ccatttctta gcttcatcta tcaccctgtc acgatcatcc tggagggaag     420
acatgctctt agtaaaggct gcaagctggg tcacagtact gtccaagttt tcctgaagtt     480
gctgaacttc cttgtctttc ttgttcaaag taacctgaat ctctccaatt gtctcttcca     540
agtggacttt ttctctgcgc aaagcatcca g                                    571
```

<210> SEQ ID NO 85
<211> LENGTH: 561
<212> TYPE: DNA
<213> ORGANISM: Homo sapien

<400> SEQUENCE: 85

```
tcattgcctg tgatggcatc tggaatgtga tgagcagcca ggaagttgta gatttcattc      60
aatcaaagga ttcagcatgt ggtggaagct gtgaggcaag agaaacaaga actgtatggc     120
aagttaagaa gcacagaggc aaacaagaag gagacagaaa agcagttgca ggaagctgag     180
caagaaatgg aggaaatgaa agaaaagatg agaaagtttg ctaaatctaa acagcagaaa     240
atcctagagc tggaagaaga gaatgaccgg cttagggcag aggtgcaccc tgcaggagat     300
acagctaaag agtgtatgga aacacttctt tcttccaatg ccagcatgaa ggaagaactt     360
gaagggtcaa aatggagta tgaaacccct tctaagaagt ttcagtcttt aatgtctgag     420
aaagactctc taagtgaaga ggttcaagat ttaaagcatc agatagaagg taatgtatct     480
aaacaagcta acctagaggc caccgagaaa catgataacc aaacgaatgt cactgaagag     540
ggaacacagt ctataccagg t                                               561
```

<210> SEQ ID NO 86
<211> LENGTH: 795
<212> TYPE: DNA
<213> ORGANISM: Homo sapien

<400> SEQUENCE: 86

```
aagccaataa tcaccattta ttacttaata tatgccaacc actgtacttg gcagttcaca      60
aattctcacc gttacaacaa ccccatgagg tatttattcc cattctatag atagggaaac     120
cacagctcaa gtaagttagg aaactgagcc aagtatacac agaatacgaa gtggcaaaac     180
tagaaggaaa gactgacact gctatctgct ggcctccagt gtcctggctc ttttcacacg     240
ggttcaatgt ctccagcgct gctgctgctg ctgcattacc atgccctcat tgttttttctt     300
cctctggtgt tcaactgcat ccttcaaaga atctaactca ttccagagac cacttatttc     360
tttctctctt tctgaaatta cttttaataa ttcttcatga gggggaaaag aagatgcctg     420
ttggtagttt tgttgtttaa gctgctcaat ttgggactta acaatttgt tttcatcttg     480
tacatcctgt aacagctgtg ttttgctaga aagatcactc tccctctctt ttagcatggc     540
ttctaacctc ttcaattcat tttccttttc tttcaacaca atctcaagtt cttcaaactg     600
tgatgcagaa gaggcctctt tcaagttatg ttgtgctact tcctgaacat gtgcttttaa     660
```

```
agattcattt tcttcttgaa gatcctgtaa ccacttccct gtattggcta ggtctttctc      720
tttctcttcc aaaacagcct tcatggtatt catctgttcc tcttttcctt ttaataagtt      780
caggagcttc agaac                                                       795
```

<210> SEQ ID NO 87
<211> LENGTH: 594
<212> TYPE: DNA
<213> ORGANISM: Homo sapien

<400> SEQUENCE: 87

```
caagctttt ttttttttt aaaaagtgtt agcattaatg ttttattgtc acgcagatgg       60
caactgggtt tatgtcttca tattttatat ttttgtaaat taaaaaaatt acaagttta     120 aatagccaat ggctggttat atttttcagaa aacatgatta gactaattca ttaatggtgg    180
cttcaagctt ttccttattg gctccagaaa attcacccac cttttgtccc ttcttaaaaa    240
actggaatgt tggcatgcat ttgacttcac actctgaagc aacatcctga cagtcatcca    300
catctacttc aaggaatatc acgttggaat acttttcaga gagggaatga agaaaaggct    360
tgatcatttt gcaaggccca caccacgtgg ctgagaagtc aactactaca agtttatcac    420
ctgcagcgtc caaggcttcc tgaaaagcag tcttgctctc gatctgcttc accatcttgg    480
ctgctggagt ctgacgagcg gctgtaagga ccgatggaaa tggatccaaa gcaccaaaca    540
gagcttcaag actcgctgct tggcttgaat tcggatccga tatcgccatg gcct          594
```

<210> SEQ ID NO 88
<211> LENGTH: 557
<212> TYPE: DNA
<213> ORGANISM: Homo sapien

<400> SEQUENCE: 88

```
aagtgttagc attaatgttt tattgtcacg cagatggcaa ctgggtttat gtcttcatat     60
tttatatttt tgtaaattaa aaaaattmca agtttaaat agccaatggc tggttatatt   120
ttcagaaaac atgattagac taattcatta atggtggctt caagcttttc cttattggct   180
ccagaaaatt cacccacctt ttgtcccttc taaaaaaact ggaatgttgg catgcatttg   240
acttcacact ctgaagcaac atcctgacag tcatccacat ctacttcaag gaatatcacg   300
ttggaatact tttcagagag ggaatgaaag aaaggcttga tcattttgca aggcccacac   360
cacgtggctg agaagtcaac tactacaagt ttatcacctg cagcgtccaa ggcttcctga   420
aaagcagtct tgctctcgat ctgcttcacc atcttggctg ctggagtctg acgagcggct   480
gtaaggaccg atggaaatgg atccaaagca ccaaacagag cttcaagact cgctgcttgg   540
catgaattcg gatccga                                                   557
```

<210> SEQ ID NO 89
<211> LENGTH: 561
<212> TYPE: DNA
<213> ORGANISM: Homo sapien
<220> FEATURE:
<221> NAME/KEY: misc_feature
<222> LOCATION: (1)...(561)
<223> OTHER INFORMATION: n = A,T,C or G

<400> SEQUENCE: 89

```
tacaaacttt attgaaacgc acacgcgcac acacacaaac acccctgtgg atagggaaaa     60
gcacctggcc acagggtcca ctgaaacggg gaggggatgg cagcttgtaa tgtggctttt   120
```

```
gccacaaccc ccttctgaca gggaaggcct tagattgagg ccccacctcc catggtgatg      180
gggagctcag aatggggtcc agggagaatt tggttagggg gaggtgctag ggaggcatga      240
gcagagggca ccctccgagt gggtcccga gggctgcaga gtcttcagta ctgtccctca      300
cagcagctgt ctcaaggctg ggtccctcaa aggggcgtcc cagcgcgggg cctccctgcg      360
caaacacttg gtaccctgg ctgcgcagcg aagccagca ggacagcagt ggcgccgatc       420
agcacaacag acgccctggc ggtagggaca gcaggcccag ccctgtcggt tgtctcggca      480
gcaggtctgg ttatcatggc agaagtgtcc ttcccacact tcacgtcctt cacacccacg      540
tganggctac nggccaggaa g                                                561

<210> SEQ ID NO 90
<211> LENGTH: 561
<212> TYPE: DNA
<213> ORGANISM: Homo sapien

<400> SEQUENCE: 90
cccgtgggtg ccatccacgg agttgttacc tgatctttgg aagcaggatc gcccgtctgc       60
actgcagtgg aagccccgtg ggcagcagtg atggccatcc ccgcatgcca cggcctctgg      120 gaagggcag caactggaag tccctgagac ggtaaagatg caggagtggc cggcagagca       180
gtgggcatca acctggcagg ggccacccag atgcctgctc agtgttgtgg gccatttgtc      240
cagaagggga cggcagcagc tgtagctggc tcctccgggg tccaggcagc aggccacagg      300
gcagaactga ccatctgggc accgcgttcc agccaccagc cctgctgtta aggccaccca     360
gctcaccagg gtccacatgg tctgcctgcg tccgactccg cggtccttgg gccctgatgg      420
ttctacctgc tgtgagctgc ccagtgggaa gtatggctgc tgccaatgcc caacgccacc      480
tgctgctccg atcacctgca ctgctgcccc aagacactgt gtgtgacctg atccagagta     540
agtgcctctc caaggagaac g                                                561

<210> SEQ ID NO 91
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 91
gaatcacctt tctggtttag ctagtacttt gtacagaaca atgaggtttc ccacagcgga       60
gtctccctgg gctctgtttg gctctcggta aggcaggcct cacctttttc ctctcctcta      120
tggagagggg aatatgcatt aaggtgaaaa gtcaccttcc aaaagtgaga aagggattcg      180
attgctgctt caggactgtg gaattatttg gaatgtttta caaatggttg ctacaaaaca      240
acaaaaaagg taattacaaa atgtgtacat cacaacatgc ttttttaaga cattatgcat      300
tgtgctcaca ttcccttaaa tgttgtttcc aaaggtgctc agcctctagc ccagctggat      360
tctccgggaa gaggcagaga cagtttggcg aaaaagacac agggaaggag ggggtggtga      420
aaggagaaag cagccttcca gttaaagatc agccctcagt taaaggtcag cttcccgcan      480
gctggcctca ncggagtct gggtcagagg gaggagcagc agcagggtgg gactggggcg      540
t                                                                      541

<210> SEQ ID NO 92
<211> LENGTH: 551
```

<212> TYPE: DNA
<213> ORGANISM: Homo sapien

<400> SEQUENCE: 92

| aaccgagcg | cgagcagtag | ctgggtgggc | accatggctg | ggatcaccac | catcgaggcg | 60 |
| gtgaagcgca | agatccaggt | tctgcagcag | caggcagatg | atgcagagga | gcgagctgag | 120 |
| cgcctccagc | gagaagttga | gggagaaagg | cgggcccggg | aacaggctga | ggctgaggtg | 180 |
| gcctccttga | accgtaggat | ccagctggtt | gaagaagagc | tggaccgtgc | tcaggagcgc | 240 |
| ctggccactg | ccctgcaaaa | gctggaagaa | gctgaaaaag | ctgctgatga | gagtgagaga | 300 |
| ggtatgaagg | ttattgaaaa | ccgggcctta | aagatgaag | aaaagatgga | actccaggaa | 360 |
| atccaactca | aagaagctaa | gcacattgca | gaagaggcag | ataggaagta | tgaagaggtg | 420 |
| gctcgtaagt | tggtgatcat | tgaaggagac | ttggaacgca | cagaggaacg | agctgagctg | 480 |
| gcagagtccc | gttgccgaga | gatggatgag | cagattagac | tgatggacca | gaacctgaag | 540 |
| tgtctgagtg | c | | | | | 551 |

<210> SEQ ID NO 93
<211> LENGTH: 531
<212> TYPE: DNA
<213> ORGANISM: Homo sapien

<400> SEQUENCE: 93

| gagaacttgg | cctttattgt | gggcccagga | gggcacaaag | gtcaggaggc | ccaagggagg | 60 |
| gatctggttt | tctggatagc | caggtcatag | catgggtatc | agtaggaatc | cgctgtagct | 120 |
| gcacaggcct | cacttgctgc | agttccgggg | agaacacctg | cactgcatgg | cgttgatgac | 180 |
| ctcgtggtac | acgacagagc | cattggtgca | gtgcaagggc | acgcgcatgg | gctccgtcct | 240 |
| cgagggcagg | cagcaggagc | attgctcctg | cacatcctcg | atgtcaatgg | agtacacagc | 300 |
| tttgctggca | cactttccct | ggcagtaatg | aatgtccact | tcctcttggg | acttacaatc | 360 |
| tcccactttg | atgtactgca | ccttggctgt | gatgtctttg | caatcaggct | cctcacatgt | 420 |
| gtcacagcag | gtgcctggaa | ttttcacgat | tttgcctcct | tcagccagac | acttgtgttc | 480 |
| atcaaatggt | gggcagcccg | tgaccctctt | ctcccagatg | tactctcctc | t | 531 |

<210> SEQ ID NO 94
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 94

| gcctggacct | tgccggatca | gtgccacaca | gtgacttgct | tggcaaatgg | ccagaccttg | 60 |
| ctgcagagtc | atcgtgtcaa | ttgtgaccat | ggaccccggc | cttcatgtgc | caacagccag | 120 |
| tctcctgttc | gggtggagga | gacgtgtggc | tgccgctgga | cctgcccttg | tgtgtgcacg | 180 |
| ggcagttcca | ctcggcacat | cgtcaccttc | gatgggcaga | atttcaagct | tactggtagc | 240 |
| tgctcctatg | tcatctttca | aaacaaggag | caggacctgg | aagtgctcct | ccacaatggg | 300 |
| gcctgcagcc | ccggggcaaa | acaagcctgc | atgaagtcca | ttgagattaa | gcatgctggc | 360 |
| gtctctgctg | agctgcacag | taacatggag | atggcagtgg | atgggagact | ggtccttgcc | 420 |
| ccgtacgttg | gtgaaaacat | ggaagtcagc | atctacggcg | ctatcatgta | tgaagtcagg | 480 |

```
tttacccatc ttggccacat cctcacatac accgccncaa acaacgagt              531

<210> SEQ ID NO 95
<211> LENGTH: 605
<212> TYPE: DNA
<213> ORGANISM: Homo sapien

<400> SEQUENCE: 95
agatcaacct ctgctggtca ggaggaatgc cttccttgtc ttggatcttt gctttgacgt    60
tctcgatagt rwcaactkkr ytsramskma agkgyratgr wmttksywgw rasyktmwwm   120
rsgraraytt agacaycccm cctcwgagac gsagkaccar gtgcagaggt ggactctttc   180
tggatgttgt agtcagacag ggtgcgtcca tcttccagct gtttcccagc aaagatcaac   240
ctctgctgat caggagggat gccttcctta tcttggatct ttgccttgac attctcgatg   300
gtgtcactgg gctccacctc gagggtgatg gtcttaccag tcagggtctt cacgaagaty   360
tgcatcccac ctctgagacg gagcaccagg tgcagggtrg actctttctg gatgttgtag   420
tcagacaggg tgcgyccatc ttccagctgc tttccsagca aagatcaacc tctgctggtc   480
aggaggratg ccttccttgt cytggatctt tgcyttgacr ttctcratgg tgtcactcgg   540
ctccacttcg agagtgatgg tcttaccagt cagggtcttc acgaagatct gcatcccacc   600
tctaa                                                              605

<210> SEQ ID NO 96
<211> LENGTH: 531
<212> TYPE: DNA
<213> ORGANISM: Homo sapien

<400> SEQUENCE: 96
aagtcacaaa cagacaaaga ttattaccag ctgcaagcta tattagaagc tgaacgaaga    60
gacagaggtc atgattctga gatgattgga gaccttcaag ctcgaattac atctttacaa   120
gaggaggtga agcatctcaa acataatctc gaaaaagtgg aaggagaaag aaaagaggct   180
caagacatgc ttaatcactc agaaaaggaa aagaataatt tagagataga tttaaactac   240
aaacttaaat cattacaaca acggttagaa caagaggtaa atgaacacaa agtaaccaaa   300
gctcgtttaa ctgacaaaca tcaatctatt gaagaggcaa agtctgtggc aatgtgtgag   360
atggaaaaaa agctgaaaga agaaagagaa gctcgagaga aggctgaaaa tcgggttgtt   420
cagattgaga acagtgttc catgctagac gttgatctga agcaatctca gcagaaacta   480
gaacatttga ctggaaataa agaaaggatg gaggatgaag ttaagaatct a            531

<210> SEQ ID NO 97
<211> LENGTH: 1017
<212> TYPE: DNA
<213> ORGANISM: Homo sapien
<220> FEATURE:
<221> NAME/KEY: misc_feature
<222> LOCATION: (1)...(1017)
<223> OTHER INFORMATION: n = A,T,C or G

<400> SEQUENCE: 97
cgcctccacc atgtccatca gggtgaccca gaagtcctac aaggtgtcca cctctggccc    60
ccgggccttc agcagccgct cctacacgag tgggcccggt tcccgcatca gctcctcgag   120
cttctcccga gtgggcagca gcaactttcg cggtggcctg gcggcgggct atggtggggc   180
cagcggcatg ggaggcatca ccgcagttac ggtcaaccag agcctgctga gcccccttgt   240
cctggaggtg gaccccaaca tccaggccgt gcgcacccag gagaaggagc agatcaagac   300
```

```
cctcaacaac aagtttgcct ccttcataga caaggtacgg ttcctggagc agcagaacaa    360
gatgctggag accaagtgga gcctcctgca gcagcagaag acggctcgaa gcaacatgga    420
caacatgttc gagagctaca tcaacarcct taggcggcag ctggagactc tgggccagga    480
gaagctgaag ctggaggcgg agcttggcaa catgcagggg ctggtggagg acttcaagaa    540
caagtatgag gatgagatca ataagcgtac agagatggag aacgaatttg tcctcatcaa    600
gaaggatgtg gatgaagctt acatgaacaa ggtagagctg gagtctcgcc tggaagggct    660
gaccgacgag atcaacttcc tcaggcagct gtatgaagag gagatccggg agctgcagtc    720
ccagatctcg gacacatctg tggtgctgtc catggacaac agccgctccc tggacatgga    780
cagcatcatt gctgaggtca aggcacagta cgaggatatt gccaaccgca gccgggctga    840
ggctgagagc atgtaccagg tcaagtatga ggagctgcag agcctggctg ggaagcacgg    900
ggatgacctg cggcgcacaa agactgagat ctctgagatg aacccggaac atcagcccgg    960
ctncaggctg agattgaggg cctcaaaggc cagaggcett ncctggangn ccgccat     1017
```

<210> SEQ ID NO 98
<211> LENGTH: 561
<212> TYPE: DNA
<213> ORGANISM: Homo sapien

<400> SEQUENCE: 98

```
cccggagcca gccaacgagc ggaaaatggc agacaatttt tcgctccatg atgcgttatc     60
tgggtctgga aacccaaacc ctcaaggatg gcctggcgca tgggggaacc agcctgctgg    120 ggcaggggc tacccagggg cttcctatcc tggggcctac cccgggcagg cacccccagg    180
ggcttatcct ggacaggcac ctccaggcgc ctaccctgga gcacctggag cttatcccgg    240
agcacctgca cctggagtct acccaggcc acccagcggc cctggggcct acccatcttc    300
tggacagcca agtgccaccg gagcctaccc tgccactggc ccctatggcg ccctgctgg    360 gccactgatt gtgccttata acctgccttt gcctggggga gtggtgcctc gcatgctgat    420
aacaattctg ggcacggtga agcccaatgc aaacagaatt gctttagatt tccaaagagg    480
gaatgatgtt gccttccact ttaacccacg cttcaatgag aacaacagga gagtcattgg    540
ttgcaataca aagctggata a                                              561
```

<210> SEQ ID NO 99
<211> LENGTH: 636
<212> TYPE: DNA
<213> ORGANISM: Homo sapien

<400> SEQUENCE: 99

```
gggaatgcaa caactttatt gaaaggaaag tgcaatgaaa tttgttgaaa ccttaaaagg     60
ggaaacttag acaccccccc tcragcgmag kaccargtgc araggtggac tctttctgga    120
tgttgtagtc agacagggtr cgwccatctt ccagctgttt yccrgcaaag atcaacctct    180
gctgatcagg aggratgcct tccttatctt ggatctttgc cttgacattc tcgatggtgt    240
cactgggctc cacctcgagg gtgatggtct taccagtcag ggtcttcacg aagatytgca    300
tcccacctct gagacggagc accaggtgca gggtrgactc tttctggatg ttgtagtcag    360
acagggtgcg yccatcttcc agctgctttc csagcaaaga tcaacctctg ctggtcagga    420
ggratgcctt cctgtcytg gatctttgcy ttgacrttct caatggtgtc actcggctcc    480
acttcgagag tgatggtctt accagtcagg gtcttcacga agatctgcat cccacctcta    540
```

| | |
|---|---|
| agacggagca ccaggtgcag ggtggactct ttctggatgg ttgtagtcag acagggtgcg | 600 |
| tccatcttcc agctgtttcc cagcaaagat caacct | 636 |

<210> SEQ ID NO 100
<211> LENGTH: 697
<212> TYPE: DNA
<213> ORGANISM: Homo sapien

<400> SEQUENCE: 100

| | |
|---|---|
| aggttgatct ttgctgggaa acagctggaa gatggacgca ccctgtctga ctacaaccat | 60 |
| ccagaaagag tccaccctgc acctggtgct ccgtcttaga ggtgggatgc agatcttcgt | 120 |
| gaagaccctg actggtaaga ccatcactct cgaagtggag ccgagtgaca ccattgagaa | 180 |
| ygtcaargca aagatccarg acaaggaagg catycctcct gaccagcaga ggttgatctt | 240 |
| tgctsggaaa gcagctggaa gatggrcgca ccctgtctga ctacaacatc cagaaagagt | 300 |
| cyaccctgca cctggtgctc cgtctcagag gtgggatgca ratcttcgtg aagaccctga | 360 |
| ctggtaagac catcaccctc gaggtggagc ccagtgacac catcgagaat gtcaaggcaa | 420 |
| agatccaaga taaggaaggc atccctcctg atcagcagag gttgatcttt gctgggaaac | 480 |
| agctggaaga tggacgcacc ctgtctgact acaacatcca gaaagagtcc acctytgcac | 540 |
| ytggtmctbc gtctyagagg kgggrtgcaa atctwmgtkw agacactcac tkkyaagryy | 600 |
| atcamcmwtg akktcgakys castkwcact wtcrakaamg tyrwwgcawa gatccmagac | 660 |
| aaggaaggca ttcctcctga ccagcagagg ttgatct | 697 |

<210> SEQ ID NO 101
<211> LENGTH: 451
<212> TYPE: DNA
<213> ORGANISM: Homo sapien

<400> SEQUENCE: 101

| | |
|---|---|
| atggagtctc actctgtcga ccaggctgga gcgctgtggt gcgatatcgg ctcactgcag | 60 |
| tctccacttc ctgggttcaa gcgatcctcc tgcctcagcc tcccgagtag ctgggactac | 120 |
| aggcaggcgt caccataatt tttgtatttt tagtagagac atggtttcgc catgttggct | 180 |
| gggctggtct cgaactcctg acctcaagtg atctgtcctg gcctcccaaa gtgttgggat | 240 |
| tacaggcgaa agccaacgct cccggccagg gaacaacttt agaatgaagg aaatatgcaa | 300 |
| agaacatca catcaaggat caattaatta ccatctatta attactatat gtgggtaatt | 360 |
| atgactattt cccaagcatt ctacgttgac tgcttgagaa gatgtttgtc ctgcatggtg | 420 |
| gagagtggag aagggccagg attcttaggt t | 451 |

<210> SEQ ID NO 102
<211> LENGTH: 571
<212> TYPE: DNA
<213> ORGANISM: Homo sapien

<400> SEQUENCE: 102

| | |
|---|---|
| agcgcggtct tccggcgcga gaaagctgaa ggtgatgtgg ccgccctcaa ccgacgcatc | 60 |
| cagctcgttg aggaggagtt ggacagggct caggaacgac tggccacggc cctgcagaag | 120 |
| ctggaggagg cagaaaaagc tgcagatgag agtgagagag gaatgaaggt gatagaaaac | 180 |
| cgggccatga aggatgagga gagatggag attcaggaga tgcagctcaa agaggccaag | 240 |
| cacattgcgg aagaggctga ccgcaaatac gaggaggtag ctcgtaagct ggtcatcctg | 300 |
| gagggtgagc tggagagggc agaggagcgt gcggaggtgt ctgaactaaa atgtggtgac | 360 |

```
ctggaagaag aactcaagaa tgttactaac aatctgaaat ctctggaggc tgcatctgaa      420
aagtattctg aaaaggagga caaatatgaa gaagaaatta aacttctgtc tgacaaactg      480
aaagaggctg agacccgtgc tgaatttgca gagagaacgg ttgcaaaact ggaaaagaca      540
attgatgacc tggaagagaa acttgcccag c                                    571
```

<210> SEQ ID NO 103
<211> LENGTH: 451
<212> TYPE: DNA
<213> ORGANISM: Homo sapien

<400> SEQUENCE: 103

```
gtgcacaggt cccatttatt gtagaaaata ataataatta cagtgatgaa tagctcttct       60
taaattacaa aacagaaacc acaaagaagg aagaggaaaa accccaggac ttccaagggt      120
gaagctgtcc cctcctccct gccaccctcc caggctcatt agtgtccttg aagggggcag      180
aggactcaga ggggatcagt ctccaggggc cctgggctga agcgggtgag gcagagagtc      240
ctgaggccac agagctgggc aacctgagcc gcctctctgg cccctcccc caccactgcc       300 caaacctgtt tacagcacct tcgcccctcc cctctaaacc cgtccatcca ctctgcactt      360
cccaggcagg tgggtgggcc aggcctcagc catactcctg ggcgcgggtt tcggtgagca      420
aggcacagtc ccagaggtga tatcaaggcc t                                    451
```

<210> SEQ ID NO 104
<211> LENGTH: 441
<212> TYPE: DNA
<213> ORGANISM: Homo sapien

<400> SEQUENCE: 104

```
gcaaggaact ggtctgctca cacttgctgg cttgcgcatc aggactggct ttatctcctg       60
actcacggtg caaaggtgca ctctgcgaac gttaagtccg tccccagcgc ttggaatcct      120
acggccccca cagccggatc ccctcagcct tccaggtcct caactcccgt ggacgctgaa      180
caatggcctc catgggcta caggtaatgg gcatcgcgct ggccgtcctg ggctggctgg       240
ccgtcatgct gtgctgcgcg ctgcccatgt ggcgcgtgac ggccttcatc ggcagcaaca      300
ttgtcacctc gcagaccatc tgggagggcc tatggatgaa ctgcgtggtg cagagcaccg      360
gccagatgca gtgcaaggtg tacgactcgc tgctggcact ccgcaggac ctgcaggcgg       420 cccgcgccct cgtcatcatc a                                              441
```

<210> SEQ ID NO 105
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 105

```
tgcaaaaggg acacagggg tcaaaaataa aaatttctct tcccccctccc caaacctgta       60 ccccagctcc ccgaccacaa cccccttcct ccccgggga agcaagaag gagcaggtgt       120 ggcatctgca gctgggaaga gagaggccgg ggaggtgccg agctcggtgc tggtctcttt      180
ccaaatataa atacntgtgt cagaactgga aaatcctcca gcacccacca cccaagcact      240
ctccgttttc tgccggtgtt tggagagggg cggggggcag gggcgccagg caccggctgg      300
```

```
ctgcggtcta ctgcatccgc tgggtgtgca ccccgcgagc ctcctgctgc tcattgtaga    360
agagatgaca ctcggggtcc ccccggatgg tgggggctcc ctggatcagc ttccggtgt     420 tggggttcac acaccagcac tccccacgct gcccgttcag agacatcttg cactgtttga    480
ggttgtacag gccatgcttg tcacagttg                                      509
```

<210> SEQ ID NO 106
<211> LENGTH: 571
<212> TYPE: DNA
<213> ORGANISM: Homo sapien

<400> SEQUENCE: 106

```
gggttggagg gactggttct ttatttcaaa aagacacttg tcaatattca gtatcaaaac    60
agttgcacta ttgatttctc tttctcccaa tcggccccaa agagaccaca taaaaggaga   120
gtacatttta agccaataag ctgcaggatg tacacctaac agacctccta gaaaccttac    180
cagaaaatgg ggactgggta gggaaggaaa cttaaaagat caacaaactg ccagcccacg    240
gactgcagag gctgtcacag ccagatgggg tggccagggt gccacaaacc caaagcaaag    300
tttcaaaata atataaaatt taaaaagttt tgtacataag ctattcaaga tttctccagc    360
actgactgat acaaagcaca attgagatgg cacttctaga gacagcagct tcaaacccag    420
aaaagggtga tgagatgagt ttcacatggc taaatcagtg gcaaaaacac agtcttcttt    480 cttttctttct ttcaaggagg caggaaagca attaagtggt cacctcaaca taaggggac    540 atgatccatt ctgtaagcag ttgtgaaggg g                                   571
```

<210> SEQ ID NO 107
<211> LENGTH: 555
<212> TYPE: DNA
<213> ORGANISM: Homo sapien

<400> SEQUENCE: 107

```
caggaaccgg agcgcgagca gtagctgggt gggcaccatg gctgggatca ccaccatcga    60
ggcggtgaag cgcaagatcc aggttctgca gcagcaggca gatgatgcag aggagcgagc    120
tgagcgcctc cagcgagaag ttgagggaga aaggcgggcc cgggaacagg ctgaggctga    180
ggtggcctcc ttgaaccgta ggatccagct ggttgaagaa gagctggacc gtgctcagga    240
gcgcctggcc actgccctgc aaaagctgga agaagctgaa aaagctgctg atgagagtga    300
gagaggtatg aaggttattg aaaaccgggc cttaaaagat gaagaaaaga tggaactcca    360
ggaaatccaa ctcaaagaag ctaagcacat tgcagaagag gcagatagga agtatgaaga    420
ggtggctcgt aagttggtga tcattgaagg agacttggaa cgcacagagg aacgagctga    480
gctggcagag tcccgttgcc gagagatgga tgagcagatt agactgatgg accagaacct    540
gaagtgtctg agtgc                                                     555
```

<210> SEQ ID NO 108
<211> LENGTH: 541
<212> TYPE: DNA
<213> ORGANISM: Homo sapien

<400> SEQUENCE: 108

```
atctacgtca tcaatcaggc tggagacacc atgttcaatc gagctaagct gctcaatatt    60
ggctttcaag aggccttgaa ggactatgat tacaactgct ttgtgttcag tgatgtggac    120
ctcattccga tggacgaccg taatgcctac aggtgttttt cgcagccacg gcacatttct    180
gttgcaatgg acaagttcgg gtttagcctg ccatatgttc agtattttgg aggtgtctct    240
```

```
gctctcagta acaacagtt tcttgccatc aatggattcc ctaataatta ttggggttgg      300
ggaggagaag atgacgacat ttttaacaga ttagttcata aaggcatgtc tatatcacgt      360
ccaaatgctg tagtagggag gtgtcgaatg atccggcatt caagagacaa gaaaaatgag      420
cccaatcctc agaggtttga ccggatcgca catacaaagg aaacgatgcg cttcgatggt      480
ttgaactcac ttacctacaa ggtgttggat gtcagagata cccgttatat acccaaatca      540
c                                                                    541
```

<210> SEQ ID NO 109
<211> LENGTH: 411
<212> TYPE: DNA
<213> ORGANISM: Homo sapien

<400> SEQUENCE: 109

```
ctagacctct aattaaaagg cacaatcatg ctggagaatg aacagtctga ccccgagggc      60
cacagcgaat tttagggaag gaggcaaaga ggtgagaagg gaaaggaaag aaggaaggaa     120
ggagaacaat aagaactgga gacgttgggt gggtcaggga gtgtggtgga ggctcggaga     180
gatggtaaac aaacctgact gctatgagtt ttcaacccca tagtctaggg ccatgagggc     240
gtcagttctt ggtggctgag ggtccttcca cccagcccac ctgggggagt ggagtgggga     300
gttctgccag gtaagcagat gttgtctccc aagttcctga cccagatgtc tggcaggata     360
acgctgacct gttccctcaa caagggacct gaaagtaatt ttgctctttta c           411
```

<210> SEQ ID NO 110
<211> LENGTH: 451
<212> TYPE: DNA
<213> ORGANISM: Homo sapien

<400> SEQUENCE: 110

```
ccgaattcaa gcgtcaacga tccytcccctt accatcaaat caattggcca ccaatggtac      60
tgaacctacg agtacaccga ctacgggcgg actaatcttc aactcctaca tacttccccc     120
attattccta gaaccaggcg acctgcgact ccttgacgtt gacaatcgag tagtactccc     180
gattgaagcc cccattcgta taataattac atcacaagac gtcttgcact catgagctgt     240
ccccacatta ggcttaaaaa cagatgcaat tcccggacgt ctaagccaaa ccactttcac     300
cgctacacga ccgggggtat actacggtca atgctctgaa atctgtggag caaaccacag     360
tttcatgccc atcgtcctag aattaattcc cctaaaaatc tttgaaatag ggcccgtatt     420
taccctatag caccccctct accccctcta g                                    451
```

<210> SEQ ID NO 111
<211> LENGTH: 541
<212> TYPE: DNA
<213> ORGANISM: Homo sapien

<400> SEQUENCE: 111

```
gctcttcaca cttttattgt taattctctt cacatggcag atacagagct gtcgtcttga      60
agaccaccac tgaccaggaa atgccacttt tacaaaatca tccccccttt tcatgattgg     120
aacagttttc ctgaccgtct gggagcgttg aagggtgacc agcacatttg cacatgcaaa     180
aaaggagtga ccccaaggcc tcaaccacac ttcccagagc tcaccatggg ctgcaggtga     240
cttgccaggt ttggggttcg tgagctttcc ttgctgctgc ggtggggagg ccctcaagaa     300
ctgagaggcc ggggtatgct tcatgagtgt taacatttac gggacaaaag cgcatcatta     360
```

```
ggataaggaa cagccacagc acttcatgct tgtgagggtt agctgtagga gcgggtgaaa      420
ggattccagt ttatgaaaat ttaaagcaaa caacggtttt tagctgggtg ggaaacagga      480
aaactgtgat gtcggccaat gaccaccatt tttctgccca tgtgaaggtc cccatgaaac      540
c                                                                     541
```

<210> SEQ ID NO 112
<211> LENGTH: 521
<212> TYPE: DNA
<213> ORGANISM: Homo sapien

<400> SEQUENCE: 112

```
caagcgcttg gcgtttggac ccagttcagt gaggttcttg ggttttgtgc ctttggggat       60
tttggtttga cccagggtc agccttagga aggtcttcag gaggaggccg agttcccctt      120
cagtaccacc cctctctccc cactttccct ctcccggcaa catctctggg aatcaacagc      180
atattgacac gttggagccg agcctgaaca tgcccctcgg ccccagcaca tggaaaaccc      240
ccttccttgc ctaaggtgtc tgagtttctg gctcttgagg catttccaga cttgaaattc      300
tcatcagtcc attgctcttg agtctttgca gagaacctca gatcaggtgc acctgggaga      360
aagactttgt ccccacttac agatctatct cctcccttgg gaaggcagg gaatgggggac      420 ggtgtatgga ggggaaggga tctcctgcgc ccttcattgc cacacttggt gggaccatga      480
acatctttag tgtctgagct ctcaaatta ctgcaatagg a                          521
```

<210> SEQ ID NO 113
<211> LENGTH: 568
<212> TYPE: DNA
<213> ORGANISM: Homo sapien

<400> SEQUENCE: 113

```
agcgtcaaat cagaatggaa aagactcaaa accatcatca acaccaagat caaaaggaca       60
agratccttc aagaaacagg aaaaaactcc taaaacacca aaaggaccta gttctgtaga      120
agacattaaa gcaaaatgc aagcaagtat agaaaaaggt ggttctcttc ccaaagtgga      180
agccaaattc atcaattatg tgaagaattg cttccggatg actgaccaag aggctattca      240
agatctctgg cagtggagga agtctctta agaaaatagt ttaaacaatt tgttaaaaaa      300
ttttccgtct tatttcattt ctgtaacagt tgatatctgg ctgtcctttt tataatgcag      360
agtgagaact ttccctaccg tgtttgataa atgttgtcca ggttctattg ccaagaatgt      420
gttgtccaaa atgcctgttt agttttaaa gatggaactc cacccttgc ttggttttaa      480 gtatgtatgg aatgttatga taggacatag tagtagcggt ggtcagacat ggaaatggtg      540
ggsmgacaaa aatatacatg tgaaataa                                         568
```

<210> SEQ ID NO 114
<211> LENGTH: 483
<212> TYPE: DNA
<213> ORGANISM: Homo sapien

<400> SEQUENCE: 114

```
tccgaattcc aagcgaatta tggacaaacg attcctttta gaggattact tttttcaatt       60
tcggttttag taatctaggc tttgcctgta aagaatacaa cgatggattt taaatactgt      120
ttgtggaatg tgtttaaagg attgattcta gaacctttgt atatttgata gtatttctaa      180 cttcatttc tttactgttt gcagttaatg ttcatgttct gctatgcaat cgtttatatg      240
cacgtttctt taattttttt agatttcct ggatgtatag tttaaacaac aaaagtcta      300
```

```
tttaaaactg tagcagtagt ttacagttct agcaaagagg aaagttgtgg ggttaaactt        360
tgtattttct ttcttataga ggcttctaaa aaggtatttt tatatgttct ttttaacaaa        420
tattgtgtac aacctttaaa acatcaatgt ttggatcaaa acaagaccca gcttattttc        480
tgc                                                                      483
```

<210> SEQ ID NO 115
<211> LENGTH: 521
<212> TYPE: DNA
<213> ORGANISM: Homo sapien

<400> SEQUENCE: 115

```
tgtggtggcg cgggctgagg tggaggccca ggactctgac cctgcccctg ccttcagcaa         60
ggcccccggc agcgccggcc actacgaact gccgtgggtt gaaaaatata ggccagtaaa        120
gctgaatgaa attgtcggga atgaagcacg cgtgagcagg ctagaggtct ttgcaaggga        180
aggaaatgtg cccaacatca tcattgcggg ccctccagga accggcaaga ccacaagcat        240
tctgtgcttg gcccgggccc tgctgggccc agcactcaaa gatgccatgt tggaactcaa        300
tgcttcaaat gacaggggca ttgacgttgt gaggaataaa attaaaatgt ttgctcaaca        360
aaaagtcact cttcccaaag gccgacataa gatcatcatt ctggatgaag cagacagcat        420
gaccgacgga gcccagcaag ccttgaggag aaccatggaa atctactcta aaaccactcg        480
ttcgcccttg cttgtaatgc ttcggataag atcatcgagc c                           521
```

<210> SEQ ID NO 116
<211> LENGTH: 501
<212> TYPE: DNA
<213> ORGANISM: Homo sapien

<400> SEQUENCE: 116

```
ctttgcaaag ctttttattc atgtctgcgg catggaatcc acctgcacat ggcatcttag         60
ctgtgaagga gaaagcagtg cacgagaagg aatgagtggg cggaaccaac ggcctccaca        120
agctgccttc cagcagcctg ccaaggccat ggcagagaga gactgcaaac aaacacaagc        180
aaacagagtc tcttcacagc tggagtctga aagctcatag tggcatgtgt gaatctgaca        240
aaattaaaag tgtgcatagt ccattacatg cataaaacac taataataat cctgtttaca        300
cgtgactgca gcaggcaggt ccagctccac cactgccctc ctgccacatc acatcaagtg        360
ccatggttta gagggttttt catatgtaat tcttttattc tgtaaaaggt aacaaaatat        420
acagaacaaa actttccctt tttaaaacta atgttacaaa tctgtattat cacttggata        480
taaatagtat ataagctgat c                                                  501
```

<210> SEQ ID NO 117
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 117

```
caagggatat atgttgaggg tacrgrgtga cactgaacag atcacaaagc acgagaaaca         60
ttagttctct ccctccccag cgtctccttc gtctccctgg ttttccgatg tccacagagt        120
gagattgtcc ctaagtaact gcatgatcag agtgctgkct ttataagact cttcattcag        180
```

```
cgtatccaat tcagcaattg cttcatcaaa tgccgttttt gccaggctac aggccttttc      240
aggagagttt agaatctcat agtaaaagac tgagaaattt agtgccagac caagacgaat      300
tgggtgtgta ggctgcattn cttctttact aatttcaaat gcttcctggt aagcctgctg      360
ggagttcgac acaagtggtt tgtttgttgc tccagatgcc acttcagaaa gatacctaaa      420
ataatctcct ttcattttca aagtagaaca c                                    451
```

<210> SEQ ID NO 118
<211> LENGTH: 501
<212> TYPE: DNA
<213> ORGANISM: Homo sapien

<400> SEQUENCE: 118

```
tccggagccg gggtagtcgc cgccgccgcc gccggtgcag ccactgcagg caccgctgcc       60
gccgcctgag tagtgggctt aggaaggaag aggtcatctc gctcggagct tcgctcggaa      120
gggtctttgt tccctgcagc cctcccacgg gaatgacaat ggataaaagt gagctggtac      180
agaaagccaa actcgctgag caggctgagc gatatgatga tatggctgca gccatgaagg      240
cagtcacaga acagggcat gaactctcca cgaagagag aaatctgctc tctgttgcct        300
acaagaatgt ggtaaggccg cccgccgctc ttcctggcgt gtcatctcca gcattgagca      360
gaaaacagag aggaatgaga agaagcagca gatgggcaaa gagtaccgtg agaagataga      420
ggcagaactg caggacatct gcaatgatgt tctggagctt gttggacaaa tatcttattc      480
caatgctaca caacccagaa a                                                501
```

<210> SEQ ID NO 119
<211> LENGTH: 391
<212> TYPE: DNA
<213> ORGANISM: Homo sapien

<400> SEQUENCE: 119

```
aaaaagcagc argttcaaca caaaatagaa atctcaaatg taggatagaa caaaaccaag       60
tgtgtgaggg gggaagcaac agcaaaagga agaaatgaga tgttgcaaaa aagatggagg      120
agggttcccc tctcctctgg ggactgactc aaacactgat gtggcagtat acaccattcc      180
agagtcaggg gtgttcattc tttttttggga gtaagaaaag gtggggatta agaagacgtt      240
tctggaggct tagggaccaa ggctggtctc tttccccccct cccaaccccc ttgatccctt      300
tctctgatca ggggaaagga gctcgaatga gggaggtaga gttggaaagg gaaaggattc      360
cacttgacag aatgggacag actccttccc a                                    391
```

<210> SEQ ID NO 120
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 120

```
tggcaatagc acagccatcc aggagctctt cargcgcatc tcggagcagt tcactgccat       60
gttccgccgg aaggccttcc tccactggta cacaggcgag ggcatggacg agatggagtt      120
caccgaggct gagagcaaca tgaacgacct cgtctctgag tatcaagcag taccaggatg      180
ccaccgcaga agaggaggag gatttcggtg aggaggccga agaggaggcc taaggcagag      240
cccccatcac ctcaggcttc tcagttccct tagccgtctt actcaactgc cccttttcctc     300
```

```
tccctcagaa tttgtgtttg ctgcctctat cttgttttt gttttttctt ctggggggt      360 ctagaacagt gcctggcaca tagtaggcgc tcaataaata cttggttgnt gaatgtctcc      420
t                                                                      421
```

<210> SEQ ID NO 121
<211> LENGTH: 206
<212> TYPE: DNA
<213> ORGANISM: Homo sapien

<400> SEQUENCE: 121

```
agctggcgct agggctcggt tgtgaaatac agcgtrgtca gcccttgcgc tcagtgtaga       60
aacccacgcc tgtaaggtcg gtcttcgtcc atctgctttt ttctgaaata cactaagagc      120
agccacaaaa ctgtaaccte aaggaaacca taaagcttgg agtgccttaa tttttaacca     180
gtttccaata aaacggttta ctacct                                           206
```

<210> SEQ ID NO 122
<211> LENGTH: 131
<212> TYPE: DNA
<213> ORGANISM: Homo sapien

<400> SEQUENCE: 122

```
ggagatgaag atgaggaagc tgagtcagct acgggcargc gggcagctga agatgatgag       60
gatgacgatg tcgataccaa gaagcagaag accgacgagg atgactagac agcaaaaaag     120
gaaaagttaa a                                                           131
```

<210> SEQ ID NO 123
<211> LENGTH: 231
<212> TYPE: DNA
<213> ORGANISM: Homo sapien
<220> FEATURE:
<221> NAME/KEY: misc_feature
<222> LOCATION: (1)...(231)
<223> OTHER INFORMATION: n = A,T,C or G

<400> SEQUENCE: 123

```
gatgaaaatt aaatacttaa attaatcaaa aggcactacg ataccaccta aaacctactg       60
cctcagtggc agtakgctaa kgaagatcaa gctacagsac atyatctaat atgaatgtta     120
gcaattacat akcargaagc atgtttgctt tccagaagac tatggnacaa tggtcattwg     180
ggcccaagag gatatttggc cnggaaagga tcaagataga tnaangtaaa g               231
```

<210> SEQ ID NO 124
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 124

```
gagtagcaac gcaaagcgct tggtattgag tctgtgggsg acttcggttc cggtctctgc       60
agcagccgtg atcgcttagt ggagtgctta gggtagttgg ccaggatgcc gaatatcaaa     120
atcttcagca ggcagctccc accaggactt atctcasaaa attgctgacc gcctgggcct     180
ggagctaggc aagtggtgga ctaagaaatt cagcaaccag gagacctgtg tggaaattgg     240
tgaaagtgta ccgtggagag gatgtctaca ttgttcagag tggntgtggc gaaatcaatg     300
```

```
acaatttaat ggagcttttg atcatgatta atgcctgcaa gattgcttca gccagccggg      360
ttactgcagt catcccatgc ttcccttatg ccccggcagg ataagaaaga tnagagccgg      420
gccgccaatc tcagccaagc ttggtgcaaa tatgctatct gtagcagtgc agatcatatt      480
atcaccatgg acctacatgc ttctcaaatt canggctttt t                          521

<210> SEQ ID NO 125
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 125
atgcaaaagg ggacacaggg ggttcaaaaa taaaaatttc tcttcccct ccccaaacct       60 gtaccccagc tccccgacca cacccccctt cctccccgg ggaaagcaag aaggagcagg      120
tgtggcatct gcagctggga agagagaggc cggggaggtg ccgagctcgg tgctggtctc    180
tttccaaata taaatacgtg tgtcagaact ggaaaatcct ccagcaccca ccacccaagc    240
actctccgtt ttctgccggt gtttggagag gggcggnggg caggggcgcc aggcaccggc    300
tggctgcggt ctactgcatc cgctgggtgt gcaccccgcg a                         341

<210> SEQ ID NO 126
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 126
aggttggaga aggtcatgca ggtgcagatt gtccaggskc agccacaggg tcaagcccaa      60
caggcccaga gtggcactgg acagaccatg caggtgatgc agcagatcat cactaacaca    120
ggagagatcc agcagatccc ggtgcagctg aatgccggcc agctgcagta tatccgctta    180
gcccagcctg tatcaggcac tcaagttgtg cagggacaga tccagacact tgccaccaat    240
gctcaacaga ttacacagac agaggtccag caaggacagc agcagttcaa gccagttcac    300
aagatggaca gcagctctac cagatccagc aagtcaccat gcctgcgggc cangacctcg    360
ccagcccatg ttcatccagt caagccaacc agcccttcna cgggcaggcc cccaggtga    420 ccggcgactg aagggcctga gctggcaagg ccaangacac ccaacacaat ttttgccata    480
cagcccccag gcaatgggca cagcctttct tcccagagga c                         521

<210> SEQ ID NO 127
<211> LENGTH: 351
<212> TYPE: DNA
<213> ORGANISM: Homo sapien

<400> SEQUENCE: 127
tgagatttat tgcatttcat gcagcttgaa gtccatgcaa aggrgactag cacagttttt      60
aatgcattta aaaaataaaa gggaggtggg cagcaaacac acaaagtcct agtttcctgg    120
gtccctggga gaaaagagtg tggcaatgaa tccacccact ctccacaggg aataaatctg    180
tctcttaaat gcaaagaatg tttccatggc ctctggatgc aaatacacag agctctgggg    240
tcagagcaag ggatggggag aggaccacga gtgaaaaagc agctacacac attcacctaa    300
```

```
ttccatctga gggcaagaac aacgtggcaa gtcttgggggg tagcagctgt t                351
```

<210> SEQ ID NO 128
<211> LENGTH: 521
<212> TYPE: DNA
<213> ORGANISM: Homo sapien

<400> SEQUENCE: 128

```
tccagacatg ctcctgtcct aggcggggag caggaaccag acctgctatg ggaagcagaa         60
agagttaagg gaaggtttcc tttcattcct gttccttctc ttttgctttt gaacagtttt        120
taaatatact aatagctaag tcatttgcca gccaggtccc ggtgaacagt agagaacaag        180
gagcttgcta agaattaatt ttgctgtttt tcaccccatt caaacagagc tgccctgttc        240
cctgatggag ttccattcct gccagggcac ggctgagtaa cacgaagcca ttcaagaaag        300
gcgggtgtga atcactgcc accccatgga cagacccctc actcttcctt cttagccgca         360
gcgctactta ataaatatat ttatactttg aaattatgat aaccgatttt tcccatgcgg        420
catcctaagg gcacttgcca gctcttatcc ggacagtcaa gcactgttgt tggacaacag        480
ataaaggaaa agaaaaagaa gaaaacaacc gcaacttctg t                           521
```

<210> SEQ ID NO 129
<211> LENGTH: 521
<212> TYPE: DNA
<213> ORGANISM: Homo sapien

<400> SEQUENCE: 129

```
tgagacggac cactggcctg gtccccctc atktgctgtc gtaggacctg acatgaaacg          60
cagatctagt ggcagagagg aagatgatga ggaacttctg agacgtcggc agcttcaaga       120
agagcaatta atgaagctta actcaggcct gggacagttg atcttgaaag aagagatgga       180
gaaagagagc cgggaaaggt catctctgtt agccagtcgc tacgattctc ccatcaactc       240
agcttcacat attccatcat ctaaaactgc atctctccct ggctatggaa gaaatgggct       300
tcaccggcct gtttctaccg acttcgctca gtataacagc tatgggatg tcagcggggg        360
agtgcgagat taccagacac ttccagatgg ccacatgcct gcaatgagaa tggaccgagg       420
agtgtctatg cccaacatgt tggaaccaaa gatatttcca tatgaaatgc tcatggtgac       480
caacagaggg ccgaaaccaa atctcagaga ggtggacaga a                           521
```

<210> SEQ ID NO 130
<211> LENGTH: 270
<212> TYPE: DNA
<213> ORGANISM: Homo sapien

<400> SEQUENCE: 130

```
tcactttatt tttcttgtat aaaaacccta tgttgtagcc acagctggag cctgagtccg         60
ctgcacggag actctggtgt gggtcttgac gaggtggtca gtgaactcct gatagggaga       120
cttggtgaat acagtctcct tccagaggtc gggggtcagg tagctgtagg tcttagaaat       180
ggcatcaaag gtggccttgg cgaagttgcc cagggtggca gtgcagcccc gggctgaggt       240
gtagcagtca tcgataccag ccatcatgag                                         270
```

<210> SEQ ID NO 131
<211> LENGTH: 341
<212> TYPE: DNA
<213> ORGANISM: Homo sapien

<400> SEQUENCE: 131

```
ctggaatata gacccgtgat cgacaaaact ttgaacgagg ctgactgtgc caccgtcccg      60
ccagccattc gctcctactg atgagacaag atgtggtgat gacagaatca gcttttgtaa     120
ttatgtataa tagctcatgc atgtgtccat gtcataactg tcttcatacg cttctgcact     180
ctggggaaga aggagtacat tgaagggaga ttggcaccta gtggctggga gcttgccagg     240
aacccagtgg ccagggagcg tggcacttac ctttgtccct tgcttcattc ttgtgagatg     300
ataaaactgg gcacagctct taaataaaat ataaatgaac a                         341
```

<210> SEQ ID NO 132
<211> LENGTH: 844
<212> TYPE: DNA
<213> ORGANISM: Homo sapien
<220> FEATURE:
<221> NAME/KEY: misc_feature
<222> LOCATION: (1)...(844)
<223> OTHER INFORMATION: n = A,T,C or G

<400> SEQUENCE: 132

```
tgaatgggga ggagctgacc caggaaatgg agcttgngga gaccaggcct gcagggatg       60
gaaccttcca gaagtgggca tctgtggtgg tgcctcttgg gaaggagcag aagtacacat    120
gccatgtgga acatgagggg ctgcctgagc ccctcaccct gagatggggc aaggaggagc    180
ctccttcatc caccaagact aacacagtaa tcattgctgt tccggttgtc cttggagctg    240
tggtcatcct tggagctgtg atggcttttg tgatgaagag gaggagaaac acaggtggaa    300
aaggagggga ctatgctctg gctccaggct cccagagctc tgatatgtct ctcccagatt    360
gtaaagtgtg aagacagctg cctggtgtgg acttggtgac agacaatgtc ttcacacatc    420
tcctgtgaca tccagagacc tcagttctct ttagtcaagt gtctgatgtt ccctgtgagt    480
ctgcgggctc aaagtgaaga actgtggagc ccagtccacc cctgcacacc aggaccctat    540
ccctgcactg ccctgtgttc ccttccacag ccaaccttgc tgctccagcc aaacattggt    600
ggacatctgc agcctgtcag ctccatgcta ccctgacctt caactcctca cttccacact    660
gagaataata atttgaatgt gggtggctgg agagatggct cagcgctgac tgctcttcca    720
aaggtcctga gttcaaatcc cagcaaccac atggtggctc acaaccatct gtaatgggat    780
ctaatacccct cttctgcagt gtctgaagac asctacagtg tacttacata taataataaa    840
taag                                                                  844
```

<210> SEQ ID NO 133
<211> LENGTH: 601
<212> TYPE: DNA
<213> ORGANISM: Homo sapien

<400> SEQUENCE: 133

```
ggccgggcgc gcgcgccccc gccacacgca cgccgggcgt gccagtttat aaagggagag      60
agcaagcagc gagtcttgaa gctctgtttg gtgctttgga tccatttcca tcggtcctta    120
cagccgctcg tcagactcca gcagccaaga tggtgaagca gatcgagagc aagactgctt    180
ttcaggaagc cttggacgct gcaggtgata aacttgtagt agttgacttc tcagccacgt    240
ggtgtgggcc ttgcaaaatg atcaagcctt tctttcattc cctctctgaa agtattcca     300
acgtgatatt ccttgaagta gatgtggatg actgtcagga tgttgcttca gagtgtgaag    360
tcaaatgcat gccaacattc cagtttttta agaagggaca aaaggtgggt gaattttctg    420
gagccaataa ggaaaagctt gaagccacca ttaatgaatt agtctaatca tgttttctga    480
```

```
aaatataacc agccattggc tatttaaaac ttgtaattt tttaatttac aaaaatataa      540
aatatgaaga cataaacccm gttgccatct gcgtgacaat aaaacattaa tgctaacact     600
t                                                                    601

<210> SEQ ID NO 134
<211> LENGTH: 421
<212> TYPE: DNA
<213> ORGANISM: Homo sapien

<400> SEQUENCE: 134
tcacataaga aatttaagca agttacrcta tcttaaaaaa cacaacgaat gcattttaat      60
agagaaaccc ttccctccct ccacctccct cccccaccct cctcatgaat taagaatcta     120
agagaagaag taaccataaa accaagtttt gtggaatcca tcatccagag tgcttacatg     180
gtgattaggt taatattgcc ttcttacaaa atttctattt taaaaaaaat tataaccttg     240
attgcttatt acaaaaaaat tcagtacaaa agttcaatat attgaaaaat gcttttcccc     300
tccctcacag caccgtttta tatatagcag agaataatga agagattgct agtctagatg     360
gggcaatctt caaattacac caagacgcac agtggtttat ttaccctccc cttctcataa     420
g                                                                    421

<210> SEQ ID NO 135
<211> LENGTH: 511
<212> TYPE: DNA
<213> ORGANISM: Homo sapien

<400> SEQUENCE: 135
ggaaaggatt caagaattag aggacttgct tgctrragaa aaagacaact ctcgtcgcat      60
gctgacagac aaagagagag agatggcgga aataagggat caaatgcagc aacagctgaa     120
tgactatgaa cagcttcttg atgtaaagtt agccctggac atggaaatca gtgcttacag     180
gaaactctta gaaggcgaag aagagaggtt gaagctgtct ccaagccctt cttcccgtgt     240
gacagtatcc cgagcatcct caagtcgtag tgtaccgtac aactagagga aagcggaaga     300
gggttgatgt ggaagaatca gaggcgaagt agtagtgtta gcatctctca ttccgcctca     360
accactggaa atgtttgcat cgaagaaatt gatgttgatg ggaaatttat cccgcttgaa     420
gaacacttct gaacaggatc aaccaatggg aaggcttggg agatgatcag aaaaattgga     480
gacacatcag tcagttataa atatacctca a                                    511

<210> SEQ ID NO 136
<211> LENGTH: 341
<212> TYPE: DNA
<213> ORGANISM: Homo sapien

<400> SEQUENCE: 136
catgggtttc accaggttgg ccaggctgct cttgaactsc tgacctcagg tgatccaccc      60
gcctcggcct cccaaagtgc tgggattaca ggcgtgagcc accacgcccg gcccccaaag     120
ctgtttcttt tgtctttagc gtaaagctct cctgccatgc agtatctaca taactgacgt     180
gactgccagc aagctcagtc actccgtggt cttttttctct ttccagttct tctctctctc     240
ttcaagttct gcctcagtga aagctgcagg tccccagtta agtgatcagg tgagggttct     300
ttgaacctgg ttctatcagt cgaattaatc cttcatgatg g                         341

<210> SEQ ID NO 137
```

<211> LENGTH: 551
<212> TYPE: DNA
<213> ORGANISM: Homo sapien

<400> SEQUENCE: 137

| | | |
|---|---|---|
| gatgtgttgg accctctgtg tcaaaaaaaa cctcacaaag aatcccctgc tcattacaga | 60 |
| agaagatgca tttaaaatat gggttatttt caactttta tctgaggaca agtatccatt | 120 |
| aattattgtg tcagaagaga ttgaatacct gcttaagaag cttacagaag ctatgggagg | 180 |
| aggttggcag caagaacaat ttgaacatta taaaatcaac tttgatgaca gtaaaaatgg | 240 |
| cctttctgca tgggaactta ttgagcttat tggaaatgga cagtttagca aaggcatgga | 300 |
| ccggcagact gtgtctatgg caattaatga agtctttaat gaacttatat tagatgtgtt | 360 |
| aaagcagggt tacatgatga aaaagggcca cagacggaaa aactggactg aaagatggtt | 420 |
| tgtactaaaa cccaacataa tttcttacta tgtgagtgag gatctgaagg ataagaaagg | 480 |
| agacattctc ttggatgaaa attgctgtgt agaagtcctt gcctgacaaa agatggaaag | 540 |
| aaatgccttt t | 551 |

<210> SEQ ID NO 138
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 138

| | | |
|---|---|---|
| gactggttct ttatttcaaa aagacacttg tcaatattca gtrtcaaaac agttgcacta | 60 |
| ttgatttctc tttctcccaa tcggccccaa agagaccaca taaaaggaga gtacatttta | 120 |
| agccaataag ctgcaggatg tacacctaac agacctccta gaaaccttac cagaaaatgg | 180 |
| ggactgggta gggaaggaaa cttaaaagat caacaaactg ccagcccacg gactgcagag | 240 |
| gctgtcacag ccagatgggg tggccagggt gccacaaacc caaagcaaag tttcaaaata | 300 |
| atataaaatt taaaaagttt tgtacataag ctattcaaga tttctccagc actgactgat | 360 |
| acaaagcaca attgagatgg cacttctaga gacagcagct tcaaacccag aaaagggtga | 420 |
| tgagatgaag tttcacatgg ctaaatcagt ggcaaaaaca cagtcttctt tctttctttc | 480 |
| tttcaaggan gcaggaaagc aattaagtgg tcaccttaac ataaggggga c | 531 |

<210> SEQ ID NO 139
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 139

| | | |
|---|---|---|
| tgggtgggca ccatggctgg gatcaccacc atcgaggcgg tgaagcgcaa gatccaggtt | 60 |
| ctgcagcagc aggcagatga tgcagaggag cgagctgagc gcctccagcg agaagttgag | 120 |
| ggagaaaggc gggcccggga acaggctgag gctgaggtgg cctccttgaa ccgtaggatc | 180 |
| cagctggttg aagaagagct ggaccgtgct caggagcgcc tggccactgc cctgcaaaag | 240 |
| ctggaagaag ctgaaaaagc tgctgatgag agtgagagag gtatgaaggt tattgaaaac | 300 |
| cgggccttaa aagatgaaga aaagatggaa ctccaggaaa tccaactcaa agaagctaag | 360 |

```
cacattgcag aagaggcaga taggaagtat gaagaggtgg ctcgtaagtt ggtgatcatt    420
gaaggagact tggaaccgca cagaaggaac gagcttgagc ttggcaaaag tcccgttgcc    480
cagagatggg atgaaccaga ttagactgat ggaccanaac c                       521
```

<210> SEQ ID NO 140
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 140

```
aggggcngcg ggtgcgtggg ccactgggtg accgacttag cctggccaga ctctcagcac     60
ctggaagcgc cccgagagtg acagcgtgag gctgggaggg aggacttggc ttgagcttgt    120
taaactctgc tctgagcctc cttgtcgcct gcatttagat ggctcccgca agaagggtg    180 gcgagaagaa aaagggccgt tctgccatca acgaagtggt aacccgagaa tacaccatca    240
acattcacaa gcgcatccat ggagtgggct tcaagaagcg tgcacctcgg gcactcaaag    300
agattcggaa atttgccatg aaggagatgg gaactccaga tgtgcgcatt gacaccaggc    360
tcaacaaagc tgtctgggcc aaaggaataa ggaatgtgcc ataccgaatc cggtgtgcgg    420
ctgtccagaa aacgtaatga ggatgaagat tcaccaaata agctatatac tttggttacc    480
tatgtacctg ttaccacttt caaaaatcta cagacagtca atgtggatga aactaatcg    540 ctgatcgtca gatcaaataa agttataaaa t                                   571
```

<210> SEQ ID NO 141
<211> LENGTH: 531
<212> TYPE: DNA
<213> ORGANISM: Homo sapien

<400> SEQUENCE: 141

```
tcgggagcca cacttggccc tcttcctctc caaagsgcca gaacctcctt ctctttggag     60
aatggggagg cctcttggag acacagaggg tttcaccttg gatgacctct agagaaattg    120
cccaagaagc ccaccttctg gtcccaacct gcagacccca cagcagtcag ttggtcaggc    180
cctgctgtag aaggtcactt ggctccattg cctgcttcca accaatgggc aggagagaag    240
gcctttattt ctcgcccacc cattcctcct gtaccagcac ctccgttttc agtcagtgtt    300
gtccagcaac ggtaccgttt acacagtcac ctcagacaca ccatttcacc tcccttgcca    360
agctgttagc cttagagtga ttgcagtgaa cactgtttac acaccgtgaa tccattccca    420
tcagtccatt ccagttggca ccagcctgaa ccatttggta cctggtgtta actggagtcc    480
tgtttacaag gtggagtcgg ggcttgctga cttctcttca tttgagggca c            531
```

<210> SEQ ID NO 142
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 142

```
acctagacag aaggtgggtg agggaggact ggtaggaggc tgaggcaatt ccttggtagt     60
```

-continued

| | |
|---|---|
| ttgtcctgaa acccctactgg agaagtcagc atgaggcacc tactgagaga agtgcccaga | 120 |
| aactgctgac tgcatctgtt aagagttaac agtaaagagg tagaagtgtg tttctgaatc | 180 |
| agagtggaag cgtctcaagg gtcccacagt ggaggtccct gagctacctc ccttccgtga | 240 |
| gtgggaagag tgaagcccat gaagaactga gatgaagcaa ggatggggtt cctgggctcc | 300 |
| aggcaagggc tgtgctctct gcagcaggga gccccacgag tcagaagaaa gaactaatc | 360 |
| atttgttgca agaaaccttg cccggatact agcggaaaac tggaggcggn ggtgggggca | 420 |
| caggaaagtg gaagtgattt gatggagagc agagaagcct atgcacagtg gccgagtcca | 480 |
| cttgtaaagt g | 491 |

<210> SEQ ID NO 143
<211> LENGTH: 515
<212> TYPE: DNA
<213> ORGANISM: Homo sapien

<400> SEQUENCE: 143

| | |
|---|---|
| ttcaagcaat tgtaacaagt atatgtagat tagagtgagc aaaatcatat acaattttca | 60 |
| tttccagttg ctattttcca aattgttctg taatgtcgtt aaaattactt aaaaattaac | 120 |
| aaagccaaaa attatattta tgacaagaaa gccatcccta cattaatctt acttttccac | 180 |
| tcaccggccc atctccttcc tcttttttcct aactatgcca ttaaaactgt tctactgggc | 240 |
| cgggcgtgtg gctcatgcct gtaatcccag cattttggga ggccaaggca ggcggatcat | 300 |
| gaggtcaaga gattgagacc atcctggcca acatggtgaa accccgcctc gactaagaat | 360 |
| acaaaaatta gctgggcatg gtggcgcatg cctgtagtct cagctactcg ggaggctgag | 420 |
| gcagaagaat cgcttgaacc cgggaggcag aggatgcagt gagccccgat cgcgccactg | 480 |
| cactctagcc tgggcgacag actgagactc tgctc | 515 |

<210> SEQ ID NO 144
<211> LENGTH: 340
<212> TYPE: DNA
<213> ORGANISM: Homo sapien

<400> SEQUENCE: 144

| | |
|---|---|
| tgtgccagtc tacaggccta tcagcagcga ctccttcagc aacagatggg gtccctgtt | 60 |
| cagcccaacc ccatgagccc ccagcagcat atgctcccaa atcaggccca gtccccacac | 120 |
| ctacaaggcc agcagatccc taattctctc tccaatcaag tgcgctctcc ccagcctgtc | 180 |
| ccttctccac ggccacagtc ccagcccccc cactccagtc cttccccaag gatgcagcct | 240 |
| cagccttctc cacaccacgt ttccccacag acaagttccc cacatcctgg actggtagtt | 300 |
| gcccaggcca accccatgga acaagggcat tttgccagcc | 340 |

<210> SEQ ID NO 145
<211> LENGTH: 630
<212> TYPE: DNA
<213> ORGANISM: Homo sapien

<400> SEQUENCE: 145

| | |
|---|---|
| tgtaaaaact tgtttttaat tttgtataaa ataaaggtgg tccatgccca cggggggctgt | 60 |
| aggaaatcca agcagaccag ctgggggtggg gggatgtagc ctacctcggg ggactgtctg | 120 |
| tcctcaaaac gggctgagaa ggcccgtcag gggcccaggt cccacagaga ggcctgggat | 180 |
| actccccccaa cccgaggggc agactgggca gtggggagcc cccatcgtgc cccagaggtg | 240 |
| gccacaggct gaaggagggg cctgaggcac cgcagcctgc aaccccccagg gctgcagtcc | 300 |

```
actaactttt tacagaataa aaggaacatg gggatgggga aaaaagcacc aggtcaggca    360
gggcccgagg gccccagatc ccaggagggc caggactcag gatgccagca ccaccctagc    420
agctcccaca gctcctggca caggaggccg ccacggattg gcacaggccg ctgctggcca    480
tcacgccaca tttggagaac ttgtcccgac agaggtcagc tcggaggagc tcctcgtggg    540
cacacactgt acgaacacag atctccttgt taatgacgta cacacggcgg aggctgcggg    600
gacagggcac gggaggtctc agccccactt                                    630
```

<210> SEQ ID NO 146
<211> LENGTH: 521
<212> TYPE: DNA
<213> ORGANISM: Homo sapien

<400> SEQUENCE: 146

```
atggctgctg gatttaggtg gtaataggg ctgtgggcca taaatctgaa gccttgagaa    60
ccttgggtct ggagagccat gaagagggaa ggaaaagagg gcaagtcctg aacctaacca   120
atgacctgat ggattgctcg accaagacac agaagtgaag tctgtgtctg tgcacttccc   180
acagactgga gttttggtg ctgaatagag ccagttgcta aaaaattggg ggtttggtga    240
agaaatctga ttgttgtgtg tattcaatgt gtgatttaa aataaacag caacaacaat     300 aaaaaccctg actggctgtt ttttcccctgt attctttaca actatttttt gaccctctga   360
aaattattat acttcaccta aatggaagac tgctgtgttt gtggaaattt tgtaattttt    420
taatttattt tattctctct ccttttttatt ttgcctgcag aatccgttga gagactaata   480
aggcttaata tttaattgat ttgtttaata tgtatataaa t                       521
```

<210> SEQ ID NO 147
<211> LENGTH: 562
<212> TYPE: DNA
<213> ORGANISM: Homo sapien

<400> SEQUENCE: 147

```
ggcatgcgag cgcactcggc ggacgcaagg gcggcgggga gcacacggag cactgcaggc    60
gccgggttgg gacagcgtct tcgctgctgc tggatagtcg tgttttcggg gatcgaggat   120
actcaccaga aaccgaaaat gccgaaacca atcaatgtcc gagttaccac catggatgca   180
gagctggagt ttgcaatcca gccaaataca actggaaaac agcttttga tcaggtggta    240 aagactatcg gcctccggga agtgtggtac tttggcctcc actatgtgga taataaagga   300
tttcctacct ggctgaagct ggataagaag gtgtctgccc aggaggtcag gaaggagaat   360
cccctccagt tcaagttccg ggccaaagtt ctaccctgaa gatgtggctg aggagctcat   420
ccaggacatc acccagaaac ttttcttcct tcaagtgaag gaaggaatcc ttagcgatga   480
gatctactgc ccccttgar actgccgtgc tcttggggtc ctacgcttgt gcatgccaag   540
tttggggact accaccaaga ag                                            562
```

<210> SEQ ID NO 148
<211> LENGTH: 820
<212> TYPE: DNA
<213> ORGANISM: Homo sapien

<400> SEQUENCE: 148

```
gaaggagtcg ggatactcag cattgatgca ccccaatttc aaagcggcat tcttcggcag    60
gtctctggga caatctctag ggtcactacc tggaaactcg ttagggtaca actgaatgct   120
```

-continued

| | |
|---|---|
| gaaaggaaag aacacctgca gaaccggaca gaaattcacc ccggcgatca gctgattgat | 180 |
| ctcggtcgac cagaagtcat ggctaaagat gacgaggacg ttgtcaattc cctgggcttt | 240 |
| tcgaagtgag tccagcagca gtctgaggta ttcgggccgg ttatgcacct ggaccaccag | 300 |
| caccagctcc cggggggccc aggtgccagc cttatctaca ttcctcaggg tctgatcaaa | 360 |
| gttcagctgg taccaggg accggtaccg cagcgtcagg ttgtccgctc gggctggggg | 420 |
| accgccggga ccagggaagc cgccgacacg ttggagaccc tgcggatgcc cacagccaca | 480 |
| gagggtggt ccccaccgcg gccgccggca ccccgcgcgg gttcggcgtc cagcaacggt | 540 |
| ggggcgaggg cctcgttctt cctttgtcgc ccattgctgc tccagaggac gaagccgcag | 600 |
| gcggccacca cgagcgtcag gattagcacc ttccgtttgt agatgcggaa cctcatggtc | 660 |
| tccagggccg ggagcgcagc tacagctcga gcgtcggcgc cgccgctagg agccgcggct | 720 |
| cggcttcgtc tccgtcctct ccattcagca ccacgggtcc cggaaaaagc tcagccscgg | 780 |
| tcccaaccgc accctagctt cgttacctgc gcctcgcttg | 820 |

<210> SEQ ID NO 149
<211> LENGTH: 501
<212> TYPE: DNA
<213> ORGANISM: Homo sapien

<400> SEQUENCE: 149

| | |
|---|---|
| cagatttta tttgcagtcg tcactggggc cgtttcttgc tgcttatttg tctgctagcc | 60 |
| tgctcttcca gctgcatggc caggcgcaag gccttgatga catctcgcag ggctgagaaa | 120 |
| tgcttggctt gctgggccag agcagattcc gctttgttca caaaggtctc caggtcatag | 180 |
| tctggctgct cggtcatctc agagagctca agccagtctg gtccttgctg tatgatctcc | 240 |
| ttgagctctt ccatagcctt ctcctccagc tccctgatct gagtcatggc ttcgttaaag | 300 |
| ctggacatct gggaagacag ttcctcctct tccttggata aattgcctgg aatcagcgcc | 360 |
| ccgttagagc aggcttccat ctcttctgtt tccatttgaa tcaactgctc tccactgggc | 420 |
| ccactgtggg ggctcagctc cttgaccctg ctgcatatct taagggtgtt taaaggatat | 480 |
| tcacaggagc ttatgcctgg t | 501 |

<210> SEQ ID NO 150
<211> LENGTH: 511
<212> TYPE: DNA
<213> ORGANISM: Homo sapien
<220> FEATURE:
<221> NAME/KEY: misc_feature
<222> LOCATION: (1)...(511)
<223> OTHER INFORMATION: n = A,T,C or G

<400> SEQUENCE: 150

| | |
|---|---|
| ctcctcttgg tacatgaacc caagttgaaa gtggacttaa caaagtatct ggagaaccaa | 60 |
| gcattctgct ttgactttgc atttgatgaa acagcttcga atgaagttgt ctacaggttc | 120 |
| acagcaaggc cactggtaca gacaatcttt gaaggtggaa aagcaacttg ttttgcatat | 180 |
| ggccagacag gaagtggcaa gacacatact atgggcggag acctctctgg gaaagcccag | 240 |
| aatgcatcca aagggatcta tgccatggcc ttccggacg tcttcttctg aagaatcaac | 300 |
| cctgctaccg gaagttgggc ctggaagtct atgtgacatt cttcgagatc tacaatggga | 360 |
| agctgtttga cctgctcaac aagaaggcca agcttgcgcg tgctggaaga cggcaagcaa | 420 |
| caggtgcaag tggtgggggc ttgcaggaac atctggntaa ctctgcttga tgatggcant | 480 |
| caagatgatc gacatgggca gcgcctgcag a | 511 |

<210> SEQ ID NO 151
<211> LENGTH: 566
<212> TYPE: DNA
<213> ORGANISM: Homo sapien

<400> SEQUENCE: 151

| | | | | | |
|---|---|---|---|---|---|
| tcccgaattc | aagcgacaaa | ttggawagtg | aaatggaaga | tgcctatcat | gaacatcagg | 60 |
| caaatctttt | gcgccaagat | ctgatgagac | gacaggaaga | attaagacgc | atggaagaac | 120 |
| ttcacaatca | agaaatgcag | aaacgtaaag | aaatgcaatt | gaggcaagag | gaggaacgac | 180 |
| gtagaagaga | ggaagagatg | atgattcgtc | aacgtgagat | ggaagaacaa | atgaggcgcc | 240 |
| aaagagagga | aagttacagc | cgaatgggct | acatggatcc | acgggaaaga | gacatgcgaa | 300 |
| tgggtggcgg | aggagcaatg | aacatgggag | atccctatgg | ttcaggaggc | agaaatttc | 360 |
| cacctctagg | aggtggtggt | ggcataggtt | atgaagctaa | tcctggcgtt | ccaccagcaa | 420 |
| ccatgagtgg | ttccatgatg | ggaagtgaca | tgcgtactga | gcgctttggg | cagggaggtg | 480 |
| cggggcctgt | gggtggacag | ggtcctagag | gaatggggcc | tggaactcca | gcaggatatg | 540 |
| gtagagggag | agaagagtac | gaaggc | | | | 566 |

<210> SEQ ID NO 152
<211> LENGTH: 518
<212> TYPE: DNA
<213> ORGANISM: Homo sapien

<400> SEQUENCE: 152

| | | | | | |
|---|---|---|---|---|---|
| ttcgtgaaga | ccctgactgg | taagaccatc | actctcgaag | tggagcccga | gtgacaccat | 60 |
| tgagaatgtc | aaggcaaaga | tccaagacaa | ggaaggcatc | cctcctgacc | agcakaggtt | 120 |
| gatctttgct | gggaaacagc | tggaagatgg | acgcaccctg | tctgactaca | acatccagaa | 180 |
| agagtccacc | ctgcacctgg | tgctccgtct | cagaggtggg | atgcaaatct | tcgtgaagac | 240 |
| cctgactggt | aagaccatca | ccctcgaggt | ggagcccagt | gacaccatcg | agaatgtcaa | 300 |
| ggcaaagatc | caagataagg | aaggcatccc | tcctgatcag | cagaggttga | tctttgctgg | 360 |
| gaaacagctg | gaagatggac | gcaccctgtc | tgactacaac | atccagaaag | agtccactct | 420 |
| gcacttggtc | ctgcgcttga | gggggggtgt | ctaagtttcc | ccttttaagg | tttcaacaaa | 480 |
| tttcattgca | ctttcctttc | aataaagttg | ttgcattc | | | 518 |

<210> SEQ ID NO 153
<211> LENGTH: 542
<212> TYPE: DNA
<213> ORGANISM: Homo sapien

<400> SEQUENCE: 153

| | | | | | |
|---|---|---|---|---|---|
| gcgcgggtgc | gtgggccact | gggtgaccga | cttagcctgg | ccagactctc | agcacctgga | 60 |
| agcgccccga | gagtgacagc | gtgaggctgg | gagggaggac | ttggcttgag | cttgttaaac | 120 |
| tctgctctga | gcctccttgt | cgcctgcatt | tagatggctc | ccgcaaagaa | gggtggcgag | 180 |
| aagaaaaagg | gccgttctgc | catcaacgaa | gtggtaaccc | gagaatacac | catcaacatt | 240 |
| cacaagcgca | tccatggagt | gggcttcaag | aagcgtgcac | ctcgggcact | caaagagatt | 300 |
| cggaaatttg | ccatgaagga | gatgggaact | ccagatgtgc | gcattgacac | caggctcaac | 360 |
| aaagctgtct | gggccaaagg | aataaggaat | gtgccatacc | gaatccgtgt | gcggctgtcc | 420 |
| agaaaacgta | atgaggatga | agattcacca | aataagctat | atactttggt | tacctatgta | 480 |

```
cctgttacca ctttcaaaaa tctacagaca gtcaatgtgg atgagaacta atcgctgatc    540
gt                                                                   542

<210> SEQ ID NO 154
<211> LENGTH: 411
<212> TYPE: DNA
<213> ORGANISM: Homo sapien

<400> SEQUENCE: 154
aattctttat ttaaatcaac aaactcatct tcctcaagcc ccagaccatg gtaggcagcc     60
ctccctctcc atccctcac cccaccccctt agccacagtg aagggaatgg aaaatgagaa   120
gccacgaggg cccctgccag ggaaggctgc cccagatgtg tggtgagcac agtcagtgca   180
gctgtggctg gggcagcagc tgccacaggc tcctccctat aaattaagtt cctgcagcca   240
cagctgtggg agaagcatac ttgtagaagc aaggccagtc cagcatcaga aggcagaggc   300
agcatcagtg actcccagcc atggaatgaa cggaggacac agagctcaga gacagaacag   360
gccaggggga agaaggagag acagaatagg ccagggcatg gcggtgaggg a            411

<210> SEQ ID NO 155
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 155
tgatgaatct gggtgggctg gcagtagccc gagatgatgg gctcttctct ggggatccca     60
actggttccc taagaaatcc aaggagaatc ctcggaactt ctcggataac cagctgcaag   120
agggcaagaa cgtgatcggg ttacagatgg gcaccaaccg cggggcgtct cangcaggca   180
tgactggcta cgggatgcca cgccagatcc tctgatccca ccccaggcct tgcccctgcc   240
ctcccacgaa tggttaatat atatgtagat atatatttta gcagtgacat tcccagagag   300
ccccagagct ctcaagctcc tttctgtcag ggtgggggt tcaagcctgt cctgtcacct   360
ctgaagtgcc tgctggcatc ctctccccca tgcttactaa tacattccct tccccatagc   420
c                                                                    421

<210> SEQ ID NO 156
<211> LENGTH: 670
<212> TYPE: DNA
<213> ORGANISM: Homo sapien

<400> SEQUENCE: 156
agcggagctc cctcccctgg tggctacaac ccacacacgc caggctcagg catcgagcag     60
aactccagcg actgggtaac cactgacatt caggtgaagg tgcgggacac ctacctggat   120
acacaggtgg tgggacagac agtgtgtcatc cgcagtgtca cggggggcat gtgctctgtg   180
tacctgaagg acagtgagaa ggttgtcagc atttccagtg agcacctgga gcctatcacc   240
cccaccaaga acaacaaggt gaaagtgatc ctgggcgagg atcgggaagc cacgggcgtc   300
ctactgagca ttgatggtga ggatggcatt gtccgtatgg accttgatga gcagctcaag   360
atcctcaacc tccgcttcct ggggaagctc ctggaagcct gaagcaggca gggccggtgg   420
acttcgtcgg atgaagagtg atcctccttc cttccctggc ccttggctgt gacacaagat   480
cctcctgcag ggctaggcgg attgttctgg atttcctttt gtttttcctt ttaggtttcc   540
```

```
atcttttccc tccctggtgc tcattggaat ctgagtagag tctggggag ggtccccacc    600 ttcctgtacc tcctccccac agcttgcttt tgttgtaccg tctttcaata aaaagaagct    660
gtttggtcta                                                           670

<210> SEQ ID NO 157
<211> LENGTH: 421
<212> TYPE: DNA
<213> ORGANISM: Homo sapien

<400> SEQUENCE: 157
ggttcacagc actgctgctt gtgtgttgcc ggccaggaat tccaggctca caaggctatc     60
ttagcagctc gttctccggt ttttagtgcc atgtttgaac atgaaatgga ggagagcaaa    120
aagaatcgag ttgaaatcaa tgatgtggag cctgaagttt ttaaggaaat gatgtgcttc    180
atttacacgg ggaaggctcc aaacctcgac aaaatggctg atgatttgct ggcagctgct    240
gacaagtatg ccctggagcg cttaaaggtc atgtgtgagg atgccctctg cagtaacctg    300
tccgtggaga acgctgcaga aattctcatc ctggccgacc tccacagtgc agatcagttg    360
aaaactcagg cagtggattt catcaactat catgcttcgg atgtcttgga gacctcttgg    420
g                                                                    421

<210> SEQ ID NO 158
<211> LENGTH: 321
<212> TYPE: DNA
<213> ORGANISM: Homo sapien

<400> SEQUENCE: 158
tcgtagccat ttttctgctt ctttggagaa tgacgccaca ctgactgctc attgtcgttg     60
gttccatgcc aattggtgaa atagaacctc atccggtagt ggagccggag ggacatcttg    120
tcatcaacgg tgatggtgcg atttggagca taccagagct tggtgttctc gccatacagg    180
gcaaagaggt tgtgacaaag aggagagata cggcatgcct gtgcagccct gatgcacagt    240
tcctctgctg tgtactctcc actgcccagc cggaggggct ccctgtccga cagatagaag    300
atcacttcca ccctggctt g                                               321

<210> SEQ ID NO 159
<211> LENGTH: 596
<212> TYPE: DNA
<213> ORGANISM: Homo sapien

<400> SEQUENCE: 159
tggcacactg ctcttaagaa actatgawga tctgagattt ttttgtgtat gttttttgact    60 cttttgagtg gtaatcatat gtgtctttat agatgtacat acctccttgc acaaatggag    120
gggaattcat tttcatcact gggagtgtcc ttagtgtata aaaaccatgc tggtatatgg    180
cttcaagttg taaaaatgaa agtgacttta aagaaaata ggggatggtc caggatctcc    240
actgataaga ctgttttta gtaacttaag gacctttggg tctacaagta tatgtgaaaa    300
aaatgagact tactgggtga ggaaattcat tgtttaaaga tggtcgtgtg tgtgtgtgtg    360
tgtgtgtgtg ttgtgttgtg tttgttttt taagggaggg aatttattat ttaccgttgc    420
ttgaaattac tgkgtaaata tatgtytgat aatgatttgc tyttttgvcma ctaaaattag    480 gvctgtataa gtwctaratg cmtccctggg kgttgatytt ccmagatatt gatgataamcc    540 cttaaaattg taaccygcct ttttcccttt gctytcmatt aaagtctatt cmaaag         596
```

<210> SEQ ID NO 160
<211> LENGTH: 515
<212> TYPE: DNA
<213> ORGANISM: Homo sapien

<400> SEQUENCE: 160

| | | | | | |
|---|---|---|---|---|---|
| gggggtaggc | tctttattag | acggttattg | ctgtactaca | gggtcagagt | gcagtgtaag | 60 |
| cagtgtcaga | ggcccgcgtt | cagcccaaga | atgtggattt | tctctcccta | ttgatcacag | 120 |
| tgggtgggtt | tcttcagaaa | agccccagag | gcagggacca | gtgagctcca | aggttagaag | 180 |
| tggaactgga | aggcttcagt | cacatgctgc | ttccacgctt | ccaggctggg | cagcaaggag | 240 |
| gagatgccca | tgacgtgcca | ggtctcccca | tctgacacca | gtgaagtctg | gtaggacagc | 300 |
| agccgcacgc | ctgcctctgc | caggaggcca | atcatggtag | gcagcattgc | aggtcagag | 360 |
| gtctgagtcc | ggaataggag | caggggcagg | tccctgcgga | gaggcacttc | tggcctgaag | 420 |
| acagctccat | tgagcccctg | cagtacaggy | gtagtgcctt | ggaccaagcc | cacagcctgg | 480 |
| taagggcgc | ctgccagggc | cacggccagg | aggca | | | 515 |

<210> SEQ ID NO 161
<211> LENGTH: 936
<212> TYPE: DNA
<213> ORGANISM: Homo sapien

<400> SEQUENCE: 161

| | | | | | |
|---|---|---|---|---|---|
| taatttctta | gtcgtttgga | atccttaagc | atgcaaaagc | tttgaacaga | agggttcaca | 60 |
| aaggaaccag | ggttgtctta | tggcatccag | ttaagccaga | gctgggaatg | cctctgggtc | 120 |
| atccacatca | ggagcagaag | cacttgactt | gtcggtcctg | ctgccacggt | ttgggcgccc | 180 |
| accacgccca | cgtccacctc | gtcctcccct | gccgccacgt | cctgggcggc | caaggtctcc | 240 |
| aaaattgatc | tccagctgag | acgttatatc | atttgctggc | ttccggaaat | gatggtccat | 300 |
| aaccgaatct | tcagcatgag | cctcttcact | ctttgattta | tgaagaacaa | atcccttctt | 360 |
| ccactgccca | tcagcacctt | catttggttt | tcggatatta | aattctactt | ttgcccggtc | 420 |
| cttattttga | atagccttcc | actcatccaa | agtcatctct | tttggaccct | cctcttttac | 480 |
| ctcttcaact | tcattctcct | tattttcagt | gtctgccact | ggatgatgtt | cttcaccttc | 540 |
| aggtgtttcc | tcagtcacat | ttgattgatc | caagtcagtt | aattcgtctt | tgacagttcc | 600 |
| ccagttgtga | gatccgctac | ctccacgttt | gtcctcgtgc | ttcaggccag | atctatcact | 660 |
| tccactatgc | ctatcaaatt | cacgtttgcc | acgagaatca | aatccatctc | ctcggcccat | 720 |
| tccacgtcca | cggccccctc | gacctcttcc | aagaccacca | cgacctcgaa | taggtcggtc | 780 |
| aataatcggt | ctatcaactg | aaaattcgcc | tccttcaccc | ttttcttcaa | gtggcttttc | 840 |
| gaatcttcgt | tcacgaggtg | gtcgcctttc | tggtcttcta | tcaattattt | tcccttcacc | 900 |
| ctgaagttgt | tgatcaggtc | ttcttccaac | tcgtgc | | | 936 |

<210> SEQ ID NO 162
<211> LENGTH: 950
<212> TYPE: DNA
<213> ORGANISM: Homo sapien

<400> SEQUENCE: 162

| | | | | | |
|---|---|---|---|---|---|
| aagcggatgg | acctgagtca | gccgaatcct | agccccttcc | cttgggcctg | ctgtggtgct | 60 |
| cgacatcagt | gacagacgga | agcagcagac | catcaaggct | acgggaggcc | cggggcgctt | 120 |
| gcgaagatga | agtttggctg | cctctccttc | cggcagcctt | atgctggctt | tgtcttaaat | 180 |

```
ggaatcaaga ctgtggagac gcgctggcgt cctctgctga gcagccagcg gaactgtacc      240
atcgccgtcc acattgctca cagggactgg gaaggcgatg cctgtcggga gctgctggtg      300
gagagactcg ggatgactcc tgctcagatt caggccttgc tcaggaaagg ggaaaagttt      360
ggtcgaggag tgatagcggg actcgttgac attggggaaa cttttgcaatg ccccgaagac     420 ttaactcccg atgaggttgt ggaactagaa atcaagctg cactgaccaa cctgaagcag       480
aagtacctga ctgtgatttc aaacccccagg tggttactgg agcccatacc taggaaagga     540
ggcaaggatg tattccaggt agacatccca gagcacctga tccctttggg gcatgaagtg      600
tgacaagtgt gggctcctga aaggaatgtt ccrgagaaac cagctaaatc atggcacctt      660
caatttgcca tcgtgacgca gacctgtata aattaggtta aagatgaatt tccactgctt      720
tggagagtcc cacccactaa gcactgtgca tgtaaacagg ttcctttgct cagatgaagg      780
aagtaggggg tggggctttc cttgtgtgat gcctccttag gcacacaggc aatgtctcaa      840
gtactttgac cttagggtag aaggcaaagc tgccagtaaa tgtctcagca ttgctgctaa      900
ttttggtcct gctagtttct ggattgtaca aataaatgtg ttgtagatga                 950

<210> SEQ ID NO 163
<211> LENGTH: 475
<212> TYPE: DNA
<213> ORGANISM: Homo sapien
<220> FEATURE:
<221> NAME/KEY: misc_feature
<222> LOCATION: (1)...(475)
<223> OTHER INFORMATION: n = A,T,C or G

<400> SEQUENCE: 163
tcgagcggcc gcccgggcag gtgtcggagt ccagcacggg aggcgtggtc ttgtagttgt       60
tctccggctg cccattgctc tcccactcca cggcgatgtc gctgggatag aagcctttga      120
ccaggcaggt caggctgacc tggttcttgg tcatctcctc ccgggatggg ggcagggtgt      180
acacctgtgg ttctcgggc tgccctttgg ctttggagat ggttttctcg atgggggctg       240
ggagggcttt gttggagacc ttgcacttgt actccttgcc attcaaccag tcctggtgca      300
ngacggtgag gacgctnacc acacggtacg ngctggtgta ctgctcctcc cgcggctttg      360
tcttggcatt atgcacctcc acgccgtcca cgtaccaatt gaacttgacc tcaggtctct      420
cgtggctcac gtccaccacc acgcatgtaa cctcaaanct cggncgcgan cacgc           475

<210> SEQ ID NO 164
<211> LENGTH: 476
<212> TYPE: DNA
<213> ORGANISM: Homo sapien

<400> SEQUENCE: 164
agcgtggtcg cggccgaggt ctgaggttac atgcgtggtg gtggacgtga gccacgaaga       60
ccctgaggtc aagttcaact ggtacgtgga cggcgtggag gtgcataatg ccaagacaaa      120
gccgcgggag gagcagtaca acagcacgta ccgtgtggtc agcgtcctca ccgtcctgca      180
ccaggactgg ctgaatggca aggagtacaa gtgcaaggtc tccaacaaag ccctcccagc      240
ccccatcgag aaaaccatct ccaaagccaa agggcagccc cgagaaccac aggtgtacac      300
cctgccccca tcccgggagg agatgaccaa gaaccaggtc agcctgacct gcctggtcaa      360
aggcttctat cccagcgaca tcgcccgtgg agtgggagag caatgggcag ccggagaaca      420
actacaagac cacgcctccc gtgctggact ccgacacctg ccgggcggcc gctcga          476
```

<210> SEQ ID NO 165
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 165

| | | | | | |
|---|---|---|---|---|---|
| agcgtggttn | cggccgaggt | cccaaccaag | gctgcancct | ggatgccatc | aaagtcttct | 60 |
| gcaacatgga | gactggtgag | acctgcgtgt | accccactca | gcccagtgtg | gcccagaaga | 120 |
| actggtacat | cagcaagaac | cccaaggaca | agaggcatgt | ctggttcggc | gagagcatga | 180 |
| ccgatggatt | ccagttcgag | tatggcggcc | agggctccga | ccctgccgat | gtggacctgc | 240 |
| ccgggcggnc | gctcga | | | | | 256 |

<210> SEQ ID NO 166
<211> LENGTH: 332
<212> TYPE: DNA
<213> ORGANISM: Homo sapien

<400> SEQUENCE: 166

| | | | | | |
|---|---|---|---|---|---|
| agcgtggtcg | cggccgaggt | caagaacccc | gcccgcacct | gccgtgacct | caagatgtgc | 60 |
| cactctgact | ggaagagtgg | agagtactgg | attgacccca | accaaggctg | caacctggat | 120 |
| gccatcaaag | tcttctgcaa | catggagact | ggtgagacct | gcgtgtaccc | cactcagccc | 180 |
| agtgtggccc | agaagaactg | gtacatcagc | aagaacccca | aggacaagag | gcatgtctgg | 240 |
| ttcggcgaga | gcatgaccga | tggattccag | ttcgagtatg | gcggcagggg | ctccgaccct | 300 |
| gccgatgtgg | acctgcccgg | gcggccgctc | ga | | | 332 |

<210> SEQ ID NO 167
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 167

| | | | | | |
|---|---|---|---|---|---|
| tcgagcggtc | gcccgggcag | gtccacatcg | gcagggtcgg | agccctggcc | gccatactcg | 60 |
| aactggaatc | catcggncat | gctctcgccg | aaccagacat | gcctcttgnc | cttggggttc | 120 |
| ttgctgatgt | accagntctt | ctgggccaca | ctgggctgag | tggggtacac | gcaggtctca | 180 |
| ccantctcca | tgttgcanaa | gactttgatg | gcatccaggt | tgcagccttg | gttggggtca | 240 |
| atccagtact | ctccactctt | ccagacagag | tggcacatct | tgaggtcacg | gcaggtgcgg | 300 |
| gcggggttct | tgacctcggt | cgcgaccacg | ct | | | 332 |

<210> SEQ ID NO 168
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 168

| | | | | | |
|---|---|---|---|---|---|
| tcgagcggcc | gcccgggcag | gtcctcctca | gagcggtagc | tgttcttatt | gccccggcag | 60 |

```
cctccataga tnaagttatt gcangagttc ctctccacgt caaagtacca gcgtgggaag    120
gatgcacggc aaggcccagt gactgcgttg gcggtgcagt attcttcata gttgaacata    180
tcgctggagt ggacttcaga atcctgcctt ctgggagcac ttgggacaga ggaatccgct    240
gcattcctgc tggtggacct cggccgcgac cacgct                              276
```

<210> SEQ ID NO 169
<211> LENGTH: 276
<212> TYPE: DNA
<213> ORGANISM: Homo sapien

<400> SEQUENCE: 169

```
agcgtggtcg cggccgaggt ccaccagcag gaatgcagcg gattcctctg tcccaagtgc     60
tcccagaagg caggattctg aagaccactc cagcgatatg ttcaactatg aagaatactg    120
caccgccaac gcagtcactg ggccttgccg tgcatccttc ccacgctggt actttgacgt    180
ggagaggaac tcctgcaata acttcatcta tggaggctgc cggggcaata agaacagcta    240
ccgctctgag gaggacctgc ccgggcggcc gctcga                              276
```

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170

```
tcgagcggcc gcccgggcag gtccacatcg gcagggtcgg agccctggcc gccatactcg     60
aactggaatc catcggtcat gctctcgccg aaccagacat gcctcttgtc cttgggttc    120 ttgctgatgt accagttctt ctgggccaca ctgggctgag tggggtacac gcaggtctca    180
ccagtctcca tgttgcagaa gactttgatg gcatccaggt tgcagccttg gttggggtca    240
atccagtact ctccactctt ccagccagaa tggcacatct tgaggtcacg gcangtgcgg    300
gcggggttct tgacctcggc cgcgaccacg ct                                  332
```

<210> SEQ ID NO 171
<211> LENGTH: 333
<212> TYPE: DNA
<213> ORGANISM: Homo sapien

<400> SEQUENCE: 171

```
agcgtggtcg cggccgaggt caagaaaccc cgcccgcacc tgccgtgacc tcaagatgtg     60
ccactctggc tggaagagtg gagagtactg gattgacccc aaccaaggct gcaacctgga    120
tgccatcaaa gtcttctgca acatggagac tggtgagacc tgcgtgtacc ccactcagcc    180
cagtgtggcc cagaagaact ggtacatcag caagaacccc aaggacaaga ggcatgtctg    240
gctcggcgag agcatgaccg atggattcca gttcgagtat ggcggccagg gctccgaccc    300
tgccgatgtg gacctgcccg ggcggccgct cga                                 333
```

<210> SEQ ID NO 172
<211> LENGTH: 527
<212> TYPE: DNA
<213> ORGANISM: Homo sapien
<220> FEATURE:
<221> NAME/KEY: misc_feature
<222> LOCATION: (1)...(527)

<223> OTHER INFORMATION: n = A,T,C or G

<400> SEQUENCE: 172

```
agcgtggtcg cggccgaggt cctgtcagag tggcactggt agaagntcca ggaaccctga    60
actgtaaggg ttcttcatca gtgccaacag gatgacatga aatgatgtac tcagaagtgt   120
cctgnaatgg ggcccatgan atggttgnct gagagagagc ttcttgtcct acattcggcg   180
ggtatggtct tggcctatgc cttatggggg tggccgttgn gggcggtgng gtccgcctaa   240
aaccatgttc ctcaaagatc atttgttgcc caacactggg ttgctgacca naagtgccag   300
gaagctgaat accatttcca gtgtcatacc agggtgggt gacgaaaggg gtctttgaa    360
ctgtggaagg aacatccaag atctctgntc catgaagatt ggggtgtgga agggttacca   420
gttggggaag ctcgctgtct ttttccttcc aatcangggc tcgctcttct gaatattctt   480
cagggcaatg acataaattg tatattcggt tcccggttcc aggccag                 527
```

<210> SEQ ID NO 173
<211> LENGTH: 635
<212> TYPE: DNA
<213> ORGANISM: Homo sapien
<220> FEATURE:
<221> NAME/KEY: misc_feature
<222> LOCATION: (1)...(635)
<223> OTHER INFORMATION: n = A,T,C or G

<400> SEQUENCE: 173

```
tcgagcggcc gcccgggcag gtccaccaca cccaattcct tgctggtatc atggcagccg    60
ccacgtgcca ggattaccgg ctacatcatc aagtatgaga agcctgggtc tcctcccaga   120
gaagtggtcc ctcggccccg ccctggtgtc acagaggcta ctattactgg cctggaaccg   180
ggaaccgaat atacaattta tgtcattgcc ctgaagaata atcagaagag cgagcccctg   240
attggaagga aaaagacaga cgagcttccc caactggtaa cccttccaca ccccaatctt   300
catggaccag agatcttgga tgttccttcc acagttcaaa agacccctt cgtcacccac   360
cctgggtatg acactggaaa tggtattcag cttcctggca cttctggtca gcaacccagt   420
gttgggcaac aaatgatctt tgangaacat ggntttaggc ggaccacacc ggccacaacg   480
ggcacccca taaggcatag gccaagaaca tacccgncga atgtaggaca agaagctctn   540
tctcanacaa ncatctcatg ggccccattc cangacactt ctgagtacat canttcatgg   600
catcctggtg gcactgataa aaacccttac agtta                              635
```

<210> SEQ ID NO 174
<211> LENGTH: 572
<212> TYPE: DNA
<213> ORGANISM: Homo sapien
<220> FEATURE:
<221> NAME/KEY: misc_feature
<222> LOCATION: (1)...(572)
<223> OTHER INFORMATION: n = A,T,C or G

<400> SEQUENCE: 174

```
agcgtggtcg cgggcgaggt cctgtcagag tggcactggt agaagttcca ggaaccctga    60
actgtaaggg ttcttcatca gtgccaacag gatgacatga aatgatgtac tcagaagtgt   120
cctggaatgg ggcccatgag atggttgtct gagagagagc ttcttgtcct acattcggcg   180
ggtatggtct tggcctatgc cttatggggg tggccgttgt gggcggtgtg gtccgcctaa   240
aaccatgttc ctcaaagatc atttgttgcc caacactggg ttgctgacca gaagtgccag   300
gaagctgaat accatttcca gtgtcatacc agggtgggt gacgaaaggg gtctttgaa    360
```

```
ctgtggaagg aacatccaag atctctggtc catgaagatt ggggtgtgga agggttacca        420
gttggggaag ctcgtctgtc ttttccttc caatcanggg ctcgctcttc tgattattct         480
tcagggcaat gacataaatt gtatattcgg ntcccgggtn cagccaataa taataaccct        540
ctgtgacacc anggcggggc cgaagganca ct                                     572
```

<210> SEQ ID NO 175
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 175

```
agcgtggtcg cggccgaggt cctcaccaga ggtaccacct acaacatcat agtggaggca         60
ctgaaagacc agcagaggca taaggttcgg gaagaggttg ttaccgtggg caactctgtc        120
aacgaaggct tgaaccaacc tacgatgac tcgtgctttg accctacac agtttcccat         180 tatgccgttg gagatgagtg ggaacgaatg tctgaatcag gctttaaact gttgtgccag        240
tgcttangct ttggaagtgg tcatttcaga tgtgattcat ctagatggtg ccatgacaat        300
ggtgtgaact acaagattgg agagaagtgg gaccgtcagg gagaaaatgg acctgcccgg       360
gcggccgctc ga                                                            372
```

<210> SEQ ID NO 176
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 176

```
tcgagcggcc gcccgggcag gtccattttc tccctgacgg tcccacttct ctccaatctt         60
gtagttcaca ccattgtcat ggcaccatct agatgaatca catctgaaat gaccacttcc        120
aaagcctaag cactggcaca acagtttaaa gcctgattca gacattcgtt cccactcatc       180
tccaacggca taatgggaaa ctgtgtaggg gtcaaagcac gagtcatccg taggttggtt        240
caagccttcg ntgacagagt tgcccacggt aacaacctct tcccgaacct tatgcctctg       300
ctggtctttc agtgcctcca ctatgatgtt gtaggtggta cctctggtga ggacctcggc       360
cgcgaccacg ct                                                            372
```

<210> SEQ ID NO 177
<211> LENGTH: 269
<212> TYPE: DNA
<213> ORGANISM: Homo sapien
<220> FEATURE:
<221> NAME/KEY: misc_feature
<222> LOCATION: (1)...(269)
<223> OTHER INFORMATION: n = A,T,C or G

<400> SEQUENCE: 177

```
agcgtggccg cggccgaggt ccattggctg gaacggcatc aacttggaag ccagtgatcg         60
tctcagcctt ggttctccag ctaatggtga tggnggtctc agtagcatct gtcacacgag        120
cccttcttgg tgggctgaca ttctccagag tggtgacaac accctgagct ggtctgcttg       180
```

```
tcaaagtgtc cttaagagca tagacactca cttcatattt ggcgnccacc ataagtcctg    240
atacaaccac ggaatgacct gtcaggaac                                      269
```

<210> SEQ ID NO 178
<211> LENGTH: 529
<212> TYPE: DNA
<213> ORGANISM: Homo sapien

<400> SEQUENCE: 178

```
tcgagcggcc gcccgggcag gtcctcagac cgggttctga gtacacagtc agtgtggttg     60
ccttgcacga tgatatggag agccagcccc tgattggaac ccagtccaca gctattcctg    120
caccaactga cctgaagttc actcaggtca caccccacaag cctgagcgcc cagtggacac    180
cacccaatgt tcagctcact ggatatcgag tgcgggtgac ccccaaggag aagaccggac    240
caatgaaaga aatcaacctt gctcctgaca gctcatccgt ggttgtatca ggacttatgg    300
cggccaccaa atatgaagtg agtgtctatg ctcttaagga cactttgaca agcagaccag    360 ctcaggggtgt tgtcaccact ctggagaatg tcagcccacc aagaagggct cgtgtgacag    420
atgctactga gaccaccatc accattagct ggagaaccaa gactgagacg atcactggct    480
tccaagttga tgccgttcca gccaatggac ctcggccgcg accacgctt                529
```

<210> SEQ ID NO 179
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 179

```
agcgtggtcg cggccgaggt ctggccgaac tgccagtgta cagggaagat gtacatgtta     60
tagntcttct cgaagtcccg ggccagcagc tccacggggt ggtctcctgc ctccaggcgc    120
ttctcattct catggatctt cttcacccgc agcttctgct tctcagtcag aaggttgttg    180
tcctcatccc tctcatacag ggtgaccagg acgttcttga gccagtcccg catgcgcagg    240
gggaattcgg tcagctcaga gtccaggcaa gggggggatgt atttgcaagg cccgatgtag    300
tccaagtgga gcttgtggcc cttcttggtg ccctccaagg tgcactttgt ggcaaagaag    360
tggcaggaag agtcgaaggt cttgttgtca ttgctgcaca ccttctcaaa ctcgccaatg    420
ggggctgggc agacctgccc gggcggccgc tcga                                454
```

<210> SEQ ID NO 180
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 180

```
tcgagcggcc gcccgggcag gtctgcccag cccccattgg cgagtttgag aaggngtgca     60
gcaatgacaa caagaccttc gactcttcct gccacttctt tgccacaaag tgcaccctgg    120
agggcaccaa gaagggccac aagtccacc tggactacat cgggccttgc aaatacatcc    180
ccccttgcct ggactctgag ctgaccgaat tcccctgcg catgcgggac tggctcaaga    240
acgtcctggt caccctgtat gagagggatg aggacaacaa ccttctgact gagaagcana    300
```

```
agctgcgggt gaagaanatc catgagaatg anaagcgcct gnaggcanga gaccaccccg      360
tggagctgct ggcccgggac ttcgagaaga actataacat gtacatcttc cctgtacact      420
ggcagttcgg ccagacctcg gccgcgacca cgct                                  454
```

<210> SEQ ID NO 181
<211> LENGTH: 102
<212> TYPE: DNA
<213> ORGANISM: Homo sapien
<220> FEATURE:
<221> NAME/KEY: misc_feature
<222> LOCATION: (1)...(102)
<223> OTHER INFORMATION: n = A,T,C or G

<400> SEQUENCE: 181

```
agcgtggntg cggacgacgc ccacaaagcc attgtatgta gttttanttc agctgcaaan       60
aataccncca gcatccacct tactaaccag catatgcaga ca                         102
```

<210> SEQ ID NO 182
<211> LENGTH: 337
<212> TYPE: DNA
<213> ORGANISM: Homo sapien
<220> FEATURE:
<221> NAME/KEY: misc_feature
<222> LOCATION: (1)...(337)
<223> OTHER INFORMATION: n = A,T,C or G

<400> SEQUENCE: 182

```
tcgagcggtc gcccgggcag gtctgggcgg atagcaccgg gcatattttg gaatggatga       60
ggtctggcac cctgagcagc ccagcgagga cttggtctta gttgagcaat ttggctagga     120
ggatagtatg cagcacggtt ctgagtctgt gggatagctg ccatgaagna acctgaagga     180
ggcgctggct ggtangggtt gattacaggg ctgggaacag ctcgtacact tgccattctc     240
tgcatatact ggntagtgag gcgagcctgg cgctcttctt tgcgctgagc taaagctaca     300
tacaatggct ttgnggacct cggccgcgac cacgctt                              337
```

<210> SEQ ID NO 183
<211> LENGTH: 374
<212> TYPE: DNA
<213> ORGANISM: Homo sapien

<400> SEQUENCE: 183

```
tcgagcggcc gcccgggcag gtccattttc tccctgacgg tcccacttct ctccaatctt       60
gtagttcaca ccattgtcat gacaccatct agatgaatca catctgaaat gaccacttcc     120
aaagcctaag cactggcaca acagtttaaa gcctgattca gacattcgtt cccactcatc     180
tccaacggca taatgggaaa ctgtgtaggg gtcaaagcac gagtcatccg taggttggtt     240
caagccttcg ttgacagaag ttgcccacgg taacaacctc ttcccgaacc ttatgcctct     300
gctggtcttt caagtgcctc cactatgatg ttgtaggtgg cacctctggt gaggacctcg     360
gccgcgacca cgct                                                        374
```

<210> SEQ ID NO 184
<211> LENGTH: 375
<212> TYPE: DNA
<213> ORGANISM: Homo sapien
<220> FEATURE:
<221> NAME/KEY: misc_feature
<222> LOCATION: (1)...(375)
<223> OTHER INFORMATION: n = A,T,C or G

<400> SEQUENCE: 184

```
agcgtggttt gcggccgagg tcctcaccan aggtgccacc tacaacatca tagtggaggc      60
actgaaagac cagcagaggc ataaggttcg ggaagaggtt gttaccgtgg gcaactctgt     120
caacgaaggc ttgaaccaac ctacggatga ctcgtgcttt gacccctaca cagnttccca    180
ttatgccgtt ggagatgagt gggaacgaat gtctgaatca ggctttaaac tgttgtgcca    240
gtgcttangc tttggaagtg gtcatttcag atgtgattca tctanatggt gtcatgacaa    300
tggtgngaac tacaagattg gagagaagtg gnaccgtcag gggannaaaat ggacctgccc    360
gggcggcncg ctcga                                                      375
```

<210> SEQ ID NO 185
<211> LENGTH: 148
<212> TYPE: DNA
<213> ORGANISM: Homo sapien
<220> FEATURE:
<221> NAME/KEY: misc_feature
<222> LOCATION: (1)...(148)
<223> OTHER INFORMATION: n = A,T,C or G

<400> SEQUENCE: 185

```
agcgtggtcg cggccgaggt ctggcttnct gctcangtga ttatcctgaa ccatccaggc      60
caaataagcg ccggctatgc ccctgnattg gattgccaca cggctcacat tgcatgcaag    120
tttgctgagc tgaaggaaaa gattgatc                                        148
```

<210> SEQ ID NO 186
<211> LENGTH: 397
<212> TYPE: DNA
<213> ORGANISM: Homo sapien
<220> FEATURE:
<221> NAME/KEY: misc_feature
<222> LOCATION: (1)...(397)
<223> OTHER INFORMATION: n = A,T,C or G

<400> SEQUENCE: 186

```
tcgagcggcc gcccgggcag gtccaattga acaaacagt tctgagaccg ttcttccacc      60
actgattaag agtggggngg cgggtattag ggataatatt catttagcct tctgagcttt    120
ctgggcagac ttggtgacct tgccagctcc agcagccttc tggtccactg ctttgatgac    180
acccaccgca actgtctgtc tcatatcacg aacagcaaag cgacccaaag gtggatagtc    240
tgagaagctc tcaacacaca tgggcttgcc aggaaccata tcaacaatgg gcagcatcac    300
cagacttcaa gaatttaagg gccatcttcc agcttttttac cagaacggcg atcaatcttt    360
tccttcagct cagcaaactt gcatgcaatg tgagccg                              397
```

<210> SEQ ID NO 187
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 187

```
tcgagcggcc gcccgggcag gtccagaggg ctgtgctgaa gtttgctgct gccactggag      60
ccactccaat tgctggccgc ttcactcctg gaaccttcac taaccagatc caggcagcct    120
tccgggagcc acggcttctt gtggntactg acccagggc tgaccaccag cctctcacgg    180
aggcatctta tgttaaccta cctaccattg cgctgtgtaa cacagattct cctctgcgct    240
```

```
atgtggacat tgccatccca tgcaacaaca agggagctca ctcagngggg tttgatgtgg    300
tggatgctgg ctcgggaagt tctgcgcatg cgtggcacca tttcccgtga acacccatgg    360
gangncatgc ctgatctgga cttctacaga gatcctgaag agattgaaaa agaagaacag    420
gctgnttgct ganaaagcaa gtgaccaagg angaaatttc angggtgaaa nggactgctc    480
ccgctcctga attcactgct actcaacctg angntgcaga ctggtcttga aggngnacan    540
gggccctctg ggcctattta agcancttcg gtcgcgaaca cgnt                     584
```

<210> SEQ ID NO 188
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 188

```
agcgtgngtc gcggccgagg tgctgaatag gcacagaggg cacctgtaca ccttcagacc    60
agtctgcaac ctcaggctga gtagcagtga actcaggagc gggagcagtc cattcaccct    120
gaaattcctc cttggncact gccttctcag cagcagcctg ctcttctttt tcaatctctt    180
caggatctct gtagaagtac agatcaggca tgacctccca tgggtgttca cgggaaatgg    240
tgccacgcat gcgcagaact tcccgagcca gcatccacca catcaaaccc actgagtgag    300
ctcccttgtt gttgcatggg atgggcaatg tccacatagc gcagaggaga atctgtgtta    360
cacagcgcaa tggtaggtag gttaacataa gatgcctccg cgagaagctg gtggtcagcc    420
ctggggtcaa gtaaccacaa gaagccgtgg ctcccggaag gctgcctgga tctggttagt    480
gaaggntcca ggagtgaagc ggccaacaat tggagtggct tcagtggcaa gcagcaaact    540
tcagcacaag ccctctggac ctgcccggcg gccgctcga                           579
```

<210> SEQ ID NO 189
<211> LENGTH: 374
<212> TYPE: DNA
<213> ORGANISM: Homo sapien
<220> FEATURE:
<221> NAME/KEY: misc_feature
<222> LOCATION: (1)...(374)
<223> OTHER INFORMATION: n = A,T,C or G

<400> SEQUENCE: 189

```
tcgagcggcc gccgggcag gtccattttc tccctgacgg ncccacttct ctccaatctt    60
gtagttcaca ccattgtcat ggcaccatct agatgaatca catctgaaat gaccacttcc    120
aaagcctaag cactggcaca acagtttaaa gcctgattca gacattcgtt cccactcatc    180
tccaacggca taatgggaaa ctgtgtaggg gtcaaagcac gagtcatccg taggttggtt    240
caagccttcg ttgacagagt tgcccacggt aacaacctcn tccccgaacc ttatgcctct    300
gctgggcttt cagngcctcc actatgatgn tgtaggggg cacctctggn gangacctcg    360
gccgcgacca cgct                                                      374
```

<210> SEQ ID NO 190
<211> LENGTH: 373
<212> TYPE: DNA
<213> ORGANISM: Homo sapien
<220> FEATURE:
<221> NAME/KEY: misc_feature
<222> LOCATION: (1)...(373)

<223> OTHER INFORMATION: n = A,T,C or G

<400> SEQUENCE: 190

| | | | | | |
|---|---|---|---|---|---|
| agcgtggtcg | cggccgaggt | cctcaccaga | ggtgccacct | acaacatcat | agtggaggca | 60 |
| ctgaaagacc | agcagaggca | taaggctcgg | aagaggttg | ttaccgtggg | caactctgtc | 120 |
| aacgaaggct | tgaaccaacc | tacgatgac | tcgtgctttg | accctacac | agtttcccat | 180 |
| tatgccgttg | gagatgagtg | ggaacgaatg | tctgaatcag | gctttaaact | gttgtgccag | 240 |
| tgcttangct | ttggaagtgg | gtcatttcag | atgtgattca | tctagatggt | gccatgacaa | 300 |
| tggngngaac | tacaagattg | gagagaagtg | gnaccgncag | ggagaaaatg | gacctgcccg | 360 |
| ggcggccgct | cga | | | | | 373 |

<210> SEQ ID NO 191
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 191

| | | | | | |
|---|---|---|---|---|---|
| agcgtggtcg | cggccgaggt | ccacatcggc | agggtcggag | ccctggccgc | catactcgaa | 60 |
| ctggaatcca | tcggtcatgc | tctcgccgaa | ccagacatgc | ctcttgtcct | tgggttctt | 120 |
| gctgatgtac | cagttcttct | gggccacact | gggctgagtg | gggtacacgc | aggtctcacc | 180 |
| agtctccatg | ttgcagaaga | ctttgatggc | atccaggntg | caaccttggt | tggggtcaat | 240 |
| ccagtactct | ccactcttcc | agccagagtg | gcacatcttg | aggtcacggc | aggtgcggnc | 300 |
| ggggntttt | gcggctgccc | tctggncttc | ggntgtnctc | natctgctgg | ctca | 354 |

<210> SEQ ID NO 192
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 192

| | | | | | |
|---|---|---|---|---|---|
| tcgagcggcc | gcccgggcag | gtctcgcggt | cgcactggtg | atgctggtcc | tgttggtccc | 60 |
| cccggccctc | ctggacctcc | tggcccccct | ggtcctccca | gcgctggttt | cgacttcagc | 120 |
| ttcctgcccc | agccacctca | agagaaggct | cacgatggtg | gccgctacta | ccgggctgat | 180 |
| gatgccaatg | tggttcgtga | ccgtgacctc | gaggtggaca | ccaccctcaa | gagcctgagc | 240 |
| cagcagatcg | agaacatccg | gagcccagag | ggcagncgca | agaacccgc | cgcacctgc | 300 |
| cgtgacctca | agatgtgcca | ctctgactgg | aagagtggag | agtactggat | tgaccccaac | 360 |
| caagctgcaa | cctggatgcc | atcaaagtct | tctgcaacat | ggagactggt | gagacctgcg | 420 |
| tgtaccccac | tcagcccagt | gtggcccaaa | agaactggta | catcagcaag | aaccccaagg | 480 |
| acaagaagca | tgtctggttc | ggcgagaaca | tgaccgatgg | attccagttc | gagtatggcg | 540 |
| ggcagggctc | cgaccctgcc | gatggggacc | ttggccgcga | acacgct | | 587 |

<210> SEQ ID NO 193
<211> LENGTH: 98
<212> TYPE: DNA
<213> ORGANISM: Homo sapien
<220> FEATURE:
<221> NAME/KEY: misc_feature
<222> LOCATION: (1)...(98)
<223> OTHER INFORMATION: n = A,T,C or G

<400> SEQUENCE: 193
agcgtggnng cggccgaggt ataaatatcc agnccatatc ctccctccac acgctganag    60
atgaagctgt ncaaagatct cagggtggan aaaaccat                            98

<210> SEQ ID NO 194
<211> LENGTH: 240
<212> TYPE: DNA
<213> ORGANISM: Homo sapien

<400> SEQUENCE: 194
tcgagcggcc gcccgggcag gtccttcaga cttggactgt gtcacactgc caggcttcca    60
gggctccaac ttgcagacgg cctgttgtgg gacagtctct gtaatcgcga aagcaaccat   120
ggaagacctg ggggaaaaca ccatggtttt atccaccctg agatctttga acaacttcat   180
ctctcagcgt gcggagggag gctctggact ggatatttct acctcggccg cgaccacgct   240

<210> SEQ ID NO 195
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 195
cgagcgggcg accgggcagg tncagactcc aatccanana accatcaagc cagatgtcag    60
aagctacacc atcacaggtt tacaaccagg cactgactac aaganctacc tgcacacctt   120
gaatgacaat gctcggagct cccctgtggt catcgacgcc tccactgcca ttgatgcacc   180
atccaacctg cgtttcctgg ccaccacacc caattccttg ctggtatcat ggcagccgcc   240
acgtgccagg attaccggta catcatcnag tatganaagc ctgggcctcc tcccagagaa   300
gnggtccctc ggccccgccc tgntgtccca naggntacta ttactgngcc ngcaaccggc   360
aaccgatatc nattttgnca ttggccttca acaataatta                         400

<210> SEQ ID NO 196
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 196 gcgtggttc gcggccgang tcctgtcaga gtggcactgg tagaagttcc aggaaccctg    60 actgtaagg gttcttcatc agngccaaca ggatgacatg aaatgatgta ctcagaagtg   120 cctggaatg gggcccatga gatggttgtc tgagagagag cttcttgncc tgtcttttc    180 ttccaatca ggggctcgct cttctgatta ttcttcaggg caatgacata aattgtatat   240 cgggtcccg gntccaggcc agtaatagta ncctctgtga caccagggcg gngccgaggg   300 ccacttctc tgggaggaga cccaggcttc tcatacttga tgatgtaacc ggtaatcctg   360 cacgtggcg gctgccatga taccagcaag gaattgggt gtggtggcca ggaaacgcag    420

```
ttggatggn gcatcaatgg cagtggaggc cgtcgatgac cacaggggga gctccgacat    480
tgtcattcaa ggtg                                                    494
```

<210> SEQ ID NO 197
<211> LENGTH: 118
<212> TYPE: DNA
<213> ORGANISM: Homo sapien
<220> FEATURE:
<221> NAME/KEY: misc_feature
<222> LOCATION: (1)...(118)
<223> OTHER INFORMATION: n = A,T,C or G

<400> SEQUENCE: 197

```
agcgtggncg cggccgaggt gcagcgcggg ctgtgccacc ttctgctctc tgcccaacga    60
taaggagggt ncctgccccc aggagaacat taactntccc cagctcggcc tctgccgg    118
```

<210> SEQ ID NO 198
<211> LENGTH: 403
<212> TYPE: DNA
<213> ORGANISM: Homo sapien
<220> FEATURE:
<221> NAME/KEY: misc_feature
<222> LOCATION: (1)...(403)
<223> OTHER INFORMATION: n = A,T,C or G

<400> SEQUENCE: 198

```
tcgagcggcc gcccgggcag gttttttttg ctgaaagtgg ntactttatt ggntgggaaa    60
gggagaagct gtggtcagcc caagaggaa tacagagncc cgaaaaaggg gagggcaggt   120
gggctggaac cagacgcagg gccaggcaga aactttctct cctcactgct cagcctggtg   180
gtggctggag ctcanaaatt gggagtgaca caggacacct tcccacagcc attgcggcgg   240
catttcatct ggccaggaca ctggctgtcc acctggcact ggtcccgaca gaagcccgag   300
ctggggaaag ttaatgttca cctgggggca ggaaccctcc ttatcattgn gcagagagca   360
gaaggtggca cagcccgcgc tgcacctcgg ccgcgaccac gct                     403
```

<210> SEQ ID NO 199
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 199

```
tcgagcggcc gcccgggcag gtccaccata agtcctgata caaccacgga tgagctgtca    60
ggagcaaggt tgatttcttt cattggtccg gncttctcct tgggggncac ccgcactcga   120
tatccagtga gctgaacatt gggtggcgtc cactgggcgc tcaggct                167
```

<210> SEQ ID NO 200
<211> LENGTH: 252
<212> TYPE: DNA
<213> ORGANISM: Homo sapien
<220> FEATURE:
<221> NAME/KEY: misc_feature
<222> LOCATION: (1)...(252)
<223> OTHER INFORMATION: n = A,T,C or G

<400> SEQUENCE: 200

```
tcgagcggtt cgcccgggca ggtccaccac acccaattcc ttgctggtat catggcagcc    60
gccacgtgcc aggattaccg gctacatcat caagtatgag aagcctgggt ctcctcccag   120
```

```
agaagcggtc cctcggcccc gccctggtgt cacagaggct actattactg gcctggaacc    180
gggaaccgaa tatacaattt atgtcattgn cctgaagaat aatcannaan agcgancccc    240
tgattggaag ga                                                        252
```

<210> SEQ ID NO 201
<211> LENGTH: 91
<212> TYPE: DNA
<213> ORGANISM: Homo sapien

<400> SEQUENCE: 201

```
agcgtggtcg cggccgaggt tgtacaagct tttttttttt tttttttttt tttttttttt    60
tttttttttt tttttttttt tttttttttt t                                   91
```

<210> SEQ ID NO 202
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 202

```
tcgagcggnc gcccgggcag gtctgccaac accaagattg gcccccgccg catccacaca    60
gtccgtgtgc ggggaggtaa caagaaatac cgtgccctga ggttggacgt ggggaatttc    120
tcctggggct cagagtgttg tactcgtaaa acaaggatca tcgatgttgt ctacaatgca    180
tctaataacg agctggttcg taccaagacc ctggtgaaga attgcatcgt gctcatcgac    240
agcacaccgt accgacagtg gtacgagtcc cactatgcgc tgccctggg ccgcaagaag    300 ggagccaagc tgactcctga ggaagaagag attttaaaca aaaacgatc taanaaaaaa    360 aaaacaat                                                             368
```

<210> SEQ ID NO 203
<211> LENGTH: 340
<212> TYPE: DNA
<213> ORGANISM: Homo sapien

<400> SEQUENCE: 203

```
agcgtggtcg cggccgaggt gaaatggtat tcagcttcct ggcacttctg gtcagcaacc    60
cagtgttggg caacaaatga tctttgagga acatggtttt aggcggacca caccgcccac    120
aacggccacc cccataaggc ataggccaag accatacccg ccgaatgtag dacaagaagc    180
tctctctcag acaaccatct catgggcccc attccaggac acttctgagt acatcatttc    240
atgtcatcct gttggcactg atgaagaacc cttacagttc agggttcctg gaacttctac    300
cagtgccact ctgacaggac ctgcccgggc ggccgctcga                          340
```

<210> SEQ ID NO 204
<211> LENGTH: 341
<212> TYPE: DNA
<213> ORGANISM: Homo sapien

<400> SEQUENCE: 204

```
tcgagcggcc gcccgggcag gtcctgtcag agtggcactg gtagaagttc caggaaccct    60
gaactgtaag ggttcttcat cagtgccaac aggatgacat gaaatgatgt actcagaagt    120
gtcctggaat ggggcccatg agatggttgt ctgagagaga gcttcttgtc ctacattcgg    180
```

-continued

| | | |
|---|---|---|
| cgggtatggt cttggcctat gccttatggg ggtggccgtt gtgggcggtg tggtccgcct | 240 |
| aaaaccatgt tcctcaaaga tcatttgttg cccaacactg ggttgctgac cagaagtgcc | 300 |
| aggaagctga ataccatttc acctcggccg cgaccacgct a | 341 |

<210> SEQ ID NO 205
<211> LENGTH: 770
<212> TYPE: DNA
<213> ORGANISM: Homo sapien
<220> FEATURE:
<221> NAME/KEY: misc_feature
<222> LOCATION: (1)...(770)
<223> OTHER INFORMATION: n = A,T,C or G

<400> SEQUENCE: 205

| | |
|---|---|
| tcgagcggcc gcccgggcag gtctcccttc ttgcggccca ggggcagcgc atagtgggac | 60 |
| tcgtaccact gtcggtacgg tgtgctgtcg atgagcacga tgcaattctt caccagggtc | 120 |
| ttggtacgaa ccagctcgtt attagatgca ttgtagacaa catcgatgat ccttgtttta | 180 |
| cgagtacaac actctgagcc ccaggagaaa ttccccacgt ccaacctcag ggcacggtat | 240 |
| ttcttgttac ctccccgcac acggactgtg tggatgcggc gggggccaag ctgactcctg | 300 |
| aggaagaaga gattttaaac aaaaaacgat ctaaaaaaat tcagaagaaa tatgatgaaa | 360 |
| ggaaaaagaa tgccaaaatc agcagtctcc tggaggagca gttccagcag ggcaagcttc | 420 |
| ttgcgtgcat cgcttcaagg ccgggacagt gtgaccgagc agatggctat gtgctagagg | 480 |
| gcaaagaagt ggagttctat cttaagaaaa tcagggccca gaatggtgng tcttcaacta | 540 |
| atccaaaggg gagtttcaga ccagtgcaat cagcaaaaac attgatactg ntggccaaat | 600 |
| ttattggtgc agggcttgca cantangann ggctgggtct tggggcttgg attggnacaa | 660 |
| gctttggcag ccttttcttt ggttttgcca aaaaccttttt gntgaagang anacctnggg | 720 |
| cggacccctt aaccgattcc acnccnggng gcgttctang gnccncttg | 770 |

<210> SEQ ID NO 206
<211> LENGTH: 810
<212> TYPE: DNA
<213> ORGANISM: Homo sapien
<220> FEATURE:
<221> NAME/KEY: misc_feature
<222> LOCATION: (1)...(810)
<223> OTHER INFORMATION: n = A,T,C or G

<400> SEQUENCE: 206

| | |
|---|---|
| agcgtggtcg cggccgaggt ctgctgcttc agcgaagggt ttctggcata accaatgata | 60 |
| aggctgccaa agactgttcc aataccagca ccagaaccag ccactcctac tgttgcagca | 120 |
| cctgcaccaa taaatttggc agcagtatca atgtctctgc tgattgcact ggtctgaaac | 180 |
| tccctttgga ttagctgaga cacaccattc tgggccctga ttttcctaag atagaactcc | 240 |
| aactctttgc cctctagcac atagccatct gctcggtcac actgtcccgg ccttgaagcg | 300 |
| atgcacgcaa gaagcttgcc ctgctggaac tgctcctcca ggagactgct gattttggca | 360 |
| ttctttttcc tttcatcata tttcttctga attttttttag atcgttttttt gtttaaaatc | 420 |
| tcttcttcct caggagtcag cttggccccc gccgcatcca cacagtccgt gtgcggggag | 480 |
| gtaacaagaa ataccgtgcc ctgaggttgg acgtggggaa tttctcctgg ggctcagagt | 540 |
| ggtgtactcg taaaacaagg atcatcgatg gtgnctacaa tgcatctaat aacgagctgg | 600 |
| gtcggaccca agaacctggg ngaanaaatg gatcgnctca tcgacaggac accgtacccg | 660 |
| acaggggnac gantcccact atgcgcttgc ccctgggccg caanaaagga aaactgcccg | 720 |

```
ggcggccntc gaaagcccaa ttntggaaaa aatccatcac actgggnggc cngtcgagca    780
tgcatntana ggggcccatt cccctnann                                     810
```

<210> SEQ ID NO 207
<211> LENGTH: 257
<212> TYPE: DNA
<213> ORGANISM: Homo sapien

<400> SEQUENCE: 207

```
tcgagcggcc gcccgggcag gtccccaacc aaggctgcaa cctggatgcc atcaaagtct    60
tctgcaacat ggagactggt gagacctgcg tgtaccccac tcagcccagt gtggcccaga    120
agaactggta catcagcaag aaccccaagg acaagaggca tgtctggttc ggcgagagca    180
tgaccgatgg attccagttc gagtatggcg gccagggctc cgaccctgcc gatgtggacc    240
tcggccgcga ccacgct                                                    257
```

<210> SEQ ID NO 208
<211> LENGTH: 257
<212> TYPE: DNA
<213> ORGANISM: Homo sapien

<400> SEQUENCE: 208

```
agcgtggtcg cggccgaggt ccacatcggc agggtcggag ccctggccgc catactcgaa    60
ctggaatcca tcgtcatgc tctcgccgaa ccagacatgc tcttgtcct tggggttctt    120 gctgatgtac cagttcttct gggccacact gggctgagtg gggtacacgc aggtctcacc    180
agtctccatg ttgcagaaga ctttgatggc atccaggttg cagccttggt tggggacctg    240
cccgggcggc cgctcga                                                    257
```

<210> SEQ ID NO 209
<211> LENGTH: 747
<212> TYPE: DNA
<213> ORGANISM: Homo sapien
<220> FEATURE:
<221> NAME/KEY: misc_feature
<222> LOCATION: (1)...(747)
<223> OTHER INFORMATION: n = A,T,C or G

<400> SEQUENCE: 209

```
tcgagcggcc gcccgggcag gtccaccaca cccaattcct tgctggtatc atggcagccg    60
ccacgtgcca ggattaccgg ctacatcatc aagtatgaga agcctgggtc tcctcccaga    120
gaagtggtcc ctcggccccg ccctggtgtc acagaggcta ctattactgg cctggaaccg    180
ggaaccgaat atacaattta tgtcattgcc ctgaagaata atcagaagag cgagcccctg    240
attggaagga aaagacaga cgagcttccc caactggtaa cccttccaca ccccaatctt    300
catggaccag agatcttgga tgttccttcc acagttcaaa agaccccttt cgtcacccac    360
cctgggtatg acactggaaa tggtattcag cttcctggca cttctggtca gcaacccagt    420
gttgggcaac aaatgatctt tgaggaacat ggntttaggc ggaccacacc gcccacaacg    480
gccaccccca taaggcatag gccaagacca tacccgccga atgtaggaca agaagctntn    540
tntcanacac catntnatgg gccccattcc aggacacttc tgagtacatc atttatgnca    600
tctgtggcac ttgatgaaaa cccttacagt tcagggttct ggaacttta ccaggcctnt    660 tacaggactn ggccggacnc cttaagccna ttncaccctg gggcgttcta nggtcccact    720
cgnncactgg ngaaaatggc tactgtn                                         747
```

<210> SEQ ID NO 210
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 210

| | | | | | |
|---|---|---|---|---|---|
| agcgtggtcg | cggccgaggt | ccactagagg | tctgtgtgcc | attgcccagg | cagagtctct | 60 |
| gcgttacaaa | ctcctaggag | ggcttgctgt | gcggagggcc | tgctatggtg | tgctgcggtt | 120 |
| catcatggag | agtggggcca | aaggctgcga | ggttgtggtg | tctgngaaac | tccnaggaca | 180 |
| ngagggctaa | attccatgaa | gtttgtggat | ggcctgatga | tccacaatcg | gagaccctgt | 240 |
| taactactac | cgtctnaccn | cctgctgtnc | nccccntttt | ctgctnaana | catngggntn | 300 |
| ntncttgncc | ntccttgggt | ngaanatnna | atngcctncc | cnttcntanc | nctactngnt | 360 |
| ccananttgg | cctttaaana | atccncccttg | ccttnnncac | tgttcanntn | tttnntcgta | 420 |
| aaccctatna | nttnnattan | atnntnnnnn | nctcacccccc | ctcntcattn | anccnatang | 480 |
| ctnnnaantc | cttnanncct | cccncccnnt | ncnctcntac | tnantncttc | tnncccatta | 540 |
| cnnagctctt | tcntttaana | taatgnngcc | nngctctnca | tntctacnat | ntgnnnaatn | 600 |
| ccccncccc | cnancgnntt | tttgacctnn | naacctcctt | tcctcttccc | tncnnaaatt | 660 |
| ncnnanttcc | ncnttccnnc | ntttcggntn | ntcccatnct | ttccannnct | tcantctanc | 720 |
| ncnctncaac | ttattttcct | ntcatcccctt | nttctttaca | nnccccctnn | tctactcnnc | 780 |
| nnttncatta | natttgaaac | tnccacnnct | anttnccctcn | ctctacnntt | ttattttncg | 840 |
| ntcnctctac | ntaatantt | aatnanttnt | cn | | | 872 |

<210> SEQ ID NO 211
<211> LENGTH: 517
<212> TYPE: DNA
<213> ORGANISM: Homo sapien
<220> FEATURE:
<221> NAME/KEY: misc_feature
<222> LOCATION: (1)...(517)
<223> OTHER INFORMATION: n = A,T,C or G

<400> SEQUENCE: 211

| | | | | | |
|---|---|---|---|---|---|
| tcgagcggcc | gcccgggcag | gtctgccaag | gagaccctgt | tatgctgtgg | ggactggctg | 60 |
| gggcatggca | ggcggctctg | gcttcccacc | cttctgttct | gagatggggg | tggtgggcag | 120 |
| tatctcatct | ttgggttcca | caatgctcac | gtggtcaggc | aggggcttct | tagggccaat | 180 |
| cttaccagtt | gggtcccagg | gcagcatgat | cttcaccttg | atgcccagca | caccctgtct | 240 |
| gagcaacacg | tggcgcacaa | gcagtgtcaa | cgtagtaagt | taacagggtc | tccgctgtgg | 300 |
| atcatcaggc | catccacaaa | cttcatggat | ttagccctct | gtcctcggag | tttcccagac | 360 |
| accacaacct | cgcagccttt | ggccccactc | tccatgatga | accgcagcac | accatagcag | 420 |
| gccctccgca | caagcaagcc | ctcctaagaa | tttgtaacgc | ananactctg | ctggcaatgg | 480 |
| cacacaaacc | tctagtggac | ctcggncgcg | accacgc | | | 517 |

<210> SEQ ID NO 212
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 212

```
tcgagcggcc gcccgggcag gtctggtcca ggatagcctg cgagtcctcc tactgctact      60
ccagacttga catcatatga atcatactgg ggagaatagt tctgaggacc agtagggcat     120
gattcacaga ttccaggggg gccaggagaa ccaggggacc ctggttgtcc tggaatacca     180
gggtcaccat ttctcccagg aataccagga gggcctggat ctcccttggg gccttgaggt     240
ccttgaccat taggagggcg agtaggagca gttggaggct gtgggcaaac tgcacaacat     300
tctccaaatg gaatttctgg gttggggcag tctaattctt gatccgtcac atattatgtc     360
atcgcagaga acgatcctg agtcacagac acatatttgg catggttctg cttccagac       420
atctctatcc gncataggac tgaccaagat gggaacatcc tccttcaaca gcttnctgt      480
tgtgccaaaa ataatagtgg gatgaagcag accgagaagt anccagctcc cctttttgca     540
caaagcntca tcatgtctaa atatcagaca tgagacttct ttgggcaaaa aaggagaaaa     600
agaaaaagca gttcaaagta nccnccatca agttggttcc ttgcccnttc agcacccggg     660
ccccgttata aaacacctng ggccggaccc ccctt                                695
```

<210> SEQ ID NO 213
<211> LENGTH: 804
<212> TYPE: DNA
<213> ORGANISM: Homo sapien
<220> FEATURE:
<221> NAME/KEY: misc_feature
<222> LOCATION: (1)...(804)
<223> OTHER INFORMATION: n = A,T,C or G

<400> SEQUENCE: 213

```
agcgtggtcg cggccgaggt gttttatgac gggcccggtg ctgaagggca gggaacaact      60
tgatggtgct actttgaact gcttttcttt tctccttttt gcacaaagag tctcatgtct     120
gatatttaga catgatgagc tttgtgcaaa aggggagctg gctacttctc gctctgcttc     180
atcccactat tattttggca acacaggaag ctgttgaagg aggatgttcc catcttggtc     240
agtcctatgc ggatagagat gtctggaagc cagaaccatg ccaaatatgt gtctgtgact     300
caggatccgt tctctgcgat gacataatat gtgacgatca agaattagac tgccccaacc     360
cagaaattcc atttggagaa tgttgtgcag tttgcccaca gcctccaact gctcctactc     420
gccctcctaa tggtcaagga cctcaaggcc ccaaggagaa tccaggccct cctggtattc     480
ctgggagaaa tggtgaccct ggtattccag acaaccagg gtcccctggt tctcctggcc      540
cccctggaat cnggngaatc atgccctact ggtcctcaaa ctattctccc anatgattca     600
tatgatgtca agtctgggat agcnagtang ganggactcg caggctattc tggaccanac     660
ctgccggggg ggcgttcgaa agcccgaatc tgcananntn cnttcacact ggcggccgtc     720
gagctgcttt aaaagggcca ttccnccttt agngngggg antacaatta ctnggcggcg      780
ttttanancg cgngnctggg aaat                                             804
```

<210> SEQ ID NO 214
<211> LENGTH: 594
<212> TYPE: DNA
<213> ORGANISM: Homo sapien
<220> FEATURE:
<221> NAME/KEY: misc_feature
<222> LOCATION: (1)...(594)
<223> OTHER INFORMATION: n = A,T,C or G

<400> SEQUENCE: 214

```
agcgtggtcg cggccgaggt ccacatcggc agggtcggag ccctggccgc catactcgaa      60
ctggaatcca tcggtcatgc tctcgccgaa ccagacatgc tcttgtcct tggggttctt     120
gctgatgtac cagttcttct gggccacact gggctgagtg gggtacacgc aggtctcacc    180
agtctccatg ttgcagaaga ctttgatggc atccaggttg cagccttggt tggggtcaat    240
ccagtactct ccactcttcc agtcagagtg gcacatcttg aggtcacggc aggtgcgggc    300
ggggttcttg cggctgccct ctgggctccg gatgttctcg atctgctggc tcaggctctt    360
gagggtggtg tccacctcga ggtcacggtc acgaaccaca ttggcatcat cagcccggta    420
gtagcggcca ccatcgtgag ccttctcttg angtggctgg ggcaggaact gaagtcgaaa    480
ccagcgctgg gaggaccagg gggaccaana ggtccaggaa gggcccgggg gggaccaaca    540
ggaccagcat caccaagtgc gacccgcgag aacctgcccg gccgnccgct cgaa          594
```

<210> SEQ ID NO 215
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 215

```
tcgagcgnnc gcccgggcag gtctcgcggt cgcactggtg atgctggtcc tgttggtccc     60
cccggccctc ctggacctcc tggtccccct ggtcctccca gcgctggttt cgacttcagc    120
ttcctgcccc agccacctca agagaaggct cacgatggtg gccgctacta ccgggctgat    180
gatgccaatg tggttcgtga ccgtgacctc gaggtggaca ccaccctcaa gagcctgagc    240
cagcagatcg agaacatccg gagcccagag gcagccgca agaacccgc cgcacctgc      300
cgtgacctca agatgtgcca ctctgactgg aagagtggag agtactggat tgaccccaac    360
caaggctgca acctggatgc catcaaagtc ttctgcaaca tggagactgg tgagacctgc    420
gtgtacccca ctcagcccag tgtggcccag aagaactggt acatcagcaa gaaccccaag    480
gacaagaggc atgtctggtt cggcgagagc atgaccgatg gattccagtt cgagtatggc    540
ggccagggct cccaccctgc cgatgtggac ctccggccgc gaccaccctt                590
```

<210> SEQ ID NO 216
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 216

```
tngagcggcc gcccgggcag gntgnnaacg ctggtcctgc tggtcctcct ggcaaggctg      60
gtgaagatgg tcaccctgga aacccggac gacctggtga gagaggagtt gttggaccac     120
aggtgctcg tggtttccct ggaactcctg gacttcctgg cttcaaaggc attaggggac     180
acaatggtct ggatggattg aagggacagc ccggtgctcc tggtgtgaag ggtgaacctg    240
gtgcccctgg tgaaaatgga actccaggtc aaacaggagc ccgtgggctt cctggtgaga    300
gaggaccgtg ttggtgcccc tggcccanac ctcgccgcg accacgctaa gcccgaattt     360
ccagcacact ggnggccgtt actantggat ccgagctcgg taccaagctt ggcgtaatca    420
```

```
tggtcatagc tgtttcctgn gtgaaattgt tatccgctca caatttcaca cancatacga      480
agccggaaag cataaagtgt aaagccttgg ggtgctaatg agtgagctaa ctcncattaa      540
attgcgttgc gctcactgcc cgcttttcca nnngggaaac cntggcntng ccngcttgcn      600
ttaantgaaa tccgccnacc cccgggaaa agncggtttg cngtattggg gcncttttc        660 cctttcctcg gnttacttga nttantgggc tttggncgnt tcgggttgng gcgancnggt      720
tcaacntcac nccaaaggng gnaanacggt tttcccanaa tccgggggnt ancccaangn      780
aaaacatnng ncnaangggc t                                                801

<210> SEQ ID NO 217
<211> LENGTH: 349
<212> TYPE: DNA
<213> ORGANISM: Homo sapien
<220> FEATURE:
<221> NAME/KEY: misc_feature
<222> LOCATION: (1)...(349)
<223> OTHER INFORMATION: n = A,T,C or G

<400> SEQUENCE: 217
agcgtggttn gcggccgagg tctgggccag ggcaccaac acgtcctctc tcaccaggaa       60
gcccacgggc tcctgtttga cctggagttc cattttcacc aggggcacca ggttcaccct     120
tcacaccagg agcaccgggc tgtcccttca atccatncag accattgtgn ccctaatgc      180 ctttgaagcc aggaagtcca ggagttccag ggaaaccacc gagcacctg tggtccaaca      240 actcctctct caccaggtcg tccgggtttt ccagggtgac catcttcacc agccttgcca     300
ggaggaccag caggaccagc gttaccaacc tgcccgggcg gccgctcga                 349

<210> SEQ ID NO 218
<211> LENGTH: 372
<212> TYPE: DNA
<213> ORGANISM: Homo sapien

<400> SEQUENCE: 218
tcgagcggcc gcccgggcag gtccattttc tccctgacgg tcccacttct ctccaatctt      60
gtagttcaca ccattgtcat ggcaccatct agatgaatca catctgaaat gaccacttcc     120
aaagcctaag cactggcaca acagtttaaa gcctgattca gacattcgtt cccactcatc     180
tccaacggca taatgggaaa ctgtgtaggg gtcaaagcac gagtcatccg taggttggtt     240
caagccttcg ttgacagagt tgcccacggt aacaacctct tcccgaacct tatgcctctg    300
ctggtctttc agtgcctcca ctatgatgtt gtaggtggca cctctggtga ggacctcggc    360
cgcgaccacg ct                                                         372

<210> SEQ ID NO 219
<211> LENGTH: 374
<212> TYPE: DNA
<213> ORGANISM: Homo sapien

<400> SEQUENCE: 219
agcgtggtcg cggccgaggt cctcaccaga ggtgccacct acaacatcat agtggaggca     60
ctgaaagacc agcagaggca taaggttcgg gaagaggttg ttaccgtggg caactctgtc    120
aacgaaggct tgaaccaacc tacggatgac tcgtgctttg accctacac agtttcccat    180 tatgccgttg agatgagtg ggaacgaatg tctgaatcag gctttaaact gttgtgccag    240
tgcttaggct ttgaagtgg tcatttcaag atgtgattca tctagatggt gccatgacaa    300
```

```
tggtgtgaac tacaagattg gagagaagtg ggaccgtcag ggagaaaatg gacctgcccg      360
ggccggccgc tcga                                                        374
```

<210> SEQ ID NO 220
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 220

```
tcgagcgnnc gcccgggcag gtccagtagt gccttcggga ctgggttcac ccccaggtct       60
gcggcagttg tcacagcgcc agccccgctg gcctccaaag catgtgcagg agcaaatggc      120
accgagatat tccttctgcc actgttctcc tacgtggtat gtcttcccat catcgtaaca      180
cgttgcctca tgagggtcac acttgaattc tccttttccg ttcccaagac atgtgcagct      240
catttggctg gctctatagt ttggggaaag tttgttgaaa ctgtgccact gacctttact      300
tcctccttct ctactggagc tttcgtacct tccacttctg ctgttggtaa aatggtggat      360
cttctatcaa tttcattgac agtacccact tctcccaaac atccaggaa atagtgattt       420 cagagcgatt aggagaacca aattatgggg cagaaataag gggcttttcc acaggttttc      480
ctttggagga agatttcagt ggtgacttta aaagaatact caacagtgtc ttcatcccca      540
tagcaaaaga agaaacngta aatgatgaa ngcttctgga gatgccnnca tttaagggac       600
ncccagaact tcaccatcta caggacctac ttcagtttac annaagncac atantctgac      660
tcanaaagga cccaagtagc nccatggnca gcactttnag cctttcccct ggggaaaann      720
ttacnttctt aaanccctngg ccnngacccc cttaagncca aattntggaa aanttccntn      780
cnnctggggg gcngttcnac atgcnttna agggcccaat tncccnt                     828
```

<210> SEQ ID NO 221
<211> LENGTH: 476
<212> TYPE: DNA
<213> ORGANISM: Homo sapien

<400> SEQUENCE: 221

```
tcgagcggcc gcccgggcag gtgtcggagt ccagcacggg aggcgtggtc ttgtagttgt       60
tctccggctg cccattgctc tcccactcca cggcgatgtc gctgggatag aagcctttga      120
ccaggcaggt caggctgacc tggttcttgg tcatctcctc ccgggatggg ggcagggtgt      180
acacctgtgg ttctcggggc tgccctttgg ctttggagat ggttttctcg atgggggctg      240
ggagggcttt gttggagacc ttgcacttgt actccttgcc attcagccag tcctggtgca      300
ggacggtgag gacgctgacc acacggtacg tgctgttgta ctgctcctcc cgcggctttg      360
tcttggcatt atgcacctcc acgccgtcca cgtaccagtt gaacttgacc tcaggtctt      420 cgtggctcac gtccaccacc acgcatgtaa cctcagacct cggccgcgac cacgct          476
```

<210> SEQ ID NO 222
<211> LENGTH: 477
<212> TYPE: DNA
<213> ORGANISM: Homo sapien

<400> SEQUENCE: 222

```
agcgtggtcg cggccgaggt ctgaggttac atgcgtggtg gtggacgtga gccacgaaga       60
ccctgaggtc aagttcaact ggtacgtgga cggcgtggag gtgcataatg ccaagacaaa      120
```

```
gccgcgggag gagcagtaca acagcacgta ccgtgtggtc agcgtcctca ccgtcctgca    180
ccaggactgg ctgaatggca aggagtacaa gtgcaaggtc tccaacaaag ccctcccagc    240
ccccatcgag aaaaccatct ccaaagccaa agggcaagcc ccgagaacca caggtgtaca    300
ccctgccccc atcccgggag gagatgacca gaaccaggt cagcctgacc tgcctggtca     360
aaggcttcta tcccagcgac atcgccgtgg agtgggagag caatgggcag ccggagaaca    420
actacaagac cacgcctccc gtgctggact ccgacacctg cccgggcggc cgctcga       477
```

<210> SEQ ID NO 223
<211> LENGTH: 361
<212> TYPE: DNA
<213> ORGANISM: Homo sapien

<400> SEQUENCE: 223

```
tcgagcggcc gcccgggcag gttgaatggc tcctcgctga ccaccccggt gctggtggtg    60
ggtacagagc tccgatgggt gaaaccattg acatagagac tgtccctgtc cagggtgtag   120
gggcccagct cagtgatgcc gtgggtcagc tggctcagct tccagtacag ccgctctctg   180
tccagtccag ggcttttggg gtcaggacga tgggtgcaga cagcatccac tctggtggct   240
gccccatcct tctcaggcct gagcaaggtc agtctgcaac cagagtacag agagctgaca   300
ctggtgttct tgaacaaggg cataagcaga ccctgaagga cacctcggcc gcgaccacgc   360
t                                                                   361
```

<210> SEQ ID NO 224
<211> LENGTH: 361
<212> TYPE: DNA
<213> ORGANISM: Homo sapien

<400> SEQUENCE: 224

```
agcgtggtcg cggccgaggt gtccttcagg gtctgcttat gcccttgttc aagaacacca    60
gtgtcagctc tctgtactct ggttgcagac tgaccttgct caggcctgag aaggatgggg   120
cagccaccag agtggatgct gtctgcaccc atcgtcctga cccaaaaagc cctggactgg   180
acagagagcg gctgtactgg aagctgagcc agctgaccca cggcatcact gagctgggcc   240
cctacaccct ggacagggac agtctctatg tcaatggttt cacccatcgg agctctgtac   300
ccaccaccag caccggggtg gtcagcgagg agccattcaa cctgcccggg cggccgctcg   360
a                                                                   361
```

<210> SEQ ID NO 225
<211> LENGTH: 766
<212> TYPE: DNA
<213> ORGANISM: Homo sapien
<220> FEATURE:
<221> NAME/KEY: misc_feature
<222> LOCATION: (1)...(766)
<223> OTHER INFORMATION: n = A,T,C or G

<400> SEQUENCE: 225

```
agcgtggtcg cggccgaggt cctgtcagag tggcactggt agaagttcca ggaaccctga    60
actgtaaggg ttcttcatca gtgccaacag gatgacatga aatgatgtac tcagaagtgt   120
cctggaatgg ggcccatgag atggttgtct gagagagagc ttcttgtcct acattcggcg   180
ggtatggtct tggcctatgc cttatggggg tggccgttgt gggcggtgtg gtccgcctaa   240
aaccatgttc ctcaaagatc atttgttgcc caacactggg ttgctgacca gaagtgccag   300
```

| | |
|---|---|
| gaagctgaat accatttcca gtgtcatacc cagggtgggt gacgaaaggg gtcttttgaa | 360 |
| ctgtggaagg aacatccaag atctctggtc catgaagatt ggggtgtgga agggttacca | 420 |
| gttggggaag ctcgtctgtc ttttttccttc caatcagggg ctcgctcttc tgattattct | 480 |
| tcagggcaat gacataaatt gtatattcgg tcccggttcc aggccagtaa tagtagcctc | 540 |
| tgtgacacca gggcggggcc gagggaccct tctnttggaa gagaccagct tctcatactt | 600 |
| gatgatgagn ccggtaatcc tggcacgtgg nggttgcatg atnccaccaa ggaaatnggn | 660 |
| gggggnggac ctgcccggcg gccgttcnaa agcccaattc cacacacttg gnggccgtac | 720 |
| tatggatccc actcngtcca acttggngga atatggcata actttt | 766 |

<210> SEQ ID NO 226
<211> LENGTH: 364
<212> TYPE: DNA
<213> ORGANISM: Homo sapien

<400> SEQUENCE: 226

| | |
|---|---|
| tcgagcggcc gcccgggcag gtccttgacc ttttcagcaa gtgggaaggt gtaatccgtc | 60 |
| tccacagaca aggccaggac tcgtttgtac ccgttgatga tagaatgggg tactgatgca | 120 |
| acagttgggt agccaatctg cagacagaca ctggcaacat tgcggacacc ctccaggaag | 180 |
| cgagaatgca gagtttcctc tgtgatatca agcacttcag ggttgtagat gctgccattg | 240 |
| tcgaacacct gctggatgac cagcccaaag gagaaggggg agatgttgag catgttcagc | 300 |
| agcgtggctt cgctggctcc cactttgtct ccagtcttga tcagacctcg gccgcgacca | 360 |
| cgct | 364 |

<210> SEQ ID NO 227
<211> LENGTH: 275
<212> TYPE: DNA
<213> ORGANISM: Homo sapien

<400> SEQUENCE: 227

| | |
|---|---|
| agcgtggtcg cggccgaggt ctgtcctaca gtcctcagga ctctactccc tcagcagcgt | 60 |
| ggtgaccgtg ccctccagca acttcggcac ccagacctac acctgcaacg tagatcacaa | 120 |
| gcccagcaac accaaggtgg acaagagagt tgagcccaaa tcttgtgaca aaactcacac | 180 |
| atgcccaccg tgcccagcac ctgaactcct ggggggaccg tcagtcttcc tcttccccccg | 240 |
| catccccctt ccaaacctgc ccgggcggcc gctcg | 275 |

<210> SEQ ID NO 228
<211> LENGTH: 275
<212> TYPE: DNA
<213> ORGANISM: Homo sapien

<400> SEQUENCE: 228

| | |
|---|---|
| cgagcggccg cccgggcagg tttggaaggg ggatgcgggg gaagaggaag actgacggtc | 60 |
| cccccaggag ttcaggtgct gggcacggtg gcatgtgtg agttttgtca caagatttgg | 120 |
| gctcaactct cttgtccacc ttggtgttgc tgggcttgtg atctacgttg caggtgtagg | 180 |
| tctgggtgcc gaagttgctg gagggcacgg tcaccacgct gctgagggag tagagtcctg | 240 |
| aggactgtag gacagacctc ggccgcgacc acgct | 275 |

<210> SEQ ID NO 229
<211> LENGTH: 40
<212> TYPE: DNA
<213> ORGANISM: Homo sapien

```
<220> FEATURE:
<221> NAME/KEY: misc_feature
<222> LOCATION: (1)...(40)
<223> OTHER INFORMATION: n = A,T,C or G

<400> SEQUENCE: 229
nggnnggtcc ggncngncag gaccactcnt cttcgaaata                            40

<210> SEQ ID NO 230
<211> LENGTH: 208
<212> TYPE: DNA
<213> ORGANISM: Homo sapien

<400> SEQUENCE: 230
agcgtggtcg cggccgaggt cctcacttgc ctcctgcaaa gcaccgatag ctgcgctctg      60
gaagcgcaga tctgttttaa agtcctgagc aatttctcgc accagacgct ggaagggaag    120
tttgcgaatc agaagttcag tggacttctg ataacgtcta atttcacgga gcgccacagt    180
accaggacct gcccgggcgg ccgctcga                                       208

<210> SEQ ID NO 231
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 231
tcgagcggcc gcccgggcag gtcctggtac tgnggcgctc cgtgaaatta gacgttatca     60
gaagtccact gaacttctga ttcgcaaact tcccttccag cgtctggtgc gagaaattgc    120
tcaggacttt aaaacagatc tgcgcttcca gagcgcagct atcggtgctt tgcaggaggc    180
aagtgaggac ctcggccgcg accacgct                                       208

<210> SEQ ID NO 232
<211> LENGTH: 332
<212> TYPE: DNA
<213> ORGANISM: Homo sapien

<400> SEQUENCE: 232
tcgagcggcc gcccgggcag gtccacatcg gcagggtcgg agccctggcc gccatactcg     60
aactggaatc catcggtcat gctctcgccg aaccagacat gcctcttgtc cttggggttc    120
ttgctgatgt accagttctt ctgggccaca ctggctgag tggggtacac gcaggtctca    180
ccagtctcca tgttgcagaa gactttgatg gcatccaggt tgcagccttg gttggggtca    240
atccagtact ctccactctt ccagtcagag tggcacatct tgaggtcacg gcaggtgcgg    300
gcggggttct tgacctcggc cgcgaccacg ct                                  332

<210> SEQ ID NO 233
<211> LENGTH: 415
<212> TYPE: DNA
<213> ORGANISM: Homo sapien
<220> FEATURE:
<221> NAME/KEY: misc_feature
<222> LOCATION: (1)...(415)
<223> OTHER INFORMATION: n = A,T,C or G

<400> SEQUENCE: 233
gtgggnttga acccntttna nctccgcttg gtaccgagct cggatccact agtaacggcc     60
```

```
gccagtgtgc tggaattcgg cttagcgtgg tcgcggccga ggtcaagaac cccgcccgca    120
cctgccgtga cctcaagatg tgccactctg actggaagag tggagagtac tggattgacc    180
ccaaccaagg ctgcaacctg gatgccatca agtcttctg caacatggag actggtgaga    240
cctgcgtgta ccccactcag cccagtgtgg cccagaagaa ctggtacatc agcaagaacc    300
ccaaggacaa gaggcatgtc tggttcggcg agagcatgac cgatggattc cagttcgagt    360
atggcggcca gggctccgac cctgccgatg tggacctgcc cgggcggccg ctcga         415
```

<210> SEQ ID NO 234
<211> LENGTH: 776
<212> TYPE: DNA
<213> ORGANISM: Homo sapien
<220> FEATURE:
<221> NAME/KEY: misc_feature
<222> LOCATION: (1)...(776)
<223> OTHER INFORMATION: n = A,T,C or G

<400> SEQUENCE: 234

```
agcgtggtcg cggccgaggt ctgggatgct cctgctgtca cagtgagata ttacaggatc     60
acttacggag aaacaggagg aaatagccct gtccaggagt tcactgtgcc tgggagcaag    120
tctacagcta ccatcagcgg ccttaaacct ggagttgatt ataccatcac tgtgtatgct    180
gtcactggcc gtggagacag ccccgcaagc agcaagccaa tttccattaa ttaccgaaca    240
gaaattgaca aaccatccca gatgcaagtg accgatgttc aggacaacag cattagtgtc    300
aagtggctgc cttcaagttc ccctgttact ggttacagag taaccaccac tcccaaaaat    360
ggaccaggac caacaaaaac taaaactgca ggtccagatc aaacagaaat gactattgaa    420
ggcttgcagc ccacagtgga gtatgtggtt aagtgtctat gctcagaatc caagcggaga    480
gaagtcagcc tctggttcag actgnaagta accaacattg atcgcctaaa ggactggcat    540
tcactgatgn ggatgccgat tccatcaaaa ttgnttggga aaaccacag gggcaagttt    600 ncangtcnag gnggacctac tcgagccctg aggatggaat ccttgactnt tccttnncct    660
gatggggaaa aaaaccttn aaaacttgaa ggacctgccc gggcggccgt ncaaaaccca    720
attccacccc cttgggggcg ttctatgggn cccactcgga ccaaacttgg ggtaan        776
```

<210> SEQ ID NO 235
<211> LENGTH: 805
<212> TYPE: DNA
<213> ORGANISM: Homo sapien
<220> FEATURE:
<221> NAME/KEY: misc_feature
<222> LOCATION: (1)...(805)
<223> OTHER INFORMATION: n = A,T,C or G

<400> SEQUENCE: 235

```
tcgagcggcc gcccgggcag gtccttgcag ctctgcagtg tcttcttcac catcaggtgc     60
agggaatagc tcatggattc catcctcagg gctcgagtag gtcaccctgt acctggaaac    120
ttgcccctgt gggctttccc aagcaatttt gatggaatcg gcatccacat cagtgaatgc    180
cagtccttta gggcgatcaa tgttggttac tgcagtctga accagaggct gactctctcc    240
gcttggattc tgagcataga cactaaccac atactccact gtgggctgca agccttcaat    300
agtcatttct gtttgatctg gacctgcagt tttagttttt gttggtcctg gtccattttt    360
gggagtggtg gttactctgt aaccagtaac aggggaactt gaaggcagcc acttgacact    420
aatgctgttg tcctgaacat cggtcacttg catctgggat ggtttgtcaa tttctgttcg    480
gtaattaatg gaaattggct tgctgcttgc ggggcttgtc tccacggcca gtgacagcat    540
```

```
acacagtgat ggtataatca actccaggtt taagccgctg atggtagctg aaactttgct    600
ccaggcacaa gtgaactcct gacagggcta tttcctnctg ttctccgtaa gtgatcctgt    660
aatatctcac tgggacagca ggangcattc caaaacttcg ggcgngaccc cctaagccga    720
attntgcaat atncatcaca ctggcgggcg ctcgancatt cattaaaagg cccaatcncc    780
cctataggga gtntantaca attng                                          805

<210> SEQ ID NO 236
<211> LENGTH: 262
<212> TYPE: DNA
<213> ORGANISM: Homo sapien

<400> SEQUENCE: 236
tcgagcggcc gcccgggcag gtcacttttg gtttttggtc atgttcggtt ggtcaaagat     60
aaaaactaag tttgagagat gaatgcaaag gaaaaaaata ttttccaaag tccatgtgaa    120
attgtctccc attttttttgg cttttgaggg ggttcagttt gggttgcttg tctgtttccg    180
ggttgggggg aaagttggtt gggtgggagg gagccaggtt gggatggagg gagtttacag    240
gaagcagaca gggccaacgt cg                                             262

<210> SEQ ID NO 237
<211> LENGTH: 372
<212> TYPE: DNA
<213> ORGANISM: Homo sapien

<400> SEQUENCE: 237
agcgtggtcg cggccgaggt cctcaccaga ggtgccacct acaacatcat agtggaggca     60
ctgaaagacc agcagaggca taaggttcgg gaagaggttg ttaccgtggg caactctgtc    120
aacgaaggct tgaaccaacc tacgatgac tcgtgctttg accctacac agtttcccat    180 tatgccgttg gagatgagtg ggaacgaatg tctgaatcag gctttaaact gttgtgccag    240
tgcttaggct ttggaagtgg tcatttcaga tgtgattcat ctagatggtg ccatgacaat    300
ggtgtgaact acaagattgg agagaagtgg gaccgtcagg gagaaaatgg acctgcccgg    360
gcggccgctc ga                                                       372

<210> SEQ ID NO 238
<211> LENGTH: 372
<212> TYPE: DNA
<213> ORGANISM: Homo sapien

<400> SEQUENCE: 238
tcgagcggcc gcccgggcag gtccattttc tccctgacgg tcccacttct ctccaatctt     60
gtagttcaca ccattgtcat ggcaccatct agatgaatca catctgaaat gaccacttcc    120
aaagcctaag cactggcaca acagtttaaa gcctgattca gacattcgtt cccactcatc    180
tccaacggca taatgggaaa ctgtgtaggg gtcaaagcac gagtcatccg taggttggtt    240
caagccttcg ttgacagagt tgcccacggt aacaacctct tcccgaacct tatgcctctg    300
ctggtctttc agtgcctcca ctatgatgtt gtaggtggca cctctggtga ggacctcggc    360
cgcgaccacg ct                                                       372

<210> SEQ ID NO 239
<211> LENGTH: 720
<212> TYPE: DNA
<213> ORGANISM: Homo sapien
<220> FEATURE:
```

<221> NAME/KEY: misc_feature
<222> LOCATION: (1)...(720)
<223> OTHER INFORMATION: n = A,T,C or G

<400> SEQUENCE: 239

| | | | | | |
|---|---|---|---|---|---|
| tcgagcggcc | gcccgggcag | gtccaccata | agtcctgata | caaccacgga | tgagctgtca | 60 |
| ggagcaaggt | tgatttcttt | cattggtccg | gtcttctcct | tggggtcac | ccgcactcga | 120 |
| tatccagtga | gctgaacatt | gggtggtgtc | cactgggcgc | tcaggcttgt | gggtgtgacc | 180 |
| tgagtgaact | tcaggtcagt | tggtgcagga | atagtggtta | ctgcagtctg | aaccagaggc | 240 |
| tgactctctc | cgcttggatt | ctgagcatag | acactaacca | catactccac | tgtgggctgc | 300 |
| aagccttcaa | tagtcatttc | tgtttgatct | ggacctgcag | ttttagtttt | tgttggtcct | 360 |
| ggtccatttt | tgggagtggt | ggttactctg | taaccagtaa | caggggaact | tgaaggcagc | 420 |
| cacttgacac | taatgctgtt | gtcctgaaca | tcggtcactt | gcatctggga | tggtttgnca | 480 |
| atttctgttc | ggtaattaat | ggaaattggc | ttgctgcttg | cggggctgtc | tccacggcca | 540 |
| gtgacagcat | acacagngat | ggnatnatca | actccaagtt | taaggccctg | atggtaactt | 600 |
| taaacttgct | cccagccagn | gaacttccgg | acagggtatt | tcttctggtt | ttccgaaagn | 660 |
| gancctggaa | tnntctcctt | ggancagaag | gancntccaa | aacttgggcc | ggaaccccttt | 720 |

<210> SEQ ID NO 240
<211> LENGTH: 691
<212> TYPE: DNA
<213> ORGANISM: Homo sapien
<220> FEATURE:
<221> NAME/KEY: misc_feature
<222> LOCATION: (1)...(691)
<223> OTHER INFORMATION: n = A,T,C or G

<400> SEQUENCE: 240

| | | | | | |
|---|---|---|---|---|---|
| agcgtggtcg | cggccgaggt | cctgtcagag | tggcactggt | agaagttcca | ggaaccctga | 60 |
| actgtaaggg | ttcttcatca | gtgccaacag | gatgacatga | aatgatgtac | tcagaagtgt | 120 |
| cctggaatgg | ggcccatgag | atggttgtct | gagagagagc | ttcttgtcct | acattcggcg | 180 |
| ggtatggtct | tggcctatgc | cttatggggg | tggccgttgt | gggcggtgtg | gtccgcctaa | 240 |
| aaccatgttc | ctcaaagatc | atttgttgcc | caacactggg | ttgctgacca | gaagtgccag | 300 |
| gaagctgaat | accatttcca | gtgtcatacc | cagggtgggt | gacgaaaggg | gtcttttgaa | 360 |
| ctgtggaagg | aacatccaag | atctctggtc | catgaagatt | ggggtgtgga | agggttacca | 420 |
| gttggggaag | ctcgtctgtc | tttttccttc | caatcagggg | ctcgctcttc | tgattattct | 480 |
| tcagggcaat | gacataaatt | gtatattcgg | ttcccggttc | caggccagta | atagtagcct | 540 |
| cttgtgacac | caggcggggc | ccanggacca | cttctctggg | angagaccca | gcttctcata | 600 |
| cttgatgatg | taacccggta | atcctgcacg | tggcggctgn | catgatacca | ncaaggaatt | 660 |
| gggtgnggng | gacctgcccg | gcggccctcn | a | | | 691 |

<210> SEQ ID NO 241
<211> LENGTH: 808
<212> TYPE: DNA
<213> ORGANISM: Homo sapien
<220> FEATURE:
<221> NAME/KEY: misc_feature
<222> LOCATION: (1)...(808)
<223> OTHER INFORMATION: n = A,T,C or G

<400> SEQUENCE: 241

| | | | | | |
|---|---|---|---|---|---|
| agcgtggtcg | cggccgaggt | ctgggatgct | cctgctgtca | cagtgagata | ttacaggatc | 60 |

```
acttacggag aaacaggagg aaatagccct gtccaggagt tcactgtgcc tgggagcaag        120
tctacagcta ccatcagcgg ccttaaacct ggagttgatt ataccatcac tgtgtatgct        180
gtcactggcc gtggagacag ccccgcaagc agcaagccaa tttccattaa ttaccgaaca        240
gaaattgaca aaccatccca gatgcaagtg accgatgttc aggacaacag cattagtgtc        300
aagtggctgc cttcaagttc ccctgttact ggttacagag taaccaccac tcccaaaaat        360
ggaccaggac caacaaaaac taaaactgca ggtccagatc aaacagaaat gactattgaa        420
ggcttgcagc ccacagtgga gtatgtggtt agtgtctatg ctcagaatcc aagcggagag        480
agtcagcctc tggttcagac tgcagtaacc actattcctg caccaactga cctgaagttc        540
actcaggtca cacccacaag cctgagccgc agtggacac  cacccaatgt tcactcactg        600
gatatcgagt gcgggtgacc cccaaggaga agacccggac ccatgaaaga aatcaacctt        660
gctcctgaca gctcatccgn gggtgtatca ggacttatgg gggactgccc cggcnggccg        720
ntcgaaancg aattntgaaa tttccttcnc actgggnggc gnttcgagct tncttntana        780
nggcccaatt cncctntagn gggtcgtn                                          808

<210> SEQ ID NO 242
<211> LENGTH: 26
<212> TYPE: DNA
<213> ORGANISM: Homo sapien
<220> FEATURE:
<221> NAME/KEY: misc_feature
<222> LOCATION: (1)...(26)
<223> OTHER INFORMATION: n = A,T,C or G

<400> SEQUENCE: 242
agcgtggtcg cggccgaggt cnagga                                             26

<210> SEQ ID NO 243
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 243
tcgagcggcc gcccgggcag gtccaccaca cccaattcct tgctggtatc atggcagccg         60
ccacgtgcca ggattaccgg ctacatcatc aagtatgaga agcctgggtc tcctcccaga        120
gaagtggtcc ctcggccccg ccctggtgtc acagaggcta ctattactgg cctggaaccg        180
ggaaccgaat atacaattta tgtcattgcc ctgaagaata atcagaagag cgagcccctg        240
attggaagga aaagacaga cgagcttccc caactggtaa cccttccaca ccccaatctt         300
catggaccag agatcttgga tgttccttcc acagttcaaa agacccccttt cgtcacccac        360 cctgggtatg acactggaaa tggtattcag cttcctggca cttctggtca gcaacccagt        420
gttgggcaac aaatgatctt tgaggaacat ggttttaggc ggaccacacc gcccacaacg        480
ggcaccccca taaggnatag gccaagacca taccccgccg aatgtaggac aagaagctct        540
ntctcaacaa ccatctcatg ggccccattc aggacactt ctgagtacat catttcatgt        600
catcctggtg ggcacttgat gaanaaccct tacagttcag ggttcctgga acttctacca        660
gngccacttc tgacagganc ttgggcgnga ccaccct                                 697

<210> SEQ ID NO 244
```

```
<211> LENGTH: 373
<212> TYPE: DNA
<213> ORGANISM: Homo sapien

<400> SEQUENCE: 244
agcgtggtcg cggccgaggt ccatttctc cctgacggtc ccacttctct ccaatcttgt      60
agttcacacc attgtcatgg caccatctag atgaatcaca tctgaaatga ccacttccaa    120
agcctaagca ctggcacaac agtttaaagc ctgattcaga cattcgttcc cactcatctc    180
caacggcata atgggaaact gtgtaggggt caaagcacga gtcatccgta ggttggttca    240
agccttcgtt gacagagttg cccacggtaa caacctcttc ccgaaccttta tgcctctgct    300 ggtctttcag tgcctccact atgatgttgt aggtggcacc tctggtgagg acctgcccgg    360
gcggcccgct cga                                                        373

<210> SEQ ID NO 245
<211> LENGTH: 307
<212> TYPE: DNA
<213> ORGANISM: Homo sapien

<400> SEQUENCE: 245
agcgtggtcg cggccgaggt gtgccccaga ccaggaattc ggcttcgacg ttggccctgt      60
ctgcttcctg taaactccct ccatcccaac ctggctccct cccacccaac caactttccc    120
cccaacccgg aaacagacaa gcaacccaaa ctgaaccccc tcaaaagcca aaaaaatggg    180
agacaatttc acatggactt tggaaaatat ttttttcctt tgcattcatc tctcaaactt    240
agtttttatc tttgaccaac cgaacatgac caaaaaccaa aagtgacctg cccgggcggc    300
cgctcga                                                               307

<210> SEQ ID NO 246
<211> LENGTH: 372
<212> TYPE: DNA
<213> ORGANISM: Homo sapien

<400> SEQUENCE: 246
tcgagcggcc gcccgggcag gtcctcacca gaggtgccac ctacaacatc atagtggagg      60
cactgaaaga ccagcagagg cataaggttc gggaagaggt tgttaccgtg ggcaactctg    120
tcaacgaagg cttgaaccaa cctacggatg actcgtgctt tgaccctac acagtttccc    180 attatgccgt tggagatgag tgggaacgaa tgtctgaatc aggctttaaa ctgttgtgcc    240
agtgcttagg cttttggaagt ggtcatttca gatgtgattc atctagatgg tgccatgaca    300
atggtgtgaa ctacaagatt ggagagaagt gggaccgtca gggagaaaat ggacctcggc    360
cgcgaccacg ct                                                         372

<210> SEQ ID NO 247
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 247
tcgagcggcc gcccgggcag gtaccggggt ggtcagcgag gagccattca cactgaactt      60
caccatcaac aacctgcggt atgaggagaa catgcagcac cctggctcca ggaagttcaa    120
caccacggag agggtccttc agggcctgct caggtccctg ttcaagagca ccagtgttgg    180
```

```
ccctctgtac tctggctgca gactgacttt gctcagacct gagaaacatg gggcagccac    240
tggagtggac gccatctgca ccctccgcct tgatcccact ggtnctggac tggacanana    300
gcggctatac ttgggagctg anccnaacct ttggcggnga cnccnctt                 348
```

<210> SEQ ID NO 248
<211> LENGTH: 304
<212> TYPE: DNA
<213> ORGANISM: Homo sapien
<220> FEATURE:
<221> NAME/KEY: misc_feature
<222> LOCATION: (1)...(304)
<223> OTHER INFORMATION: n = A,T,C or G

<400> SEQUENCE: 248

```
gaggactggc tcagctccca gtatagccgc tctctgtcca gtccaggacc agtgggatca    60
aggcggaggg tgcagatggc gtccactcca gtggctgccc catgtttctc aagtctgagc   120
aaagncagtc tgcagccaga gtacagaggg ccaacactgg tgctcttgaa cagggacctg   180
agcaggccct gaaggaccct ctccgtggtg ttgaacttcc tggagccagg gtgctgcatg   240
ttctcctcat accgcaggtt gttgatggtg aagttcagtg tgaatggctc ctcgctgacc   300
accc                                                                304
```

<210> SEQ ID NO 249
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 249

```
agcgtggtcg cggccgaggt ccaccacacc caattccttg ctggtatcat ggcagccgcc    60
acgtgccagg attaccggct acatcatcaa gtatgagaag cctgggtctc ctcccagaga   120
agtggtccct cggccccgcc ctggtgtcac agaggctact attactggcc tggaaccggg   180
aaccgaatat acaatttatg tcattgccct gaagaataat cagaagagcg agccctgat    240 tggaaggaaa aagacagacg agcttcccca actggtaacc cttccacacc ccaatcttca   300
tggaccanan ancttggatn gtcctttcac nggttnaaaa aacccttttc gcccccccac   360
cttgggattt aaccttggga aangggggatt tnaccnttcc                        400
```

<210> SEQ ID NO 250
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 250

```
tcgagcggcc gcccgggcag gtcctgtcag agtggcactg gtagaagttc caggaaccct    60
gaactgtaag ggttcttcat cagtgccaac aggatgacat gaaatgatgt actcagaagt   120
gtcctggaat ggggcccatg agatggttgt ctgagagaga gcttcttgtc ctacattcgg   180
cgggtatggt cttggcctat gccttatggg ggtggccgtt gtgggcggtg tggtccgcct   240
aaaaccatgt tcctcaaaga tcatttgttg cccaacactg ggttgctgac cagaagtgcc   300
```

| aggaagctga ataccatttc cagtgtcata cccagggngg gtgaccaaag ggggtcnttt | 360 |
| ngacctggng aaaggaacca tccaaaanct ctgncccatg | 400 |

<210> SEQ ID NO 251
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 251

| agcgtggncg cggccgaggt ctgaggatgt aaactcttcc caggggaagg ctgaagtgct | 60 |
| gaccatggtg ctactgggtc cttctgagtc agatatgtga ctgatgngaa ctgaagtagg | 120 |
| tactgtagat ggtgaagtct gggtgtccct aaatgctgca tctccagagc cttccatcat | 180 |
| taccgtttct tcttttgcta tgggatgaga cactgttgag tattctctaa agtcaccact | 240 |
| gaaatcttcc tccaaaggaa aacctgtgga aaagccccctt atttctgccc cataatttgg | 300 |
| ttctcctaat cnctctgaaa tcactatttc cctggaangt ttgggaaaaa nngggcnacc | 360 |
| tgncantgga aantggatan aaagatccca ccattttacc caacnagcag aaagtgggaa | 420 |
| nggtaccgaa aagctccaag taanaaaaag gagggaagta aaggtcaagt gggcaccagt | 480 |
| ttcaaacaaa actttcccca aactatanaa ccca | 514 |

<210> SEQ ID NO 252
<211> LENGTH: 501
<212> TYPE: DNA
<213> ORGANISM: Homo sapien
<220> FEATURE:
<221> NAME/KEY: misc_feature
<222> LOCATION: (1)...(501)
<223> OTHER INFORMATION: n = A,T,C or G

<400> SEQUENCE: 252

| aagcggccgc ccgggcaggn ncagnagtgc cttcgggact gggntcaccc ccaggtctgc | 60 |
| ggcagttgtc acagcgccag ccccgctggc ctccaaagca tgtgcaggag caaatggcac | 120 |
| cgagatattc cttctgccac tgttctccta cgtggtatgt cttcccatca tcgtaacacg | 180 |
| ttgcctcatg agggtcacac ttgaattctc cttttccgtt cccaagacat gtgcagctca | 240 |
| tttggctggc tctatagttt ggggaaagtt tgttgaaact gtgccactga cctttacttc | 300 |
| ctccttctct actggagctt tccgtacctt ccacttctgc tgntggnaaa aagggnggaa | 360 |
| cntcttatca atttcattgg acagtanccc nctttctncc caaaacatnc aagggaaaat | 420 |
| attgattncn agagcggatt aaggaacaac ccnaattatg ggggccagaa ataaagggg | 480 |
| cttttccaca ggtnttttcc t | 501 |

<210> SEQ ID NO 253
<211> LENGTH: 226
<212> TYPE: DNA
<213> ORGANISM: Homo sapien

<400> SEQUENCE: 253

| tcgagcggcc gcccgggcag gtctgcaggc tattgtaagt gttctgagca catatgagat | 60 |
| aacctgggcc aagctatgat gttcgatacg ttaggtgtat taaatgcact tttgactgcc | 120 |
| atctcagtgg atgacagcct tctcactgac agcagagatc ttcctcactg tgccagtggg | 180 |
| caggagaaag agcatgctgc gactggacct cggccgcgac cacgct | 226 |

<210> SEQ ID NO 254
<211> LENGTH: 226
<212> TYPE: DNA
<213> ORGANISM: Homo sapien

<400> SEQUENCE: 254

```
agcgtggtcg cggccgaggt ccagtcgcag catgctcttt ctcctgccca ctggcacagt      60
gaggaagatc tctgctgtca gtgagaaggc tgtcatccac tgagatggca gtcaaaagtg     120
catttaatac acctaacgta tcgaacatca tagcttggcc caggttatct catatgtgct     180
cagaacactt acaatagcct gcagacctgc ccgggcggcc gctcga                    226
```

<210> SEQ ID NO 255
<211> LENGTH: 427
<212> TYPE: DNA
<213> ORGANISM: Homo sapien
<220> FEATURE:
<221> NAME/KEY: misc_feature
<222> LOCATION: (1)...(427)
<223> OTHER INFORMATION: n = A,T,C or G

<400> SEQUENCE: 255

```
cgagcggccg cccgggcagg tccagactcc aatccagaga accaccaagc cagatgtcag      60
aagctacacc atcacaggtt tacaaccagg cactgactac aagatctacc tgtacacctt     120
gaatgacaat gctcggagct cccctgtggt catcgacgcc tccactgcca ttgatgcacc     180
atccaacctg cgtttcctgg ccaccacacc caattccttg ctggtatcat ggcagccgcc     240
acgtgccagg attaccggct acatcatcaa gtatgagaag cctgggtctc ctcccagaga     300
agtggtccct cggccccgcc ctggtgncac agaagctact attactggcc tggaaccggg     360
aaccgaatat acaatttatg tcattgccct gaagaataat canaagagcg agccctgat     420 tggaagg                                                               427
```

<210> SEQ ID NO 256
<211> LENGTH: 535
<212> TYPE: DNA
<213> ORGANISM: Homo sapien
<220> FEATURE:
<221> NAME/KEY: misc_feature
<222> LOCATION: (1)...(535)
<223> OTHER INFORMATION: n = A,T,C or G

<400> SEQUENCE: 256

```
agcgtggtcg cggccgaggt cctgtcagag tggcactggt agaagttcca ggaaccctga      60
actgtaaggg ttcttcatca gtgccaacag gatgacatga aatgatgtac tcagaagtgt     120
cctggaatgg ggcccatgag atggttgtct gagagagagc ttcttgtcct gtcttttcc     180 ttccaatcag gggctcgctc ttctgattat tcttcagggc aatgacataa attgtatatt     240
cggttcccgg ttccaggcca gtaatagtag cctctgtgac accagggcgg ggccgaggga     300
ccacttctct gggaggagac ccaggcttct catacttgat gatgtanccg gtaatcctgg     360
caccgtggcg gctgccatga taccagcaag gaattgggtg tggtggccaa gaaacgcagg     420
ttggatggtg catcaatggc agtggaggcg tcgatnacca caggggagct ccgancattg     480
tcattcaagg tggacaggta gaatcttgta atcaggtgcc tggtttgtaa acctg          535
```

<210> SEQ ID NO 257
<211> LENGTH: 544
<212> TYPE: DNA

<213> ORGANISM: Homo sapien
<220> FEATURE:
<221> NAME/KEY: misc_feature
<222> LOCATION: (1)...(544)
<223> OTHER INFORMATION: n = A,T,C or G

<400> SEQUENCE: 257

| | | | | | |
|---|---|---|---|---|---|
| tcgagcggcc | gcccgggcag | gtttcgtgac | cgtgacctcg | aggtggacac | cacccctcaag | 60 |
| agcctgagcc | agcagatcga | gaacatccgg | agcccagagg | gcagccgcaa | gaaccccgcc | 120 |
| cgcacctgcc | gtgacctcaa | gatgtgccac | tctgactgga | gagtggaga | gtactggatt | 180 |
| gaccccaacc | aaggctgcaa | cctggatgcc | atcaaagtct | tctgcaacat | ggagactggt | 240 |
| gagacctgcg | tgtaccccac | tcagcccagt | gtggcccaga | gaactggta | catcagcaag | 300 |
| aaccccaagg | acaagaagca | tgtctggttc | ggcgaaagca | tgaccgatgg | attccagttc | 360 |
| gagtatggcg | ccagggctc | cgaccctgcc | gatgtggacc | tcggccgcga | ccacgctaag | 420 |
| cccgaattcc | agcacactgg | cggccgttac | tagtgggatc | cgagcttcgg | taccaagctt | 480 |
| ggcgtaatca | tgggncatag | ctgtttcctg | ngtgaaaatg | gtattccgct | tcacaatttc | 540 |
| ccac | | | | | 544 |

<210> SEQ ID NO 258
<211> LENGTH: 418
<212> TYPE: DNA
<213> ORGANISM: Homo sapien

<400> SEQUENCE: 258

| | | | | | |
|---|---|---|---|---|---|
| agcgtggtcg | cggccgaggt | ccacatcggc | agggtcggag | ccctggccgc | catactcgaa | 60 |
| ctggaatcca | tcggtcatgc | tctcgccgaa | ccagacatgc | tcttgtcct | tgggggttctt | 120 |
| gctgatgtac | cagttcttct | gggccacact | gggctgagtg | gggtacacgc | aggtctcacc | 180 |
| agtctccatg | ttgcagaaga | ctttgatggc | atccaggttg | cagccttggt | tggggtcaat | 240 |
| ccagtactct | ccactcttcc | agtcagagtg | gcacatcttg | aggtcacggc | aggtgcgggc | 300 |
| ggggttcttg | cggctgccct | ctgggctccg | gatgttctcg | atctgctggc | tcaagctctt | 360 |
| gaagggtggt | gtccacctcg | aggtcacggt | cacgaaacct | gcccgggcgg | ccgctcga | 418 |

<210> SEQ ID NO 259
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 259

| | | | | | |
|---|---|---|---|---|---|
| agcgtggtcg | cggccgaggt | caagaaccc | gcccgcacct | gccgtgacct | caagatgtgc | 60 |
| cactctgact | ggaagagtgg | agagtactgg | attgacccca | accaaggctg | caacctggat | 120 |
| gccatcaaag | tcttctgcaa | catggagact | ggtgagacct | gcgtgtaccc | cactcagccc | 180 |
| agtgtggccc | agaagaactg | gtacatcagc | aagaacccca | aggacaagag | gcatgtctgg | 240 |
| ttcggcgaga | gcatgaccga | tggattccag | ttcgagtatg | gcggccaggg | ctccgacccc | 300 |
| gccgatgtgg | acctgcccgn | gccggnccgc | tcgaaaagcc | cnaatttcca | gncacacttg | 360 |
| gccggccgtt | actactg | | | | 377 |

<210> SEQ ID NO 260
<211> LENGTH: 332

```
<212> TYPE: DNA
<213> ORGANISM: Homo sapien

<400> SEQUENCE: 260
tcgagcggcc gcccgggcag gtccacatcg gcagggtcgg agccctggcc gccatactcg      60
aactggaatc catcggtcat gctctcgccg aaccagacat gcctcttgtc cttggggttc     120
ttgctgatgt accagttctt ctgggccaca ctgggctgag tggggtacac gcaggtctca     180
ccagtctcca tgttgcagaa gactttgatg gcatccaggt tgcagccttg gttggggtca     240
atccagtact ctccactctt ccagtcagag tggcacatct tgaggtcacg gcaggtgcgg     300
gcggggttct tgacctcggc cgcgaccacg ct                                   332

<210> SEQ ID NO 261
<211> LENGTH: 94
<212> TYPE: DNA
<213> ORGANISM: Homo sapien

<400> SEQUENCE: 261
cgagcggccg cccgggcagg tcccccccct tttttttttt tttttttttt tttttttttt      60
tttttttttt tttttttttt tttttttttt tttt                                  94

<210> SEQ ID NO 262
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 262
agcgtggtcg cggccgaggt ctggcattcc ttcgacttct ctccagccga gcttcccaga      60
acatcacata tcactgcaaa aatagcattg catacatgga tcaggccagt ggaaatgtaa     120
agaaggccct gaagctgatg gggtcaaatg aaggtgaatt caaggctgaa ggaaatagca     180
aattcaccta cacagttctg gaggatggtt gcacgaaaca cactggggaa tggagcaaaa     240
cagtctttga atatcgaaca cgcaaggctg tgagactacc tattgtagat attgcaccct     300
atgacattgg tggtcctgat caagaatttg gtgtggacgt tggccctgtt tgcttttat      360 aaaccaaact ctatctgaaa tcccaacaaa aaaatttaa ctccatatgt gntcctcttg      420
ttctaatctt ggcaaccagt gcaagtgacc gacaaaattc cagttattta tttccaaaat    480
gtttggaaac agtataattt gacaaagaaa aaggatact tctctttttt tggctggtcc      540
accaaataca attcaaaagg cttttggtt ttattttttt anccaattcc aatttcaaaa     600
tgtctcaatg gngcttataa taaaataaac tttcacccctt nttttntgat              650

<210> SEQ ID NO 263
<211> LENGTH: 573
<212> TYPE: DNA
<213> ORGANISM: Homo sapien
<220> FEATURE:
<221> NAME/KEY: misc_feature
<222> LOCATION: (1)...(573)
<223> OTHER INFORMATION: n = A,T,C or G

<400> SEQUENCE: 263
agcgtggtcg cggccgaggt ctgggatgct cctgctgtca cagtgagata ttacaggatc      60
acttacggag aaacaggagg aaatagccct gtccaggagt tcactgtgcc tgggagcaag     120
```

-continued

| | |
|---|---|
| tctacagcta ccatcagcgg ccttaaacct ggagttgatt ataccatcac tgtgtatgct | 180 |
| gtcactggcc gtggagacag ccccgcaagc agcaagccaa tttccattaa ttaccgaaca | 240 |
| gaaattgaca aaccatccca gatgcaagtg accgatgttc aggacaacag cattagtgtc | 300 |
| aagtggctgc cttcaagttc ccctgttact ggttacagaa gtaaccacca ctcccaaaaa | 360 |
| tggaccagga ccaacaaaaa ctaaaactgc aggtccagat caaacagaaa atggactatt | 420 |
| gaaggcttgc agcccacagt ggaagtatgt ggntaggngt ctatgctcag aatcccaagc | 480 |
| cggagaaagt cagccttctg gtttagactg cagtaaccaa cattgatcgc cctaaaggac | 540 |
| tggncattca cttggatggt ggatgtccaa ttc | 573 |

<210> SEQ ID NO 264
<211> LENGTH: 550
<212> TYPE: DNA
<213> ORGANISM: Homo sapien
<220> FEATURE:
<221> NAME/KEY: misc_feature
<222> LOCATION: (1)...(550)
<223> OTHER INFORMATION: n = A,T,C or G

<400> SEQUENCE: 264

| | |
|---|---|
| tcgagcggcc gcccgggcag gtccttgcag ctctgcagng tcttcttcac catcaggtgc | 60 |
| agggaatagc tcatggattc catcctcagg gctcgagtag gtcaccctgt acctggaaac | 120 |
| ttgcccctgt gggctttccc aagcaatttt gatggaatcg acatccacat cagngaatgc | 180 |
| cagtccttta gggcgatcaa tgttggttac tgcagtctga accagaggct gactctctcc | 240 |
| gcttggattc tgagcataga cactaaccac atactccact gtgggctgca agccttcaat | 300 |
| agtcatttct gtttgatctg gacctgcagt tttaagtttt tggtggtcct gncccatttt | 360 |
| tgggaagtgg ggggttactc tgtaaccagt aacagggaa cttgaaggca gccacttgac | 420 |
| actaatgctg ttgtcctgaa catcggtcac ttgcatctgg gatggtttt gacaatttct | 480 |
| ggttcggcaa attaatggaa attggcttgc tgcttggcgg ggctgnctcc acgggccagt | 540 |
| gacagcatac | 550 |

<210> SEQ ID NO 265
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 265

| | |
|---|---|
| tcgagcggcc gcccgggcag gtccttgcag ctctgcagtg tcttcttcac catcaggtgc | 60 |
| agggaatagc tcatggattc catcctcagg gctcgagtag gtcaccctgt acctggaaac | 120 |
| ttgcccctgt gggctttccc aagcaatttt gatggaatcg acatccacat cagtgaatgc | 180 |
| cagtccttta gggcgatcaa tgttggttac tgcagtctga accagaggct gactctctcc | 240 |
| gcttggattc tgagcataga cactaaccac atactccact gtgggctgca agccttcaat | 300 |
| agtcatttct gtttgatctg gacctgcagt tttaagtttt tgttggncct gnnccatttt | 360 |
| tggggaaggg gtggttactc ttgtaaccag taacagggga acttgaagca gccacttgac | 420 |
| actaatgctg gtggcctgaa catcggtcac ttgcatctgg gatggtttgg tcaatttctg | 480 |
| ttcggtaatt aatgggaaat tggcttactg gcttgcgggg gctgtctcca cggncagtga | 540 |
| caagcataca caggngatgg gtataatcaa ctccaggttt aaggccnctg atggta | 596 |

<210> SEQ ID NO 266
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 266

| | | | | | |
|---|---|---|---|---|---|
| agcgtggtcg | cggccgaggt | ctgggatgct | cctgctgtca | cagtgagata | ttacaggatc | 60 |
| acttacggag | aaacaggagg | aaatagccct | gtccaggagt | tcactgtgcc | tgggagcaag | 120 |
| tctacagcta | ccatcagcgg | ccttaaacct | ggagttgatt | ataccatcac | tgtgtatgct | 180 |
| gtcactggcc | gtggagacag | ccccgcaagc | agtaagccaa | tttccattaa | ttaccgaaca | 240 |
| gaaattgaca | aaccatccca | gatgcaagtg | accgatgttc | aggacaacag | cattagtgtc | 300 |
| aagtggctgc | cttcaagttc | cctgttact | ggttacagag | taaccaccac | tcccaaaaat | 360 |
| gggaccagga | ccaacaaaaa | actaaaactg | canggtccag | atcaaacaga | aatgactatt | 420 |
| gaaggcttgc | agcccacagt | ggagtatgtg | ggttagtgtc | tatgctcaga | atnccaagcg | 480 |
| gagagagtca | gcctctggtt | cagact | | | | 506 |

<210> SEQ ID NO 267
<211> LENGTH: 548
<212> TYPE: DNA
<213> ORGANISM: Homo sapien
<220> FEATURE:
<221> NAME/KEY: misc_feature
<222> LOCATION: (1)...(548)
<223> OTHER INFORMATION: n = A,T,C or G

<400> SEQUENCE: 267

| | | | | | |
|---|---|---|---|---|---|
| tcgagcggcc | gcccgggcag | gtcagcgctc | tcaggacgtc | accaccatgg | cctgggctct | 60 |
| gctcctcctc | accctcctca | ctcagggcac | agggtcctgg | gcccagtctg | ccctgactca | 120 |
| gcctccctcc | gcgtccgggt | ctcctggaca | gtcagtcacc | atctcctgca | ctggaaccag | 180 |
| cagtgacgtt | ggtgcttatg | aatttgtctc | ctggtaccaa | caacacccag | gcaaggcccc | 240 |
| caaactcatg | atttctgagg | tcactaagcg | gccctcaggg | gtccctgatc | gcttctctgg | 300 |
| ctccaagtct | ggcaacacgg | cctccctgac | cgtctctggg | ctccangctg | aggatgangc | 360 |
| tgattattac | tggaagctca | tatgcaggca | acaacaattg | ggtgttcggc | ggaagggacc | 420 |
| aagctgaccg | tnctaaggtc | aagcccaagg | cttgccccc | tcggtcactc | tgttcccacc | 480 |
| ctcctctgaa | gaagctttca | agccaacaan | gncacactgg | gtgtgtctca | taagtggact | 540 |
| ttctaccc | | | | | | 548 |

<210> SEQ ID NO 268
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 268

| | | | | | |
|---|---|---|---|---|---|
| agcgtggtcg | cggccgaggt | ctgtagcttc | tgtgggactt | ccactgctca | ggcgtcaggc | 60 |
| tcaggtagct | gctggccgcg | tacttgttgt | tgctttgntt | ggagggtgtg | gtggtctcca | 120 |

```
ctcccgcctt gacggggctg ctatctgcct tccaggccac tgtcacggct cccgggtaga    180
agtcacttat gagacacacc agtgtggcct tgttggcttg aagctcctca gaggagggtg    240
ggaacagagt gaccgagggg gcagccttgg gctgacctag gacggtcagc ttggtccctc    300
cgccgaacac ccaattgttg ttgcctgcat atgagctgca gtaataatca gcctcatcct    360
cagcctggag cccagagacn gtcaaggag gcccgtgttt gccaagactt ggaagccaga    420
naagcgatca gggacccctg agggccgctt tacngacctc aaaaaatcat gaatttgggg    480
ggcctttgcc tgggngttgg ttggtnacca gnaaaacaaa atttcataaa gcaccaacgt    540
cactgctggt ttccagtgca ngaanatggt gaactgaant gtcc                    584
```

<210> SEQ ID NO 269
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 269

```
agcgtggtcg cggccgaggt ccagcatcag gagccccgcc ttgccggctc tggtcatcgc     60
cttctttttt gtggcctgaa acgatgtcat caattcgcag tagcagaact gccgtctcca    120
ctgctgtctt ataagtctgc agcttcacag ccaatggctc ccatatgccc agttccttca    180
tgtccaccaa agtaccgtc tcaccattta caccccaggt ctcacagttc tcctgggtgt    240
gcttggcccg aagggaggta agtanacgga tggtgctggt cccacagttc tggatcaggg    300
tacgaggaat gacctctagg gcctgggcna caagccctgt atggacctgc ccgggcgggc    360
ccgctcga                                                            368
```

<210> SEQ ID NO 270
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 270

```
tcgagcggcc gcccgggcag gtccatacag ggctgttgcc caggccctag aggncattcc     60
ttgtaccctg atccagaact gtgggaccag caccatccgt ctacttacct cccttcgggc    120
caagcacacc caggagaact gtgagacctg gggtgtaaat ggngagacgg gtactttggt    180
ggacatgaag gaactgggca tatgggagcc attggctgng aagctgcana cttataagac    240
agcagtggag acggcagttc tgctactgcg aattgatgac atcgtttcag gccacaaaaa    300
gaaaggcgat gaccanagcc ggcaaggcgg ggcttcctga tgctggacct cggccgccga    360
ccacgctt                                                            368
```

<210> SEQ ID NO 271
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 271

```
agcgtggtcg cggccgaggt ccactagagg tctgtgtgcc attgcccagg cagagtctct    60
gcgttacaaa ctcctaggag ggcttgctgt gcggagggcc tgctatggtg tgctgcggtt   120
catcatggag agtggggcca aaggctgcga ggttgtggtg tctgggaaac tccgaggaca   180
gagggctaaa tccatgaagt ttgtggatgg cctgatgatc cacagcggag accctgttaa   240
ctactacgtt gacactgctg tgcgccacgt gttgctcana caggtgtgc tgggcatcaa    300
ggtgaagatc atgctgccct gggacccanc tggcaaaaat ggcccttaaa aacccttgc    360
cntgaccacg tgaaccattt gtgngaaccc aagatgaan atacttgccc accaccccc    420
attc                                                                424
```

<210> SEQ ID NO 272
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 272

```
tcgagcggcc gcccgggcag gtctgccaag gagaccctgt tatgctgtgg ggactggctg    60
gggcatggca ggcggctctg gcttcccacc cttctgttct gagatggggg tggtgggcag   120
tatctcatct ttgggttcca caatgctcac gtggtcaggc aggggcttct tagggccaat   180
cttaccagtt gggtcccagg gcagcatgat cttcaccttg atgcccagca caccctgtct   240
gagcaacacg tggcgcacag cagtgtcaac gtagtagtta acagggtctc cgctgtggat   300
catcaggcca tccacaaact tcatggattt agccctctgt cctcggagtt tcccaaaaca   360
ccacaacctc gccagccttt gggccccact tcttcatgaa tgaaaccgca gcacaccatt   420
ancaaggccc ttccgcacag gnaagccctt cctaaggagt tttgtaaacg caaaaaactc   480
ttgcctgggg caaatgggca cacagacctn tantnggacc ttggnccgcg aaccaccgct   540
t                                                                   541
```

<210> SEQ ID NO 273
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 273

```
agcgtggtcg cggccgaggt ctggccctcc tggcaaggct ggtgaagatg gtcaccctgg    60
aaaacccgga cgacctggtg agagaggagt tgttggacca caggtgctc gtggtttccc   120
tggaactcct ggacttcctg gcttcaaagg cattagggga cacaatggtc tggatggatt   180
gaagggacag cccggtgctc ctggtgtgaa gggtgaacct ggngccctg gtgaaaatgg   240
aactccaggt caaacaggag cccgngggct tcctggngag agaggacgtg ttggtgcccc   300
tggcccanac ctgcccggc ggccgctcna aagccgaaa tccagnacac tggcggccgn    360
tactantgga atccgaactt cggtaccaaa gcttggccgt aatcatggcc atagcttgtt   420
ccctggggng gaaattggta ttccgctncc aattccacac aacataccga acccggaaag   480
cattaaagtg taaaagccct gggggggcct aaatgangtg agcntaactc ncatttaatt   540
```

```
ggcgttgcgc ttcactgccc cgcttttcca gtccgggna                                    579

<210> SEQ ID NO 274
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 274
tcgagcggcc gcccgggcag gtctgggcca ggggcaccaa cacgtcctct ctcaccagga             60
agcccacggg ctcctgtttg acctggagtt ccattttcac caggggcacc aggttcaccc           120
ttcacaccag gagcaccggg ctgtcccttc aatccatcca gaccattgtg nccctaatg            180 cctttgaagc caggaagtcc aggagttcca gggaaaccac gagcacctg tggtccaaca            240 actcctctct caccaggtcg tccgggtttt ccaggtgac catcttcacc agccttgcca            300
ggagggccag acctcggccg cgaccacgct                                             330

<210> SEQ ID NO 275
<211> LENGTH: 97
<212> TYPE: DNA
<213> ORGANISM: Homo sapien
<220> FEATURE:
<221> NAME/KEY: misc_feature
<222> LOCATION: (1)...(97)
<223> OTHER INFORMATION: n = A,T,C or G

<400> SEQUENCE: 275
ancgtggtcg cggccgaggt cctcaccaga ggtgncacct acaacatcat agtggaggca             60
ctgaaagacc ancagaggca taaggttcgg gaagagg                                      97

<210> SEQ ID NO 276
<211> LENGTH: 610
<212> TYPE: DNA
<213> ORGANISM: Homo sapien
<220> FEATURE:
<221> NAME/KEY: misc_feature
<222> LOCATION: (1)...(610)
<223> OTHER INFORMATION: n = A,T,C or G

<400> SEQUENCE: 276
tcgagcggcc gcccgggcag gtccattttc tccctgacgg tcccacttct ctccaatctt             60
gtagttcaca ccattgtcat ggcaccatct agatgaatca catctgaaat gaccacttcc           120
aaagcctaag cactggcaca acagtttaaa gcctgattca gacattcgtt cccactcatc           180
tccaacggca taatgggaaa ctgtgtaggg gtcaaagcac gagtcatccg taggttggtt           240
caagccttcg ttgacagagt tgtccacggt aacaacctct tcccgaacct tatgcctctg           300
ctggtctttc agtgcctcca ctatgatgtt gtaggtggca cctctggtga ggacctcngn           360
ccngaacaac gcttaagccc gnattctgca gaataatccc atcacacttg gcggccgctt           420
cgancatgca tcntaaaagg ggccccaatt tccccttat aagngaancc gtatttncca            480
atttcactgg ncccgccgnt tttacaaacg ncggtgaact ggggaaaaac cctggcggtt           540
acccaacttt aatcgccntt ggcagcacaa tccccctttt tcgnccancn tgggcgtaaa           600
taaccgaaaa                                                                   610

<210> SEQ ID NO 277
<211> LENGTH: 38
```

```
<212> TYPE: DNA
<213> ORGANISM: Homo sapien
<220> FEATURE:
<221> NAME/KEY: misc_feature
<222> LOCATION: (1)...(38)
<223> OTHER INFORMATION: n = A,T,C or G

<400> SEQUENCE: 277
ancgnggtcg cggccgangt nttttttctt nttttttt                              38

<210> SEQ ID NO 278
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 278
agcgtggtcg cggccgaggt ctgaggttac atgcgtggtg gtggacgtga gccacgaaga      60
ccctgaggtc aagttcaact ggtacgtgga cggcgtggag gtgcataatg ccaagacaaa     120
gccgcgggag gagcagtaca acagcacgta ccggngggtc agcgtcctca ccgtcctgca     180
ccagaattgg ttgaatggca aggagtacaa gngcaaggtt ccaacaaag ccntcccagc      240 ccccntcgaa aaaccattt ccaaagccaa agggcagccc cgagaaccac aggtgtacac      300
cctgccccca tcccgggagg aaaagancaa naaccnggtt cagccttaac ttgcttggtc     360
naangctttt tatcccaacg nacttcccc ntggaantgg gaaaaaccaa tgggccaanc      420
cgaaaaacaa ttacaanaac ccc                                            443

<210> SEQ ID NO 279
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 279
tcgagcggcc gcccgggcag gtgtcggagt ccagcacggg aggcgtggtc ttgtagttgt      60
tctccggctg cccattgctc tcccactcca cggcgatgtc gctgggatag aagcctttga     120
ccaggcaggt caggctgacc tggttcttgg tcatctcctc ccgggatggg ggcagggtga     180
acacctgggg ttctcggggc ttgcccttg gttttgaana tggttttctc gatggggct       240 ggaagggctt tgttgnaaac cttgcacttg actccttgcc attcacccag ncctggngca     300
ggacggngag gacnctnacc acacggaacc gggctggtgg actgctcc                 348

<210> SEQ ID NO 280
<211> LENGTH: 149
<212> TYPE: DNA
<213> ORGANISM: Homo sapien
<220> FEATURE:
<221> NAME/KEY: misc_feature
<222> LOCATION: (1)...(149)
<223> OTHER INFORMATION: n = A,T,C or G

<400> SEQUENCE: 280
agcgtggtcg cggacgangt cctgtcagag tggnactggt agaagttcca ngaaccctga      60
actgtaaggg ttcttcatca gtgccaacag gatgacatga aatgatgtac tcagaagngn     120
```

```
cctggaatgg ggcccatgan atggttgcc                                149
```

<210> SEQ ID NO 281
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 281

```
tcgagcggcc gcccgggcag gtccaccaca cccaattcct tgctggtatc atggcagccg    60
ccacgtgcca ggattaccgg ctacatcatc aagtatgaga agcctgggtc tcctcccaga   120
gaagtggtcc ctcggccccg ccctggtgtc acagaggcta ctattactgg cctggaaccg   180
ggaaccgaat atacaattta tgtcattgcc ctgaagaata tcagaagag cgagcccctg    240
attggaagga aaagacaga cgagcttccc caactggtaa cccttccaca ccccaatctt    300
catggaccag agatcttgga tgttccttcc acagttcaaa agacccctt cggcacccccc   360
cctgggtatg aacctgggaa aanggnantt aanctttcct ggca                   404
```

<210> SEQ ID NO 282
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 282

```
agcgtggtcg cggccgaggt ctgggatgct cctgctgtca cagtgagata ttacaggatc    60
acttacgag aaacaggagg aaatagccct gtccaggagt tcactgtgcc tgggagcaag   120
tctacagcta ccatcagcgg ccttaaacct ggagttgatt ataccatcac tgtgtatgct   180
gtcactggcc gtggagacag ccccgcaagc agcaagccaa tttccattaa ttaccgaaca   240
gaaattgaca aaccatccca gatgcaagtg accgatgttc aggacaacag cattagtgtc   300
aagtggctgc cttcaaggtn ccctggtact gggttacaga ntaaccacca ctcccaaaaa   360
tggaccagga accacaaaaa cttaaactgc agggtccaga tcaaaacaga aatgactatt   420
gaangcttgc agcccacagt gggagtatgn gggtagtgnc tatgcttcag aatccaagcg   480
gaaaaangtc aagccttntg ggttcaa                                      507
```

<210> SEQ ID NO 283
<211> LENGTH: 325
<212> TYPE: DNA
<213> ORGANISM: Homo sapien
<220> FEATURE:
<221> NAME/KEY: misc_feature
<222> LOCATION: (1)...(325)
<223> OTHER INFORMATION: n = A,T,C or G

<400> SEQUENCE: 283

```
tcgagcggcc gcccgggcag gtccttgcag ctctgcagtg tcttcttcac catcaggtgc    60
agggaatagc tcatggattc catcctcagg gctcgagtag gtcaccctgt acctggaaac   120
ttgcccctgt gggctttccc aagcaatttt gatggaatcg acatccacat cagtgaatgc   180
cagtccttta gggcgatcaa tgttggttac tgcagnctga accagaggct gactctctcc   240
gcttggattc tgagcataga cactaaccac atactccact gtgggctgca anccttcaat   300
```

```
aanncatttc tgtttgatct ggacc                                      325
```

<210> SEQ ID NO 284
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 284

```
tcgagcggcc gcccgggcag gtctggtggg gtcctggcac acgcacatgg gggngttgnt    60
ctnatccagc tgcccagccc ccattggcga gtttgagaag gtgtgcagca atgacaacaa   120
naccttcgac tcttcctgcc acttctttgc cacaaagtgc accctggagg gcaccaagaa   180
gggccacaag ctccacctgg actacatcgg gccttgcaaa tacatccccc cttgcctgga   240
ctctgagctg accgaattcc cccttgcgca tgcgggactg gctcaagaac cgtcctggca   300
cccttgtatg anagggatga agacacnacc c                                   331
```

<210> SEQ ID NO 285
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 285

```
agcgtggtcg cggccgaggt ctgtcctaca gtcctcagga ctctactccc tcagcagcgt    60
ggtgaccgtg ccctccagca acttcggcac ccagacctac acctgcaacg tagatcacaa   120
gcccagcaac accaaggtgg acaagagagt tgagcccaaa tcttgtgaca aaactcacac   180
atgcccaccg tgcccagcac ctgaactcct ggggggaccg tcagtcttcc tcttcccccg   240
catcccccctt ccaaacctgc ccgggcggcc gctcgaaagc cgaattccag cacactggcg   300
gccggtacta gtgganccna acttggnanc caacctggng gaantaatgg gcataanctg   360
tttctggggg gaaattggta tccngtttac aattcccnca caacatacga gccggaagca   420
taaaagngta aaagcctggg ggnggcctan tgaagtgaag ctaaactcac attaattngc   480
gttgccgctc actggcccgc ttttccagc                                      509
```

<210> SEQ ID NO 286
<211> LENGTH: 336
<212> TYPE: DNA
<213> ORGANISM: Homo sapien
<220> FEATURE:
<221> NAME/KEY: misc_feature
<222> LOCATION: (1)...(336)
<223> OTHER INFORMATION: n = A,T,C or G

<400> SEQUENCE: 286

```
tcgagcggcc gcccgggcag gtttggaagg gggatgcggg ggaagaggaa gactgacggt    60
ccccccagga gttcaggtgc tgggcacggt gggcatgtgt gagttttgtc acaagatttg   120
ggctcaactc tcttgtccac cttggtgttg ctgggcttgt gatctacgtt gcaggtgtag   180
gtctgggngc cgaagttgct ggagggcacg gtcaccacgg tgctgaggga gtagagtcct   240
gaggactgta ngacagacct cggccgngac cacgctaagc cgaattctgc agatatccat   300
```
cacactggcg gccgctccga gcatgcattt tagagg 336

<210> SEQ ID NO 287
<211> LENGTH: 30
<212> TYPE: DNA
<213> ORGANISM: Homo sapien
<220> FEATURE:
<221> NAME/KEY: misc_feature
<222> LOCATION: (1)...(30)
<223> OTHER INFORMATION: n = A,T,C or G

<400> SEQUENCE: 287
agcgtggncg cggacganga caacaacccc 30

<210> SEQ ID NO 288
<211> LENGTH: 316
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 288
tcgagcggcc gcccgggcag gnccacatcg gcagggtcgg agccctggcc gccatactcg 60
aactggaatc catcggtcat gctcttgccg aaccagacat gcctcttgtc cttggggttc 120
ttgctgatgn accagttctt ctgggccaca ctgggctgag tggggtacac gcaggtctca 180
ccagtctcca tgttgcagaa gactttgatg catccaggt tgcagccttg gttggggtca 240
atccagtact ctccactctt ccagtcagag tggcacatct tgaggtcacg gcaggtgcgg 300
gcggggttct tgacct 316

<210> SEQ ID NO 289
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 289
agcgtggtcg cggccgaggt ccagcctgga gataanggtg aagtggtgc ccccggactt 60 ccaggtatag ctggacctcg tggtagccct ggtgagagag gtgaaactgg ccctccagga 120
cctgctggtt tccctggtgc tcctggacag aatggtgaac ctggnggtaa aggagaaaga 180
ggggctccgg ntganaaagg tgaaggaggc cctcctgnat tggcagggc cccangactt 240 agaggtggag ctggccccc tggccccgaa ggaggaaagg gtgctgctgg tcctcctggg 300
ccacctgg 308

<210> SEQ ID NO 290
<211> LENGTH: 324
<212> TYPE: DNA
<213> ORGANISM: Homo sapien
<220> FEATURE:
<221> NAME/KEY: misc_feature
<222> LOCATION: (1)...(324)
<223> OTHER INFORMATION: n = A,T,C or G

<400> SEQUENCE: 290
tcgagcggcc gcccgggcag gtctgggcca ggaggaccaa taggaccagt aggacccctt 60
gggccatctt tccctgggac accatcagca cctggaccgc ctggttcacc cttgtcaccc 120

```
tttggaccag gacttccaag acctcctctt tctccaggca ttccttgcag accaggagta        180
ccancagcac caggtggccc aggaggacca gcagcaccct ttcctccttc gggaccaggg        240
ggaccagctc cacctctaag tcctggggcc cctgccaatc aggagggcc tccttcacct         300 ttctcacccg gagcccctct ttct                                               324
```

<210> SEQ ID NO 291
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 291

```
tcgagcggcc gcccgggcag gtccaccggg atattcgggg gtctggcagg aatgggaggc        60
atccagaacg agaaggagac catgcaaagc ctgaacgacc gcctggcctc ttacctggac        120
agagtgagga gcctggagac cgacaaccgg aggctgaga gcaaaatccg ggagcacttg         180
gagaagaagg gaccccaggt cagagactgg agccattact tcaagatcat cgaggacctg       240
agggctcana tcttcgcaaa tactgcngac aatgcccg                                278
```

<210> SEQ ID NO 292
<211> LENGTH: 299
<212> TYPE: DNA
<213> ORGANISM: Homo sapien
<220> FEATURE:
<221> NAME/KEY: misc_feature
<222> LOCATION: (1)...(299)
<223> OTHER INFORMATION: n = A,T,C or G

<400> SEQUENCE: 292

```
atgcgnggtc gcggccgang accanctctg gctcatactt gactctaaag ncntcaccag        60
nanttacggn cattgccaat ctgcagaacg atgcgggcat tgtccgcant atttgcgaag        120
atctgagccc tcaggncctc gatgatcttg aagtaanggc tccagtctct gacctggggt       180
cccttcttct ccaagtgctc ccggattttg ctctccagcc tccggttctc ggtctccaag       240
ncttctcact ctgtccagga aaagaggcca ggcggncgat cagggctttt gcatggact       299
```

<210> SEQ ID NO 293
<211> LENGTH: 101
<212> TYPE: DNA
<213> ORGANISM: Homo sapien

<400> SEQUENCE: 293

```
agcgtggtcg cggccgaggt tgtacaagct tttttttttt tttttttttt tttttttttt        60
tttttttttt tttttttttt tttttttttt tttttttttt t                            101
```

<210> SEQ ID NO 294
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 294

```
tcgagcggcc gcccgggcag gtctgccaac accaagattg gccccgccg catccacaca         60
```

```
gttngtgtgc ggggaggtaa caagaaatac cgtgccctga ggntggacgn ggggaatttc      120
tcctggggct cagagtgttg tactcgtaaa acaaggatca tcgatgttgt ctacaatgca      180
tctaataacg agctggttcg taccaagacc ctggtgaaga attgcatcgt gctcatngac      240
agcacaccgt accgacagtg ggtaccgaag tcccactatg cncct                     285
```

<210> SEQ ID NO 295
<211> LENGTH: 216
<212> TYPE: DNA
<213> ORGANISM: Homo sapien

<400> SEQUENCE: 295

```
tcgagcggcc gcccgggcag gtccaccaca cccaattcct tgctggtatc atggcagccg      60
ccacgtgcca ggattaccgg ctacatcatc aagtatgaga agcctgggtc tcctcccaga      120
gaagtggtcc ctcggccccg ccctggtgtc acagaggcta ctattactgg cctggaaccg      180
ggaaccgaat atacaattta tgtcattgcc ctgaag                               216
```

<210> SEQ ID NO 296
<211> LENGTH: 414
<212> TYPE: DNA
<213> ORGANISM: Homo sapien
<220> FEATURE:
<221> NAME/KEY: misc_feature
<222> LOCATION: (1)...(414)
<223> OTHER INFORMATION: n = A,T,C or G

<400> SEQUENCE: 296

```
agcgtgntcn cggccgagga tggggaagct cgnctgtctt tttccttcca atcaggggct      60
nnntcttctg attattcttc aggcaaanga cataaattgt atattcggnt cccggttcca      120
gnccagtaat agtagcctct gtgacaccag ggcggggccg agggaccact tctctgggag      180
gagacccagg cttctcatac ttgatgatga agccggtaat cctggcacgt gggcggctgc      240
catgatacca ccaangaatt gggtgtggtg gacctgcccg ggcgggccgc tcgaaaancc      300
gaattcntgc aagaatatcc atcacacttg ggcgggccgn tcgaaccatg catcntaaaa      360
gggccccaat ttccccccta ttaggngaag ccncatttaa caaattccac ttgg           414
```

<210> SEQ ID NO 297
<211> LENGTH: 376
<212> TYPE: DNA
<213> ORGANISM: Homo sapien
<220> FEATURE:
<221> NAME/KEY: misc_feature
<222> LOCATION: (1)...(376)
<223> OTHER INFORMATION: n = A,T,C or G

<400> SEQUENCE: 297

```
tcgagcggcc gcccgggcag gtctcgcggt cgcactggtg atgctggtcc tgttggtccc      60
cccggccctc ctggacctcc tggtccccct ggtcctccca gcgctggttt cgacttcagc      120
ttcctgcccc agccacctca agagaaggct cacgatggtg gccgctacta ccgggctgat      180
gatgccaatg tggttcgtga ccgtgacctc gaggtggaca ccaccctcaa gagccttgag      240
ccagcagaat cgaaaacatt cggaacccaa gaagggcaag cccgcaaaga aaccccgccc      300
gcacctggcc gngaacctcc aagaangtgc ccacntcttg actgggaaaa aaagggaaaa      360
ntacttggaa ttggac                                                    376
```

<210> SEQ ID NO 298
<211> LENGTH: 357

<212> TYPE: DNA
<213> ORGANISM: Homo sapien
<220> FEATURE:
<221> NAME/KEY: misc_feature
<222> LOCATION: (1)...(357)
<223> OTHER INFORMATION: n = A,T,C or G

<400> SEQUENCE: 298

```
agcgtggtcg cggccgaggt ccacatcggc agggtcggag ccctggccgc catactcgaa      60
ctggaatcca tcggtcatgc tctcgccgaa ccagacatgc ctcttgtcct tggggttctt     120
gctgatgtac cagttcttct gggccacact gggctgagtg gggtacacgc aggtctcacc     180
agtctccatg ttgcagaaga ctttgatggc atccaggttg cagccttggt tggggtcaat     240
ccagtactct ccactcttcc agtcagaagt ggcacatctt gaggtcacgg cagggtgcgg     300
gcggggttct tgcgggctgc ccttctgggc tcccggaatg ttctnngaac ttgctgg        357
```

<210> SEQ ID NO 299
<211> LENGTH: 307
<212> TYPE: DNA
<213> ORGANISM: Homo sapien
<220> FEATURE:
<221> NAME/KEY: misc_feature
<222> LOCATION: (1)...(307)
<223> OTHER INFORMATION: n = A,T,C or G

<400> SEQUENCE: 299

```
agcgtggtcg cggccgaggt ccactagagg tctgtgtgcc attgcccagg cagagtctct      60
gcgttacaaa ctcctaggag ggcttgctgt gcggagggcc tgctatggtg tgctgcggtt     120
catcatggga agtggggcca aaggctgcga ggttgtggtg tctgggaaac tccgaggaca     180
gagggctaaa tccatgaagt ttgtggatgg cctgatgatc cacagcggag accctgttaa     240
ctactacgtt gacacttgct tgtgcgccac gtgttgctca nacangggtg ggctgggcat     300
caaggng                                                                307
```

<210> SEQ ID NO 300
<211> LENGTH: 351
<212> TYPE: DNA
<213> ORGANISM: Homo sapien

<400> SEQUENCE: 300

```
tcgagcggcc gcccgggcag gtctgccaag gagaccctgt tatgctgtgg ggactggctg      60
gggcatggca ggcggctctg gcttcccacc cttctgttct gagatggggg tggtgggcag     120
tatctcatct ttgggttcca caatgctcac gtggtcaggc aggggcttct tagggccaat     180
cttaccagtt gggtcccagg gcagcatgat cttcaccttg atgcccagca caccctgtct     240
gagcaacacg tggcgcacag caagtgtcaa cgtaagtaag ttaacagggt ctccgctgtg     300
gatcatcagg ccatccacaa acttcatgga tttaaccctc tgtcctcgga g              351
```

<210> SEQ ID NO 301
<211> LENGTH: 330
<212> TYPE: DNA
<213> ORGANISM: Homo sapien

<400> SEQUENCE: 301

```
tcgagcggcc gcccgggcag gtgtttcaga ggttccaagg tccactgtgg aggtcccagg      60
agtgctggtg gtgggcacag aggtccgatg ggtgaaacca ttgacataga gactgttcct     120
gtccagggtg taggggccca gctctttgat gccattggcc agttggctca gctcccagta     180
```

```
cagccgctct ctgttgagtc cagggctttt ggggtcaaga tgatggatgc agatggcatc      240
cactccagtg gctgctccat ccttctcgga cctgagagag gtcagtctgc agccagagta      300
cagagggcca acactggtgt tctttgaata                                       330
```

<210> SEQ ID NO 302
<211> LENGTH: 317
<212> TYPE: DNA
<213> ORGANISM: Homo sapien
<220> FEATURE:
<221> NAME/KEY: misc_feature
<222> LOCATION: (1)...(317)
<223> OTHER INFORMATION: n = A,T,C or G

<400> SEQUENCE: 302

```
agcgtggtcg cggccgaggt ctgtactggg agctaagcaa actgaccaat gacattgaag      60
agctgggccc ctacaccctg gacaggaaca gtctctatgt caatggtttc acccatcaga     120
gctctgtgnc caccaccagc actcctggga cctccacagt ggatttcaga acctcaggga     180
ctccatcctc cctctccagc cccacaatta tggctgctgg ccctctcctg gtaccattca     240
ccctcaactt caccatcacc aacctgcagt atggggagga catgggtcac cctgnctcca     300
ggaagttcaa caccaca                                                    317
```

<210> SEQ ID NO 303
<211> LENGTH: 283
<212> TYPE: DNA
<213> ORGANISM: Homo sapien
<220> FEATURE:
<221> NAME/KEY: misc_feature
<222> LOCATION: (1)...(283)
<223> OTHER INFORMATION: n = A,T,C or G

<400> SEQUENCE: 303

```
tcgagcggcc gcccggacag gtctgggcgg atagcaccgg gcatattttg gaatggatga      60
ggtctggcac cctgagcagt ccagcgagga cttggtctta gttgagcaat ttggctagga     120
ggatagtatg cagcacggnt ctgagnctgt gggatagctg ccatgaagta acctgaagga     180
ggtgctggct ggtangggtt gattacaggg ttgggaacag ctcgtacact tgccattctc     240
tgcatatact ggttagtgag gtgagcctgg ccctcttctt ttg                       283
```

<210> SEQ ID NO 304
<211> LENGTH: 72
<212> TYPE: DNA
<213> ORGANISM: Homo sapien
<220> FEATURE:
<221> NAME/KEY: misc_feature
<222> LOCATION: (1)...(72)
<223> OTHER INFORMATION: n = A,T,C or G

<400> SEQUENCE: 304

```
agcgtggtcg cggccgaggt gagccacagg tgaccggggc tgaagctggg gctgctggnc      60
ctgctggtcc tg                                                          72
```

<210> SEQ ID NO 305
<211> LENGTH: 245
<212> TYPE: DNA
<213> ORGANISM: Homo sapien
<220> FEATURE:
<221> NAME/KEY: misc_feature
<222> LOCATION: (1)...(245)
<223> OTHER INFORMATION: n = A,T,C or G

<400> SEQUENCE: 305

```
cagcngctcc nacggggcct gngggaccaa caacaccgtt ttcacccttta ggccctttgg     60 ctcctctttc tcctttagca ccaggttgac cagcagcncc ancaggacca gcaaatccat    120
tggggccagc aggaccgacc tcaccacgtt caccaggct tccccgagga ccagcaggac    180
cagcaggacc agcagcccca gcttcgcccc ggtcacctgt ggctcacctc ggccgcgacc    240
acgct                                                                245
```

<210> SEQ ID NO 306
<211> LENGTH: 246
<212> TYPE: DNA
<213> ORGANISM: Homo sapien
<220> FEATURE:
<221> NAME/KEY: misc_feature
<222> LOCATION: (1)...(246)
<223> OTHER INFORMATION: n = A,T,C or G

<400> SEQUENCE: 306

```
tcgagcggtc gcccgggcag gtccaccggg atagccgggg gtctggcagg aatgggaggc     60
atccagaacg agaaggagac catgcaaagc ctgaacgacc gcctggcctc ttacctggac    120
agagtgagga gcctggagac cganaaccgg aggctggana gcaaaatccg ggagcacttg    180
gagaagaagg acccccaggt caagagactg gagccattac ttcaagatca tcgagggacc    240
tggagg                                                               246
```

<210> SEQ ID NO 307
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 307

```
agcgnggtcg cggccgaggt ccagctctgt ctcatacttg actctaaagt catcagcagc     60
aagacgggca ttgtcaatct gcagaacgat gcgggcattg tccgcagtat ttgcgaagat    120
ctgagccctc aggtcctcga tgatcttgaa gtaatggctc cagtctctga cctggggtcc    180
cttcttctcc aagtgctccc ggatttgct ctccagcctc cggttctcgg tctccaggct    240
cctcactctg tccaggtaag aaggcccagg cggtcgttca ggctttgcat ggtctccttc    300
tcgttctgga tgcctcccat tcctgccaga ccc                                 333
```

<210> SEQ ID NO 308
<211> LENGTH: 310
<212> TYPE: DNA
<213> ORGANISM: Homo sapien

<400> SEQUENCE: 308

```
tcgagcggcc gcccgggcag gtcaggaagc acattggtct tagagccact gcctcctgga     60
ttccacctgt gctgcggaca tctccaggga gtgcagaagg gaagcaggtc aaactgctca    120
gatcagtcag actggctgtt ctcagttctc acctgagcaa ggtcagtctg cagccagagt    180
acagagggcc aacactggtg ttcttgaaca agggcttgag cagaccctgc agaaccctct    240
tccgtggtgt tgaacttcct ggaaaccagg gtgttgcatg ttttttcctca taatgcaagg    300 ttggtgatgg                                                           310
```

<210> SEQ ID NO 309

```
<211> LENGTH: 429
<212> TYPE: DNA
<213> ORGANISM: Homo sapien

<400> SEQUENCE: 309
agcgtggtcg cggccgaggt ccacatcggc agggtcggag ccctggccgc catactcgaa      60
ctggaatcca tcggtcatgc tctcgccgaa ccagacatgc ctcttgtcct tggggttctt     120
gctgatgtac cagttcttct gggccacact gggctgagtg gggtacaccg caggtctcac     180
cagtctccat gttgcagaag actttgatgg catccaggtt gcagccttgg ttggggtcaa     240
tccagtactc tccactcttc cagtcagaag tgggcacatc ttgaggtcac cggcaggtgc     300
cgggccgggg gttcttgcgg cttgccctct gggctccgga tgttctcgat ctgcttggct     360
caggctcttg agggtgggtg tccacctcga ggtcacggtc accgaaacct gcccgggcgg     420
cccgctcga                                                              429

<210> SEQ ID NO 310
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 310
tcgagcggtc gcccgggcag gtttcgtgac cgtgacctcg aggtggacac caccctcaag      60
agcctgagcc agcagatcga gaacatccgg agcccagagg gcagccgcaa gaaccccgcc     120
cgcacctgcc gtgacctcaa gatgtgccac tctgactgga gagtggagag tactggatt     180
gaccccaacc aaggctgcaa cctggatgcc atcaaagtct tctgcaacat ggagactggt     240
gagacctgcg tgtaccccac tcagcccagt gtgggcccag aagaaactgg tacatcagca     300
aggaaccccca aggacaagag gcattgtctt ggttcggcga gnagcatgac ccgatggatt     360
ccagtttcga gtattggcgg ccagggcttc ccgacccttg ccgatgtgga cctcggccgc     420
gaccaccgct                                                              430

<210> SEQ ID NO 311
<211> LENGTH: 2996
<212> TYPE: DNA
<213> ORGANISM: Homo sapien

<400> SEQUENCE: 311
cagccaccgg agtggatgcc atctgcaccc accgccctga ccccacaggc cctgggctgg      60
acagagagca gctgtatttg agctgagcc agctgaccca cagcatcact gagctgggcc     120
cctacaccct ggacagggac agtctctatg tcaatggttt cacacagcgg agctctgtgc     180
ccaccactag cattcctggg accccccacag tggacctggg aacatctggg actccagttt     240
ctaaacctgg tccctcggct gccagccctc tcctggtgct attcactctc aacttcacca     300
tcaccaacct gcggtatgag gagaacatgc agcaccctg ctccaggaag ttcaacacca     360
cggagagggt ccttcaggc ctggtccctg ttcaagagca ccagtgttgg ccctctgtac     420
tctggctgca gactgacttt gctcaggcct gaaaaggatg ggacagccac tggagtggat     480
gccatctgca cccaccaccc tgaccccaaa agcctaggc tggacagaga gcagctgtat     540
tgggagctga gccagctgac ccacaatatc actgagctgg gccctatgc cctggacaac     600
gacagcctct ttgtcaatgg tttcactcat cggagctctg tgtccaccac cagcactcct     660
```

```
gggacccccca cagtgtatct gggagcatct aagactccag cctcgatatt tggcccttca      720
gctgccagcc atctcctgat actattcacc ctcaacttca ccatcactaa cctgcggtat      780
gaggagaaca tgtggcctgg ctccaggaag ttcaacacta cagagagggt ccttcagggc      840
ctgctaaggc ccttgttcaa gaacaccagt gttggccctc tgtactctgg ctgcaggctg      900
accttgctca ggccagagaa agatggggaa gccaccggag tggatgccat ctgcacccac      960
cgccctgacc ccacaggccc tgggctggac agagagcagc tgtatttgga gctgagccag     1020
ctgacccaca gcatcactga gctgggcccc tacacactgg acagggacag tctctatgtc     1080
aatggtttca cccatcggag ctctgtaccc accaccagca ccggggtggt cagcgaggag     1140
ccattcacac tgaacttcac catcaacaac ctgcgctaca tggcggacat gggccaaccc     1200
ggctccctca gttcaacat cacagacaac gtcatgaagc acctgctcag tcctttgttc     1260
cagaggagca gcctgggtgc acggtacaca ggctgcaggg tcatcgcact aaggtctgtg     1320
aagaacggtg ctgagacacg ggtggacctc ctctgcacct acctgcagcc cctcagcggc     1380
ccaggtctgc ctatcaagca ggtgttccat gagctgagcc agcagaccca tggcatcacc     1440
cggctgggcc cctactctct ggacaaagac agcctctacc ttaacggtta caatgaacct     1500
ggtccagatg agcctcctac aactcccaag ccagccacca cattcctgcc tcctctgtca     1560
gaagccacaa cagccatggg gtaccacctg aagaccctca cactcaactt caccatctcc     1620
aatctccagt attcaccaga tatgggcaag ggctcagcta cattcaactc caccgagggg     1680
gtccttcagc acctgctcag acccttgttc cagaagagca gcatgggccc cttctacttg     1740
ggttgccaac tgatctccct caggcctgag aaggatgggg cagccactgg tgtggacacc     1800
acctgcacct accaccctga ccctgtgggc cccgggctgg acatacagca gctttactgg     1860
gagctgagtc agctgaccca tggtgtcacc caactgggct tctatgtcct ggacagggat     1920
agcctcttca tcaatggcta tgcaccccag aatttatcaa tccggggcga gtaccagata     1980
aatttccaca ttgtcaactg gaacctcagt aatccagacc ccacatcctc agagtacatc     2040
accctgctga gggacatcca ggacaaggtc accacactct acaaaggcag tcaactacat     2100
gacacattcc gcttctgcct ggtcaccaac ttgacgatgg actccgtgtt ggtcactgtc     2160
aaggcattgt tctcctccaa tttggacccc agcctggtgg agcaagtctt tctagataag     2220
accctgaatg cctcattcca ttggctgggc tccacctacc agttggtgga catccatgtg     2280
acagaaatgg agtcatcagt ttatcaacca acaagcagct ccagcaccca gcacttctac     2340
ctgaatttca ccatcaccaa ctaccatat tcccaggaca aagcccagcc aggcaccacc     2400
aattaccaga ggaacaaaag gaatattgag gatgcgctca ccaactctt ccgaaacagc     2460 agcatcaaga gttattttc tgactgtcaa gtttcaacat tcaggtctgt ccccaacagg     2520
caccacaccg gggtggactc cctgtgtaac ttctcgccac tggctcggag agtagacaga     2580
gttgccatct atgaggaatt tctgcggatg acccggaatg gtacccagct gcagaacttc     2640
accctggaca ggagcagtgt ccttgtggat gggtattttc ccaacagaaa tgagccctta     2700
actgggaatt ctgaccttcc cttctgggct gtcatcctca tcggcttggc aggactcctg     2760
ggactcatca catgcctgat ctgcgtgtc ctggtgacca ccgccggcg gaagaaggaa     2820 ggagaataca acgtccagca acagtgccca ggctactacc agtcacacct agacctggag     2880
gatctgcaat gactgaact tgccggtgcc tgggtgcct ttcccccagc cagggtccaa     2940
agaagcttgg ctggggcaga aataaaccat attggtcgga cacaaaaaaa aaaaaa       2996
```

<210> SEQ ID NO 312
<211> LENGTH: 914
<212> TYPE: PRT
<213> ORGANISM: Homo sapien

<400> SEQUENCE: 312

```
Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
                20                  25                  30

Asn Leu Val Pro Arg Leu Pro Ala Leu Ser Trp Cys Tyr Ser Leu Ser
            35                  40                  45

Thr Ser Pro Ser Pro Thr Cys Gly Met Arg Arg Thr Cys Ser Thr Leu
50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365

Pro Leu Phe Gln Arg Ser Ser Leu Gly Ala Arg Tyr Thr Gly Cys Arg
    370                 375                 380
```

```
Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
            405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
            435                 440                 445

Asn Glu Pro Gly Pro Asp Glu Pro Pro Thr Thr Pro Lys Pro Ala Thr
450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
            485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
            515                 520                 525

Phe Tyr Leu Gly Cys Gln Leu Ile Ser Leu Arg Pro Glu Lys Asp Gly
            530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
            565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
            595                 600                 605

Tyr Gln Ile Asn Phe His Ile Val Asn Trp Asn Leu Ser Asn Pro Asp
            610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
            645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
            675                 680                 685

Leu Asp Lys Thr Leu Asn Ala Ser Phe His Trp Leu Gly Ser Thr Tyr
690                 695                 700

Gln Leu Val Asp Ile His Val Thr Glu Met Glu Ser Ser Val Tyr Gln
705                 710                 715                 720

Pro Thr Ser Ser Ser Thr Gln His Phe Tyr Leu Asn Phe Thr Ile
            725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Leu Asn Gln Leu Phe
            755                 760                 765

Arg Asn Ser Ser Ile Lys Ser Tyr Phe Ser Asp Cys Gln Val Ser Thr
            770                 775                 780

Phe Arg Ser Val Pro Asn Arg His His Thr Gly Val Asp Ser Leu Cys
785                 790                 795                 800
```

```
                                   -continued

Asn Phe Ser Pro Leu Ala Arg Arg Val Asp Arg Val Ala Ile Tyr Glu
            805                 810                 815

Glu Phe Leu Arg Met Thr Arg Asn Gly Thr Gln Leu Gln Asn Phe Thr
                820             825             830

Leu Asp Arg Ser Ser Val Leu Val Asp Gly Tyr Phe Pro Asn Arg Asn
            835             840             845

Glu Pro Leu Thr Gly Asn Ser Asp Leu Pro Phe Trp Ala Val Ile Leu
        850             855             860

Ile Gly Leu Ala Gly Leu Leu Gly Leu Ile Thr Cys Leu Ile Cys Gly
865                 870             875                 880

Val Leu Val Thr Thr Arg Arg Arg Lys Lys Glu Gly Glu Tyr Asn Val
                885             890             895

Gln Gln Gln Cys Pro Gly Tyr Tyr Gln Ser His Leu Asp Leu Glu Asp
            900             905             910

Leu Gln
```

COMPOSITIONS AND METHODS FOR THERAPY AND DIAGNOSIS OF OVARIAN CANCER

CROSS REFERENCE TO RELATED APPLICATIONS

This application is a continuation-in-part of U.S. application Ser. No. 09/216,003, filed Dec. 17, 1998, and Ser. No. 09/215,681, filed Dec. 17, 1998.

TECHNICAL FIELD

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides antibodies and cells may be used in vaccines and pharmaceutical compositions for treatment of ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

SUMMARY OF THE INVENTION

Briefly stated, this invention provides compositions and methods for the therapy of cancer. Such as ovarian cancer. In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the polypeptide comprises a sequence that is encoded by a polynucleotide sequence selected from the group consisting of SEQ ID NOs:1–81, and complements of such polynucleotides.

The present invention further provides polynucleotides that encode a polypeptide as described above or a portion thereof, expression vectors comprising such polynucleotides and host cells transformed or transfected with such expression vectors.

Within other aspects, the present invention provides pharmaceutical compositions and vaccines. Pharmaceutical compositions may comprise a physiologically acceptable carrier or excipient in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–81; (ii) a polynucleotide encoding such a polypeptide; (iii) an antibody that specifically binds to such a polypeptide; (iv) an antigen-presenting cell that expresses such a polypeptide and/or (v) a T cell that specifically reacts with such a polypeptide. Vaccines may comprise a non-specific immune response enhancer in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–81, (ii) a polynucleotide encoding such a polypeptide; (iii) an anti-idiotypic antibody that is specifically bound by an antibody that specifically binds to such a polypeptide; (iv) an antigen-presenting cell that expresses such a polypeptide and/or (v) a T cell that specifically reacts with such a polypeptide.

The present invention further provides, in other aspects, fusion proteins that comprise at least one polypeptide as described above, as well as polynucleotides encoding such fusion proteins.

Within related aspects, pharmaceutical compositions comprising a fusion protein or polynucleotide encoding a fusion protein in combination with a physiologically acceptable carrier are provided.

Vaccines are further provided, within other aspects, comprising a fusion protein or polynucleotide encoding a fusion protein in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for stimulating and/or expanding T cells, comprising contacting T cells with (a) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–311; (b) a polynucleotide encoding such a polypeptide and/or (c) an antigen presenting cell that expresses such a polypeptide under conditions and for a time sufficient to permit the stimulation and/or expansion of T cells. Such polypeptide, polynucleotide and/or antigen presenting cell(s) may be present within a pharmaceutical composition or vaccine, for use in stimulating and/or expanding T cells in a mammal.

Within other aspects, the present invention provides methods for inhibiting the development of ovarian cancer in a patient, comprising administering to a patient T cells prepared as described above.

Within further aspects, the present invention provides methods for inhibiting the development of ovarian cancer in a patient, comprising the steps of: (a) incubating CD4$^+$ and/or CD8$^+$ T cells isolated from a patient with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–311; (ii) a polynucleotide encoding such a polypeptide; or (iii) an antigen-presenting cell that expresses such a polypeptide; such that T cells proliferate; and (b) administering to the patient an effective amount of the proliferated T cells, and thereby inhibiting the development of ovarian cancer in the patient. The proliferated cells may be cloned prior to administration to the patient.

The present invention also provides, within other aspects, methods for identifying secreted tumor antigens. Such methods comprise the steps of: (a) implanting tumor cells in an immunodeficient mammal; (b) obtaining serum from the immunodeficient mammal after a time sufficient to permit secretion of tumor antigens into the serum; (c) immunizing an immunocompetent mammal with the serum; (d) obtaining antiserum from the immunocompetent mammal; and (e) screening a tumor expression library with the antiserum, and therefrom identifying a secreted tumor antigen. A preferred method for identifying a secreted ovarian carcinoma antigen comprises the steps of: (a) implanting ovarian carcinoma cells in a SCID mouse; (b) obtaining serum from the SCID mouse after a time sufficient to permit secretion of ovarian carcinoma antigens into the serum; (c) immunizing an immunocompetent mouse with the serum; (d) obtaining antiserum from the immunocompetent mouse; and (e) screening an ovarian carcinoma expression library with the antiserum, and therefrom identifying a secreted ovarian carcinoma antigen.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A–1S (SEQ ID NOs:1–71) depict partial sequences of polynucleotides encoding representative secreted ovarian carcinoma antigens.

FIGS. 2A–2C depict full insert sequences for three of the clones of FIG. 1. FIG. 2A shows the sequence designated O7E (11731; SEQ ID NO:72), FIG. 2B shows the sequence designated O9E (11785; SEQ ID NO:73) and FIG. 2C shows the sequence designated O8E (13695; SEQ ID NO:74).

Figure 3:
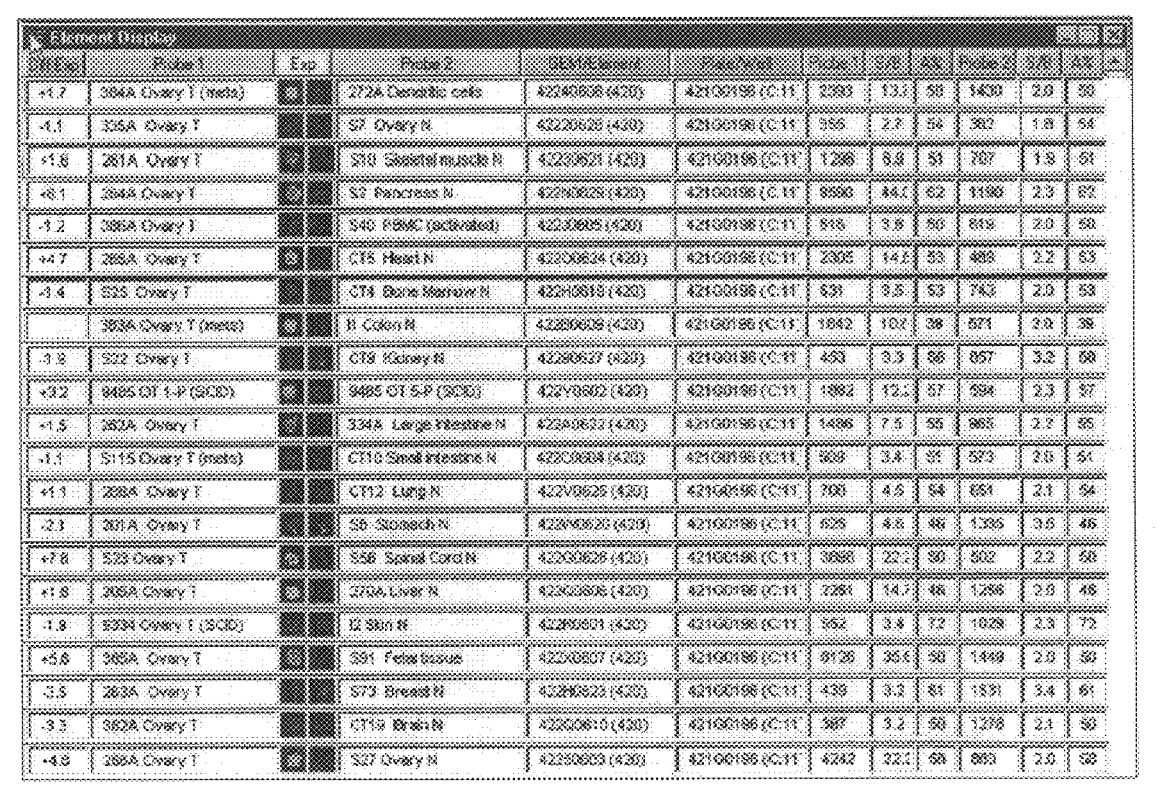

FIG. 3 presents results of microarray expression analysis of the ovarian carcinoma sequence designated O8E.

FIG. 4 presents a partial sequence of a polynucleotide (designated 3g; SEQ ID NO:75) encoding an ovarian carcinoma sequence that is a splice fusion between the human T-cell leukemia virus type I oncoprotein TAX and osteonectin.

FIG. 5 presents the ovarian carcinoma polynucleotide designated 3f (SEQ ID NO:76).

FIG. 6 presents the ovarian carcinoma polynucleotide designated 6b (SEQ ID NO:77).

FIGS. 7A and 7B present the ovarian carcinoma polynucleotides designated 8e (SEQ ID NO:78) and 8h (SEQ ID NO:79).

FIG. 8 presents the ovarian carcinoma polynucleotide designated 12c (SEQ ID NO:80).

FIG. 9 presents the ovarian carcinoma polynucleotide designated 12h (SEQ ID NO:81).

Figure 10:
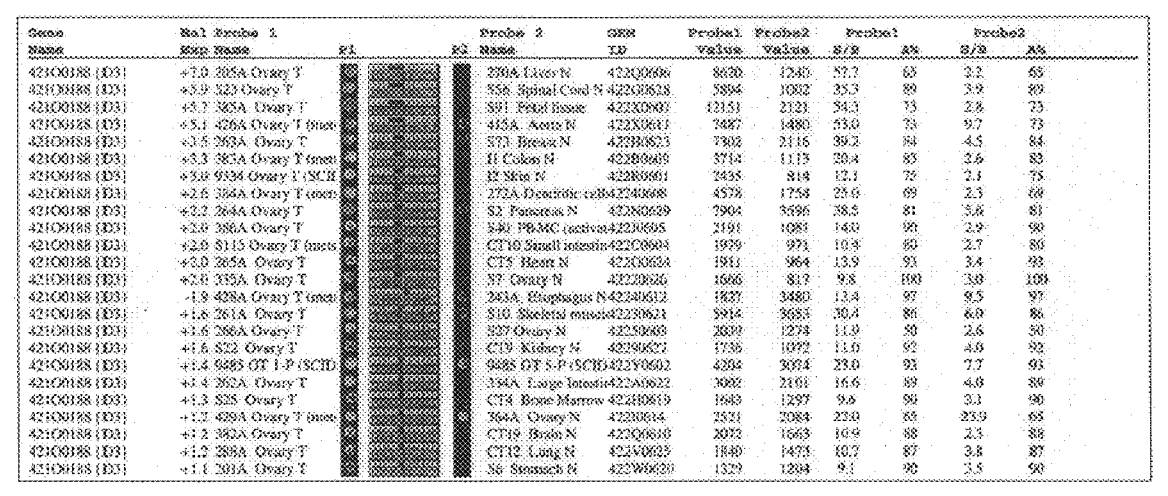

FIG. 10 depicts results of microarray expression analysis of the ovarian carcinoma sequence designated 3f.

Figure 11:
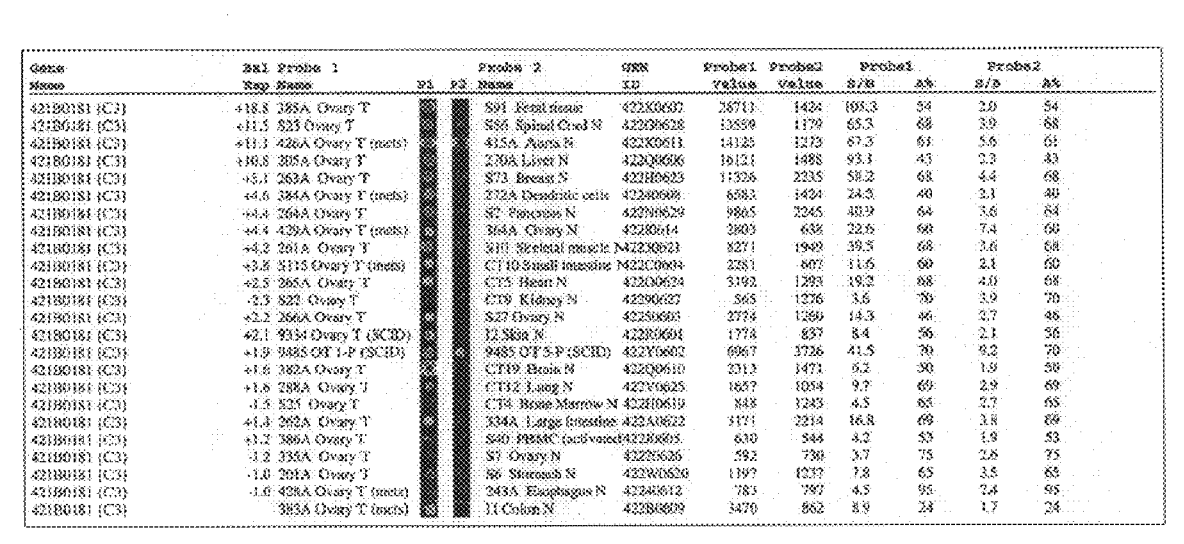

FIG. 11 depicts results of microarray expression analysis of the ovarian carcinoma sequence designated 6b.

Figure 12:
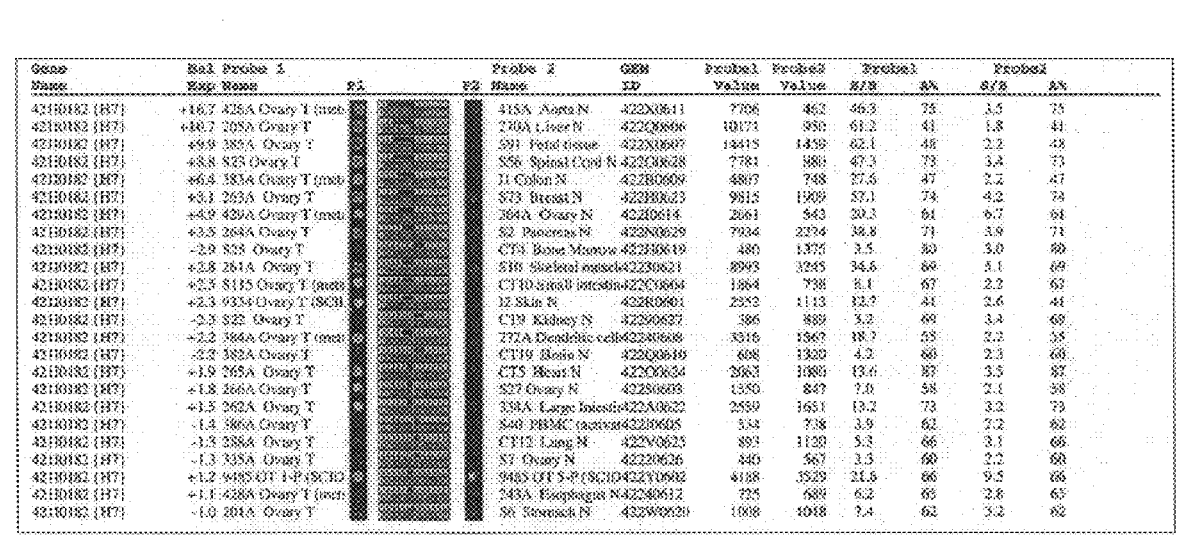

FIG. 12 depicts results of microarray expression analysis of the ovarian carcinoma sequence designated 8e.

Figure 13:
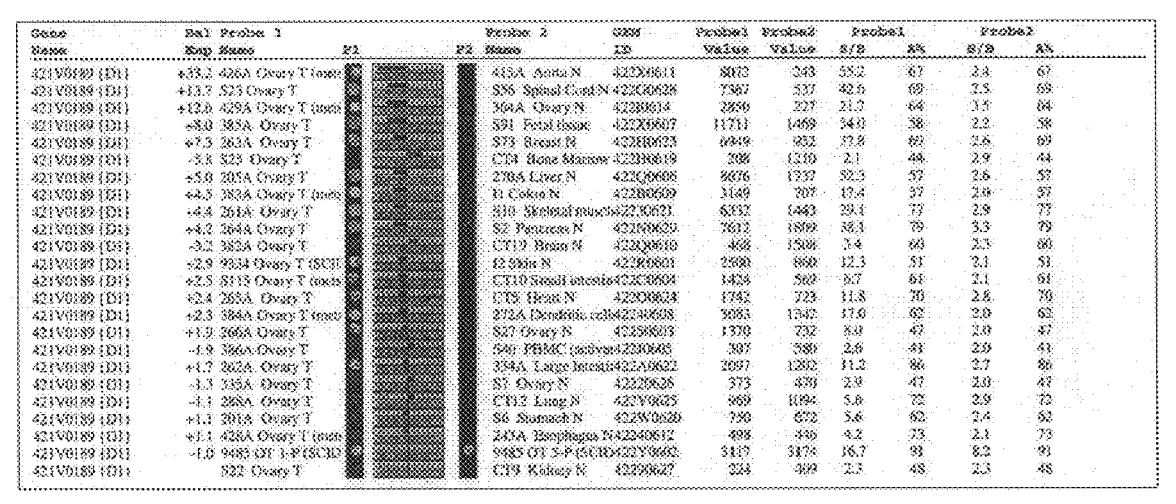

FIG. 13 depicts results of microarray expression analysis of the ovarian carcinoma sequence designated 12c.

Figure 14:
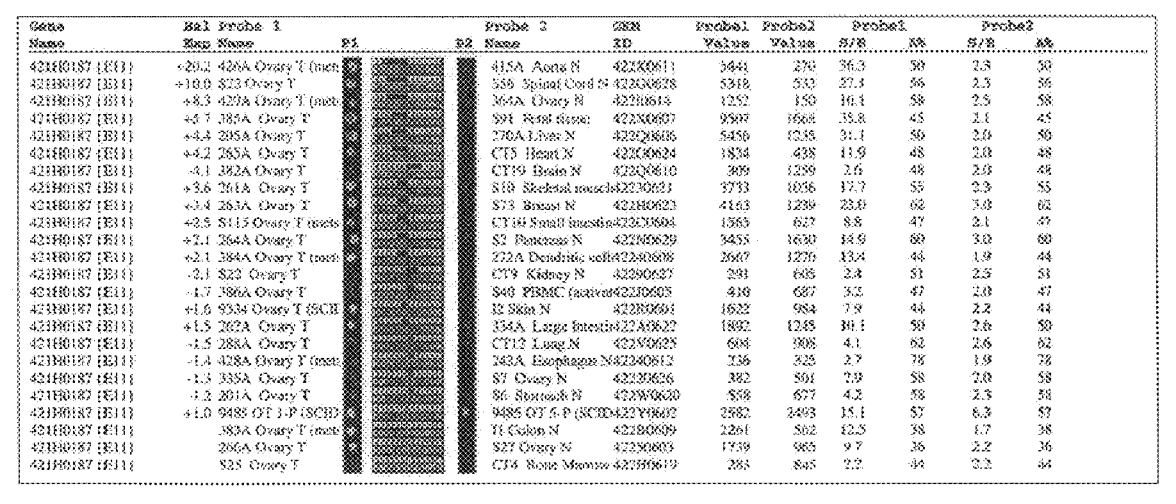

FIG. 14 depicts results of microarray expression analysis of the ovarian carcinoma sequence designated 12h.

FIGS. 15A–15Z–1 depict partial sequences of additional polynucleotides encoding representative secreted ovarian carcinoma antigens (SEQ ID NOs:82–310).

DETAILED DESCRIPTION OF THE INVENTION

As noted above, the present invention is generally directed to compositions and methods for the therapy of cancer, such as ovarian cancer. The compositions described herein may include immunogenic polypeptides, polynucleotides encoding such polypeptides, binding agents such as antibodies that bind to a polypeptide, antigen presenting cells (APCs) and/or immune system cells (e.g., T cells).

Polypeptides of the present invention generally comprise at least an immunogenic portion of an ovarian carcinoma protein or a variant thereof. Certain ovarian carcinoma proteins have been identified using an immunoassay technique, and are referred to herein as ovarian carcinoma antigens. An "ovarian carcinoma antigen" is a protein that is expressed by ovarian tumor cells (preferably human cells) at a level that is at least two fold higher than the level in normal ovarian cells. Certain ovarian carcinoma antigens react detectably (within an immunoassay, such as an ELISA or Western blot) with antisera generated against serum from an immunodeficient animal implanted with a human ovarian tumor. Such ovarian carcinoma antigens are shed or secreted from an ovarian tumor into the sera of the immunodeficient animal. Accordingly, certain ovarian carcinoma antigens provided herein are secreted antigens. Certain nucleic acid sequences of the subject invention generally comprise a DNA or RNA sequence that encodes all or a portion of such a polypeptide, or that is complementary to such a sequence.

The present invention further provides ovarian carcinoma sequences that are identified using techniques to evaluate altered expression within an ovarian tumor. Such sequences may be polynucleotide or protein sequences. Ovarian carcinoma sequences are generally expressed in an ovarian tumor at a level that is at least two fold, and preferably at least five fold, greater than the level of expression in normal ovarian tissue, as determined using a representative assay provided herein. Certain ovarian carcinoma partial polynucleotide sequences are presented in FIGS. 4–9 as well as SEQ ID NOs:75–81. Proteins encoded by genes comprising such polynucleotide sequences (or complements thereof) are also considered ovarian carcinoma proteins.

Antibodies are generally immune system proteins, or antigen-binding fragments thereof, that are capable of binding to a portion of a polypeptide as described above. T cells that may be employed within such compositions are generally T cells (e.g, $CD4^+$ and/or $CD8^+$) that are specific for a polypeptide as described above. Certain methods described herein further employ antigen-presenting cells (such as dendritic cells or macrophages) that express an ovarian carcinoma polypeptide as provided herein.

Ovarian Carcinoma Polynucleotides

Any polynucleotide that encodes an ovarian carcinoma protein or a portion or other variant thereof as described herein is encompassed by the present invention. Preferred polynucleotides comprise at least 15 consecutive nucleotides, preferably at least 30 consecutive nucleotides, and more preferably at least 45 consecutive nucleotides, that encode a portion of an ovarian carcinoma protein. More preferably, a polynucleotide encodes an immunogenic portion of an ovarian carcinoma protein, such as an ovarian carcinoma antigen. Polynucleotides complementary to any such sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an ovarian carcinoma protein or a portion thereof) or may comprise a variant of such a sequence. Polynucleotide variants may contain one or more substitutions, additions, deletions and/or insertions such that the immunogenicity of the encoded polypeptide is not diminished, relative to a native ovarian carcinoma protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native ovarian carcinoma protein or a portion thereof.

The percent identity for two polynucleotide or polypeptide sequences may be readily determined by comparing sequences using computer algorithms well known to those of ordinary skill in the art, such as Megalign, using default parameters. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned. Optimal alignment of sequences for comparison may be conducted, for example, using the Megalign program in the Lasergene suite of bioinformatics software (DNASTAR, Inc., Madison, Wis.), using default parameters. Preferably, the percentage of sequence identity is determined by comparing two optimally aligned sequences over a window of comparison of at least 20 positions, wherein the portion of the polynucleotide or polypeptide sequence in the window may comprise additions or deletions (i.e., gaps) of 20% or less, usually 5 to 15%, or 10 to 12%, relative to the reference sequence (which does not contain additions or deletions). The percent identity may be calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native ovarian carcinoma sequence (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, an ovarian carcinoma polynucleotide may be identified, as described in more detail below, by screening a late passage ovarian tumor expression library with antisera generated against sera of immunocompetent mice after injection of such mice with sera from SCID mice implanted with late passage ovarian tumors. Ovarian carcinoma polynucleotides may also be identified using any of a variety of techniques designed to evaluate differential gene expression. Alternatively, polypeptides may be amplified from cDNA prepared from ovarian tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., an ovarian carcinoma cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of ovarian carcinoma antigens are provided in FIGS. 1A–1S (SEQ ID NOS:1 to 71) and FIGS. 15A to 15Z–1 (SEQ ID NOs:82 to 310). These polynucleotides were isolated by serological screening of an ovarian tumor cDNA expression library, using a technique designed to identify secreted tumor antigens. Briefly, a late passage ovarian tumor expression library was prepared from a SCID-derived human ovarian tumor (OV9334) in the vector λ-screen (Novagen). The sera used for screening were obtained by injecting immunocompetent mice with sera from SCID mice implanted with one late passage ovarian tumors. This technique permits the identification of cDNA molecules that encode immunogenic portions of secreted tumor antigens. The polynucleotides recited herein, as well as full length polynucleotides comprising such sequences, other portions of such full length polynucleotides, and sequences complementary to all or a portion of such full length molecules, are specifically encompassed by the present invention. It will be apparent to those of ordinary skill in the art that this technique can also be applied to the identification of antigens that are secreted from other types of tumors.

The sequences provided in FIGS. 1A–1S appear to be novel. For sequences in FIGS. 15A–15Z–1, database searches revealed matches having substantial identity.

Other nucleic acid sequences of cDNA molecules encoding portions of ovarian carcinoma proteins are provided in FIGS. 4–9 (SEQ ID NOs:75–81). These sequences were identified by screening a microarray of cDNAs for tumor-associated expression (i.e., expression that is at least five fold greater in an ovarian tumor than in normal ovarian tissue, as determined using a representative assay provided herein). Such screens were performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad Sci. USA* 94:2150–2155, 1997). SEQ ID NO:311 provides a full length sequence incorporating certain of these nucleic acid sequences.

Any of a variety of well known techniques may be used to evaluate tumor-associated expression of a cDNA. For example, hybridization techniques using labeled polynucleotide probes may be employed. Alternatively, or in addition, amplification techniques such as real-time PCR may be used (see Gibson et al., *Genome Research* 6:995–1001, 1996; Heid et al., *Genome Research* 6:986–994, 1996). Real-time PCR is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR may be performed, for example, using a Perkin Elmer/Applied Biosystems (Foster City, Calif.) 7700 Prism instrument. Matching primers and fluorescent probes may be designed for genes of interest using, for example, the primer express program provided by Perkin Elmer/Applied Biosystems (Foster City, Calif.). Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). To quantitate the amount of specific RNA in a sample, a standard curve is generated alongside using a plasmid containing the gene of interest. Standard curves may be generated using the Ct values determined in the real-time PCR, which are related to the initial cDNA concentration used in the assay. Standard dilutions ranging from $10-10^6$ copies of the gene of interest are generally sufficient. In addition, a standard curve is generated for the control sequence. This permits standardization of initial RNA content of a tissue sample to the amount of control for comparison purposes.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding an ovarian carcinoma antigen, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells or tissues to facilitate the production of antisense RNA. An antisense polynucleotide may be used, as described herein, to inhibit expression of an ovarian carcinoma protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches,* Futura Publishing Co. (Mt. Kisco, N.Y.; 1994). Alternatively, an antisense molecule may be designed to hybridize with a control region of a gene (e.g., promoter, enhancer or transcription initiation site), and block transcription of the gene; or to block translation by inhibiting binding of a transcript to ribosomes.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules. microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Ovarian Carcinoma Polypeptides

Within the context of the present invention, polypeptides may comprise at least an immunogenic portion of an ovarian carcinoma protein or a variant thereof, as described herein. As noted above, certain ovarian carcinoma proteins are ovarian carcinoma antigens that are expressed by ovarian tumor cells and react detectably within an immunoassay (such as an ELISA) with antisera generated against serum from an immunodeficient animal implanted with an ovarian tumor. Other ovarian carcinoma proteins are encoded by ovarian carcinoma polynucleotides recited herein. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an ovarian carcinoma protein or a variant thereof. Preferred immunogenic portions are encoded by cDNA molecules isolated as described herein. Further immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with ovarian carcinoma protein-specific antibodies, antisera and/or T-cell lines or clones. As used herein, antisera and antibodies are "ovarian carcinoma protein-specific" if they specifically bind to an ovarian carcinoma protein (i.e., they react with the ovarian carcinoma protein in an ELISA or other immunoassay, and do not react detectably with unrelated proteins). Such antisera, antibodies and T cells may be prepared as described herein, and using well known techniques. An immunogenic portion of a native ovarian carcinoma protein is a portion that reacts with such antisera, antibodies and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length protein. Such screens may generally be performed using methods well known to those of ordinary skill in the art, such as those described in Harlow and Lane, *Antibodies: A Laboratory Manual,* Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native ovarian carcinoma protein. A polypeptide "variant," as used herein, is a polypeptide that differs from a native ovarian carcinoma protein in one or more substitutions, deletions, additions and/or insertions, such that the immunogenicity of the polypeptide is not substantially diminished. In other words, the ability of a variant to react with ovarian carcinoma protein-specific antisera may be enhanced or unchanged, relative to the native ovarian carcinoma protein, or may be diminished by less than 50%, and preferably less than 20%, relative to the native ovarian carcinoma protein. Such variants may generally be identified by modifying one of the above polypeptide sequences and evaluating the reactivity of the modified polypeptide with ovarian carcinoma protein-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity to the native polypeptide. Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli,* yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase BPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known tumor antigen, such as an ovarian carcinoma protein or a variant of such a protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen present cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae,* which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to an ovarian carcinoma protein. As used herein, an antibody, or antigen-binding fragment thereof, is said to "specifically bind" to an ovarian carcinoma protein if it reacts at a detectable level (within, for example, an ELISA) with an ovarian carcinoma protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Binding agents may be further capable of differentiating between patients with and without a cancer, such as ovarian cancer, using the representative assays provided herein. In other words, antibodies or other binding agents that bind to a ovarian carcinoma antigen will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, leukophoresis, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, and RNA molecule or a polypeptide. In a preferred embodiment, a binding agent is an antibody or an antigen-binding fragment thereof Antibodies may be prepared by any of a variety of techniques known to those of ordinary skill in the art. See, e.g. Harlow and Lane, *Antibodies: A Laboratory Manual,* Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.). may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a hotolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of an ovarian carcinoma protein. Such antibodies may be raised against an antibody, or antigen-binding fragment thereof, that specifically binds to an immunogenic portion of an ovarian carcinoma protein, using well known techniques. Anti-idiotypic antibodies that mimic an immunogenic portion of an ovarian carcinoma protein are those antibodies that bind to an antibody, or antigen-binding fragment thereof, that specifically binds to an immunogenic portion of an ovarian carcinoma protein, as described herein.

T Cells

Immunotherapeutic compositions may also, or alternatively, comprise T cells specific for an ovarian carcinoma protein. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CFPRATE™ system, available from CellPro Inc., Bothell Wash. (see also U.S. Pat. Nos. 5,240,856; 5,215,926; WO 89/06280; WO 91/16116 and WO 92/07243). Alternatively, T cells may be derived from related or unrelated humans, non-human animals, cell lines or cultures.

T cells may be stimulated with an ovarian carcinoma polypeptide, polynucleotide encoding an ovarian carcinoma polypeptide and/or an antigen presenting cell (APC) that expresses such a polypeptide. Such stimulation is performed under conditions and for a time sufficient to permit the generation of T cells that are specific for the polypeptide. Preferably, an ovarian carcinoma polypeptide or polynucleotide is present within a delivery vehicle, such as a microsphere, to facilitate the generation of specific T cells.

T cells are considered to be specific for an ovarian carcinoma polypeptide if the T cells kill target cells coated with an ovarian carcinoma polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with an ovarian carcinoma polypeptide (200 ng/ml–100 µ/ml, preferably 100 ng/ml–25 µg/ml) for 3–7 days should result in at least a two fold increase in proliferation of the T cells and/or contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998). T cells that have been activated in response to an ovarian carcinoma polypeptide, polynucleotide or ovarian carcinoma polypeptide-expressing APC may be $CD4^{30}$ and/or $CD8^+$. Ovarian carcinoma polypeptide-specific T cells may be expanded using standard techniques. Within preferred embodiments, the T cells are derived from a patient or a related or unrelated donor and are administered to the patient following stimulation and expansion.

For therapeutic purposes, $CD4^+$ or $CD8^+$ T cells that proliferate in response to an ovarian carcinoma polypeptide, polynucleotide or APC can be expanded in number either in vitro or in vivo. Proliferation of such T cells in vitro may be accomplished in a variety of ways. For example, the T cells can be re-exposed to an ovarian carcinoma polypeptide, with or without the addition of T cell growth factors, such as interleukin-2, and/or stimulator cells that synthesize an ovarian carcinoma polypeptide. Alternatively, one or more T cells that proliferate in the presence of an ovarian carcinoma polypeptide can be expanded in number by cloning. Methods for cloning cells are well known in the art, and include limiting dilution. Following expansion, the cells may be administered back to the patient as described, for example, by Chang et al., *Crit. Rev. Oncol. Hematol.* 22:213, 1996.

Pharmaceutical Compositions and Vaccines

Within certain aspects, polypeptides, polynucleotides, binding agents and/or immune system cells as described herein may be incorporated into pharmaceutical compositions or vaccines. Pharmaceutical compositions comprise one or more such compounds or cells and a physiologically acceptable carrier. Vaccines may comprise one or more such compounds or cells and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., Science 259:1745–1749, 1993 and reviewed by Cohen, Science 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and company, Inc., Rahway, N.J.), alum, biodegradable microspheres, monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peri-tumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcy receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a ovarian carcinoma antigen (or portion or other variant thereof) such that the antigen, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells. for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as ovarian cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. Within certain preferred embodiments, a patient is afflicted with ovarian cancer. Such cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immuno response-modifying agents (such as tumor vaccines, bacterial adjuvants and/or cytokines).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into stem cells taken from a patient and clonally propagated in vitro for autologous transplant back into the same patient.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration), orally or in the bed of a resected tumor. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to an ovarian carcinoma antigen generally correlate with an improved clinical outcome. Such immune responses may generally be evaluated using standard proliferation, cytotoxicity or cytokine assays, which may be performed using samples obtained from a patient before and after treatment.

Screens for Identifying Secreted Ovarian Carcinoma Antigens

The present invention provides methods for identifying secreted tumor antigens. Within such methods, tumors are implanted into immunodeficient animals such as SCID mice and maintained for a time sufficient to permit secretion of tumor antigens into serum. In general, tumors may be implanted subcutaneously or within the gonadal fat pad of an immunodeficient animal and maintained for 1–9 months, preferably 1–4 months. Implantation may generally be performed as described in WO 97/18300. The serum containing secreted antigens is then used to prepare antisera in immunocompetent mice, using standard techniques and as described herein. Briefly, 50–100 µL of sera (pooled from three sets of immunodeficient mice, each set bearing a different SCID-derived human ovarian tumor) may be mixed 1:1 (vol:vol) with an appropriate adjuvant, such as RIBI-MPL or MPL+TDM (Sigma Chemical Co., St. Louis, Mo.) and injected intraperitoneally into syngeneic immunocompetent animals at monthly intervals for a total of 5 months. Antisera from animals immunized in such a manner may be obtained by drawing blood after the third, fourth and fifth immunizations. The resulting antiserum is generally pre-cleared of E. coli and phage antigens and used (generally following dilution, such as 1:200) in a serological expression screen.

The library is typically an expression library containing cDNAs from one or more tumors of the type that was implanted into SCID mice. This expression library may be prepared in any suitable vector, such as λ-screen (Novagen). cDNAs that encode a polypeptide that reacts with the antiserum may be identified using standard techniques, and sequenced. Such cDNA molecules may be further characterized to evaluate expression in tumor and normal tissue, and to evaluate antigen secretion in patients.

The methods provided herein have advantages over other methods for tumor antigen discovery. In particular, all antigens identified by such methods should be secreted or released through necrosis of the tumor cells. Such antigens may be present on the surface of tumor cells for an amount of time sufficient to permit targeting and killing by the immune system, following vaccination.

Methods for Detecting Cancer

In general, a cancer may be detected in a patient based on the presence of one or more ovarian carcinoma antigens and/or polynucleotides encoding such proteins in a biological sample (such as blood, sera, urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, an ovarian carcinoma-associated sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual,* Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian carcinoma antigens and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer.

Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen. binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use ovarian carcinoma polypeptides to detect antibodies that bind to such polypeptides in a biological sample. The detection of such ovarian carcinoma antigen specific antibodies may correlate with the presence of a cancer.

A cancer may also, or alternatively, be detected based on the presence of T cells that specifically react with an ovarian carcinoma antigen in a biological sample. Within certain methods, a biological sample comprising $CD4^+$ and/or $CD8^+$ T cells isolated from a patient is incubated with an ovarian carcinoma antigen, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with an ovarian carcinoma antigen (e.g., 5–25 µg/ml). It may be desirable to incubate another aliquot of a T cell sample in the absence of ovarian carcinoma antigen to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding an ovarian carcinoma antigen in a biological sample. For example, at least two oligonucleotide primers may be employed in a polymerase chain reaction (PCR) based assay to amplify a portion of an ovarian carcinoma antigen cDNA derived from a biological sample, wherein at least one of the oligonucleotide primers is specific for (i.e., hybridizes to) a polynucleotide encoding the ovarian carcinoma antigen. The amplified cDNA is then separated and detected using techniques well known in the art, such as gel electrophoresis. Similarly, oligonucleotide probes that specifically hybridize to a polynucleotide encoding an ovarian carcinoma antigen may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding an ovarian carcinoma antigen that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence provided herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample such as a biopsy tissue and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, ovarian carcinoma antigens and polynucleotides encoding such proteins may be used as markers for monitoring the progression of cancer. In this embodiment, assays as described above for the diagnosis of a cancer may be performed over time, and the change in the level of reactive polypeptide(s) evaluated. For example, the assays may be performed every 24–72 hours for a period of 6 months to 1 year, and thereafter performed as needed. In general, a cancer is progressing in those patients in whom the level of polypeptide detected by the binding agent increases over time. In contrast, the cancer is not progressing when the level of reactive polypeptide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple ovarian carcinoma antigen markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to an ovarian carcinoma antigen. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding an ovarian carcinoma antigen in a biological sample. Such kits generally comprise at least one oligonucleotide probe or primer, as described above, that hybridizes to a polynucleotide encoding an ovarian carcinoma antigen. Such an oligonucleotide may be used, for example, within a PCR or hybridization assay. Additional components that may be present within such kits include a second oligonucleotide and/or a diagnostic reagent or container to facilitate the detection of a polynucleotide encoding an ovarian carcinoma antigen.

The following Examples are offered by way of illustration and not by way of limitation.

EXAMPLES

Example 1

Identification of Representative Ovarian Carcinoma Antigen cDNAs

This Example illustrates the identification of cDNA molecules encoding ovarian carcinoma antigens.

Anti-SCID mouse sera (generated against sera from SCID mice carrying late passage ovarian carcinoma) was precleared of *E. coli* and phage antigens and used at a 1:200 dilution in a serological expression screen. The library screened was made from a SCID-derived human ovarian tumor (OV9334) using a directional RH oligo(dT) priming cDNA library construction kit and the λScreen vector (Novagen). A bacteriophage lambda screen was employed. Approximately 400,000 pfu of the amplified OV9334 library were screened.

196 positive clones were isolated. Certain sequences that appear to be novel are provided in FIGS. 1A–1S and SEQ ID NOs:1 to 71. Three complete insert sequences are shown in FIGS. 2A–2C. (SEQ ID NOs:72 to 74). Other clones having known sequences are presented in FIGS. 15A–15Z–1 (SEQ ID NOs:82 to 310). Database searches identified the following sequences that were substantially identical to the sequences presented in FIGS. 15A–15Z–1.

These clones were further characterized using microarray technology to determine mRNA expression levels in a variety of tumor and normal tissues. Such analyses were performed using a Synteni (Palo Alto, Calif.) microarray, according to the manufacturer's instructions. PCR amplification products were arrayed on slides, with each product occupying a unique location in the array. mRNA was extracted from the tissue sample to be tested, reverse transcribed and fluorescent-labeled cDNA probes were generated. The microarrays were probed with the labeled cDNA probes and the slides were scanned to measure fluorescence intensity. Data was analyzed using Synteni's provided GEMtools software. The results for one clone (13695, also referred to as O8E) are shown in FIG. 3.

Example 2

Identification of Ovarian Carcinoma cDNAs Using Microarray Technology

This Example illustrates the identification of ovarian carcinoma polynucleotides by screening a microarray of cDNAs for ovarian tumor-specific expression. Such screens were performed using a Synteni (Palo Alto, Calif.) microarray, according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997).

cDNA was generated from ovarian tumor tissue and from normal ovarian tissue, and a subtracted cDNA library was prepared and arrayed on the chip. The chip was then probed with fluorescent probes generated from normal and tumor cDNA. The slides were scanned and the fluorescence intensity was measured, and the data were analyzed using Synteni's GEMtools software. In general, sequences showing at least a 5-fold increase in expression in tumor cells (relative to normal cells) were considered ovarian tumor antigens.

Using such assays, an ovarian tumor antigen was identified that is a splice fusion between the human T-cell leukemia virus type I oncoprotein TAX (see Jin et al., *Cell* 93:81–91, 1998) and an extracellular matrix protein called osteonectin. A splice junction sequence exists at the fusion point. The sequence of this clone is presented in FIG. 4 and SEQ ID NO:75. Osteonectin, unspliced and unaltered, was also identified from such assays independently.

Further clones identified by this methods are referred to herein as 3f, 6b, 8e, 8h, 12c and 12h. Sequences of these clones are shown in FIGS. 5 to 9 and SEQ ID NOs:76 to 81. Microarray analyses were performed as described above, and are presented in FIGS. 10 to 14. A full length sequence encompassing clones 3f, 6b, 8e and 12h was obtained by screening an ovarian tumor (SCID-derived) cDNA library. This 2996 base pair sequence (designated O772P) is presented in SEQ ID NO:311, and the encoded 914 amino acid protein sequence is shown in SEQ ID NO:312. PSORT analysis indicates a Type 1a transmembrane protein localized to the plasma membrane.

From the foregoing it will be appreciated that, although specific embodiments of the invention have been described herein for purposes of illustration, various modifications may be made without deviating from the spirit and scope of the invention. Accordingly, the invention is not limited except as by the appended claims.

SUMMARY OF SEQUENCE LISTING

SEQ ID NOs:1–71 are ovarian carcinoma antigen polynucleotides shown in FIGS. 1A–1S.

SEQ ID NOs:72–74 are ovarian carcinoma antigen polynucleotides shown in FIGS. 2A–2C.

SEQ ID NO:75 is the ovarian carcinoma polynucleotide 3g (FIG. 4).

SEQ ID NO:76 is the ovarian carcinoma polynucleotide 3f (FIG. 5).

SEQ ID NO:77 is the ovarian carcinoma polynucleotide 6b (FIG. 6).

SEQ ID NO:78 is the ovarian carcinoma polynucleotide 8e (FIG. 7A).

SEQ ID NO:79 is the ovarian carcinoma polynucleotide 8h (FIG. 7B).

SEQ ID NO:80 is the ovarian carcinoma polynucleotide 12e (FIG. 8).

SEQ ID NO:81 is the ovarian carcinoma polynucleotide 12h (FIG. 9).

SEQ ID NOs:82–310 are ovarian carcinoma antigen polynucleotides shown in FIGS. 15A–15Z–1.

SEQ ID NO:311 is a full length sequence of ovarian carcinoma polynucleotide O772P.

SEQ ID NO:312 is the O772P amino acid sequence.

What is claimed is:

1. An isolated polypeptide comprising a sequence consisting of at least a 10 amino acid portion of the sequence set forth in SEQ ID NO:312.

2. An isolated polypeptide comprising a sequence consisting of at least a 20 amino acid portion of the sequence set forth in SEQ ID NO:312.

3. An isolated polypeptide consisting of the sequence set forth in SEQ ID NO:312.

4. An isolated polypeptide comprising an amino acid sequence having at least 90% identity with a polypeptide sequence set forth in SEQ ID NO:312.

5. A composition comprising a polypeptide according to any one of claims 1, 2, 3 and 4 in combination with a physiologically acceptable carrier.

6. A composition comprising a polypeptide according to any one of claims 1, 2, 3 and 4, in combination with a non-specific immune response enhancer.

7. A fusion protein comprising at least one polypeptide according to any one of claims 1, 2, 3 and 4.

8. A composition comprising a fusion protein according to claim 7 in combination with a physiologically acceptable carrier.

9. A composition comprising a fusion protein according to claim 7 in combination with a non-specific immune response enhancer.

* * * * *